US009475884B2

(12) United States Patent
Govindan et al.

(10) Patent No.: US 9,475,884 B2
(45) **Date of Patent: *Oct. 25, 2016**

(54) DOSAGES OF IMMUNOCONJUGATES OF ANTIBODIES AND SN-38 FOR IMPROVED EFFICACY AND DECREASED TOXICITY

(71) Applicant: Immunomedics, Inc., Morris Plains, NJ (US)

(72) Inventors: Serengulam V. Govindan, Summit, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/669,611

(22) Filed: Mar. 26, 2015

(65) Prior Publication Data

US 2015/0196664 A1 Jul. 16, 2015

Related U.S. Application Data

(62) Division of application No. 13/948,732, filed on Jul. 23, 2013, now Pat. No. 9,028,833.

(60) Provisional application No. 61/736,684, filed on Dec. 13, 2012, provisional application No. 61/749,548, filed on Jan. 7, 2013.

(51) Int. Cl.

| | |
|---|---|
| ***A61K 47/48*** | (2006.01) |
| ***A61K 39/395*** | (2006.01) |
| ***C07K 16/00*** | (2006.01) |
| ***C07K 16/30*** | (2006.01) |
| ***A61K 31/337*** | (2006.01) |
| ***A61K 31/4184*** | (2006.01) |
| ***A61K 31/4375*** | (2006.01) |
| ***A61K 31/513*** | (2006.01) |
| ***A61K 31/675*** | (2006.01) |
| ***A61K 31/7088*** | (2006.01) |
| ***A61K 31/713*** | (2006.01) |
| ***A61K 33/24*** | (2006.01) |
| ***A61K 38/00*** | (2006.01) |

(Continued)

(52) U.S. Cl.

CPC ......... *C07K 16/3007* (2013.01); *A61K 31/337* (2013.01); *A61K 31/4184* (2013.01); *A61K 31/4375* (2013.01); *A61K 31/454* (2013.01); *A61K 31/4745* (2013.01); *A61K 31/513* (2013.01); *A61K 31/675* (2013.01); *A61K 31/7088* (2013.01); *A61K 31/713* (2013.01); *A61K 33/24* (2013.01); *A61K 38/00* (2013.01); *A61K 38/14* (2013.01); *A61K 38/19* (2013.01); *A61K 39/3955* (2013.01); *A61K 39/39533* (2013.01); *A61K 39/39558* (2013.01); *A61K 45/06* (2013.01); *A61K 47/486* (2013.01); *A61K 47/4863* (2013.01); *A61K 47/48384* (2013.01); *A61K 47/48561* (2013.01); *A61K 47/48569* (2013.01); *A61K 47/48576* (2013.01); *A61K 47/48584* (2013.01); *A61K 47/48592* (2013.01); *A61K 47/48669* (2013.01); *A61K 47/48715* (2013.01); *A61K 48/00* (2013.01); *A61K 51/1045* (2013.01); *A61K 51/1093* (2013.01); *A61N 5/00* (2013.01); *A61N 5/10* (2013.01); *C07K 16/18* (2013.01); *C07K 16/2803* (2013.01); *C07K 16/2833* (2013.01); *C07K 16/2887* (2013.01); *C07K 16/30* (2013.01); *C07K 16/303* (2013.01); *C07K 16/3015* (2013.01); *C07K 16/3023* (2013.01); *C07K 16/3061* (2013.01); *A61K 2039/505* (2013.01); *A61K 2039/507* (2013.01); *A61K 2039/545* (2013.01); *C07K 2316/96* (2013.01); *C07K 2317/76* (2013.01); *C07K 2317/92* (2013.01); *C07K 2317/94* (2013.01)

(58) Field of Classification Search

CPC ..... A61K 47/48; A61K 39/395; C07K 16/00
USPC ............ 424/181.1, 178.1, 179.1; 530/391.9, 530/388.1

See application file for complete search history.

(56) References Cited

U.S. PATENT DOCUMENTS 4,036,945 A 7/1977 Haber
4,046,722 A 9/1977 Rowland (Continued)

FOREIGN PATENT DOCUMENTS

EP 0253202 1/1988
EP 0306943 3/1989

(Continued)

OTHER PUBLICATIONS

US 6,558,648, 05/2003, Griffiths et al. (withdrawn)

(Continued)

*Primary Examiner* — Yan Xiao
(74) *Attorney, Agent, or Firm* — Richard A. Nakashima

(57) ABSTRACT

The present invention relates to therapeutic immunoconjugates comprising SN-38 attached to an antibody or antigen-binding antibody fragment. The antibody may bind to EGP-1 (TROP-2), CEACAM5, CEACAM6, CD74, CD19, CD20, CD22, CSAp, HLA-DR, AFP or MUC5ac and the immunoconjugate may be administered at a dosage of between 4 mg/kg and 24 mg/kg, preferably 4, 6, 8, 9, 10, 12, 16 or 18 mg/kg. When administered at specified dosages and schedules, the immunoconjugate can reduce solid tumors in size, reduce or eliminate metastases and is effective to treat cancers resistant to standard therapies, such as radiation therapy, chemotherapy or immunotherapy.

20 Claims, 8 Drawing Sheets

(51) Int. Cl.

| | |
|---|---|
| ***A61K 38/14*** | (2006.01) |
| ***A61K 38/19*** | (2006.01) |
| ***A61K 45/06*** | (2006.01) |
| ***A61K 48/00*** | (2006.01) |
| ***A61K 51/10*** | (2006.01) |
| ***A61N 5/00*** | (2006.01) |
| ***A61K 31/454*** | (2006.01) |
| ***A61N 5/10*** | (2006.01) |
| ***C07K 16/28*** | (2006.01) |
| ***A61K 31/4745*** | (2006.01) |
| ***C07K 16/18*** | (2006.01) |
| *A61K 39/00* | (2006.01) |

(56) References Cited

U.S. PATENT DOCUMENTS

| | | | | |
|---|---|---|---|---|
| 4,200,690 | A | 4/1980 | Root et al. | |
| 4,331,647 | A | 5/1982 | Goldenberg | |
| 4,359,457 | A | 11/1982 | Neville et al. | |
| 4,699,784 | A | 10/1987 | Shih et al. | |
| 4,704,692 | A | 11/1987 | Ladner | |
| 4,816,567 | A | 3/1989 | Cabilly et al. | |
| 4,824,659 | A | 4/1989 | Howthorne | |
| 4,916,213 | A | 4/1990 | Scannon et al. | |
| 4,918,163 | A | 4/1990 | Young et al. | |
| 4,925,922 | A | 5/1990 | Byers et al. | |
| 4,932,412 | A | 6/1990 | Goldenberg | |
| 4,946,778 | A | 8/1990 | Ladner et al. | |
| 5,057,313 | A | 10/1991 | Shih et al. | |
| 5,106,955 | A | 4/1992 | Endo et al. | |
| 5,112,954 | A | 5/1992 | Abrams et al. | |
| 5,122,368 | A | 6/1992 | Greenfield et al. | |
| 5,134,075 | A | 7/1992 | Hellstrom et al. | |
| 5,171,665 | A | 12/1992 | Hellstrom et al. | |
| 5,196,337 | A | 3/1993 | Ochi et al. | |
| 5,204,095 | A | 4/1993 | Goodall et al. | |
| 5,229,275 | A | 7/1993 | Goroff | |
| 5,443,953 | A | 8/1995 | Hansen et al. | |
| 5,484,892 | A | 1/1996 | Tedder et al. | |
| 5,525,338 | A | 6/1996 | Goldenberg | |
| 5,565,215 | A | 10/1996 | Gref et al. | |
| 5,567,610 | A | 10/1996 | Borrebaeck et al. | |
| 5,593,676 | A | 1/1997 | Bhat et al. | |
| 5,618,920 | A | 4/1997 | Robinson et al. | |
| 5,620,708 | A | 4/1997 | Amkraut et al. | |
| 5,633,425 | A | 5/1997 | Lonberg et al. | |
| 5,679,640 | A | 10/1997 | Gaeta et al. | |
| 5,686,072 | A | 11/1997 | Uhr et al. | |
| 5,693,762 | A | 12/1997 | Queen et al. | |
| 5,698,178 | A | 12/1997 | Goldenberg | |
| 5,702,727 | A | 12/1997 | Amkraut et al. | |
| 5,708,146 | A | 1/1998 | Willner et al. | |
| 5,716,595 | A | 2/1998 | Goldenberg | |
| 5,736,119 | A | 4/1998 | Goldenberg et al. | |
| 5,750,105 | A | 5/1998 | Newman et al. | |
| 5,776,456 | A | 7/1998 | Anderson et al. | |
| 5,789,554 | A | 8/1998 | Leung et al. | |
| 5,792,845 | A | 8/1998 | O'Reilly et al. | |
| 5,795,967 | A | 8/1998 | Aggarwal et al. | |
| 5,798,554 | A | 8/1998 | Grimaldi et al. | |
| 5,817,307 | A | 10/1998 | Cummins | |
| 5,824,701 | A | 10/1998 | Greenwald et al. | |
| 5,874,540 | A | 2/1999 | Hansen et al. | |
| 5,922,302 | A | 7/1999 | Goldenberg et al. | |
| 6,051,228 | A | 4/2000 | Aruffo et al. | |
| 6,051,230 | A | 4/2000 | Thorpe et al. | |
| 6,056,973 | A | 5/2000 | Allen et al. | |
| 6,077,499 | A | 6/2000 | Griffiths et al. | |
| 6,096,289 | A | 8/2000 | Goldenberg | |
| 6,156,754 | A | 12/2000 | Lerchen et al. | |
| 6,165,440 | A | 12/2000 | Esenaliev | |
| 6,183,744 | B1 | 2/2001 | Goldenberg | |
| 6,187,287 | B1 | 2/2001 | Leung et al. | |
| 6,201,104 | B1 | 3/2001 | MacDonald et al. | |
| 6,214,345 | B1 | 4/2001 | Firestone et al. | |
| 6,254,868 | B1 | 7/2001 | Leung et al. | |
| 6,306,393 | B1 | 10/2001 | Goldenberg | |
| 6,331,175 | B1 | 12/2001 | Goldenberg | |
| 6,379,698 | B1 | 4/2002 | Leamon | |
| 6,387,350 | B2 | 5/2002 | Goldenberg | |
| 6,395,276 | B1 | 5/2002 | Rybak et al. | |
| 6,530,944 | B2 | 3/2003 | West et al. | |
| 6,562,318 | B1 | 5/2003 | Filler | |
| 6,653,104 | B2 | 11/2003 | Goldenberg | |
| 6,716,821 | B2 | 4/2004 | Zhao et al. | |
| 7,018,809 | B1 | 3/2006 | Carter | |
| 7,074,403 | B1 | 7/2006 | Goldenberg et al. | |
| 7,122,636 | B1 | 10/2006 | Hsei et al. | |
| 7,151,164 | B2 | 12/2006 | Hansen et al. | |
| 7,238,785 | B2 | 7/2007 | Govindan et al. | |
| 7,312,318 | B2 | 12/2007 | Hansen et al. | |
| 7,387,779 | B2 | 6/2008 | Kalluri | |
| 7,585,491 | B2 | 9/2009 | Govindan et al. | |
| 7,591,994 | B2 | 9/2009 | Govindan et al. | |
| 7,772,373 | B2 | 8/2010 | Hansen et al. | |
| 7,820,161 | B1 | 10/2010 | Curd et al. | |
| 7,910,103 | B2 | 3/2011 | Goldenberg | |
| 7,931,903 | B2 | 4/2011 | Hansen et al. | |
| 7,999,083 | B2 | 8/2011 | Govindan et al. | |
| 8,080,250 | B1 | 12/2011 | Govindan et al. | |
| 8,119,101 | B2 | 2/2012 | Byrd et al. | |
| 8,268,317 | B2 | 9/2012 | Govindan et al. | |
| 8,268,319 | B2 | 9/2012 | Govindan et al. | |
| 8,420,086 | B2 | 4/2013 | Govindan et al. | |
| 8,425,912 | B2 | 4/2013 | Govindan et al. | |
| 8,658,773 | B2 | 2/2014 | Zeng et al. | |
| 9,180,205 | B2 | 11/2015 | Zeng et al. | |
| 9,226,973 | B2 * | 1/2016 | Govindan | A61K 31/454 |
| 2001/0034363 | A1 | 10/2001 | Li et al. | |
| 2002/0018749 | A1 | 2/2002 | Hudson et al. | |
| 2003/0103979 | A1 | 6/2003 | Leung et al. | |
| 2003/0133972 | A1 | 7/2003 | Danthi et al. | |
| 2004/0001838 | A1 | 1/2004 | Zhao et al. | |
| 2004/0076683 | A1 | 4/2004 | Hoarau et al. | |
| 2006/0142506 | A1 | 6/2006 | Breitenkamp et al. | |
| 2006/0193865 | A1 | 8/2006 | Govindan et al. | |
| 2007/0212350 | A1 | 9/2007 | Govindan et al. | |
| 2008/0166363 | A1 | 7/2008 | Govindan et al. | |
| 2010/0104589 | A1 | 4/2010 | Govindan et al. | |
| 2011/0070156 | A1 | 3/2011 | Govindan et al. | |
| 2011/0160159 | A1 | 6/2011 | Ryan | |
| 2011/0256053 | A1 | 10/2011 | Chang et al. | |
| 2011/0274704 | A1 | 11/2011 | Chang et al. | |
| 2011/0305631 | A1 | 12/2011 | Govindan et al. | |
| 2012/0082617 | A1 | 4/2012 | Govindan et al. | |
| 2012/0328564 | A1 | 12/2012 | Govindan et al. | |
| 2013/0090458 | A1 | 4/2013 | Govindan et al. | |
| 2013/0177526 | A1 | 7/2013 | Govindan et al. | |
| 2013/0216561 | A1 | 8/2013 | Govindan et al. | |
| 2014/0004078 | A1 | 1/2014 | Govindan et al. | |
| 2014/0178294 | A1 | 6/2014 | Zeng et al. | |
| 2016/0032008 | A1 | 2/2016 | Zeng et al. | |

FOREIGN PATENT DOCUMENTS

| | | |
|---|---|---|
| EP | 0332865 | 9/1989 |
| EP | 0510949 | 10/1992 |
| WO | 90/09196 | 8/1990 |
| WO | 91/11465 | 8/1991 |
| WO | 91/13974 | 9/1991 |
| WO | 94/27638 | 12/1994 |
| WO | 9509917 | 4/1995 |
| WO | 96/04925 | 2/1996 |
| WO | 98/04281 | 2/1998 |
| WO | 98/42378 | 10/1998 |
| WO | 98/50435 | 11/1998 |
| WO | 99/02567 | 1/1999 |
| WO | 99/54440 | 10/1999 |
| WO | 00/29584 | 5/2000 |
| WO | 00/67795 | 11/2000 |
| WO | 00/67796 | 11/2000 |
| WO | 0074718 | 12/2000 |
| WO | 0076551 | 12/2000 |

(56) References Cited

FOREIGN PATENT DOCUMENTS

| | | |
|---|---|---|
| WO | 0124763 | 4/2001 |
| WO | 2004054622 | 7/2004 |
| WO | 2007123995 | 11/2007 |
| WO | 2012151199 | 11/2012 |

OTHER PUBLICATIONS

Anbalagan et al., "Peptidomimetic Src/pretubulin inhibitor KX-01 alone and in combination with paclitaxel suppresses growth, metastasis in human ER/PR/HER2-negative tumor xenografts", Mol Cancer Ther. Sep. 2012;11 (9):1936-47.
Bennouna et al., "Therapeutic strategies for colorectal cancer in Europe and the United States: focus on chemotherapy for advanced colorectal cancer" Int. J. Clin. Oncol. (2002) 7:236-244.
Burkard et al., "Validating cancer drug targets through chemical genetics", Biochim Biophys Acta. Dec. 2010;1806 (2):251-7.
Burke et al., "Design, synthesis, and biological evaluation of antibody-drug conjugates comprised of potent camptothecin analogues", Bioconjug Chem. Jun. 2009;20(6):1242-50.
Burnham et al., "Invasion of HeLa cells by group B streptococcus requires the phosphoinositide-3-kinase signalling pathway and modulates phosphorylation of host-cell Akt and glycogen synthase kinase-3", Microbiology. Dec. 2007;153(Pt 12):4240-52.
Cao et al., "Bispecific Antibodies as Novel Bioconjugates" Bioconj. Chem. Nov.-Dec. 1998;9(6):635-44.
Cardillo et al., "Humanized anti-Trop-2 IgG—SN-38 conjugate for effective treatment of diverse epithelial cancers: preclinical studies in human cancer xenograft models and monkeys", Clin Cancer Res. May 15, 2011;17(10):3157-69.
Carter et al., Chemotherapy of Cancer; 2nd Edition; John Wiley & Sons, New York, 1981; Appendix C.
Chari et al., "Immunoconjugates Containing Novel Maytansinoids: Promising Anticancer Drugs" Cancer Res. Jan. 1, 1992;52(1):127-31.
Feldmann et al., "Design of effective immunotherapy for human autoimmunity", Nature. Jun. 2, 2005;435(7042):612-9.
Fukuda et al., "Evaluation of novel platinum complexes, inhibitors of topoisomerase I and II in non-small cell lung cancer (NSCLC) sublines resistant to cisplatin", Anticancer Res. Mar.-Apr. 1995;15(2):393-8.
Garcia-Giron et al., "Phase II trial of fortnightly irinotecan (CPT-11) in the treatment of colorectal cancer patients resistant to previous fluoropyrimidine-based chemotherapy", Clin Transl Oncol. Jul. 2005;7(6):244-9.
Gomez-Manzano et al., "Delta-24 increases the expression and activity of topoisomerase I and enhances the antiglioma effect of irinotecan", Clin Cancer Res. Jan. 15, 2006;12(2):556-62.
Govindan et al., "Milatuzumab-SN-38 conjugates for the treatment of CD74+ cancers", Mol Cancer Ther. Jun. 2013;12(6):968-78.
Gueritte-Voegelein et al., "Relationships between the Structure of Taxol Analogues and Their Antimitotic Activity" J. Med. Chem. 1991, 34, 992-998.
Guillemard et al., "Taxane-Antibody Conjugates Afford Potent Cytotoxicity, Enhanced Solubility, and Tumor Target Selectivity" Cancer Res. 61, 694-699, Jan. 15, 2001.
Gura, T., "Systems for identifying new drugs are often faulty", Science. Nov. 7, 1997;278(5340):1041-2.
Hatzakis et al., "Synthesis and single enzyme activity of a clicked lipase-BSA hetero-dimer" Chem. Commun., 2006, 2012-2014.
He et al., "Synthesis and biological evaluation of bis and monocarbonate prodrugs of 10-hydroxycamptothecins", Bioorg Med Chem. Aug. 1, 2004;12(15):4003-8.
Heindel et al., "A Novel Heterobifunctional Linker for Formyl to Thiol Coupling" Bioconjugate Chem. 1991, 2, 427-430.
Horwitz et al., "Antiviral action of camptothecin", Antimicrob Agents Chemother. Nov. 1972;2(5):395-401.
Huang et al., "The Rana catesbeiana rcr Gene Encoding a Cytotoxic Ribonuclease" J. Biol. Chem. 273 (11):6395-6401 (1998).
Kaiser, J., "Cancer. First pass at cancer genome reveals complex landscape", Science. Sep. 8, 2006;313(5792):1370.
King et al., "Monoclonal Antibody Conjugates of Doxorubicin Prepared with Branched Linkers: A Novel Method for Increasing the Potency of Doxorubicin Immunoconjugates" Bioconjugate Chem. 1999, 10, 279-288.
Kreitman et al., "Pseudomonas Exotoxin-based Immunotoxins Containing the Antibody LL2 or LL2-Fab' Induce Regression of Subcutaneous Human B-Cell Lymphoma in Mice" Cancer Res. 53, 819-825, Feb. 15, 1993.
Krontiris and Capizzi, Internal Medicine, Chapters 71-72, pp. 699-729; 4th Edition, Jay Stein (Ed.), Elsevier Science, 1994.
Kufe et al., Non-Intercalating Topoisomerase-Targeting Drugs, Holland-Frei Cancer Medicine, Hamilton (ON), BC Decker (2003).
Kufe et al., Topoisomerase Biology, 6th Ed., Holland-Frei Cancer Medicine, Hamilton (ON), BC Decker (2003).
Mahato et al., "Prodrugs for improving tumor targetability and efficiency", Adv Drug Deliv Rev. Jul. 18, 2011;63 (8):659-70.
Matsumura, Y., "Preclinical and clinical studies of NK012, an SN-38-incorporating polymeric micelles, which is designed based on EPR effect", Adv Drug Deliv Rev. Mar. 18, 2011;63(3):184-92.
Miller et al., "Development of Taxoids with Enhanced Toxicity and Solubility" Poster Presentation, 224th ACS Nat. Meeting, Aug. 18-22, 2002, Boston, MA.
Mine Safety and Health Administration (Special Hazards of Acetylene, Sep. 16, 2011).
Moon et al., "Antibody Conjugates of 7-Ethyl-10-hydroxycamptothecin (SN-38) for Targeted Cancer Chemotherapy" J. Med. Chem. 2008, 51, 6916-6926.
Newton et al., "Potent and specific antitumor effects of an anti-CD22-targeted cytotoxic ribonuclease: potential for the treatment of non-Hodgkin lymphoma" Blood, 97(2):528-35 (2001).
Paul, W., ed., Fundamental Immunology, 3rd Ed., Raven Press, New York, 1993, p. 292-295.
Perez et al., "Inhibition by the anti-mitotic drug doxorubicin of platelet-activating-factor-induced late eosinophil accumulation in rats" Eur. J. Pharmacol. Sep. 4, 1998;356(2-3):239-43.
Reddy et al., "Elimination of Fc Receptor-Dependent Effector Functions of a Modified IgG4 Monoclonal Antibody to Human CD4", J. Immunol. 164:1925-1933 (2000).
Rowlinson-Busza et al., "Targeted delivery of biologic and other antineoplastic agents" Curr. Opin. Oncol. Dec. 1992;4(6):1142-1148.
Sharkey et al., "Epratuzumab-SN-38: a new antibody-drug conjugate for the therapy of hematologic malignancies", Mol Cancer Ther. Jan. 2012;11(1):224-34.
Sharkey et al., "Combination radioimmunotherapy and chemoimmunotherapy involving different or the same targets improves therapy of human pancreatic carcinoma xenograft models", Mol Cancer Ther. Jun. 2011;10(6):1072-81.
Shih et al., "The Processing and Fate of Antibodies and Their Radiolabels Bound to the Surface of Tumor Cells In Vitro: A Comparison of Nine Radiolabels" J. Nucl. Med. 1994; 35:899-908.
Shih et al., "In vitro and in vivo reactivity of an internalizing antibody, RS7, with human breast cancer", Cancer Res. Dec. 1, 1995;55(23 Suppl):5857s-5863s.
Stanford University Environmental Health and Safety (Information on Azide Compounds, Dec. 2, 2008).
Suzawa et al., "Synthesis of a Novel Duocarmycin Derivative DU-257 and its Application to Immunoconjugate Using Poly(ethylene glycol)-dipeptidyl Linker Capable of Tumor Specific Activation" Bioorg. Med. Chem. 8(8):2175-84 (2000).
Suzawa et al., "Enhanced tumor cell selectivity of adriamycin-monoclonal antibody conjugate via a poly(ethylene glycol)-based cleavable linker" J. Control. Release 79:229-242 (2002).
Trail et al., "Carcinoma Reactive Doxorubicin (DOX) Conjugates: Comparison of BR64-DOX Conjugates Prepared With Disulfide or Thioether Linkers", Proc. Amer. Assoc. Cancer Res., vol. 34, Mar. 1993, #2858, p. 479.
Talmadge et al., "Murine models to evaluate novel and conventional therapeutic strategies for cancer", Am J Pathol. Mar. 2007;170(3):793-804.

(56) References Cited

OTHER PUBLICATIONS

Thurber et al., "Antibody tumor penetration: transport opposed by systemic and antigen-mediated clearance", Adv Drug Deliv Rev. Sep. 2008;60(12):1421-34.
Van Noort and Amor, "Cell Biology of Autoimmune Disease", vol. 178, pp. 127-206; International Rev. of Cytology, 1998.
Walker et al., "Synthesis of an Immunoconjugate of Camptothecin" Bioorg. Med. Chem. Lett. 12(2):217-219 (2002).
Bardia et al., "IMMU-132, a new antibody-drug conjugate (ADC) against Trop-2, as a novel therapeutic for patients with relapsed/refractory, metastatic, triple-negative breast cancer (TNBC): Results from Phase I/II clinical trial (NCT01631552)", Poster, San Antonio Breast Cancer Symposium, Dec. 9-13, 2014.
Goldenberg et al., "Selective in vivo therapeutic efficacies of SN-38 conjugates of an anti-CEACAM5 antibody in preclinical models of human colon carcinoma", Presentation, ASCO 2009 Gastrointestinal Cancers Symposium, San Francisco, CA, Jan. 15-17, 2009.
Goldenberg, D.M., "Challenging the Dogmas: Clinical Efficacy of SN-38-Conjugated Antibodies in Solid Tumors", 26th EORTC-NCI-AACR Symposium on Molecular Targets and Cancer Therapeutics, Barcelona, Spain, Nov. 18-21, 2014.
Goldenberg, D.M., "SN-38 Conjugates for Therapy of Advanced Solid Cancers", 5th Annual World ADC Summit in San Diego, CA, Oct. 26-29, 2014.
Goldenberg et al., "Therapy of human solid tumor xenografts with CD74-targeted milatuzumab-SN-38 immunoconjugates", Poster, 2012 ASCO Annual Meeting, Chicago, IL, Jun. 1-5, 2012.
Goldenberg et al., "Improved Therapeutic Index of IMMU-132 ADC vs. Irinotecan in Preclinical Studies", Presentation, AACR Annual Meeting, San Diego, CA, Apr. 5-9, 2014.
Gorman, G. "Focused on Therapy: Cancer, Autoimmune & Other Serious Diseases", Presentation, Oppenheimer 23rd Annual Healthcare Conference, NYC, Dec. 12, 2012.
Govindan et al., "Targeted therapy of human colonic, lung, and pancreatic cancer xenografts, growing in nude mice, with potent antibody conjugates of SN-38", Poster, AACR 100th Annual Meeting, Denver, CO, Apr. 18-22, 2009.
Govindan et al., "Efficacious therapies of two human pancreatic cancer xenografts and an aggressive human lymphoma xenograft with redesigned antibody-SN-38 conjugates", Poster, AACR 101st Annual Meeting, Washington, DC, Apr. 17-21, 2010.
Govindan et al., "Improving the Therapeutic Index in Cancer Therapy by Using Antibody-Drug Conjugates Designed with a Moderately Cytotoxic Drug", Mol Pharm. Nov. 25, 2014. [Epub ahead of print].
Govindan et al., "Optimal cleavable linker for antibody-SN-38 conjugates for cancer therapy: Impact of linker's stability on efficacy", Poster, AACR 103rd Annual Meeting, Chicago, IL, Mar. 31-Apr. 4, 2012.
Govindan et al., "CEACAM5-targeted therapy of human colonic and pancreatic cancer xenografts with potent labetuzumab-SN-38 immunoconjugates", Clin Cancer Res. Oct. 1, 2009;15(19):6052-61.
Karacay et al., "Combining antibody-targeted radiation (radioimmunotherapy) and antibody-SN-38 conjugates (ADC) improves pancreatic cancer therapy", Poster, AACR 101st Annual Meeting, Washington, DC, Apr. 17-21, 2010.
Moon et al., "Cross-linker evaluation in the design of antibody-SN-38 conjugates for cancer therapy", Poster, AACR 101st Annual Meeting, Washington, DC, Apr. 17-21, 2010.
Segal et al., "IMMU-130, an SN-38 antibody-drug conjugate (ADC) targeting CEACAM5, is therapeutically active in metastatic colorectal cancer (mCRC): Initial clinical results of two Phase I studies", Presentation, AACR Annual Meeting, San Diego, CA, Apr. 5-9, 2014.
Starodub et al., "IMMU-132, an SN-38 antibody-drug conjugate (ADC) targeting Trop-2, as a novel platform for the therapy of diverse metastatic solid cancers: Clinical results", Poster, the 2014 Annual Meeting of the American Society of Clinical Oncology (ASCO), May 30-Jun. 3, 2014.
Beckman et al., "Antibody constructs in cancer therapy: protein engineering strategies to improve exposure in solid tumors", Cancer. Jan. 15, 2007;109(2):170-9.
Berenbaum, MC., "Synergy, additivism and antagonism in immunosuppression. A critical review", Clin Exp Immunol. Apr. 1977;28(1):1-18.
Berenbaum, MC., "What is synergy?", Pharmacol Rev. Jun. 1989;41(2):93-141.
Cespedes et al., "Mouse models in oncogenesis and cancer therapy", Clin Transl Oncol. May 2006;8(5):318-29.
Dennis, C., "Cancer: off by a whisker", Nature. Aug. 17, 2006;442(7104):739-41.
Foran, JM., "Antibody-based therapy of non-Hodgkin's lymphoma", Best Pract Res Clin Haematol. Sep. 2002;15(3):449-65.
Fujimori et al., "A modeling analysis of monoclonal antibody percolation through tumors: a binding-site barrier", J Nucl Med. Jul. 1990;31(7):1191-8.
Lundberg et al., "Conjugation of an anti-B-cell lymphoma monoclonal antibody, LL2, to long-circulating drug-carrier lipid emulsions", J. Pharm. Pharmacol. 51(10):1099-105 (1999).
Mack et al., "A small bispecific antibody construct expressed as a functional single-chain molecule with high tumor cell cytotoxicity", Proc. Natl. Acad. Sci. USA 92:7021-7025 (1995).
Maloney et al., "Phase I clinical trial using escalating single-dose infusion of chimeric anti-CD20 monoclonal antibody (IDEC-C2B8) in patients with recurrent B-cell lymphoma", Blood 84(8):2457-66 (1994).
Maloney et al., "IDEC-C2B8 (Rituximab) anti-CD20 monoclonal antibody therapy in patients with relapsed low-grade non-Hodgkin's lymphoma", Blood. Sep. 15, 1997;90(6):2188-95.
Mason et al., "Value of monoclonal anti-CD22 (p135) antibodies for the detection of normal and neoplastic B lymphoid cells", Blood. Mar. 1987;69(3):836-40.
Mills et al., "Diagnostic imaging of non-Hodgkin's lymphoma with anti-lymphomas antibody labeled with Tc-99m", Proc Am Assoc Cancer Res 1993; 34:479, Abstract #2857.
Mole S. E., "Epitope Mapping", Methods in Molecular Biology, vol. 10: Immunochemical Protocols, Manson (Ed.), Humana Press, Inc. (1992).
Morrison et al., "Chimeric human antibody molecules: mouse antigen-binding domains with human constant region domains", Proc Natl Acad Sci USA Nov. 1984;81(21):6851-5.
Murthy et al., "Lymphoma imaging with a new technetium-99m labelled antibody, LL2", Eur J Nucl Med. 1992;19(6):394-401.
Ochakovskaya et al., Therapy of Disseminated B-Cell Lymphoma Xenografts in Severe Combined Immunodeficient Mice with an Anti-CD74 Antibody Conjugated with (111)Indium, (67)Gallium, or (90)Yttrium, Clin. Cancer Res. 7(6):1505-1510 (2001).
Orlandi et al., "Cloning immunoglobulin variable domains for expression by the polymerase chain reaction", Proc. Natl. Acad. Sci. USA 86:3833-3837 (1989).
Pastan et al., "Immunotoxins", Cell 47:641-648 (1986).
Pawlak-Byczkowska et al., "Two new monoclonal antibodies, EPB-1 and EPB-2, reactive with human lymphoma", Cancer Res. 49(16):4568-77 (1989).
Perrota et al., "Response of chronic relapsing ITP of 10 years duration to Rituximab", Blood, vol. 92(10 Suppl.), p. 88b, 1998, Abstract# 3360.
Press et al., "Radiolabeled-antibody therapy of B-cell lymphoma with autologous bone marrow support", N. Engl. J. Med. 329(17):1219-24 (1993).
Press et al., "Phase II trial of 131I-B1 (anti-CD20) antibody therapy with autologous stem cell transplantation for relapsed B cell lymphomas", Lancet 346:336-40 (1995).
Press et al., "Prospects for the management of non-Hodgkin's lymphomas with monoclonal antibodies and immunoconjugates", Cancer J. Sci. Am. 4(Suppl 2):S19-26 (1998).
Protheroe et al., "Remission of inflammatory arthropathy in association with anti-CD20 therapy for non-Hodgkin's lymphoma", Rheumatology (Oxford) 38(11):1150-2 (1999).
Qu et al., "Carbohydrates engineered at antibody constant domains can be used for site-specific conjugation of drugs and chelates", J. Immunol. Methods 213(2):131-44 (1998).

(56) References Cited

OTHER PUBLICATIONS

Qu et al., "Internalization and cytotoxic effects of a humanized anti-CD74 antibody, LL1", Proc Am Assoc Cancer Res 2002;43:255, Abstract # 1269.
Queen et al., "A humanized antibody that binds to the interleukin 2 receptor", Proc Natl Acad Sci U S A. Dec. 1989;86(24):10029-33.
Renner et al., "Monoclonal antibodies in the treatment of non-Hodgkin's lymphoma: recent results and future prospects", Leukemia 11(Suppl 2):S55-9 (1997).
Riechmann et al., "Reshaping human antibodies for therapy", Nature 332(6162):323-7 (1988).
Roche et al., "Cell surface HLA-DR-invariant chain complexes are targeted to endosomes by rapid internalization", Proc Natl Acad Sci U S A. Sep. 15, 1993;90(18):8581-5.
Rowan et al., "Cross-linking of the CAMPATH-1 antigen (CD52) mediates growth inhibition in human B- and T-lymphoma cell lines, and subsequent emergence of CD52-deficient cells", Immunology 95(3):427-36 (1998).
Rudikoff et al., "Single amino acid substitution altering antigen-binding specificity", Proc. Natl. Acad. Sci. USA 79(6):1979-83 (1982).
Rudnick et al., "Affinity and avidity in antibody-based tumor targeting", Cancer Biother Radiopharm. Apr. 2009;24(2):155-61.
Saltzman et al., "Transport rates of proteins in porous materials with known microgeometry", Biophys. J. 55(1):163-71 (1989).
Sandhu, J. S., "Protein engineering of antibodies", Crit. Rev. Biotechnol. 12(5-6):437-62 (1992).
Schwarts-Albiez et al., "The carbohydrate moiety of the CD22 antigen can be modulated by inhibitors of the glycosylation pathway", Leukocyte Typing IV. White Cell Differentiation Antigens, Knapp et al., (Eds.), p. 65-67, Oxford University Press, 1989.
Sherwood et al., "Controlled antibody delivery systems", Biotechnology 10(11):1446-9 (1992).
Shih et al., "Internalization and intracellular processing of an anti-B-cell lymphoma monoclonal antibody, LL2", Int J Cancer 56(4):538-45 (1994).
Singer et al., "Optimal humanization of 1B4, an anti-CD18 murine monoclonal antibody, is achieved by correct choice of human V-region framework sequences", J. Immunol. 150(7):2844-57 (1993).
Stein et al., "Epitope specificity of the anti-(B cell lymphoma) monoclonal antibody, LL2", Cancer Immunol. Immunother. 37(5):293-8 (1993).
Tallarida, RJ., Drug Synergism and Dose Effect Analysis, Ed. Chapman & Hall, 2000, pp. 1-8; 10-13; 57-71.
Taylor et al., "Human immunoglobulin transgenes undergo rearrangement, somatic mutation and class switching in mice that lack endogenous IgM", Int Immunol. Apr. 1994;6(4):579-91.
Theocharis et al., "Characterization of in vivo mutated T cell clones from patients with systemic lupus erythematosus", Clin. Immunol. Immunopathol. 74(2):135-42 (1995).
Tsang et al.,"Reactive oxygen species mediate doxorubicin induced p53-independent apoptosis", Life Sci. Sep. 5, 2003;73(16):2047-58.
Vuist et al., "Potentiation by interleukin 2 of Burkitt's lymphoma therapy with anti-pan B (anti-CD19) monoclonal antibodies in a mouse xenotransplantation model", Cancer Res. 49(14):3783-8 (1989).
Wilson et al., "cDNA cloning of the B cell membrane protein CD22: a mediator of B-B cell interactions", J Exp Med. Jan. 1, 1991;173(1):137-46.
Wilson et al., "Genomic structure and chromosomal mapping of the human CD22 gene", J Immunol. Jun. 1, 1993;150 (11):5013-24.
Wosnik et al., "Rapid construction of large synthetic genes: total chemical synthesis of two different versions of the bovine prochymosin gene", Gene. 1987;60(1):115-27.
Wurflein et al., "Evaluating antibodies for their capacity to induce cell-mediated lysis of malignant B cells", Cancer Res. Jul. 15, 1998;58(14):3051-8.
Ausubel et al., (eds.), Current Protocols in Molecular Biology, pp. 8.2.8-8.2.13, John Wiley & Sons, Inc. (1990).
Ausubel et al., (eds.), Short Protocols in Molecular Biology, pp. 8.8-8.10, John Wiley & Sons, Inc. (1995).
Baines et al., "Purification of Immunoglobulin G (IgG)", Methods in Molecular Biology, vol. 10, pp. 79-104, Manson et al., (eds.), The Human Press (1992).
Bambot et al., "Efficient total gene synthesis of 1.35-kb hybrid alpha-lytic protease gene using the polymerase chain reaction", PCR Methods Appl. Feb. 1993;2(3):266-71.
Baum et al., "Initial clinical results with technetium-99m-labeled LL2 monoclonal antibody fragment in the radioimmunodetection of B-cell lymphomas", Cancer. Feb. 1, 1994;73(3 Suppl):896-9.
Beers et al., The Merck Manual of Diagnosis and Therapy, Ch. 180, p. 1474-1476; 17th Ed., Whitehouse Station, NJ, Merck Research Labs (1999).
Belisle et al., "Epitope specificity of the anti-B-cell lymphoma monoclonal antibody, LL2", Proc Am Assoc Cancer Res 1993; 34:481, Abstr #2873.
Bendig, M., "Humanization of Rodent Monoclonal Antibodies by CDR Grafting", Academic Press Inc., New York, NY, vol. 8, (1995), pp. 83-93.
Bhat et al., "Human antilipid A monoclonal antibodies bind to human B cells and the i antigen on cord red blood cells", J Immunol. Nov. 1, 1993;151(9):5011-21.
Carter et al., "Humanization of an anti-p185HER2 antibody for human cancer therapy", Proc. Natl. Acad. Sci. USA 89(10):4285-9 (1992).
Coligan et al., (Eds.), Current Protocols in Immunology, vol. 1, pp. 2.5.1-2.6.7; pp. 2.7.1.-2.7.12; pp. 2.8.1-2.8.10; pp. 2.9.1-2.9.3; pp. 2.10.-2.10.4; John Wiley & Sons, Inc., 1991.
Coloma et al., "Design and production of novel tetravalent bispecific antibodies", Nat. Biotechnol. 15(2):159-63 (1997).
Dillon et al., "Use of Polymerase Chain Reaction for the Rapid Construction of Synthetic Genes", Methods in Molecular Biology, vol. 15: PCR Protocols: Current Methods and Applications, White (Ed.), pp. 263-268, Humana Press, Inc. (1993).
Ellis et al., "Engineered anti-CD38 monoclonal antibodies for immunotherapy of multiple myeloma", J Immunol. Jul. 15, 1995;155(2):925-37.
Flavell et al., "Systemic therapy with 3BIT, a triple combination cocktail of anti-CD19, -CD22, and -CD38-saporin immunotoxins, is curative of human B-cell lymphoma in severe combined immunodeficient mice", Cancer Res. 57:4824-9 (1997).
Foy et al., "In vivo CD40-gp39 interactions are essential for thymus-dependent humoral immunity. II. Prolonged suppression of the humoral immune response by an antibody to the ligand for CD40, gp39", J Exp Med. Nov. 1, 1993;178(5):1567-75.
French et al., "Response of B-cell lymphoma to a combination of bispecific antibodies and saporin", Leuk. Res. 20 (7):607-17 (1996).
Ghetie et al., "Evaluation of ricin a chain-containing immunotoxins directed against CD19 and CD22 antigens on normal and malignant human B-cells as potential reagents for in vivo therapy", Cancer Res. 48(9):2610-7 (1988).
Goldenberg et al., "Targeting, dosimetry, and radioimmunotherapy of B-cell lymphomas with iodine-131-labeled LL2 monoclonal antibody", J Clin Oncol. Apr. 1991;9(4):548-64.
Goldenberg, D. M., "New Developments in Monoclonal Antibodies for Cancer Detection and Therapy", CA Cancer J. Clin. 44(1):43-64 (1994).
Goldenberg et al., "Epratuzumab (Humanized Anti-CD22 MAb) Conjugated with SN-38, a New Antibody-Drug Conjugate (ADC) for the Treatment of Hematologic Tumors: Preclinical Studies Alone and in Combination with Veltuzumab, a Humanized Anti-CD20 MAb", Blood (ASH Annual Meeting Abstracts) 2010 116: Abstract 3941.
Gondo et al., "HLA class II antigen associated invariant chain gene expression in malignant lymphoma", Br. J. Haematol. 67(4):413-7 (1987).
Green et al., "Antigen-specific human monoclonal antibodies from mice engineered with human Ig heavy and light chain YACs", Nature Genetics 7:13-21 (1994).
Gussow et al., "Humanization of monoclonal antibodies", Methods Enzymol. 1991;203:99-121.

(56) References Cited

OTHER PUBLICATIONS

Hansen et al., "Internalization and catabolism of radiolabelled antibodies to the MHC class-II invariant chain by B-cell lymphomas", Biochem. J. 1996, 320:293-300.
Hashida et al., "More useful maleimide compounds for the conjugation of Fab' to horseradish peroxidase through thiol groups in the hinge", J Appl Biochem. Feb.-Apr. 1984;6(1-2):56-63.
Hekman et al., "Initial experience with treatment of human B cell lymphoma with anti-CD19 monoclonal antibody", Cancer Immunol. Immunother. 1991;32(6):364-72.
Hess et al., "Specificity of effector T lymphocytes in autologous graft-versus-host disease: role of the major histocompatibility complex class II invariant chain peptide", Blood 89(6):2203-9 (1997).
Hildebrandt et al., "Expression of CD 21, CD 22, and the mouse erythrocyte receptor on peripheral B lymphocytes in rheumatoid arthritis", Ann Rheum Dis. Jul. 1988;47(7):588-94.
Imuran patient information leaflet, GlaxoSmithKline 7076598/5093, Oct. 2004.
Inaoki et al., "CD19-regulated signaling thresholds control peripheral tolerance and autoantibody production in B lymphocytes", J Exp Med. Dec. 1, 1997;186(11):1923-31.
Jones et al., "Replacing the complementarity-determining regions in a human antibody with those from a mouse" Nature 321(6069):522-5 (1986).
Juweid et al., "99Tcm-LL1: a potential new bone marrow imaging agent", Nucl. Med. Commun. 18(2):142-8 (1997).
Juweid et al., "Treatment of non-Hodgkin's lymphoma with radiolabeled murine, chimeric, or humanized LL2, an anti-CD22 monoclonal antibody", Cancer Res. 55(23 Suppl):5899s-5907s (1995).
Kaminski et al., "Radioimmunotherapy of B-cell lymphoma with [131I]anti-B1 (anti-CD20) antibody", N. Engl. J. Med. 329(7):459-65 (1993).
Kiener et al., "Stimulation of CD40 with purified soluble gp39 induces proinflammatory responses in human monocytes", J Immunol. Nov. 15, 1995;155(10):4917-25.
Kiesel et al., "Removal of cells from a malignant B-cell line from bone marrow with immunomagnetic beads and with complement and immunoglobulin switch variant mediated cytolysis", Leuk. Res. 11(12):1119-25 (1987).
Kohler et al., "Continuous cultures of fused cells secreting antibody of predefined specificity", Nature 256:495-7 (1975).
Kreitman et al., "Pseudomonas exotoxin-based immunotoxins containing the antibody LL2 or LL2-Fab' induce regression of subcutaneous human B-cell lymphoma in mice", Cancer Res. 53(4):819-25 (1993).
Leonard et al., "Epratuzumab, a new Anti-CD22, humanized, monoclonal antibody for the therapy of non-Hodgkin's lymphoma (NHL): phase I/II trial results", Blood 94:92a-93a, Abstract # 404, (1999).
Leung et al., "Chimerization and humanization of a B-cell Lymphoma specific antibody, LL2", Proc Am Assoc Cancer Res 1993; 34:481, Abstr #2872.
Leung et al., "Chimerization of LL2, a Rapidly Internalizing Antibody Specific for B Cell Lymphoma", Hybridoma 13 (6):469-476 (1994).
Leung et al., "Construction and characterization of a humanized, internalizing, b-cell (CD22)-specific, leukemia/lymphma antibody, LL2", Mol. Immunol. 32(17/18):1413-1427 (1995).
Levine et al., "IgM antibody-related polyneuropathies: B-cell depletion chemotherapy using Rituximab", Neurology 52 (8):1701-4 (1999).
Li et al., "The epitope specificity and tissue reactivity of four murine monoclonal anti-CD22 antibodies", Cell Immunol. 118(1):85-99 (1989).
Lonberg et al., "Antigen-specific human antibodies from mice comprising four distinct genetic modifications", Nature 368:856-9 (1994).
Longo, D. L., "Immunotherapy for non-Hodgkin's lymphoma", Curr. Opin. Oncol. 8(5):353-9 (1996).
Losman et al., "Baboon anti-idiotype antibodies mimic a carcinoembryonic antigen epitope", Int J Cancer. Aug. 15, 1990;46(2):310-4.
Lundberg, B., "Preparation of drug-carrier emulsions stabilized with phosphatidylcholine-surfactant mixtures", J. Pharm. Sci. 83(1):72-5 (1994).
Lundberg et al., "Submicron lipid emulsions containing amphipathic polyethylene glycol for use as drug-carriers with prolonged circulation time", Int. J. Pharm. 134:119-127 (1996).
Faltas et al., "Sacituzumab Govitecan, a Novel Antibody-Drug Conjugate, in Patients With Metastatic Platinum-Resistant Urothelial Carcinoma", Clin Genitourin Cancer. Feb. 2016;14(1):e75-9.
Bardia et al., "Therapy of refractory/relapsed metastatic triple-negative breast cancer (TNBC) with an anti-Trop-2-SN-38 antibody-drug conjugate (ADC), sacituzumab govitecan (IMMU-132): Phase I/II clinical experience", J Clin Oncol 33, 2015 (suppl; abstr 1016), Retrieved from http://meetinglibrary.asco.org/content/150673-156.
Dang et al., "Hypoxia-inducible factor-1 target genes as indicators of tumor vessel response to vascular endothelial growth factor inhibition", Cancer Res. Mar. 15, 2008;68(6):1872-80.
Dotan et al., "A new anti-CEA-SN-38 antibody-drug conjugate (ADC), IMMU-130, is active in controlling metastatic colorectal cancer (mCRC) in patients (pts) refractory or relapsing after irinotecan-containing chemotherapies: Initial results of a phase I/II study", J Clin Oncol 33, 2015 (suppl; abstr 2505), Retrieved from http://meetinglibrary.asco.org/content/148390-156.
Goldenberg et al., "Tolerability in mice, monkeys, and rabbits of new antibody (MAb)-drug (SN-38) immunoconjugates", Proceedings of the 102nd Annual Meeting of the American Association for Cancer Research; Apr. 2-6, 2011; Orlando, FL. Cancer Res 2011;71(8 Suppl):Abstract # 3619.
Govindan et al., "IMMU-130, a unique antibody-drug conjugate (ADC) of SN-38 targeting CEACAM5 antigen: Preclinical basis for clinical activity in metastatic colorectal cancer (mCRC)", J Clin Oncol 33, 2015 (suppl 3; abstr 625), Retrieved from http://meetinglibrary.asco.org/content/139777-158.
Guarino et al., "Therapy of advanced metastatic lung cancer with an anti-Trop-2-SN-38 antibody-drug conjugate (ADC), sacituzumab govitecan (IMMU-132): Phase I/II clinical experience", J Clin Oncol 33, 2015 (suppl; abstr 2504), Retrieved from http://meetinglibrary.asco.org/content/148373-156.
NCT01270698 (Jan. 3, 2011, pp. 1-4).
NCT01605318 (May 22, 2012, pp. 1-4).
Starodub et al., "Phase I/II trial of Immu-132 (isactuzumab govitecan), an anti-Trop-2-SN-38 antibody drug conjugate (ADC): Results in patients with metastatic gastrointestinal (GI) cancers", J Clin Oncol 33, 2015 (suppl 3; abstr 703), Retrieved from http://meetinglibrary.asco.org/content/140198-158.
Declaration under 37 C.F.R. 1.132 by David M. Goldenberg, filed in U.S. Appl. No. 13/948,732 on Jun. 20, 2014.
Declaration under 37 C.F.R. 1.132 by David M. Goldenberg, filed in US Appl. No. 14/204,698 on Jan. 7, 2015
Segal et al., "IMMU-130, an SN-38 antibody-drug conjugate (ADC) targeting CEACAM5, is therapeutically active in metastatic colorectal cancer (mCRC): Initial clinical results of two Phase I studies", 2014 AACR Meeting Apr. 5-9, 2-14, San Diego, CA (Abstract No. CT211).
Seruga et al., "Failures in Phase III: Causes and Consequences", Clin Cancer Res. Oct. 15, 2015;21(20):4552-60.
Reagan-Shaw et al., "Dose translation from animal to human studies revisited", FASEB J. Mar. 2008;22(3):659-61.
Bardia et al., "Safety and efficacy of anti-Trop-2 antibody drug conjugate, sacituzumab govitecan (IMMU-132), in-heavily pretreated patients with TNBC", Poster presented at San Antonio Breast Cancer Symposium, Dec. 10, 2015, San Antonio, TX.
Bardia et al., "Safety and tumor responses of the anti-Trop-2 antibody drug conjugate, sacituzumab govitecan (IMMU-132), in refractory, metastatic, triple-negative breast cancer (TNBC): An ongoing Phase II trial", Poster presented at AACR-NCI-EORTC International Conference: Molecular Targets and Cancer Therapeutics, Nov. 8, 2015, Boston, MA.

(56) References Cited

OTHER PUBLICATIONS

Basu et al., "The epithelial/carcinoma antigen EGP-1, recognized by monoclonal antibody RS7-3G11, is phosphorylated on serine 303", Int J Cancer. Aug. 9, 1995;62(4):472-9.

Basu et al., "Epithelial glycoprotein EGP-1 recognized by MAb RS7-3G11 is phosphorylated on serine 303", Proc. Amer. Assoc. Cancer Res. 36: 439 (Abstr. #2621), 1995.

Camidge et al., "Therapy of Advanced Metastatic Lung Cancers with an Anti-Trop-2-SN-38 Antibody-Drug Conjugate, IMMU-132: Interim Phase II Clinical Results", Oral presentation at 16th World Conference on Lung Cancer (WCLC), Sep. 7, 2015, Denver, CO.

Cardillo et al., "A novel immunotoxin comprising quadruple RNase tethered to an internalizing anti-TROP-2 humanized MAb shows potent cytotoxicity against diverse solid tumors in vitro", Proc. Amer. Assoc. Cancer Res. Annual Meeting, 51:1296 (Abstr. #5346), 2010.

Cardillo et al., "Combining an anti-Trop-2 antibody-SN-38 conjugate (sacituzumab govitecan) with microtubule inhibitors (paclitaxel and eribulin mesylate) or PARP inhibitor (olaparib) significantly improves therapeutic outcome in experimental triple-negative breast cancer (TNBC)", Mol Cancer Ther 2015;14(12 Suppl 2):Abstract nr C166.

Cardillo et al., "Synthetic lethality in TNBC mediated by an anti-Trop-2 antibody-drug conjugate, sacituzumab govitecan (IMMU-132), when combined with paclitaxel or the PARP Inhibitor, olaparib", Poster presented at San Antonio Breast Cancer Symposium, Dec. 10, 2015, San Antonio, TX.

Chang et al., "In vitro and in vivo evaluation of a novel recombinant immunotoxin of ranpirnase fused to a humanized anti-EGP-1 antobody, HRS7, for the potential treatment of prostate and lung cancers", Proc. Amer. Assoc. Cancer Res. Annual Meeting, 48: (Abstr. #4795), 2007.

Goldenberg et al., Tolerability in mice, monkeys, and rabbits of new antibody (MAb)-drug (SN-38) immunoconjugates. Proc. Amer. Assoc. Cancer Res. 102nd Annual Meeting, 52: 865 (Abstr. #3619), 2011.

Goldenberg et al., "SN-38 antibody-drug conjugates as a novel platform for solid cancer therapy: preclinical science", American Association for Cancer Research (AACR) 2014 Annual Meeting, Abstr. #2904, Apr. 7, 2014.

Goldenberg et al., "Characterization of an anti-Trop-2-SN-38 antibody-drug conjugate (IMMU-132) with potent activity against solid cancers", American Society of Clinical Oncology (ASCO) 50th Annual Meeting. J Clin Oncol 32:5s, 2014 (suppl; abstr #3107), 2014.

Goldenberg et al., "IMMU-132, a potential new antibody-drug conjugate (ADC) for the treatment of triple-negative breast cancer (TNBC): Preclinical and initial clinical results", Poster P5-19-08 presented at San Antonio Breast Cancer Symposium, Dec. 9-13, 2014.

Govindan et al., "Optimal cleavable linker for antibody-SN-38 conjugates for cancer therapy: Impact of linker's stability on efficacy", Proc. Amer. Assoc. Cancer Res. 103rd Annual Meeting, 53: 611 (Abstr. #2526), 2012.

Govindan et al., "Preclinical therapy of breast cancer with a radioiodinated humanized anti-EGP-1 monoclonal antibody: advantage of a residualizing iodine radiolabel", Breast Cancer Res Treat Mar. 2004;84(2):173-82.

Govindan et al., "Conjugation of SN-38 to an anti-EGP-1 MAB, HRS7, via a cleavable linker shows selective therapeutic activity in a preclinical model of non-small cell lung cancer (NSCLC)", Proc. Eleventh Conf. on Cancer Therapy, Cancer Biotherapy & Radiopharmaceuticals, 21(4):401 (Abstr. #56), 2006.

Govindan et al., "Therapy of human colonic and lung cancer xenografts with SN-38 conjugates of anti-CEACAM5 and anti-EGP-1 humanized monoclonal antibodies", Proc. AACR Molecular Targets and Cancer Therapeutics, 347-348 (Abstr. #C287), 2007.

Govindan et al., "Efficacious therapies of two human pancreatic cancer xenografts and an aggressive human lymphoma xenograft with redesigned antibody-SN-38 conjugates", Proc. Amer. Assoc. Cancer Res. Annual Meeting, 51:591 (Abstr. #2438), 2010.

Liu et al., "Novel immunoRNases comprising multiple copies of ranpimase display potent cytotoxicity in human breast cancer cell lines expressing Trop-2", Proc. Amer. Assoc. Cancer Res. 103rd Annual Meeting, 53: 1124 (Abstr. #4636), 2012.

Ocean et al., "Interim results of IMMU-132 (sacituzumab govitecan), an anti-trop-2 antibody-drug conjugate (ADC) in patients with metastatic gastrointestinal (GI) cancers", Poster presented at ESMO's 17th World Congress on Gastrointestinal Cancer, Jul. 4, 2015.

Picozzi et al., "IMMU-132, a new antibody-drug conjugate (ADC), evaluated in patients with advanced, metastatic, pancreatic ductal adenocarcinoma (mPC): Results of a Phase I/II trial", Poster presented at American Association for Cancer Research (AACR) Special Conference on Pancreatic Cancer:Innovations in Research and Treatment, Abstr. #B99, May 18-21, 2014.

Shih et al., "Radioimmunodetection and radioimmunotherapy of xenografted human breast cancer with monoclonal antibody RS7", J. Immunother. 16: 169 (Abstr. #85), 1994.

Starodub et al., "Advanced solid cancer therapy with a novel antibody-drug conjugate (ADC), sacituzumab govitecan (IMMU-132): key preclinical and clinical results", Abstract CT236. Presented at American Association for cancer Research (AACR) 2015 Annual Meeting, Philadelphia, PA, Apr. 20, 2015.

Starodub et al., "Safety, efficacy, and pharmacokinetics of a new humanized anti-Trop-2 antibody-SN-38 conjugate (IMMU-132) for the treatment of diverse epithelial cancers: Phase I clinical experience", AACR-NCI-EORTC International Conference on Molecular Targets and Cancer Therapeutics Meeting. (Abstr. #C67), Oct. 22, 2013.

Starodub et al., "SN-38 antibody-drug conjugate (ADC) targeting Trop-2, IMMU-132, as a novel platform for the therapy of diverse metastatic solid cancers: Initial clinical results", American Association for Cancer Research (AACR) 2014 Annual Meeting, Abstr. #CT206, Apr. 7, 2014.

Starodub et al., "Therapy of gastrointestinal malignancies with an anti-Trop-2-SN-38 antibody drug conjugate (ADC) (sacituzumab govitecan): Phase I/II clinical experience", 2015 American Society of Clinical Oncology (ASCO) Annual Meeting, J Clin Oncol 33, 2015 (suppl; abstr 3546), Board 38, Jun. 1, 2015.

Stein et al., "Therapy of a breast cancer xenograft using humanized RS7 labeled with residualizing iodine", Proc. Amer. Assoc. Cancer Res. 43: 88 (Abstr. #413), 2002.

Stein et al., "Radioimmunotherapy of lung cancer with MAb RS7-3G11", Proc. Amer. Assoc. Cancer Res. 33: 318 (Abstr. #1897), 1992.

Stein et al., "Radioimmunotherapy with MAb RS7-3G11 in an animal model", Antib. Immunoconj. Radiopharm. 5: 358 (Abstr. #100), 1992.

Stein et al., "Specificity and properties of MAb RS7-3G11 and the antigen defined by this pancarcinoma monoclonal antibody", Int J Cancer. Dec. 2, 1993;55(6):938-46.

Stein et al., "Comparative biodistribution and radioimmunotherapy of monoclonal antibody RS7 and its F(ab')2 in nude mice bearing human tumor xenografts", Cancer. Feb. 1, 1994;73(3 Suppl):816-23.

Stein et al., "Murine monoclonal antibodies raised against human non-small cell carcinoma of the lung: specificity and tumor targeting", Cancer Res. Feb. 15, 1990;50(4):1330-6.

Stein et al., "Effects of radiolabeling monoclonal antibodies with a residualizing iodine radiolabel on the accretion of radioisotope in tumors", Cancer Res. Jul. 15, 1995;55(14):3132-9.

Stein et al., "Successful therapy of a human lung cancer xenograft using MAb RS7 labeled with residualizing radioiodine", Rev Oncol Hematol. Jul.-Aug. 2001;39(1-2):173-80.

Stein et al., "Assessment of combined radioimmunotherapy and chemotherapy for treatment of medullary thyroid cancer", Clin Cancer Res. 5(10 Suppl):3199s-206s, 1999.

Stein et al., Characterization of the epithelial/carcinoma antigen recognized by MAb RS7. Proc. Amer. Assoc. cancer Res. 35: 501 (Abstr. #2986), 1994.

(56) References Cited

OTHER PUBLICATIONS

Stein et al., A novel tumor-associated antigen defined by MAb RS7-3G11: Characterization and internalization properties. Proc. Amer. Assoc. Cancer Res. 33: 341, 1992.

Stein et al., "Characterization of cluster 13: the epithelial/carcinoma antigen recognized by MAb RS7", Int J Cancer Suppl. 1994;8:98-102.

Stein et al., "Targeting and therapy of human non small cell carcinoma of the lung xenografts using 131 I labeled monoclonal antibody RS7 3G11", Proc. Amer. Assoc. Cancer Res. 32: 260, 1991.

Van Rij et al., "Imaging of prostate cancer with immuno-PET and immuno-SPECT using a radiolabeled anti-EGP-1 monoclonal antibody", J Nucl Med. 52(10):1601-7, 2011.

Van Rij et al., "Pretargeting of prostate cancer with an internalizing anti-EGP-1 ×anti-I-HSG bispecific antibody", Annual Congress of the European Association of Nuclear Medicine, Birmingham, UK, Eur J Nucl Med Mol Imaging 38 (Suppl 2):S212 (Abstr. #OP582), 2011.

Vanama et al., Construction, characterization, and mammalian expression of an immunotoxin consisting of ranpimase (Rap) fused to a humanized anti-EGP-1 antibody, hRS7, as a potential therapeutic for prostate cancer. Proc. Amer. Assoc. Cancer Res., 96th Annual Meeting, 160 (Abstr. #679), 2005.

Cardillo et al., "Sacituzumab Govitecan (IMMU-132), an Anti-Trop-2/SN-38 Antibody-Drug Conjugate: Characterization and Efficacy in Pancreatic, Gastric, and Other Cancers", Bioconjug Chem. May 20, 2015;26 (5):919-31, EPUB May 8, 2015.

Goldenberg et al., "Trop-2 is a novel target for solid cancer therapy with sacituzumab govitecan (IMMU-132), an antibody-drug conjugate (ADC)", Oncotarget. Jun. 18, 2015. [Epub ahead of print].

Sharkey et al., "Enhanced Delivery of SN-38 to Human Tumor Xenografts with an Anti-Trop-2-SN-38 Antibody Conjugate (Sacituzumab Govitecan)", Clin Cancer Res. Jun. 23, 2015. pii: clincanres.0670.2015. [Epub ahead of print].

Starodub et al., "First-in-Human Trial of a Novel Anti-Trop-2 Antibody-SN-38 Conjugate, Sacituzumab Govitecan, for the Treatment of Diverse Metastatic Solid Tumors", Clin Cancer Res. May 5, 2015. [Epub ahead of print].

* cited by examiner

DOSAGES OF IMMUNOCONJUGATES OF ANTIBODIES AND SN-38 FOR IMPROVED EFFICACY AND DECREASED TOXICITY

RELATED APPLICATIONS

This application is a divisional of U.S. application Ser. No. 13/948,732, filed Jul. 23, 2013, which claims the benefit under 35 U.S.C. 119(e) of U.S. Provisional Patent Applications 61/736,684, filed Dec. 13, 2012, and 61/749,548, filed Jan. 7, 2013.

SEQUENCE LISTING

The instant application contains a Sequence Listing which has been submitted in ASCII format via EFS-Web and is hereby incorporated by reference in its entirety. Said ASCII copy, created on Jul. 17, 2013, is named IMM340US1_SL.txt and is 60,438 bytes in size.

FIELD OF THE INVENTION

The present invention relates to therapeutic use of immunoconjugates of antibodies or antigen-binding antibody fragments and camptothecins, such as SN-38, with improved ability to target various cancer cells in human subjects. In preferred embodiments, the antibodies and therapeutic moieties are linked via an intracellularly-cleavable linkage that increases therapeutic efficacy. In more preferred embodiments, the immunoconjugates are administered at specific dosages and/or specific schedules of administration that optimize the therapeutic effect. The optimized dosages and schedules of administration of SN-38-conjugated antibodies for human therapeutic use disclosed herein show unexpected superior efficacy that could not have been predicted from animal model studies, allowing effective treatment of cancers that are resistant to standard anti-cancer therapies, including the parental compound, irinotecan (CPT-11).

BACKGROUND OF THE INVENTION

For many years it has been an aim of scientists in the field of specifically targeted drug therapy to use monoclonal antibodies (MAbs) for the specific delivery of toxic agents to human cancers. Conjugates of tumor-associated MAbs and suitable toxic agents have been developed, but have had mixed success in the therapy of cancer in humans, and virtually no application in other diseases, such as infectious and autoimmune diseases. The toxic agent is most commonly a chemotherapeutic drug, although particle-emitting radionuclides, or bacterial or plant toxins, have also been conjugated to MAbs, especially for the therapy of cancer (Sharkey and Goldenberg, *CA Cancer J Clin.* 2006 July-August; 56(4):226-243) and, more recently, with radioimmunoconjugates for the preclinical therapy of certain infectious diseases (Dadachova and Casadevall, *QJ Nucl Med Mol Imaging* 2006; 50(3):193-204).

The advantages of using MAb-chemotherapeutic drug conjugates are that (a) the chemotherapeutic drug itself is structurally well defined; (b) the chemotherapeutic drug is linked to the MAb protein using very well-defined conjugation chemistries, often at specific sites remote from the MAbs' antigen binding regions; (c) MAb-chemotherapeutic drug conjugates can be made more reproducibly and usually with less immunogenicity than chemical conjugates involving MAbs and bacterial or plant toxins, and as such are more amenable to commercial development and regulatory approval; and (d) the MAb-chemotherapeutic drug conjugates are orders of magnitude less toxic systemically than radionuclide MAb conjugates, particularly to the radiation-sensitive bone marrow.

Camptothecin (CPT) and its derivatives are a class of potent antitumor agents. Irinotecan (also referred to as CPT-11) and topotecan are CPT analogs that are approved cancer therapeutics (Iyer and Ratain, *Cancer Chemother. Phamacol.* 42: S31-S43 (1998)). CPTs act by inhibiting topoisomerase I enzyme by stabilizing topoisomerase I-DNA complex (Liu, et al. in *The Camptothecins: Unfolding Their Anticancer Potential*, Liehr J. G., Giovanella, B. C. and Verschraegen (eds), NY Acad Sci., NY 922:1-10 (2000)). CPTs present specific issues in the preparation of conjugates. One issue is the insolubility of most CPT derivatives in aqueous buffers. Second, CPTs provide specific challenges for structural modification for conjugating to macromolecules. For instance, CPT itself contains only a tertiary hydroxyl group in ring-E. The hydroxyl functional group in the case of CPT must be coupled to a linker suitable for subsequent protein conjugation; and in potent CPT derivatives, such as SN-38, the active metabolite of the chemotherapeutic CPT-11, and other C-10-hydroxyl-containing derivatives such as topotecan and 10-hydroxy-CPT, the presence of a phenolic hydroxyl at the C-10 position complicates the necessary C-20-hydroxyl derivatization. Third, the lability under physiological conditions of the δ-lactone moiety of the E-ring of camptothecins results in greatly reduced antitumor potency. Therefore, the conjugation protocol is performed such that it is carried out at a pH of 7 or lower to avoid the lactone ring opening. However, conjugation of a bifunctional CPT possessing an amine-reactive group such as an active ester would typically require a pH of 8 or greater. Fourth, an intracellularly-cleavable moiety preferably is incorporated in the linker/spacer connecting the CPTs and the antibodies or other binding moieties.

A need exists for more effective methods of preparing and administering antibody-CPT conjugates, such as antibody-SN-38 conjugates. Preferably, the methods comprise optimized dosing and administration schedules that maximize efficacy and minimize toxicity of the antibody-CPT conjugates for therapeutic use in human patients.

SUMMARY OF THE INVENTION

As used herein, the abbreviation "CPT" may refer to camptothecin or any of its derivatives, such as SN-38, unless expressly stated otherwise. The present invention resolves an unfulfilled need in the art by providing improved methods and compositions for preparing and administering CPT-antibody immunoconjugates. Preferably, the camptothecin is SN-38. The disclosed methods and compositions are of use for the treatment of a variety of diseases and conditions which are refractory or less responsive to other forms of therapy, and can include diseases against which suitable antibodies or antigen-binding antibody fragments for selective targeting can be developed, or are available or known. Preferred diseases or conditions that may be treated with the subject immunoconjugates include, for example, cancer or diseases caused by infectious organisms.

Preferably, the targeting moiety is an antibody, antibody fragment, bispecific or other multivalent antibody, or other antibody-based molecule or compound. The antibody can be of various isotypes, preferably human IgG1, IgG2, IgG3 or IgG4, more preferably comprising human IgG1 hinge and constant region sequences. The antibody or fragment thereof can be a chimeric human-mouse, a chimeric human-primate, a humanized (human framework and murine hypervariable (CDR) regions), or fully human antibody, as well as variations thereof, such as half-IgG4 antibodies (referred to as "unibodies"), as described by van der Neut Kolfschoten et al. (*Science* 2007; 317:1554-1557). More preferably, the antibody or fragment thereof may be designed or selected to comprise human constant region sequences that belong to specific allotypes, which may result in reduced immunogenicity when the immunoconjugate is administered to a human subject. Preferred allotypes for administration include a non-G1m1 allotype (nG1m1), such as G1m3, G1m3,1, G1m3,2 or G1m3,1,2. More preferably, the allotype is selected from the group consisting of the nG1m1, G1m3, nG1m1,2 and Km3 allotypes.

Antibodies of use may bind to any disease-associated antigen known in the art. Where the disease state is cancer, for example, many antigens expressed by or otherwise associated with tumor cells are known in the art, including but not limited to, carbonic anhydrase IX, alpha-fetoprotein (AFP), α-actinin-4, A3, antigen specific for A33 antibody, ART-4, B7, Ba 733, BAGE, BrE3-antigen, CA125, CAMEL, CAP-1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD80, CD83, CD95, CD126, CD132, CD133, CD138, CD147, CD154, CDC27, CDK-4/m, CDKN2A, CTLA-4, CXCR4, CXCR7, CXCL12, HIF-1α, colon-specific antigen-p (CSAp), CEA (CEACAM5), CEACAM6, c-Met, DAM, EGFR, EGFRvIII, EGP-1 (TROP-2), EGP-2, ELF2-M, Ep-CAM, fibroblast growth factor (FGF), Flt-1, Flt-3, folate receptor, G250 antigen, GAGE, gp100, GRO-β, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-γ, IFN-α, IFN-β, IFN-λ, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), KC4-antigen, KS-1-antigen, KS 1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, PAM4 antigen, pancreatic cancer mucin, PD-1 receptor, placental growth factor, p53, PLAGL2, prostatic acid phosphatase, PSA, PRAME, PSMA, P1GF, ILGF, ILGF-1R, IL-6, IL-25, RS5, RANTES, T101, SAGE, 5100, survivin, survivin-2B, TAC, TAG-72, tenascin, TRAIL receptors, TNF-α, Tn antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, an oncogene marker and an oncogene product (see, e.g., Sensi et al., *Clin Cancer Res* 2006, 12:5023-32; Parmiani et al., *J Immunol* 2007, 178:1975-79; Novellino et al. *Cancer Immunol Immunother* 2005, 54:187-207). Preferably, the antibody binds to CEACAM5, CEACAM6, EGP-1 (TROP-2), MUC-16, AFP, MUC5a,c, PAM4 antigen, CD74, CD19, CD20, CD22 or HLA-DR.

Exemplary antibodies that may be utilized include, but are not limited to, hR1 (anti-IGF-1R, U.S. patent application Ser. No. 12/722,645, filed Mar. 12, 2010), hPAM4 (anti-mucin, U.S. Pat. No. 7,282,567), hA20 (anti-CD20, U.S. Pat. No. 7,251,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,541,440), hRS7 (anti-EGP-1, U.S. Pat. No. 7,238,785), hMN-3 (anti-CEACAM6, U.S. Pat. No. 7,541,440), Ab124 and Ab125 (anti-CXCR4, U.S. Pat. No. 7,138,496), the Examples section of each cited patent or application incorporated herein by reference. More preferably, the antibody is IMMU-31 (anti-AFP), hRS7 (anti-TROP-2), hMN-14 (anti-CEACAM5), hMN-3 (anti-CEACAM6), hMN-15 (anti-CEACAM6), hLL1 (anti-CD74), hLL2 (anti-CD22), hL243 or IMMU-114 (anti-HLA-DR), hA19 (anti-CD19) or hA20 (anti-CD20). As used herein, the terms epratuzumab and hLL2 are interchangeable, as are the terms veltuzumab and hA20, hL243g4P, hL243gamma4P and IMMU-114.

Alternative antibodies of use include, but are not limited to, abciximab (anti-glycoprotein IIb/IIIa), alemtuzumab (anti-CD52), bevacizumab (anti-VEGF), cetuximab (anti-EGFR), gemtuzumab (anti-CD33), ibritumomab (anti-CD20), panitumumab (anti-EGFR), rituximab (anti-CD20), tositumomab (anti-CD20), trastuzumab (anti-ErbB2), lambrolizumab (anti-PD-1 receptor), nivolumab (anti-PD-1 receptor), ipilimumab (anti-CTLA-4), abagovomab (anti-CA-125), adecatumumab (anti-EpCAM), atlizumab (anti-IL-6 receptor), benralizumab (anti-CD125), obinutuzumab (GA101, anti-CD20), CC49 (anti-TAG-72), AB-PG1-XG1-026 (anti-PSMA, U.S. patent application Ser. No. 11/983,372, deposited as ATCC PTA-4405 and PTA-4406), D2/B (anti-PSMA, WO 2009/130575), tocilizumab (anti-IL-6 receptor), basiliximab (anti-CD25), daclizumab (anti-CD25), efalizumab (anti-CD11a), GA101 (anti-CD20; Glycart Roche), muromonab-CD3 (anti-CD3 receptor), natalizumab (anti-α4 integrin), omalizumab (anti-IgE); anti-TNF-α antibodies such as CDP571 (Ofei et al., 2011, Diabetes 45:881-85), MTNFAI, M2TNFAI, M3TNFAI, M3TNFABI, M302B, M303 (Thermo Scientific, Rockford, Ill.), infliximab (Centocor, Malvern, Pa.), certolizumab pegol (UCB, Brussels, Belgium), anti-CD40L (UCB, Brussels, Belgium), adalimumab (Abbott, Abbott Park, Ill.), Benlysta (Human Genome Sciences); antibodies for therapy of Alzheimer's disease such as Alz 50 (Ksiezak-Reding et al., 1987, *J Biol Chem* 263:7943-47), gantenerumab, solanezumab and infliximab; anti-fibrin antibodies like 59D8, T2G1s, MH1; anti-CD38 antibodies such as MOR03087 (MorphoSys AG), MOR202 (Celgene), HuMax-CD38 (Genmab) or daratumumab (Johnson & Johnson); (anti-HIV antibodies such as P4/D10 (U.S. Pat. No. 8,333,971), Ab 75, Ab 76, Ab 77 (Paulik et al., 1999, *Biochem Pharmacol* 58:1781-90), as well as the anti-HIV antibodies described and sold by Polymun (Vienna, Austria), also described in U.S. Pat. Nos. 5,831,034, 5,911,989, and Vcelar et al., *AIDS* 2007; 21(16):2161-2170 and Joos et al., *Antimicrob. Agents Chemother.* 2006; 50(5):1773-9, all incorporated herein by reference; and antibodies against pathogens such as CR6261 (anti-influenza), exbivirumab (anti-hepatitis B), felvizumab (anti-respiratory syncytial virus), foravirumab (anti-rabies virus), motavizumab (anti-respiratory syncytial virus), palivizumab (anti-respiratory syncytial virus), panobacumab (anti-*Pseudomonas*), rafivirumab (anti-rabies virus), regavirumab (anti-cytomegalovirus), sevirumab (anti-cytomegalovirus), tivirumab (anti-hepatitis B), and urtoxazumab (anti-*E. coli*).

In a preferred embodiment, the chemotherapeutic moiety is selected from camptothecin (CPT) and its analogs and derivatives and is more preferably SN-38. However, other chemotherapeutic moieties that may be utilized include taxanes (e.g, baccatin III, taxol), epothilones, anthracyclines (e.g., doxorubicin (DOX), epirubicin, morpholinodoxorubicin (morpholino-DOX), cyanomorpholino-doxorubicin (cyanomorpholino-DOX), 2-pyrrolinodoxorubicin (2-PDOX) or a prodrug form of 2-PDOX (pro-2-PDOX); see, e.g., Priebe W (ed.), ACS symposium series 574, published by American Chemical Society, Washington D.C., 1995 (332 pp) and Nagy et al., *Proc. Natl. Acad. Sci. USA* 93:2464-2469, 1996), benzoquinoid ansamycins exemplified by geldanamycin (DeBoer et al., *Journal of Antibiotics* 23:442-447, 1970; Neckers et al., *Invest. New Drugs* 17:361-373, 1999), and the like. Preferably, the antibody or fragment thereof links to at least one chemotherapeutic moiety; preferably 1 to about 5 chemotherapeutic moieties; more preferably 6 or more chemotherapeutic moieties, most preferably about 6 to about 12 chemotherapeutic moieties.

An example of a water soluble CPT derivative is CPT-11. Extensive clinical data are available concerning CPT-11's pharmacology and its in vivo conversion to the active SN-38 (Iyer and Ratain, *Cancer Chemother Pharmacol.* 42:S31-43 (1998); Mathijssen et al., *Clin Cancer Res.* 7:2182-2194 (2002); Rivory, *Ann NY Acad Sci.* 922:205-215, 2000)). The active form SN-38 is about 2 to 3 orders of magnitude more potent than CPT-11. In specific preferred embodiments, the immunoconjugate may be an hMN-14-SN-38, hMN-3-SN-38, hMN-15-SN-38, IMMU-31-SN-38, hRS7-SN-38, hA20-SN-38, hL243-SN-38, hLL1-SN-38 or hLL2-SN-38 conjugate.

Various embodiments may concern use of the subject methods and compositions to treat a cancer, including but not limited to non-Hodgkin's lymphomas, B-cell acute and chronic lymphoid leukemias, Burkitt lymphoma, Hodgkin's lymphoma, acute large B-cell lymphoma, hairy cell leukemia, acute myeloid leukemia, chronic myeloid leukemia, acute lymphocytic leukemia, chronic lymphocytic leukemia, T-cell lymphomas and leukemias, multiple myeloma, Waldenstrom's macroglobulinemia, carcinomas, melanomas, sarcomas, gliomas, bone, and skin cancers. The carcinomas may include carcinomas of the oral cavity, esophagus, gastrointestinal tract, pulmonary tract, lung, stomach, colon, breast, ovary, prostate, uterus, endometrium, cervix, urinary bladder, pancreas, bone, brain, connective tissue, liver, gall bladder, urinary bladder, kidney, skin, central nervous system and testes.

In addition, the subject methods and compositions may be used to treat an infectious disease, for example diseases involving infection by pathogens such as bacteria, rickettsia, mycoplasma, protozoa, fungi, viruses, parasites, or other microbial agents. Examples include human immunodeficiency virus (HIV) causing AIDS, *Mycobacterium* of tuberculosis, *Streptococcus agalactiae*, methicillin-resistant *Staphylococcus aureus, Legionella pneumophilia, Streptococcus pyogenes, Escherichia coli, Neisseria gonorrhoeae, Neisseria meningitidis, Pneumococcus, Cryptococcus neoformans, Histoplasma capsulatum, Hemophilis influenzae* B, *Treponema pallidum*, Lyme disease spirochetes, West Nile virus, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reo virus, polio virus, simian virus 40, mouse mammary tumor virus, dengue virus, *rubella* virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orate, M. arginini, Acholeplasma laidlawii, M. salivarium* and *M. pneumoniae*. A review listing antibodies against infectious organisms (antitoxin and antiviral antibodies), as well as other targets, is contained in Casadevall, Clin Immunol 1999; 93(1):5-15, incorporated herein by reference.

In certain embodiments involving treatment of cancer, the drug conjugates may be used in combination with surgery, radiation therapy, chemotherapy, immunotherapy with naked antibodies, radioimmunotherapy, immunomodulators, vaccines, and the like. These combination therapies can allow lower doses of each therapeutic to be given in such combinations, thus reducing certain severe side effects, and potentially reducing the courses of therapy required. When there is no or minimal overlapping toxicity, full doses of each can also be given.

In infectious diseases, the drug immunoconjugates can be combined with other therapeutic drugs, immunomodulators, naked MAbs, or vaccines (e.g., MAbs against hepatitis, HIV, or papilloma viruses, or vaccines based on immunogens of these viruses, or kinase inhibitors, such as in hepatitis B). Antibodies and antigen-based vaccines against these and other viral pathogens are known in the art and, in some cases, already in commercial use. The development of anti-infective monoclonal antibodies has been reviewed recently by Reichert and Dewitz (*Nat Rev Drug Discovery* 2006; 5:191-195), incorporated herein by reference, which summarizes the priority pathogens against which naked antibody therapy has been pursued, resulting in only 2 pathogens against which antibodies are either in Phase III clinical trials or are being marketed (respiratory syncytial virus and methicillin-resistant *Staphylococcus aureus*), with 25 others in clinical studies and 20 discontinued during clinical study. For combination therapy, the use of radioimmunotherapy for the treatment of infectious organisms is disclosed, for example, in U.S. Pat. Nos. 4,925,648; 5,332,567; 5,439,665; 5,601,825; 5,609,846; 5,612,016; 6,120,768; 6,319,500; 6,458,933; 6,548,275; and in U.S. Patent Application Publication Nos. 20020136690 and 20030103982, the Examples section of each of which is incorporated herein by reference.

Preferred optimal dosing of immunoconjugates may include a dosage of between 3 mg/kg and 20 mg/kg, preferably given either weekly, twice weekly or every other week. The optimal dosing schedule may include treatment cycles of two consecutive weeks of therapy followed by one, two, three or four weeks of rest, or alternating weeks of therapy and rest, or one week of therapy followed by two, three or four weeks of rest, or three weeks of therapy followed by one, two, three or four weeks of rest, or four weeks of therapy followed by one, two, three or four weeks of rest, or five weeks of therapy followed by one, two, three, four or five weeks of rest, or administration once every two weeks, once every three weeks or once a month. Treatment may be extended for any number of cycles, preferably at least 2, at least 4, at least 6, at least 8, at least 10, at least 12, at least 14, or at least 16 cycles. The dosage may be up to 24 mg/kg. Exemplary dosages of use may include 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 22 mg/kg and 24 mg/kg. Preferred dosages are 4, 6, 8, 9, 10, 12, 14, 16 or 18 mg/kg. The person of ordinary skill will realize that a variety of factors, such as age, general health, specific organ function or weight, as well as effects of prior therapy on specific organ systems (e.g., bone marrow) may be considered in selecting an optimal dosage of immunoconjugate, and that the dosage and/or frequency of administration may be increased or decreased during the course of therapy. The dosage may be repeated as needed, with evidence of tumor shrinkage observed after as few as 4 to 8 doses. The optimized dosages and schedules of administration disclosed herein show unexpected superior efficacy and reduced toxicity in human subjects, which could not have been predicted from animal model studies. Surprisingly, the superior efficacy allows treatment of tumors that were previously found to be resistant to one or more standard anti-cancer therapies, including the parental compound, CPT-11, from which SN-38 is derived in vivo.

The subject methods may include use of CT and/or PET/CT, or MRI, to measure tumor response at regular intervals. Blood levels of tumor markers, such as CEA (carcinoembryonic antigen), CA19-9, AFP, CA 15.3, or PSA, may also be monitored. Dosages and/or administration schedules may be adjusted as needed, according to the results of imaging and/or marker blood levels.

A surprising result with the instant claimed compositions and methods is the unexpected tolerability of high doses of antibody-drug conjugate, even with repeated infusions, with only relatively low-grade toxicities of nausea and vomiting observed, or manageable neutropenia. A further surprising result is the lack of accumulation of the antibody-drug conjugate, unlike other products that have conjugated SN-38 to albumin, PEG or other carriers. The lack of accumulation is associated with improved tolerability and lack of serious toxicity even after repeated or increased dosing. These surprising results allow optimization of dosage and delivery schedule, with unexpectedly high efficacies and low toxicities. The claimed methods provide for shrinkage of solid tumors, in individuals with previously resistant cancers, of 15% or more, preferably 20% or more, preferably 30% or more, more preferably 40% or more in size (as measured by longest diameter). The person of ordinary skill will realize that tumor size may be measured by a variety of different techniques, such as total tumor volume, maximal tumor size in any dimension or a combination of size measurements in several dimensions. This may be with standard radiological procedures, such as computed tomography, ultrasonography, and/or positron-emission tomography. The means of measuring size is less important than observing a trend of decreasing tumor size with immunoconjugate treatment, preferably resulting in elimination of the tumor.

While the immunoconjugate may be administered as a periodic bolus injection, in alternative embodiments the immunoconjugate may be administered by continuous infusion of antibody-drug conjugates. In order to increase the Cmax and extend the PK of the immunoconjugate in the blood, a continuous infusion may be administered for example by indwelling catheter. Such devices are known in the art, such as HICKMAN®, BROVIAC® or PORT-A-CATH® catheters (see, e.g., Skolnik et al., *Ther Drug Monit* 32:741-48, 2010) and any such known indwelling catheter may be used. A variety of continuous infusion pumps are also known in the art and any such known infusion pump may be used. The dosage range for continuous infusion may be between 0.1 and 3.0 mg/kg per day. More preferably, these immunoconjugates can be administered by intravenous infusions over relatively short periods of 2 to 5 hours, more preferably 2-3 hours.

In particularly preferred embodiments, the immunoconjugates and dosing schedules may be efficacious in patients resistant to standard therapies. For example, an hMN-14-SN-38 immunoconjugate may be administered to a patient who has not responded to prior therapy with irinotecan, the parent agent of SN-38. Surprisingly, the irinotecan-resistant patient may show a partial or even a complete response to hMN-14-SN-38. The ability of the immunoconjugate to specifically target the tumor tissue may overcome tumor resistance by improved targeting and enhanced delivery of the therapeutic agent. Alternatively, an anti-CEACAM5 immunoconjugate, such as hMN-14, may be co-administered with an anti-CEACAM6 immunoconjugate, such as hMN-3 or hMN-15. Other antibody-SN-38 immunoconjugates may show similar improved efficacy and/or decreased toxicity, compared to alternative standard therapeutic treatments, and combinations of different SN-38 immunoconjugates, or SN-38-antibody conjugates in combination with an antibody conjugated to a radionuclide, toxin or other drug, may provide even more improved efficacy and/or reduced toxicity. A specific preferred subject may be a metastatic colon cancer patient, a triple-negative breast cancer patient, a HER+, ER+, progesterone+ breast cancer patient, a metastatic non-small-cell lung cancer (NSCLC) patient, a metastatic pancreatic cancer patient, a metastatic renal cell carcinoma patient, a metastatic gastric cancer patient, a metastatic prostate cancer patient, or a metastatic small-cell lung cancer patient.

(N=10) tumor-bearing mice (N=10) were treated twice weekly for 4 weeks with the agents indicated. All the ADCs and controls were administered in the amounts indicated (expressed as amount of SN-38 per dose; long arrows=conjugate injections, short arrows=irinotecan injections).

Figure 5A:
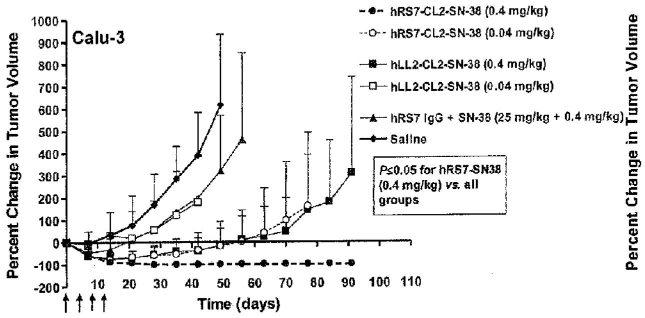
FIG. 5A. Therapeutic efficacy of hRS7-SN-38 ADC in mice bearing human non-small cell lung tumor xenografts. Mice bearing Calu-3 tumors (N=5-7) were injected with hRS7-CL2-SN-38 every 4 days for a total of 4 injections (q4d×4). All the ADCs and controls were administered in the amounts indicated (expressed as amount of SN-38 per dose; long arrows=conjugate injections, short arrows=irinotecan injections).
Figure 5B:
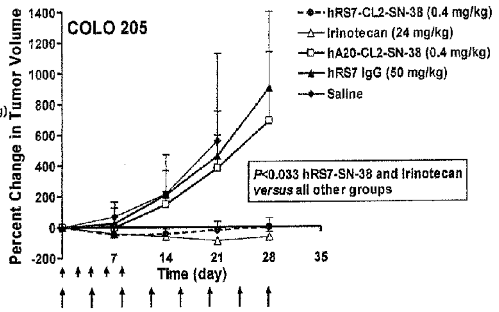
FIG. 5B. Therapeutic efficacy of hRS7-SN-38 ADC in mice bearing human colorectal tumor xenografts. COLO 205 tumor-bearing mice (N=5) were injected 8 times (q4d×8) with the ADC or every 2 days for a total of 5 injections (q2d×5) with the MTD of irinotecan. All the ADCs and controls were administered in the amounts indicated (expressed as amount of SN-38 per dose; long arrows=conjugate injections, short arrows=irinotecan injections).
Figure 5C:
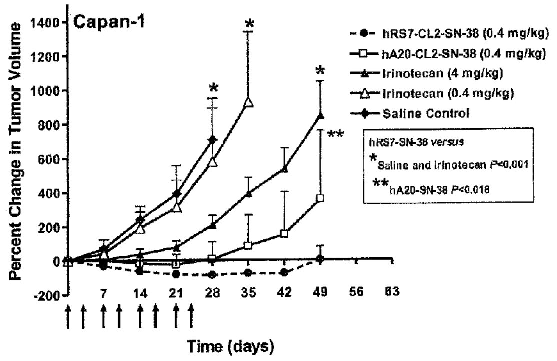
FIG. 5C. Therapeutic efficacy of hRS7-SN-38 ADC in mice bearing human pancreatic cancer xenografts. Capan-1
Figure 5D:
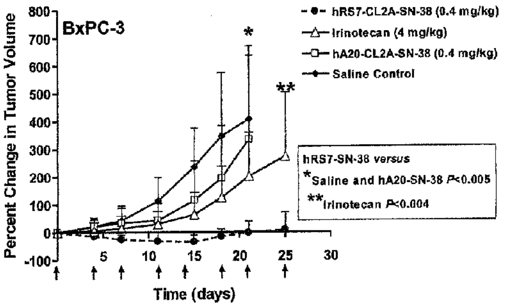

FIG. 5D. Therapeutic efficacy of hRS7-SN-38 ADC in mice bearing human pancreatic cancer xenografts. BxPC-3 tumor-bearing mice (N=10) were treated twice weekly for 4 weeks with the agents indicated. All the ADCs and controls were administered in the amounts indicated (expressed as amount of SN-38 per dose; long arrows=conjugate injections, short arrows=irinotecan injections).

Figure 5E:
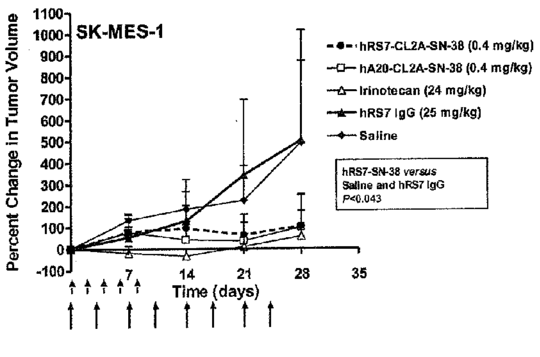

FIG. 5E. Therapeutic efficacy of hRS7-SN-38 ADC in mice bearing human squamous cell lung carcinoma xenografts. In addition to ADC given twice weekly for 4 week, SK-MES-1 tumor-bearing (N=8) mice received the MTD of CPT-11 (q2d×5). All the ADCs and controls were administered in the amounts indicated (expressed as amount of SN-38 per dose; long arrows=conjugate injections, short arrows=irinotecan injections).

Figures 6A, 6B, 6C, 6D:
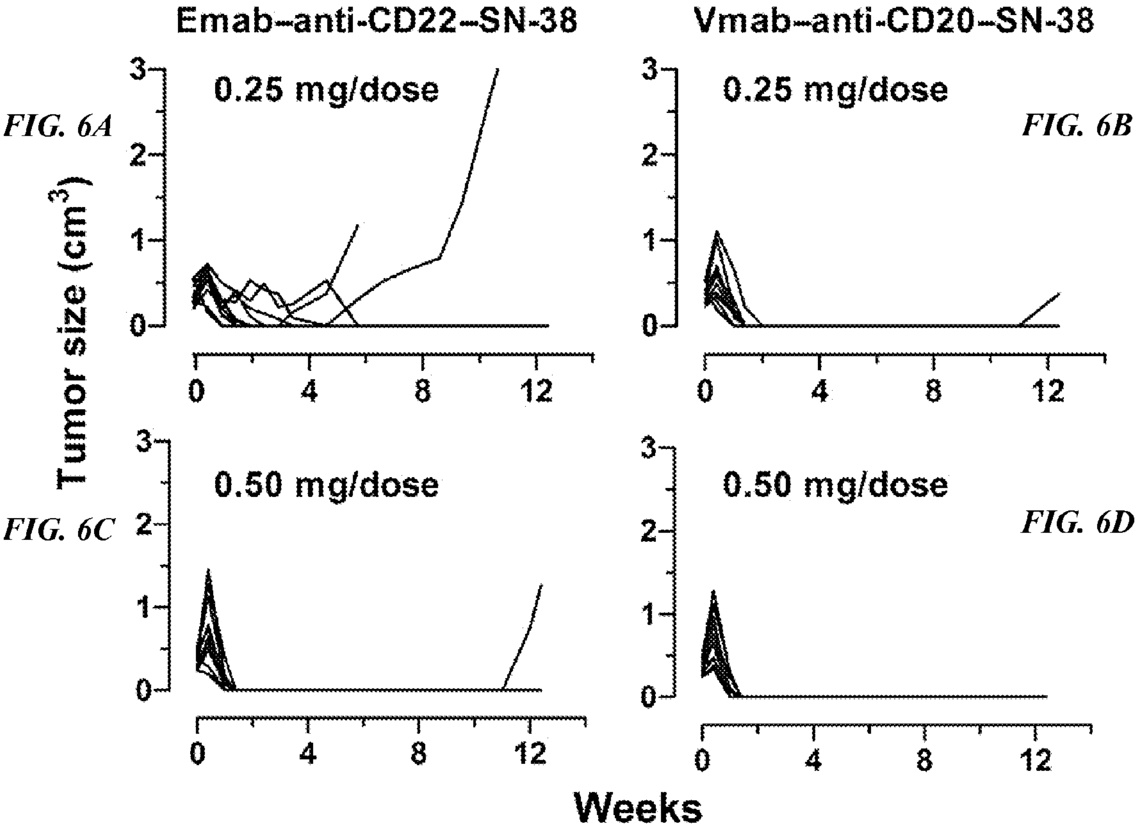

FIG. 6A. Comparative efficacy of epratuzumab (Emab)-SN-38 and veltuzumab (Vmab)-SN-38 conjugates in the subcutaneous Ramos model. Nude mice (N=10 per group) with tumors averaging approximately 0.35 $cm^3$ (0.20-0.55 $cm^3$) were administered 0.25 mg of Emab-SN-38 twice weekly for 4 weeks.

FIG. 6B. Comparative efficacy of epratuzumab (Emab)-SN-38 and veltuzumab (Vmab)-SN-38 conjugates in the subcutaneous Ramos model. Nude mice (N=10 per group) with tumors averaging approximately 0.35 $cm^3$ (0.20-0.55 $cm^3$) were administered 0.25 mg of Vmab-SN-38 twice weekly for 4 weeks.

FIG. 6C. Comparative efficacy of epratuzumab (Emab)-SN-38 and veltuzumab (Vmab)-SN-38 conjugates in the subcutaneous Ramos model. Nude mice (N=10 per group) with tumors averaging approximately 0.35 $cm^3$ (0.20-0.55 $cm^3$) were administered 0.5 mg of Emab-SN-38 twice weekly for 4 weeks.

FIG. 6D. Comparative efficacy of epratuzumab (Emab)-SN-38 and veltuzumab (Vmab)-SN-38 conjugates in the subcutaneous Ramos model. Nude mice (N=10 per group) with tumors averaging approximately 0.35 $cm^3$ (0.20-0.55 $cm^3$) were administered 0.5 mg of Vmab-SN-38 twice weekly for 4 weeks.

Figure 7A:
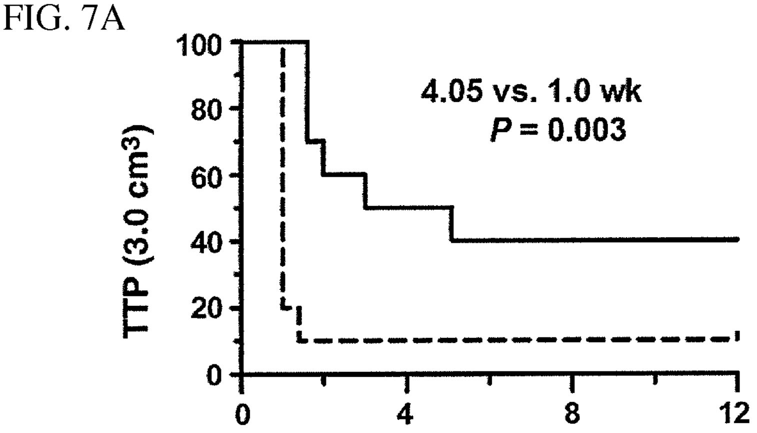

FIG. 7A. Specificity of Emab anti-CD22-SN-38 conjugate (solid line) versus an irrelevant labetuzumab (Lmab)-SN-38 conjugate (dashed line) in nude mice bearing subcutaneous Ramos tumors. Animals were given twice weekly doses of 75 μg of each conjugate per dose (54.5 μg/kg of SN-38, based on average weight of 22 g) intraperitoneally for 4 weeks. Survival based on time-to-progression (TTP) to 3.0 $cm^3$, with tumors starting at an average size of 0.4 $cm^3$. P values comparing median survival (shown) for Emab-SN-38 to Lmab-SN-38 conjugate are shown in each panel. C, survival curves (solid gray) for another group of animals given weekly intraperitoneal injections of irinotecan (6.5 μg/dose; SN-38 equivalents approximately the same as the 250-m dose of the Emab-SN-38 conjugate).

Figure 7B:
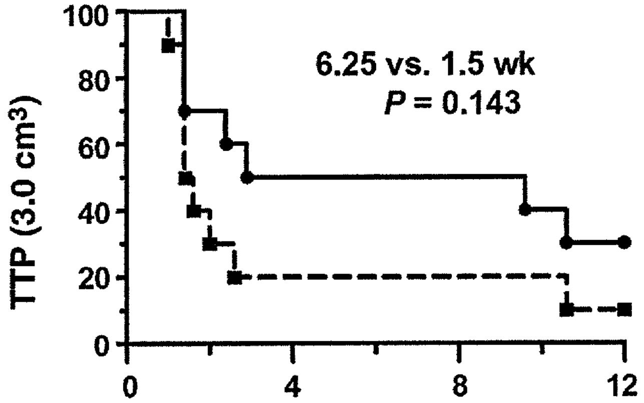

FIG. 7B. Specificity of Emab anti-CD22-SN-38 conjugate (solid line) versus an irrelevant labetuzumab (Lmab)-SN-38 conjugate (dashed line) in nude mice bearing subcutaneous Ramos tumors. Animals were given twice weekly doses of 125 μg of each conjugate per dose (91 μg/kg of SN-38, based on average weight of 22 g) intraperitoneally for 4 weeks. Survival based on time-to-progression (TTP) to 3.0 $cm^3$, with tumors starting at an average size of 0.4 $cm^3$. P values comparing median survival (shown) for Emab-SN-38 to Lmab-SN-38 conjugate are shown in each panel. C, survival curves (solid gray) for another group of animals given weekly intraperitoneal injections of irinotecan (6.5 μg/dose; SN-38 equivalents approximately the same as the 250-m dose of the Emab-SN-38 conjugate).

Figure 7C:
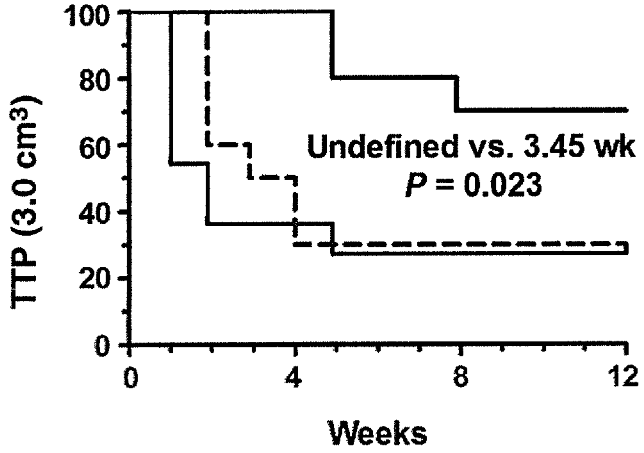

FIG. 7C. Specificity of Emab anti-CD22-SN-38 conjugate (solid line) versus an irrelevant labetuzumab (Lmab)-SN-38 conjugate (dashed line) in nude mice bearing subcutaneous Ramos tumors. Animals were given twice weekly doses of 250 μg of each conjugate per dose (182 μg/kg of SN-38, based on average weight of 22 g) intraperitoneally for 4 weeks. Survival based on time-to-progression (TTP) to 3.0 $cm^3$, with tumors starting at an average size of 0.4 $cm^3$. P values comparing median survival (shown) for Emab-SN-38 to Lmab-SN-38 conjugate are shown in each panel. Survival curves (solid gray) are also shown for another group of animals given weekly intraperitoneal injections of irinotecan (6.5 μg/dose; SN-38 equivalents approximately the same as the 250-m dose of the Emab-SN-38 conjugate).

Figure 8:
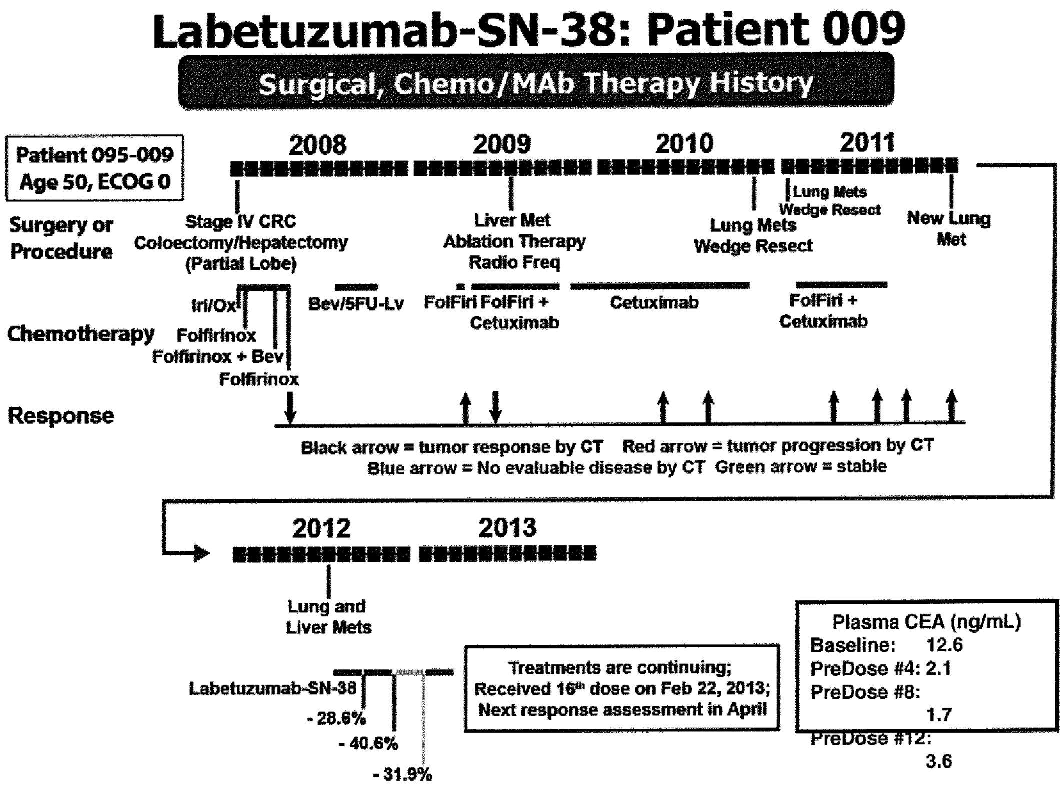

FIG. 8. History of prior treatment of patient, before administering IMMU-130 (labetuzumab-NS-38). Prior treatment included stage IV CRC coloectomy/hepatectomy (partial lobe), radiofrequency ablation therapy of liver metasteses, wedge resection of lung metasteses, and chemotherapy with irinotecan/oxaliplatin, Folfirinox, Folfirinox+bevacizumab, bevacizumab+5-FU/leucovorin, FolFiri, Folfiri+cetuximab, and cetuximab alone. The patient received doses of 16 mg/kg of IMMU-132 by slow IV infusion every other week for a total of 17 treatment doses.

DETAILED DESCRIPTION OF THE INVENTION

Definitions

In the description that follows, a number of terms are used and the following definitions are provided to facilitate understanding of the claimed subject matter. Terms that are not expressly defined herein are used in accordance with their plain and ordinary meanings.

Unless otherwise specified, a or an means "one or more."

The term about is used herein to mean plus or minus ten percent (10%) of a value. For example, "about 100" refers to any number between 90 and 110.

An antibody, as used herein, refers to a full-length (i.e., naturally occurring or formed by normal immunoglobulin gene fragment recombinatorial processes) immunoglobulin molecule (e.g., an IgG antibody) or an antigen-binding portion of an immunoglobulin molecule, such as an antibody fragment. An antibody or antibody fragment may be conjugated or otherwise derivatized within the scope of the claimed subject matter. Such antibodies include but are not limited to IgG1, IgG2, IgG3, IgG4 (and IgG4 subforms), as well as IgA isotypes. As used below, the abbreviation "MAb" may be used interchangeably to refer to an antibody, antibody fragment, monoclonal antibody or multispecific antibody.

An antibody fragment is a portion of an antibody such as $F(ab')_2$, $F(ab)_2$, Fab', Fab, Fv, scFv (single chain Fv), single domain antibodies (DABs or VHHs) and the like, including the half-molecules of IgG4 cited above (van der Neut Kolfschoten et al. (Science 2007; 317(14 September):1554-1557). Regardless of structure, an antibody fragment of use binds with the same antigen that is recognized by the intact antibody. The term "antibody fragment" also includes synthetic or genetically engineered proteins that act like an antibody by binding to a specific antigen to form a complex.

For example, antibody fragments include isolated fragments consisting of the variable regions, such as the "Fv" fragments consisting of the variable regions of the heavy and light chains and recombinant single chain polypeptide molecules in which light and heavy variable regions are connected by a peptide linker ("scFv proteins"). The fragments may be constructed in different ways to yield multivalent and/or multispecific binding forms.

A naked antibody is generally an entire antibody that is not conjugated to a therapeutic agent. A naked antibody may exhibit therapeutic and/or cytotoxic effects, for example by Fc-dependent functions, such as complement fixation (CDC) and ADCC (antibody-dependent cell cytotoxicity). However, other mechanisms, such as apoptosis, anti-angiogenesis, anti-metastatic activity, anti-adhesion activity, inhibition of heterotypic or homotypic adhesion, and interference in signaling pathways, may also provide a therapeutic effect. Naked antibodies include polyclonal and monoclonal antibodies, naturally occurring or recombinant antibodies, such as chimeric, humanized or human antibodies and fragments thereof. In some cases a "naked antibody" may also refer to a "naked" antibody fragment. As defined herein, "naked" is synonymous with "unconjugated," and means not linked or conjugated to a therapeutic agent.

A chimeric antibody is a recombinant protein that contains the variable domains of both the heavy and light antibody chains, including the complementarity determining regions (CDRs) of an antibody derived from one species, preferably a rodent antibody, more preferably a murine antibody, while the constant domains of the antibody molecule are derived from those of a human antibody. For veterinary applications, the constant domains of the chimeric antibody may be derived from that of other species, such as a primate, cat or dog.

A humanized antibody is a recombinant protein in which the CDRs from an antibody from one species; e.g., a murine antibody, are transferred from the heavy and light variable chains of the murine antibody into human heavy and light variable domains (framework regions). The constant domains of the antibody molecule are derived from those of a human antibody. In some cases, specific residues of the framework region of the humanized antibody, particularly those that are touching or close to the CDR sequences, may be modified, for example replaced with the corresponding residues from the original murine, rodent, subhuman primate, or other antibody.

A human antibody is an antibody obtained, for example, from transgenic mice that have been "engineered" to produce human antibodies in response to antigenic challenge. In this technique, elements of the human heavy and light chain loci are introduced into strains of mice derived from embryonic stem cell lines that contain targeted disruptions of the endogenous heavy chain and light chain loci. The transgenic mice can synthesize human antibodies specific for various antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, human antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993). Human antibodies may also be generated by in vitro activated B cells. See U.S. Pat. Nos. 5,567,610 and 5,229,275, the Examples section of each of which is incorporated herein by reference.

A therapeutic agent is an atom, molecule, or compound that is useful in the treatment of a disease. Examples of therapeutic agents include, but are not limited to, antibodies, antibody fragments, immunoconjugates, drugs, cytotoxic agents, pro-apopoptotic agents, toxins, nucleases (including DNAses and RNAses), hormones, immunomodulators, chelators, boron compounds, photoactive agents or dyes, radionuclides, oligonucleotides, interference RNA, siRNA, RNAi, anti-angiogenic agents, chemotherapeutic agents, cyokines, chemokines, prodrugs, enzymes, binding proteins or peptides or combinations thereof.

An immunoconjugate is an antibody, antigen-binding antibody fragment, antibody complex or antibody fusion protein that is conjugated to a therapeutic agent. Conjugation may be covalent or non-covalent. Preferably, conjugation is covalent.

As used herein, the term antibody fusion protein is a recombinantly-produced antigen-binding molecule in which one or more natural antibodies, single-chain antibodies or antibody fragments are linked to another moiety, such as a protein or peptide, a toxin, a cytokine, a hormone, etc. In certain preferred embodiments, the fusion protein may comprise two or more of the same or different antibodies, antibody fragments or single-chain antibodies fused together, which may bind to the same epitope, different epitopes on the same antigen, or different antigens.

An immunomodulator is a therapeutic agent that when present, alters, suppresses or stimulates the body's immune system. Typically, an immunomodulator of use stimulates immune cells to proliferate or become activated in an immune response cascade, such as macrophages, dendritic cells, B-cells, and/or T-cells. However, in some cases an immunomodulator may suppress proliferation or activation of immune cells. An example of an immunomodulator as described herein is a cytokine, which is a soluble small protein of approximately 5-20 kDa that is released by one cell population (e.g., primed T-lymphocytes) on contact with specific antigens, and which acts as an intercellular mediator between cells. As the skilled artisan will understand, examples of cytokines include lymphokines, monokines, interleukins, and several related signaling molecules, such as tumor necrosis factor (TNF) and interferons. Chemokines are a subset of cytokines. Certain interleukins and interferons are examples of cytokines that stimulate T cell or other immune cell proliferation. Exemplary interferons include interferon-$\alpha$, interferon-$\beta$, interferon-$\gamma$ and interferon-$\lambda$.

CPT is an abbreviation for camptothecin, and as used in the present application CPT represents camptothecin itself or an analog or derivative of camptothecin, such as SN-38. The structures of camptothecin and some of its analogs, with the numbering indicated and the rings labeled with letters A-E, are given in formula 1 in Chart 1 below.

Chart 1

(1)

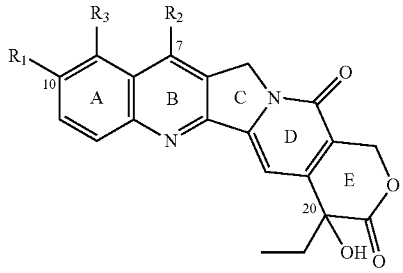

CPT: $R_1 = R_2 = R_3 = H$

10-Hydroxy-CPT: $R_1 = OH$; $R_2 = R_3 = H$

CPT-11: $R_1$ =

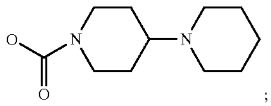

;

$R_2$ = ethyl; $R_3 = H$

SN-38: $R_1 = OH$; $R_2$ = ethyl; $R_3 = H$

Topotecan: $R_1 = OH$; $R_2 = H$; $R_3 = CH_2—N(CH_3)_2$

Camptothecin Conjugates

Non-limiting methods and compositions for preparing immunoconjugates comprising a camptothecin therapeutic agent attached to an antibody or antigen-binding antibody fragment are described below. In preferred embodiments, the solubility of the drug is enhanced by placing a defined polyethyleneglycol (PEG) moiety (i.e., a PEG containing a defined number of monomeric units) between the drug and the antibody, wherein the defined PEG is a low molecular weight PEG, preferably containing 1-30 monomeric units, more preferably containing 1-12 monomeric units.

Preferably, a first linker connects the drug at one end and may terminate with an acetylene or an azide group at the other end. This first linker may comprise a defined PEG moiety with an azide or acetylene group at one end and a different reactive group, such as carboxylic acid or hydroxyl group, at the other end. Said bifunctional defined PEG may be attached to the amine group of an amino alcohol, and the hydroxyl group of the latter may be attached to the hydroxyl group on the drug in the form of a carbonate. Alternatively, the non-azide (or acetylene) moiety of said defined bifunctional PEG is optionally attached to the N-terminus of an L-amino acid or a polypeptide, with the C-terminus attached to the amino group of amino alcohol, and the hydroxy group of the latter is attached to the hydroxyl group of the drug in the form of carbonate or carbamate, respectively.

A second linker, comprising an antibody-coupling group and a reactive group complementary to the azide (or acetylene) group of the first linker, namely acetylene (or azide), may react with the drug-(first linker) conjugate via acetylene-azide cycloaddition reaction to furnish a final bifunctional drug product that is useful for conjugating to disease-targeting antibodies. The antibody-coupling group is preferably either a thiol or a thiol-reactive group.

Methods for selective regeneration of the 10-hydroxyl group in the presence of the C-20 carbonate in preparations of drug-linker precursor involving CPT analogs such as SN-38 are provided below. Other protecting groups for reactive hydroxyl groups in drugs such as the phenolic hydroxyl in SN-38, for example t-butyldimethylsilyl or t-butyldiphenylsilyl, may also be used, and these are deprotected by tetrabutylammonium fluoride prior to linking of the derivatized drug to an antibody-coupling moiety. The 10-hydroxyl group of CPT analogs is alternatively protected as an ester or carbonate, other than 'BOC', such that the bifunctional CPT is conjugated to an antibody without prior deprotection of this protecting group. The protecting group is readily deprotected under physiological pH conditions after the bioconjugate is administered.

In the acetylene-azide coupling, referred to as 'click chemistry', the azide part may be on L2 with the acetylene part on L3. Alternatively, L2 may contain acetylene, with L3 containing azide. 'Click chemistry' refers to a copper (+1)-catalyzed cycloaddition reaction between an acetylene moiety and an azide moiety (Kolb H C and Sharpless K B, *Drug Discov Today* 2003; 8: 1128-37), although alternative forms of click chemistry are known and may be used. Click chemistry takes place in aqueous solution at near-neutral pH conditions, and is thus amenable for drug conjugation. The advantage of click chemistry is that it is chemoselective, and complements other well-known conjugation chemistries such as the thiol-maleimide reaction.

While the present application focuses on use of antibodies or antibody fragments as targeting moieties, the skilled artisan will realize that where a conjugate comprises an antibody or antibody fragment, another type of targeting moiety, such as an aptamer, avimer, affibody or peptide ligand, may be substituted.

An exemplary preferred embodiment is directed to a conjugate of a drug derivative and an antibody of the general formula 2, $$\text{MAb-[L2]-[L1]-[AA]}_m\text{-[A']-Drug} \quad (2)$$

where MAb is a disease-targeting antibody; L2 is a component of the cross-linker comprising an antibody-coupling moiety and one or more of acetylene (or azide) groups; L1 comprises a defined PEG with azide (or acetylene) at one end, complementary to the acetylene (or azide) moiety in L2, and a reactive group such as carboxylic acid or hydroxyl group at the other end; AA is an L-amino acid; m is an integer with values of 0, 1, 2, 3, or 4; and A' is an additional spacer, selected from the group of ethanolamine, 4-hydroxybenzyl alcohol, 4-aminobenzyl alcohol, or substituted or unsubstituted ethylenediamine. The L amino acids of 'AA' are selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. If the A' group contains hydroxyl, it is linked to the hydroxyl group or amino group of the drug in the form of a carbonate or carbamate, respectively.

In a preferred embodiment of formula 2, A' is a substituted ethanolamine derived from an L-amino acid, wherein the carboxylic acid group of the amino acid is replaced by a hydroxymethyl moiety. A' may be derived from any one of the following L-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

In an example of the conjugate of the preferred embodiment of formula 2, m is 0, A' is L-valinol, and the drug is exemplified by SN-38. The resultant structure is shown in formula 3.

(3)

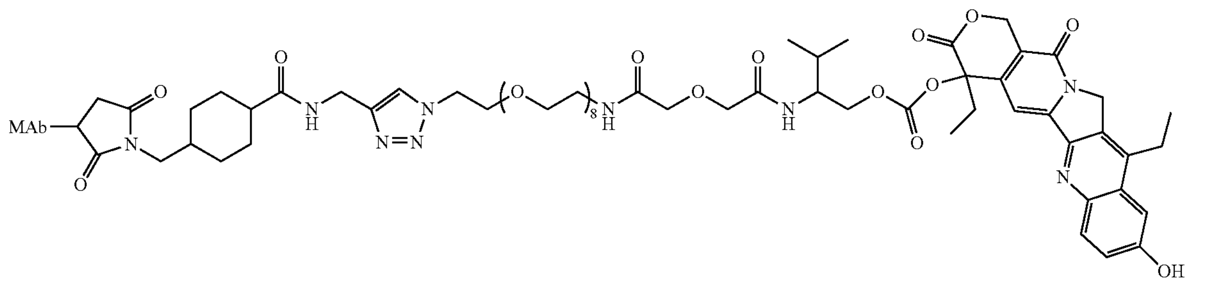

In another example of the conjugate of the preferred embodiment of formula 2, m is 1 and represented by a derivatized L-lysine, A' is L-valinol, and the drug is exemplified by SN-38. The structure is shown in formula 4.

(4)

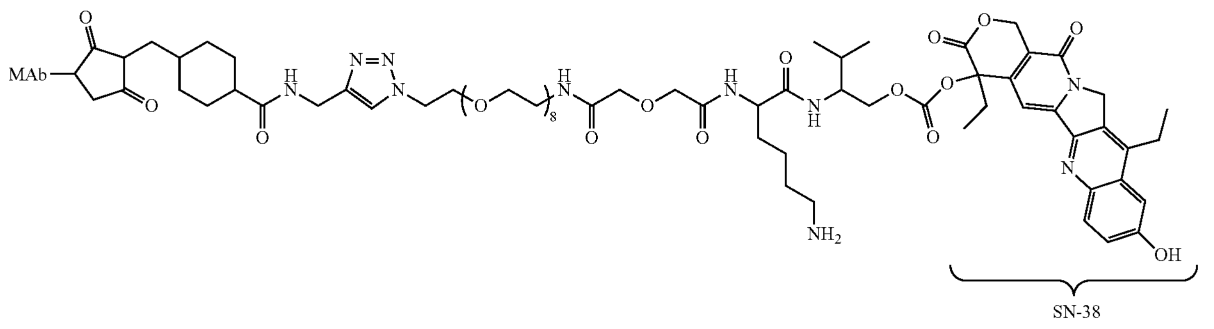

In this embodiment, an amide bond is first formed between the carboxylic acid of an amino acid such as lysine and the amino group of valinol, using orthogonal protecting groups for the lysine amino groups. The protecting group on the N-terminus of lysine is removed, keeping the protecting group on the side chain of lysine intact, and the N-terminus is coupled to the carboxyl group on the defined PEG with azide (or acetylene) at the other end. The hydroxyl group of valinol is then attached to the 20-chloroformate derivative of 10-hydroxy-protected SN-38, and this intermediate is coupled to an L2 component carrying the antibody-binding moiety as well as the complementary acetylene (or azide) group involved in the click cycloaddition chemistry. Finally, removal of protecting groups at both lysine side chain and SN-38 gives the product of this example, shown in formula 3.

While not wishing to be bound by theory, the small MW SN-38 product, namely valinol-SN-38 carbonate, generated after intracellular proteolysis, has the additional pathway of liberation of intact SN-38 through intramolecular cyclization involving the amino group of valinol and the carbonyl of the carbonate.

In another preferred embodiment, A' of the general formula 2 is A-OH, whereby A-OH is a collapsible moiety such as 4-aminobenzyl alcohol or a substituted 4-aminobenzyl alcohol substituted with a $C_1$-$C_{10}$ alkyl group at the benzylic position, and the latter, via its amino group, is attached to an L-amino acid or a polypeptide comprising up to four L-amino acid moieties; wherein the N-terminus is attached to a cross-linker terminating in the antibody-binding group.

An example of a preferred embodiment is given below, wherein the A-OH embodiment of A' of general formula (2) is derived from substituted 4-aminobenzyl alcohol, and 'AA' is comprised of a single L-amino acid with m=1 in the general formula (2), and the drug is exemplified with SN-38. The structure is represented below (formula 5, referred to as MAb-CLX-SN-38). Single amino acid of AA is selected from any one of the following L-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. The substituent R on 4-aminobenzyl alcohol moiety (A-OH embodiment of A') is hydrogen or an alkyl group selected from C1-C10 alkyl groups.

(5)

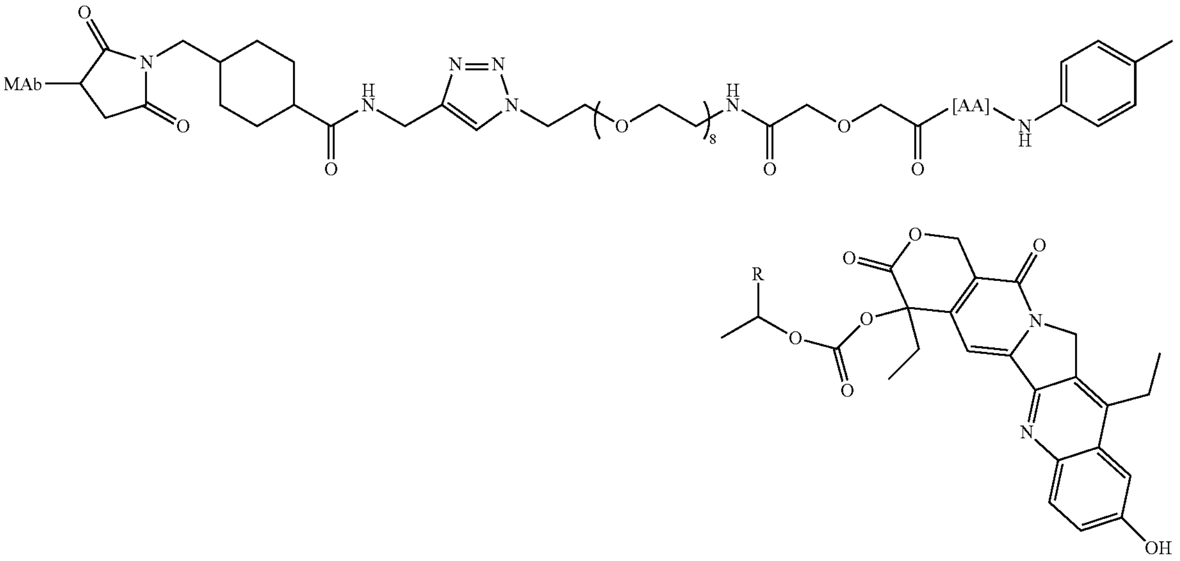

MAb-CLX-SN-38

An embodiment of MAb-CLX-SN-38 of formula 5, wherein the single amino acid AA is L-lysine and R=H, and the drug is exemplified by SN-38 (formula 6; referred to as MAb-CL2A-SN-38).

(6)

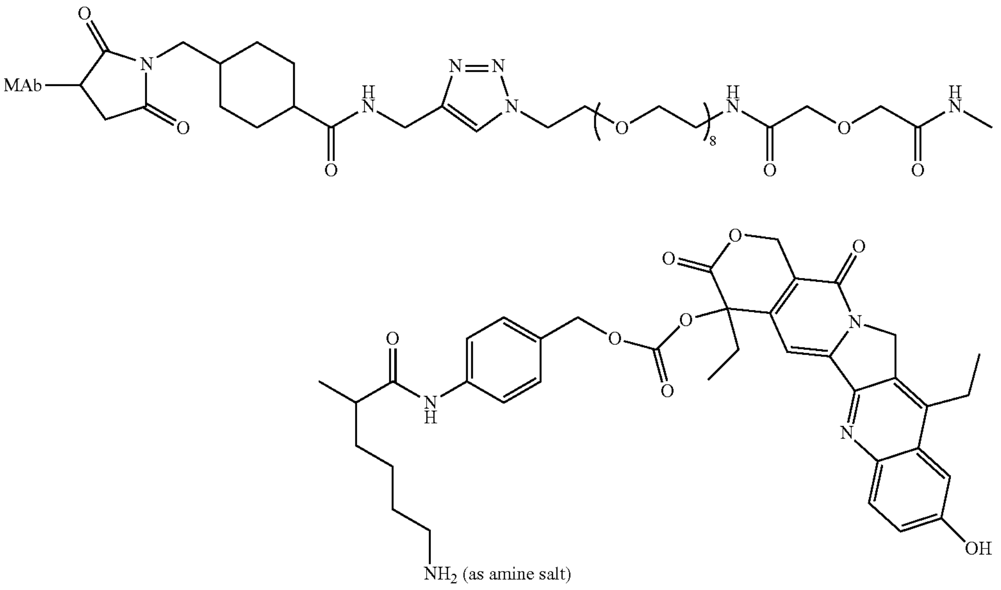

MAb-CL2A-SN-38

Other embodiments are possible within the context of 10-hydroxy-containing camptothecins, such as SN-38. In the example of SN-38 as the drug, the more reactive 10-hydroxy group of the drug is derivatized leaving the 20-hydroxyl group unaffected. Within the general formula 2, A' is a substituted ethylenediamine. An example of this embodiment is represented by the formula '7' below, wherein the phenolic hydroxyl group of SN-38 is derivatized as a carbamate with a substituted ethylenediamine, with the other amine of the diamine derivatized as a carbamate with a 4-aminobenzyl alcohol, and the latter's amino group is attached to Phe-Lys dipeptide. In this structure (formula 7), R and R' are independently hydrogen or methyl. It is referred to as MAb-CL17-SN-38 or MAb-CL2E-SN-38, when R=R'=methyl.

(7)

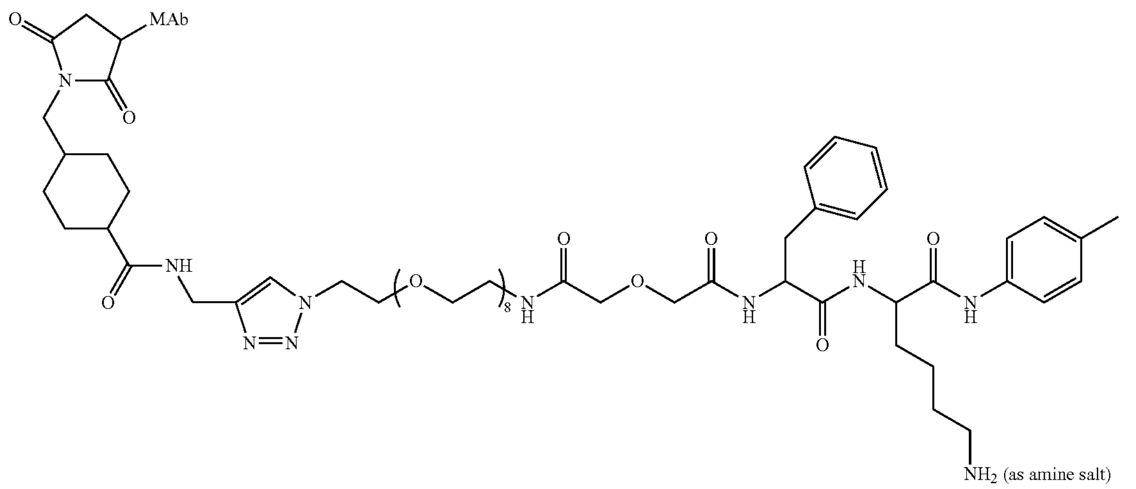

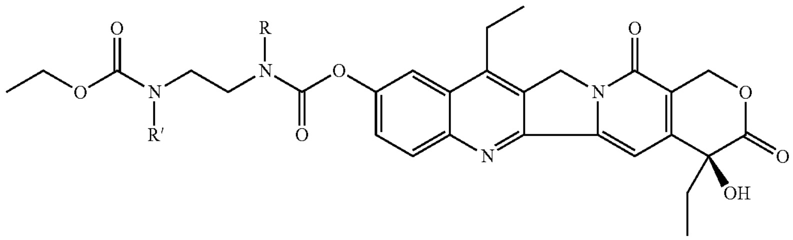

In a preferred embodiment, AA comprises a polypeptide moiety, preferably a di, tri or tetrapeptide, that is cleavable by intracellular peptidase. Examples are: Ala-Leu, Leu-Ala-Leu, and Ala-Leu-Ala-Leu (Trouet et al., 1982).

In another preferred embodiment, the L1 component of the conjugate contains a defined polyethyleneglycol (PEG) spacer with 1-30 repeating monomeric units. In a further preferred embodiment, PEG is a defined PEG with 1-12 repeating monomeric units. The introduction of PEG may involve using heterobifunctionalized PEG derivatives which are available commercially. The heterobifunctional PEG may contain an azide or acetylene group. An example of a heterobifunctional defined PEG containing 8 repeating monomeric units, with 'NHS' being succinimidyl, is given below in formula 8:

(8)

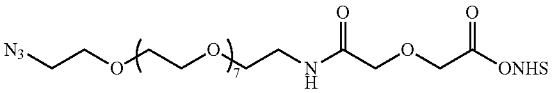

In a preferred embodiment, L2 has a plurality of acetylene (or azide) groups, ranging from 2-40, but preferably 2-20, and more preferably 2-5, and a single antibody-binding moiety.

A representative SN-38 conjugate of an antibody containing multiple drug molecules and a single antibody-binding moiety is shown below. The L2' component of this structure is appended to 2 acetylenic groups, resulting in the attachment of two azide-appended SN-38 molecules. The bonding to MAb is represented as a succinimide.

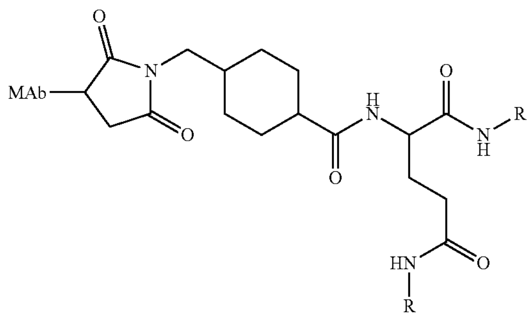

-continued

Where R residue is:

(9)

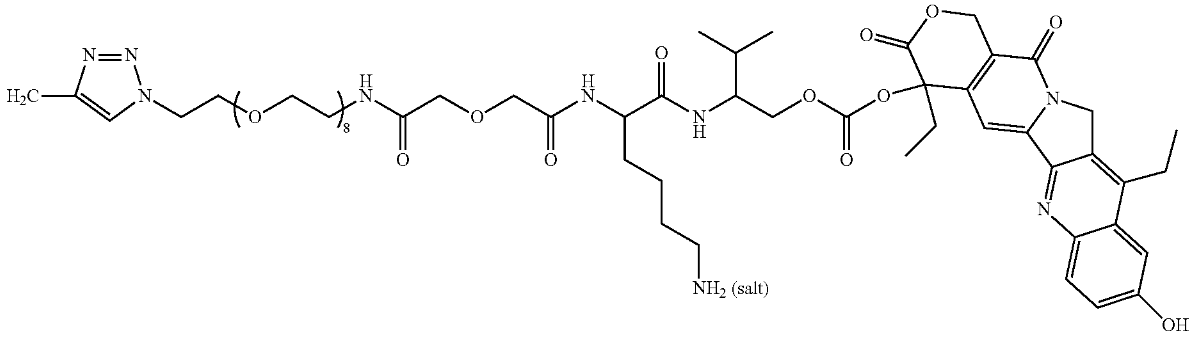

In preferred embodiments, when the bifunctional drug contains a thiol-reactive moiety as the antibody-binding group, the thiols on the antibody are generated on the lysine groups of the antibody using a thiolating reagent. Methods for introducing thiol groups onto antibodies by modifications of MAb's lysine groups are well known in the art (Wong in *Chemistry of protein conjugation and cross-linking*, CRC Press, Inc., Boca Raton, Fla. (1991), pp 20-22). Alternatively, mild reduction of interchain disulfide bonds on the antibody (Willner et al., *Bioconjugate Chem.* 4:521-527 (1993)) using reducing agents such as dithiothreitol (DTT) can generate 7-to-10 thiols on the antibody; which has the advantage of incorporating multiple drug moieties in the interchain region of the MAb away from the antigen-binding region. In a more preferred embodiment, attachment of SN-38 to reduced disulfide sulfhydryl groups results in formation of an antibody-SN-38 immunoconjugate with 6 SN-38 moieties covalently attached per antibody molecule. Other methods of providing cysteine residues for attachment of drugs or other therapeutic agents are known, such as the use of cysteine engineered antibodies (see U.S. Pat. No. 7,521,541, the Examples section of which is incorporated herein by reference.)

In alternative preferred embodiments, the chemotherapeutic moiety is selected from the group consisting of doxorubicin (DOX), epirubicin, morpholinodoxorubicin (morpholino-DOX), cyanomorpholino-doxorubicin (cyanomorpholino-DOX), 2-pyrrolino-doxorubicin (2-PDOX), Pro-2PDOX, CPT, 10-hydroxy camptothecin, SN-38, topotecan, lurtotecan, 9-aminocamptothecin, 9-nitrocamptothecin, taxanes, geldanamycin, ansamycins, and epothilones. In a more preferred embodiment, the chemotherapeutic moiety is SN-38. Preferably, in the conjugates of the preferred embodiments, the antibody links to at least one chemotherapeutic moiety; preferably 1 to about 12 chemotherapeutic moieties; most preferably about 6 to about 12 chemotherapeutic moieties.

Furthermore, in a preferred embodiment, the linker component 'L2' comprises a thiol group that reacts with a thiol-reactive residue introduced at one or more lysine side chain amino groups of said antibody. In such cases, the antibody is pre-derivatized with a thiol-reactive group such as a maleimide, vinylsulfone, bromoacetamide, or iodoacetamide by procedures well described in the art.

In the context of this work, a process was surprisingly discovered by which CPT drug-linkers can be prepared wherein CPT additionally has a 10-hydroxyl group. This process involves, but is not limited to, the protection of the 10-hydroxyl group as a t-butyloxycarbonyl (BOC) derivative, followed by the preparation of the penultimate intermediate of the drug-linker conjugate. Usually, removal of BOC group requires treatment with strong acid such as trifluoroacetic acid (TFA). Under these conditions, the CPT 20-O-linker carbonate, containing protecting groups to be removed, is also susceptible to cleavage, thereby giving rise to unmodified CPT. In fact, the rationale for using a mildly removable methoxytrityl (MMT) protecting group for the lysine side chain of the linker molecule, as enunciated in the art, was precisely to avoid this possibility (Walker et al., 2002). It was discovered that selective removal of phenolic BOC protecting group is possible by carrying out reactions for short durations, optimally 3-to-5 minutes. Under these conditions, the predominant product was that in which the 'BOC' at 10-hydroxyl position was removed, while the carbonate at '20' position was intact.

An alternative approach involves protecting the CPT analog's 10-hydroxy position with a group other than 'BOC', such that the final product is ready for conjugation to antibodies without a need for deprotecting the 10-OH protecting group. The 10-hydroxy protecting group, which converts the 10-OH into a phenolic carbonate or a phenolic ester, is readily deprotected by physiological pH conditions or by esterases after in vivo administration of the conjugate. The faster removal of a phenolic carbonate at the 10 position vs. a tertiary carbonate at the 20 position of 10-hydroxycamptothecin under physiological condition has been described by He et al. (He et al., *Bioorganic & Medicinal Chemistry* 12: 4003-4008 (2004)). A 10-hydroxy protecting group on SN-38 can be 'COR' where R can be a substituted alkyl such as "$N(CH_3)_2-(CH_2)_n-$" where n is 1-10 and wherein the terminal amino group is optionally in the form of a quaternary salt for enhanced aqueous solubility, or a simple alkyl residue such as "$CH_3-(CH_2)_n-$" where n is 0-10, or it can be an alkoxy moiety such as "$CH_3-(CH_2)$ n-O—" where n is 0-10, or "$N(CH_3)_2-(CH_2)_n-O-$" where n is 2-10, or "$R_1O-(CH_2-CH_2-O)_n-CH_2-CH_2-O-$" where $R_1$ is ethyl or methyl and n is an integer with values of 0-10. These 10-hydroxy derivatives are readily prepared by treatment with the chloroformate of the chosen reagent, if the final derivative is to be a carbonate. Typically, the 10-hydroxy-containing camptothecin such as SN-38 is treated with a molar equivalent of the chloroformate in dimethylformamide using triethylamine as the base. Under these conditions, the 20-OH position is unaffected. For forming 10-O-esters, the acid chloride of the chosen reagent is used.

In a preferred process of the preparation of a conjugate of a drug derivative and an antibody of the general formula 2, wherein the descriptors L2, L1, AA and A-X are as described in earlier sections, the bifunctional drug moiety, [L2]-[L1]-$[AA]_m$[A-X]-Drug is first prepared, followed by the conjugation of the bifunctional drug moiety to the antibody (indicated herein as "MAb").

In a preferred process of the preparation of a conjugate of a drug derivative and an antibody of the general formula 2, wherein the descriptors L2, L1, AA and A-OH are as described in earlier sections, the bifunctional drug moiety is prepared by first linking A-OH to the C-terminus of AA via an amide bond, followed by coupling the amine end of AA to a carboxylic acid group of L1. If AA is absent (i.e. m=0), A-OH is directly attached to L1 via an amide bond. The cross-linker, [L1]-$[AA]_m$[A-OH], is attached to drug's hydroxyl or amino group, and this is followed by attachment to the L1 moiety, by taking recourse to the reaction between azide (or acetylene) and acetylene (or azide) groups in L1 and L2 via click chemistry.

In one embodiment, the antibody is a monoclonal antibody (MAb). In other embodiments, the antibody may be a multivalent and/or multispecific MAb. The antibody may be a murine, chimeric, humanized, or human monoclonal antibody, and said antibody may be in intact, fragment (Fab, Fab', $F(ab)_2$, $F(ab')_2$), or sub-fragment (single-chain constructs) form, or of an IgG1, IgG2a, IgG3, IgG4, IgA isotype, or submolecules therefrom.

In a preferred embodiment, the antibody binds to an antigen or epitope of an antigen expressed on a cancer or malignant cell. The cancer cell is preferably a cell from a hematopoietic tumor, carcinoma, sarcoma, melanoma or a glial tumor. A preferred malignancy to be treated according to the present invention is a malignant solid tumor or hematopoietic neoplasm.

In a preferred embodiment, the intracellularly-cleavable moiety may be cleaved after it is internalized into the cell upon binding by the MAb-drug conjugate to a receptor thereof, and particularly cleaved by esterases and peptidases.

General Antibody Techniques

Techniques for preparing monoclonal antibodies against virtually any target antigen are well known in the art. See, for example, Köhler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art, as discussed below.

The skilled artisan will realize that the claimed methods and compositions may utilize any of a wide variety of antibodies known in the art. Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040, 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art. Isolated antibodies may be conjugated to therapeutic agents, such as camptothecins, using the techniques disclosed herein.

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, *Hybridoma* 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. Techniques for production of humanized monoclonal antibodies are well known in the art. (See, e.g., Jones et al., 1986, *Nature,* 321:522; Riechmann et al., *Nature,* 1988, 332:323; Verhoeyen et al., 1988, *Science,* 239:1534; Carter et al., 1992, *Proc. Nat'l Acad. Sci. USA,* 89:4285; Sandhu, *Crit. Rev. Biotech.,* 1992, 12:437; Tempest et al., 1991, *Biotechnology* 9:266; Singer et al., *J. Immun.,* 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., *Int. J. Cancer* 46: 310 (1990). In another embodiment, an antibody may be a human monoclonal antibody. Such antibodies may be obtained from transgenic mice that have been engineered to produce specific human antibodies in response to antigenic challenge, as discussed below.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the μ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual*, Barbas et al. (eds), 1st edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A non-limiting example of such a system is the XENOMOUSE® (e.g., Green et al., 1999, *J. Immunol. Methods* 231:11-23, incorporated herein by reference) from Abgenix (Fremont, Calif.). In the XENOMOUSE® and similar animals, the mouse antibody genes have been inactivated and replaced by functional human antibody genes, while the remainder of the mouse immune system remains intact.

The XENOMOUSE® was transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XENOMOUSE® immunized with a target antigen will produce human antibodies by the normal immune response, which may be harvested and/or produced by standard techniques discussed above. A variety of strains of XENOMOUSE® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XENOMOUSE® system but may utilize any transgenic animal that has been genetically engineered to produce human antibodies.

Production of Antibody Fragments

Some embodiments of the claimed methods and/or compositions may concern antibody fragments. Such antibody fragments may be obtained, for example, by pepsin or papain digestion of whole antibodies by conventional methods. For example, antibody fragments may be produced by enzymatic cleavage of antibodies with pepsin to provide a 5S fragment denoted $F(ab')_2$. This fragment may be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment. Exemplary methods for producing antibody fragments are disclosed in U.S. Pat. Nos. 4,036,945; 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, *Proc. Nat'l. Acad. Sci. USA,* 69:2659. Alternatively, the variable chains may be linked by an intermolecular disulfide bond or cross-linked by chemicals such as glutaraldehyde. See Sandhu, 1992, *Crit. Rev. Biotech.,* 12:437.

Preferably, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell, such as *E. coli*. The recombinant host cells synthesize a single polypeptide chain with a linker peptide bridging the two V domains. Methods for producing scFvs are well-known in the art. See Whitlow et al., 1991, *Methods: A Companion to Methods in Enzymology* 2:97; Bird et al., 1988, *Science,* 242:423; U.S. Pat. No. 4,946,778; Pack et al., 1993, *Bio/Technology,* 11:1271, and Sandhu, 1992, *Crit. Rev. Biotech.,* 12:437.

Another form of an antibody fragment is a single-domain antibody (dAb), sometimes referred to as a single chain antibody. Techniques for producing single-domain antibodies are well known in the art (see, e.g., Cossins et al., *Protein Expression and Purification,* 2007, 51:253-59; Shuntao et al., *Molec Immunol* 2006, 43:1912-19; Tanha et al., *J. Biol. Chem.* 2001, 276:24774-780). Other types of antibody fragments may comprise one or more complementarity-determining regions (CDRs). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, *Methods: A Companion to Methods in Enzymology* 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.)

Antibody Variations

In certain embodiments, the sequences of antibodies, such as the Fc portions of antibodies, may be varied to optimize the physiological characteristics of the conjugates, such as the half-life in serum. Methods of substituting amino acid sequences in proteins are widely known in the art, such as by site-directed mutagenesis (e.g. Sambrook et al., *Molecular Cloning, A laboratory manual,* $2^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, *J Nucl Med* 41:355-62; Hinton et al., 2006, *J Immunol* 176:346-56; Petkova et al. 2006, *Int Immunol* 18:1759-69; U.S. Pat. No. 7,217,797; each incorporated herein by reference).

Target Antigens and Exemplary Antibodies

In a preferred embodiment, antibodies are used that recognize and/or bind to antigens that are expressed at high levels on target cells and that are expressed predominantly or exclusively on diseased cells versus normal tissues. More preferably, the antibodies internalize rapidly following binding. An exemplary rapidly internalizing antibody is the LL1 (anti-CD74) antibody, with a rate of internalization of approximately $8\times10^6$ antibody molecules per cell per day (e.g., Hansen et al., 1996, *Biochem J.* 320:293-300). Thus, a "rapidly internalizing" antibody may be one with an internalization rate of about $1\times10^6$ to about $1\times10^7$ antibody molecules per cell per day. Antibodies of use in the claimed compositions and methods may include MAbs with properties as recited above. Exemplary antibodies of use for therapy of, for example, cancer include but are not limited to LL1 (anti-CD74), LL2 or RFB4 (anti-CD22), veltuzumab (hA20, anti-CD20), rituxumab (anti-CD20), obinutuzumab (GA101, anti-CD20), lambrolizumab (anti-PD-1 receptor), nivolumab (anti-PD-1 receptor), ipilimumab (anti-CTLA-4), RS7 (anti-epithelial glycoprotein-1 (EGP-1, also known as TROP-2)), PAM4 or KC4 (both anti-mucin), MN-14 (anti-carcinoembryonic antigen (CEA, also known as CD66e or CEACAM5), MN-15 or MN-3 (anti-CEACAM6), Mu-9 (anti-colon-specific antigen-p), Immu 31 (an anti-alpha-fetoprotein), R1 (anti-IGF-1R), A19 (anti-CD19), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), L243 (anti-HLA-DR) alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); tositumomab (anti-CD20); PAM4 (aka clivatuzumab, anti-mucin) and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20050271671; 20060193865; 20060210475; 20070087001; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMMU-31 (U.S. Pat. No. 7,300,655), hLL1 (U.S. Pat. No. 7,312,318), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772,645), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575) the text of each recited patent or application is incorporated herein by reference with respect to the Figures and Examples sections.

Other useful antigens that may be targeted using the described conjugates include carbonic anhydrase IX, B7, CCCL19, CCCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM6, CTLA-4, alpha-fetoprotein (AFP), VEGF (e.g., AVASTIN®, fibronectin splice variant), ED-B fibronectin (e.g., L19), EGP-1 (TROP-2), EGP-2 (e.g., 17-1A), EGF receptor (ErbB1) (e.g., ERBITUX®), ErbB2, ErbB3, Factor H, FHL-1, Flt-3, folate receptor, Ga 733, GRO-β, HMGB-1, hypoxia inducible factor (HIF), HM1.24, HER-2/neu, insulin-like growth factor (ILGF), IFN-γ, IFN-α, IFN-β, IFN-λ, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5ac, placental growth factor (P1GF), PSA (prostate-specific antigen), PSMA, PAM4 antigen, PD-1 receptor, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), TROP-2, VEGFR, RANTES, T101, as well as cancer stem cell antigens, complement factors C3, C3a, C3b, C5a, C5, and an oncogene product.

A comprehensive analysis of suitable antigen (Cluster Designation, or CD) targets on hematopoietic malignant cells, as shown by flow cytometry and which can be a guide to selecting suitable antibodies for drug-conjugated immunotherapy, is Craig and Foon, *Blood* prepublished online Jan. 15, 2008; DOL 10.1182/blood-2007-11-120535.

The CD66 antigens consist of five different glycoproteins with similar structures, CD66a-e, encoded by the carcinoembryonic antigen (CEA) gene family members, BCG, CGM6, NCA, CGM1 and CEA, respectively. These CD66 antigens (e.g., CEACAM6) are expressed mainly in granulocytes, normal epithelial cells of the digestive tract and tumor cells of various tissues. Also included as suitable targets for cancers are cancer testis antigens, such as NY-ESO-1 (Theurillat et al., *Int. J. Cancer* 2007; 120(11):2411-7), as well as CD79a in myeloid leukemia (Kozlov et al., *Cancer Genet. Cytogenet.* 2005; 163(1):62-7) and also B-cell diseases, and CD79b for non-Hodgkin's lymphoma (Poison et al., *Blood* 110(2):616-623). A number of the aforementioned antigens are disclosed in U.S. Provisional Application Ser. No. 60/426,379, entitled "Use of Multi-specific, Non-covalent Complexes for Targeted Delivery of Therapeutics," filed Nov. 15, 2002. Cancer stem cells, which are ascribed to be more therapy-resistant precursor malignant cell populations (Hill and Penis, *J. Natl. Cancer Inst.* 2007; 99:1435-40), have antigens that can be targeted in certain cancer types, such as CD133 in prostate cancer (Maitland et al., *Ernst Schering Found. Sympos. Proc.* 2006; 5:155-79), non-small-cell lung cancer (Donnenberg et al., *J. Control Release* 2007; 122(3):385-91), and glioblastoma (Beier et al., *Cancer Res.* 2007; 67(9):4010-5), and CD44 in colorectal cancer (Dalerba er al., *Proc. Natl. Acad. Sci. USA* 2007; 104(24)10158-63), pancreatic cancer (Li et al., *Cancer Res.* 2007; 67(3):1030-7), and in head and neck squamous cell carcinoma (Prince et al., *Proc. Natl. Acad. Sci. USA* 2007; 104(3)973-8).

For multiple myeloma therapy, suitable targeting antibodies have been described against, for example, CD38 and CD138 (Stevenson, *Mol Med* 2006; 12(11-12):345-346; Tassone et al., *Blood* 2004; 104(12):3688-96), CD74 (Stein et al., ibid.), CS1 (Tai et al., *Blood* 2008; 112(4):1329-37, and CD40 (Tai et al., 2005; *Cancer Res.* 65(13):5898-5906).

Macrophage migration inhibitory factor (MIF) is an important regulator of innate and adaptive immunity and apoptosis. It has been reported that CD74 is the endogenous receptor for MIF (Leng et al., 2003, *J Exp Med* 197:1467-76). The therapeutic effect of antagonistic anti-CD74 antibodies on MIF-mediated intracellular pathways may be of use for treatment of a broad range of disease states, such as cancers of the bladder, prostate, breast, lung, colon and chronic lymphocytic leukemia (e.g., Meyer-Siegler et al., 2004, *BMC Cancer* 12:34; Shachar & Haran, 2011, *Leuk Lymphoma* 52:1446-54); autoimmune diseases such as rheumatoid arthritis and systemic lupus erythematosus (Morand & Leech, 2005, *Front Biosci* 10:12-22; Shachar & Haran, 2011, *Leuk Lymphoma* 52:1446-54); kidney diseases such as renal allograft rejection (Lan, 2008, *Nephron Exp Nephrol.* 109:e79-83); and numerous inflammatory diseases (Meyer-Siegler et al., 2009, *Mediators Inflamm* epub Mar. 22, 2009; Takahashi et al., 2009, *Respir Res* 10:33; Milatuzumab (hLL1) is an exemplary anti-CD74 antibody of therapeutic use for treatment of MIF-mediated diseases.

Anti-TNF-α antibodies are known in the art and may be of use to treat immune diseases, such as autoimmune disease, immune dysfunction (e.g., graft-versus-host disease, organ transplant rejection) or diabetes. Known antibodies against TNF-α include the human antibody CDP571 (Ofei et al., 2011, *Diabetes* 45:881-85); murine antibodies MTNFAI, M2TNFAI, M3TNFAI, M3TNFABI, M302B and M303 (Thermo Scientific, Rockford, Ill.); infliximab (Centocor, Malvern, Pa.); certolizumab pegol (UCB, Brussels, Belgium); and adalimumab (Abbott, Abbott Park, Ill.). These and many other known anti-TNF-α antibodies may be used in the claimed methods and compositions. Other antibodies of use for therapy of immune dysregulatory or autoimmune disease include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD11a); muromonab-CD3 (anti-CD3 receptor); anti-CD40L (UCB, Brussels, Belgium); natalizumab (anti-α4 integrin) and omalizumab (anti-IgE).

Type-1 and Type-2 diabetes may be treated using known antibodies against B-cell antigens, such as CD22 (epratuzumab and hRFB4), CD74 (milatuzumab), CD19 (hA19), CD20 (veltuzumab) or HLA-DR (hL243) (see, e.g., Winer et al., 2011, *Nature Med* 17:610-18). Anti-CD3 antibodies also have been proposed for therapy of type 1 diabetes (Cernea et al., 2010, *Diabetes Metab Rev* 26:602-05).

The pharmaceutical composition of the present invention may be used to treat a subject having a metabolic disease, such amyloidosis, or a neurodegenerative disease, such as Alzheimer's disease. Bapineuzumab is in clinical trials for Alzheimer's disease therapy. Other antibodies proposed for therapy of Alzheimer's disease include Alz 50 (Ksiezak-Reding et al., 1987, *J Biol Chem* 263:7943-47), gantenerumab, and solanezumab. Infliximab, an anti-TNF-α antibody, has been reported to reduce amyloid plaques and improve cognition.

In a preferred embodiment, diseases that may be treated using the claimed compositions and methods include cardiovascular diseases, such as fibrin clots, atherosclerosis, myocardial ischemia and infarction. Antibodies to fibrin (e.g., scFv(59D8); T2G1s; MH1) are known and in clinical trials as imaging agents for disclosing said clots and pulmonary emboli, while anti-granulocyte antibodies, such as MN-3, MN-15, anti-NCA95, and anti-CD15 antibodies, can target myocardial infarcts and myocardial ischemia. (See, e.g., U.S. Pat. Nos. 5,487,892; 5,632,968; 6,294,173; 7,541,440, the Examples section of each incorporated herein by reference) Anti-macrophage, anti-low-density lipoprotein (LDL), anti-MIF, and anti-CD74 (e.g., hLL1) antibodies can be used to target atherosclerotic plaques. Abciximab (anti-glycoprotein IIb/IIIa) has been approved for adjuvant use for prevention of restenosis in percutaneous coronary interventions and the treatment of unstable angina (Waldmann et al., 2000, *Hematol* 1:394-408). Anti-CD3 antibodies have been reported to reduce development and progression of atherosclerosis (Steffens et al., 2006, *Circulation* 114:1977-84). Antibodies against oxidized LDL induced a regression of established atherosclerosis in a mouse model (Ginsberg, 2007, *J Am Coll Cardiol* 52:2319-21). Anti-ICAM-1 antibody was shown to reduce ischemic cell damage after cerebral artery occlusion in rats (Zhang et al., 1994, *Neurology* 44:1747-51). Commercially available monoclonal antibodies to leukocyte antigens are represented by: OKT anti-T-cell monoclonal antibodies (available from Ortho Pharmaceutical Company) which bind to normal T-lymphocytes; the monoclonal antibodies produced by the hybridomas having the ATCC accession numbers HB44, HB55, HB12, HB78 and HB2; G7E11, W8E7, NKP15 and GO22 (Becton Dickinson); NEN9.4 (New England Nuclear); and FMC11 (Sera Labs). A description of antibodies against fibrin and platelet antigens is contained in Knight, *Semin. Nucl. Med.*, 20:52-67 (1990).

In another preferred embodiment, antibodies are used that internalize rapidly and are then re-expressed, processed and presented on cell surfaces, enabling continual uptake and accretion of circulating conjugate by the cell. An example of a most-preferred antibody/antigen pair is LL1, an anti-CD74 MAb (invariant chain, class II-specific chaperone, Ii) (see, e.g., U.S. Pat. Nos. 6,653,104; 7,312,318; the Examples section of each incorporated herein by reference). The CD74 antigen is highly expressed on B-cell lymphomas (including multiple myeloma) and leukemias, certain T-cell lymphomas, melanomas, colonic, lung, and renal cancers, glioblastomas, and certain other cancers (Ong et al., *Immunology* 98:296-302 (1999)). A review of the use of CD74 antibodies in cancer is contained in Stein et al., *Clin Cancer Res.* 2007 Sep. 15; 13(18 Pt 2):5556s-5563s, incorporated herein by reference.

The diseases that are preferably treated with anti-CD74 antibodies include, but are not limited to, non-Hodgkin's lymphoma, Hodgkin's disease, melanoma, lung, renal, colonic cancers, glioblastome multiforme, histiocytomas, myeloid leukemias, and multiple myeloma. Continual expression of the CD74 antigen for short periods of time on the surface of target cells, followed by internalization of the antigen, and re-expression of the antigen, enables the targeting LL1 antibody to be internalized along with any chemotherapeutic moiety it carries. This allows a high, and therapeutic, concentration of LL1-chemotherapeutic drug conjugate to be accumulated inside such cells. Internalized LL1-chemotherapeutic drug conjugates are cycled through lysosomes and endosomes, and the chemotherapeutic moiety is released in an active form within the target cells.

In another preferred embodiment, the therapeutic conjugates can be used against pathogens, since antibodies against pathogens are known. For example, antibodies and antibody fragments which specifically bind markers produced by or associated with infectious lesions, including viral, bacterial, fungal and parasitic infections, for example caused by pathogens such as bacteria, rickettsia, mycoplasma, protozoa, fungi, and viruses, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444,744, 4,818,709 and 4,624,846, the Examples section of each incorporated herein by reference, and in Reichert and Dewitz, cited above. A review listing antibodies against infectious organisms (antitoxin and antiviral antibodies), as well as other targets, is contained in Casadevall, *Clin Immunol* 1999; 93(1):5-15, incorporated herein by reference.

In a preferred embodiment, the pathogens are selected from the group consisting of HIV virus, *Mycobacterium tuberculosis, Streptococcus agalactiae*, methicillin-resistant *Staphylococcus aureus, Legionella pneumophilia, Streptococcus pyogenes, Escherichia coli, Neisseria gonorrhoeae, Neisseria meningitidis, Pneumococcus, Cryptococcus neoformans, Histoplasma capsulatum, Hemophilis influenzae* B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japonicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orate, M. arginini, Acholeplasma laidlawii, M. salivarium* and *M. pneumoniae*, as disclosed in U.S. Pat. No. 6,440,416, the Examples section of which is incorporated herein by reference.

In a more preferred embodiment, drug conjugates of the present invention comprising anti-gp120 and other such anti-HIV antibodies can be used as therapeutics for HIV in AIDS patients; and drug conjugates of antibodies to *Mycobacterium tuberculosis* are suitable as therapeutics for drug-refractive tuberculosis. Fusion proteins of anti-gp120 MAb (anti HIV MAb) and a toxin, such as *Pseudomonas* exotoxin, have been examined for antiviral properties (Van Oigen et al., *J Drug Target,* 5:75-91, 1998). Attempts at treating HIV infection in AIDS patients failed, possibly due to insufficient efficacy or unacceptable host toxicity. The CPT drug conjugates of the present invention advantageously lack such toxic side effects of protein toxins, and are therefore advantageously used in treating HIV infection in AIDS patients. These drug conjugates can be given alone or in combination with other antibiotics or therapeutic agents that are effective in such patients when given alone. Candidate anti-HIV antibodies include the P4/D10 anti-envelope antibody described by Johansson et al. (*AIDS.* 2006 Oct. 3; 20(15): 1911-5), as well as the anti-HIV antibodies described and sold by Polymun (Vienna, Austria), also described in U.S. Pat. Nos. 5,831,034, 5,911,989, and Vcelar et al., *AIDS* 2007; 21(16):2161-2170 and Joos et al., *Antimicrob. Agents Chemother.* 2006; 50(5):1773-9, all incorporated herein by reference. A preferred targeting agent for HIV is various combinations of these antibodies in order to overcome resistance.

Antibodies of use to treat autoimmune disease or immune system dysfunctions (e.g., graft-versus-host disease, organ transplant rejection) are known in the art and may be conjugated to SN-38 using the disclosed methods and compositions. Antibodies of use to treat autoimmune/immune dysfunction disease may bind to exemplary antigens including, but not limited to, BCL-1, BCL-2, BCL-6, CD1a, CD2, CD3, CD4, CD5, CD7, CD8, CD10, CD11b, CD11c, CD13, CD14, CD15, CD16, CD19, CD20, CD21, CD22, CD23, CD25, CD33, CD34, CD38, CD40, CD40L, CD41a, CD43, CD45, CD55, TNF-alpha, interferon and HLA-DR. Antibodies that bind to these and other target antigens, discussed above, may be used to treat autoimmune or immune dysfunction diseases. Autoimmune diseases that may be treated with immunoconjugates may include acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, bullous pemphigoid, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis or fibrosing alveolitis.

The antibodies discussed above and other known antibodies against disease-associated antigens may be used as CPT-conjugates, more preferably SN-38-conjugates, in the practice of the claimed methods and compositions.

Bispecific and Multispecific Antibodies

Bispecific antibodies are useful in a number of biomedical applications. For instance, a bispecific antibody with binding sites for a tumor cell surface antigen and for a T-cell surface receptor can direct the lysis of specific tumor cells by T cells. Bispecific antibodies recognizing gliomas and the CD3 epitope on T cells have been successfully used in treating brain tumors in human patients (Nitta, et al. *Lancet.* 1990; 355:368-371). A preferred bispecific antibody is an anti-CD3×anti-CD19 antibody. In alternative embodiments, an anti-CD3 antibody or fragment thereof may be attached to an antibody or fragment against another B-cell associated antigen, such as anti-CD3×anti-CD20, anti-CD3×anti-CD22, anti-CD3×anti-HLA-DR or anti-CD3×anti-CD74. In certain embodiments, the techniques and compositions for therapeutic agent conjugation disclosed herein may be used with bispecific or multispecific antibodies as the targeting moieties.

Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, *Nature,* 1983; 305:537-540).

Another method for producing bispecific antibodies uses heterobifunctional cross-linkers to chemically tether two different monoclonal antibodies (Staerz, et al. *Nature,* 1985; 314:628-631; Perez, et al. *Nature,* 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. *Proc Natl Acad Sci USA.* 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte, et al. *Proc Natl Acad Sci USA.* 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. Nos. 4,946,778 and 5,132,405, the Examples section of each of which is incorporated herein by reference. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL) has been utilized to produce combinations of virtually any desired antibodies, antibody fragments and other effector molecules (see, e.g., U.S. Pat. Nos. 7,521,056; 7,527,787; 7,534,866; 7,550,143; 7,666,400; 7,858,070; 7,871,622; 7,906,121; 7,906,118; 8,163,291; 7,901,680; 7,981,398; 8,003,111 and 8,034,352, the Examples section of each of which incorporated herein by reference). The technique utilizes complementary protein binding domains, referred to as anchoring domains (AD) and dimerization and docking domains (DDD), which bind to each other and allow the assembly of complex structures, ranging from dimers, trimers, tetramers, quintamers and hexamers. These form stable complexes in high yield without requirement for extensive purification. The DNL technique allows the assembly of monospecific, bispecific or multispecific antibodies. Any of the techniques known in the art for making bispecific or multispecific antibodies may be utilized in the practice of the presently claimed methods.

In various embodiments, a conjugate as disclosed herein may be part of a composite, multispecific antibody. Such antibodies may contain two or more different antigen binding sites, with differing specificities. The multispecific composite may bind to different epitopes of the same antigen, or alternatively may bind to two different antigens. Some of the more preferred target combinations include those listed in Table 1. This is a list of examples of preferred combinations, but is not intended to be exhaustive.

TABLE 1

| Some Examples of multispecific antibodies. | |
|---|---|
| First target | Second target |
| MIF | A second proinflammatory effector cytokine, especially HMGB-1, TNF-α, IL-1, or IL-6 |
| MIF | Proinflammatory effector chemokine, especially MCP-1, RANTES, MIP-1A, or MIP-1B |
| MIF | Proinflammatory effector receptor, especially IL-6R, IL-13R, and IL-15R |
| MIF | Coagulation factor, especially TF or thrombin |
| MIF | Complement factor, especially C3, C5, C3a, or C5a |
| MIF | Complement regulatory protein, especially CD46, CD55, CD59, and mCRP |
| MIF | Cancer associated antigen or receptor |
| HMGB-1 | A second proinflammatory effector cytokine, especially MIF, TNF-α, IL-1, or IL-6 |
| HMGB-1 | Proinflammatory effector chemokine, especially MCP-1, RANTES, MIP-1A, or MIP-1B |
| HMGB-1 | Proinflammatory effector receptor especially MCP-1, RANTES, MIP-1A, or MIP-1B |
| HMGB-1 | Coagulation factor, especially TF or thrombin |
| HMGB-1 | Complement factor, especially C3, C5, C3a, or C5a |
| HMGB-1 | Complement regulatory protein, especially CD46, CD55, CD59, and mCRP |
| HMGB-1 | Cancer associated antigen or receptor |
| TNF-α | A second proinflammatory effector cytokine, especially MIF, HMGB-1, TNF-α, IL-1, or IL-6 |
| TNF-α | Proinflammatory effector chemokine, especially MCP-1, RANTES, MIP-1A, or MIP-1B |
| TNF-α | Proinflammatory effector receptor, especially IL-6R IL-13R, and IL-15R |
| TNF-α | Coagulation factor, especially TF or thrombin |
| TNF-α | Complement factor, especially C3, C5, C3a, or C5a |
| TNF-α | Complement regulatory protein, especially CD46, CD55, CD59, and mCRP |
| TNF-α | Cancer associated antigen or receptor |
| LPS | Proinflammatory effector cytokine, especially MIF, HMGB-1, TNF-α, IL-1, or IL-6 |
| LPS | Proinflammatory effector chemokine, especially MCP-1, RANTES, MIP-1A, or MIP-1B |
| LPS | Proinflammatory effector receptor, especially IL-6R IL-13R, and IL-15R |
| LPS | Coagulation factor, especially TF or thrombin |
| LPS | Complement factor, especially C3, C5, C3a, or C5a |
| LPS | Complement regulatory protein, especially CD46, CD55, CD59, and mCRP |
| TF or thrombin | Proinflammatory effector cytokine, especially MIF, HMGB-1, TNF-α, IL-1, or IL-6 |
| TF or thrombin | Proinflammatory effector chemokine, especially MCP-1, RANTES, MIP-1A, or MIP-1B |
| TF or thrombin | Proinflammatory effector receptor, especially IL-6R IL-13R, and IL-15R |
| TF or thrombin | Complement factor, especially C3, C5, C3a, or C5a |
| TF or thrombin | Complement regulatory protein, especially CD46, CD55, CD59, and mCRP |
| TF or thrombin | Cancer associated antigen or receptor |

Still other combinations, such as are preferred for cancer therapies, include CD20+CD22 antibodies, CD74+CD20 antibodies, CD74+CD22 antibodies, CEACAM5 (CEA)+ CEACAM6 (NCA) antibodies, insulin-like growth factor (ILGF)+CEACAM5 antibodies, EGP-1 (e.g., RS-7)+ILGF antibodies, CEACAM5+EGFR antibodies, IL6+CEACAM6 antibodies. Such antibodies need not only be used in combination, but can be combined as fusion proteins of various forms, such as IgG, Fab, scFv, and the like, as described in U.S. Pat. Nos. 6,083,477; 6,183,744 and 6,962,702 and U.S. Patent Application Publication Nos. 20030124058; 20030219433; 20040001825; 20040202666; 20040219156; 20040219203; 20040235065; 20050002945; 20050014207; 20050025709; 20050079184; 20050169926; 20050175582; 20050249738; 20060014245 and 20060034759, the Examples section of each incorporated herein by reference.

DOCK-AND-LOCK™ (DNL™)

In preferred embodiments, a bivalent or multivalent antibody is formed as a DOCK-AND-LOCK™ (DNL™) complex (see, e.g., U.S. Pat. Nos. 7,521,056; 7,527,787; 7,534,866; 7,550,143; 7,666,400; 7,858,070; 7,871,622; 7,906,121; 7,906,118; 8,163,291; 7,901,680; 7,981,398; 8,003,111 and 8,034,352, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., *FEBS Letters.* 2005; 579: 3264. Wong and Scott, *Nat. Rev. Mol. Cell Biol.* 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Although the standard DNL™ complex comprises a trimer with two DDD-linked molecules attached to one AD-linked molecule, variations in complex structure allow the formation of dimers, trimers, tetramers, pentamers, hexamers and other multimers. In some embodiments, the DNL™ complex may comprise two or more antibodies, antibody fragments or fusion proteins which bind to the same antigenic determinant or to two or more different antigens. The DNL™ complex may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

PKA, which plays a central role in one of the best studied signal transduction pathways triggered by the binding of the second messenger cAMP to the R subunits, was first isolated from rabbit skeletal muscle in 1968 (Walsh et al., *J. Biol. Chem.* 1968; 243:3763). The structure of the holoenzyme consists of two catalytic subunits held in an inactive form by the R subunits (Taylor, *J. Biol. Chem.* 1989; 264:8443). Isozymes of PKA are found with two types of R subunits (RI and RII), and each type has α and β isoforms (Scott, *Pharmacol. Ther.* 1991; 50:123). Thus, the four isoforms of PKA regulatory subunits are RIα, RIβ, RIIα and RIIβ. The R subunits have been isolated only as stable dimers and the dimerization domain has been shown to consist of the first 44 amino-terminal residues of RIIα (Newlon et al., *Nat. Struct. Biol.* 1999; 6:222). As discussed below, similar portions of the amino acid sequences of other regulatory subunits are involved in dimerization and docking, each located near the N-terminal end of the regulatory subunit. Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., *J. Biol. Chem.* 1990; 265; 21561)

Since the first AKAP, microtubule-associated protein-2, was characterized in 1984 (Lohmann et al., *Proc. Natl. Acad. Sci USA.* 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, *Nat. Rev. Mol. Cell Biol.* 2004; 5:959). The AD of AKAPs for PKA is an amphipathic helix of 14-18 residues (Carr et al., *J. Biol. Chem.* 1991; 266:14188). The amino acid sequences of the AD are quite varied among individual AKAPs, with the binding affinities reported for RII dimers ranging from 2 to 90 nM (Alto et al., *Proc. Natl. Acad. Sci. USA.* 2003; 100:4445). AKAPs will only bind to dimeric R subunits. For human RIIα, the AD binds to a hydrophobic surface formed by the 23 amino-terminal residues (Colledge and Scott, *Trends Cell Biol.* 1999; 6:216). Thus, the dimerization domain and AKAP binding domain of human RIIα are both located within the same N-terminal 44 amino acid sequence (Newlon et al., *Nat. Struct. Biol.* 1999; 6:222; Newlon et al., *EMBO J.* 2001; 20:1651), which is termed the DDD herein.

We have developed a platform technology to utilize the DDD of human PKA regulatory subunits and the AD of AKAP as an excellent pair of linker modules for docking any two entities, referred to hereafter as A and B, into a noncovalent complex, which could be further locked into a DNL™ complex through the introduction of cysteine residues into both the DDD and AD at strategic positions to facilitate the formation of disulfide bonds. The general methodology of the approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., *Proc. Natl. Acad. Sci. USA.* 2001; 98:8480) to ligate site-specifically. Using various combinations of linkers, adaptor modules and precursors, a wide variety of DNL™ constructs of different stoichiometry may be produced and used (see, e.g., U.S. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL™ construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., *Molecular Cloning, A laboratory manual, $2^{nd}$* Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

In various embodiments, an antibody or antibody fragment may be incorporated into a DNL™ complex by, for example, attaching a DDD or AD moiety to the C-terminal end of the antibody heavy chain, as described in detail below. In more preferred embodiments, the DDD or AD moiety, more preferably the AD moiety, may be attached to the C-terminal end of the antibody light chain (see, e.g., U.S. patent application Ser. No. 13/901,737, filed May 24, 2013, the Examples section of which is incorporated herein by reference.)

Structure-Function Relationships in AD and DDD Moieties

For different types of DNL™ constructs, different AD or DDD sequences may be utilized. Exemplary DDD and AD sequences are provided below.

```
DDD1
                                        (SEQ ID NO: 1)
SHIQIPPGLTELLQGYTVEVLRQQPPDLVEFAVEYFTRLREARA

DDD2
                                        (SEQ ID NO: 2)
CGHIQIPPGLTELLQGYTVEVLRQQPPDLVEFAVEYFTRLREARA

AD1
                                        (SEQ ID NO: 3)
QIEYLAKQIVDNAIQQA

AD2
                                        (SEQ ID NO: 4)
CGQIEYLAKQIVDNAIQQAGC
```

The skilled artisan will realize that DDD1 and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                        (SEQ ID NO: 5)
SLRECELYVQKHNIQALLKDSIVQLCTARPERPMAFLREYFERLEKEEAK

DDD3C
                                        (SEQ ID NO: 6)
MSCGGSLRECELYVQKHNIQALLKDSIVQLCTARPERPMAFLREYFERLE

KEEAK

AD3
                                        (SEQ ID NO: 7)
CGFEELAWKIAKMIWSDVFQQGC
```

In other alternative embodiments, other sequence variants of AD and/or DDD moieties may be utilized in construction of the DNL™ complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

```
PKA RIα
                                        (SEQ ID NO: 8)
SLRECELYVQKHNIQALLKDVSIVQLCTARPERPMAFLREYFEKLEKEEAK

PKA RIβ
                                        (SEQ ID NO: 9)
SLKGCELYVQLHGIQQVLKDCIVHLCISKPERPMKFLREHFEKLEKEENR

QILA
```

-continued

```
PKA RIIα
                                        (SEQ ID NO: 10)
SHIQIPPGLTELLQGYTVEVGQQPPDLVDFAVEYFTRLREARRQ

PKA RIIβ
                                        (SEQ ID NO: 11)
SIEIPAGLTELLQGFTVEVLRHQPADLLEFALQHFTRLQQENER
```

The structure-function relationships of the AD and DDD domains have been the subject of investigation. (See, e.g., Burns-Hamuro et al., 2005, *Protein Sci* 14:2982-92; Carr et al., 2001, *J Biol Chem* 276:17332-38; Alto et al., 2003, *Proc Natl Acad Sci USA* 100:4445-50; Hundsrucker et al., 2006, *Biochem J* 396:297-306; Stokka et al., 2006, *Biochem J* 400:493-99; Gold et al., 2006, *Mol Cell* 24:383-95; Kinderman et al., 2006, *Mol Cell* 24:397-408, the entire text of each of which is incorporated herein by reference.)

For example, Kinderman et al. (2006, *Mol Cell* 24:397-408) examined the crystal structure of the AD-DDD binding interaction and concluded that the human DDD sequence contained a number of conserved amino acid residues that were important in either dimer formation or AKAP binding, underlined in SEQ ID NO:1 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

```
                                        (SEQ ID NO: 1)
SHIQIPPGLTELLQGYTVEVLRQQPPDLVEFAVEYFTRLREARA
```

As discussed in more detail below, conservative amino acid substitutions have been characterized for each of the twenty common L-amino acids. Thus, based on the data of Kinderman (2006) and conservative amino acid substitutions, potential alternative DDD sequences based on SEQ ID NO:1 are shown in Table 2. In devising Table 2, only highly conservative amino acid substitutions were considered. For example, charged residues were only substituted for residues of the same charge, residues with small side chains were substituted with residues of similar size, hydroxyl side chains were only substituted with other hydroxyls, etc. Because of the unique effect of proline on amino acid secondary structure, no other residues were substituted for proline. A limited number of such potential alternative DDD moiety sequences are shown in SEQ ID NO:12 to SEQ ID NO:31 below. The skilled artisan will realize that an almost unlimited number of alternative species within the genus of DDD moieties can be constructed by standard techniques, for example using a commercial peptide synthesizer or well known site-directed mutagenesis techniques. The effect of the amino acid substitutions on AD moiety binding may also be readily determined by standard binding assays, for example as disclosed in Alto et al. (2003, *Proc Natl Acad Sci USA* 100:4445-50).

TABLE 2

Conservative Amino Acid Substitutions in DDD1 (SEQ ID NO: 1). Consensus sequence disclosed as SEQ ID NO: 87.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T | K<br>R | | N | | | | A | | S | D | | | N | A | | S | | D | | | K |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N | N | | | E | | | D | | L<br>I<br>V | | D | | | S | K | | K | D | L<br>I<br>V | K | L<br>I<br>V |

THIQIPPGLTELLQGYTVEVLRQQPPDLVEFAVEYFTRLREARA (SEQ ID NO: 12)

SKIQIPPGLTELLQGYTVEVLRQQPPDLVEFAVEYFTRLREARA (SEQ ID NO: 13)

SRIQIPPGLTELLQGYTVEVLRQQPPDLVEFAVEYFTRLREARA(SEQ ID NO: 14)

SHINIPPGLTELLQGYTVEVLRQQPPDLVEFAVEYFTRLREARA (SEQ ID NO: 15)

SHIQIPPALTELLQGYTVEVLRQQPPDLVEFAVEYFTRLREARA (SEQ ID NO: 16)

SHIQIPPGLSELLQGYTVEVLRQQPPDLVEFAVEYFTRLREARA (SEQ ID NO: 17)

SHIQIPPGLTDLLQGYTVEVLRQQPPDLVEFAVEYFTRLREARA (SEQ ID NO: 18)

SHIQIPPGLTELLNGYTVEVLRQQPPDLVEFAVEYFTRLREARA (SEQ ID NO: 19)

SHIQIPPGLTELLQAYTVEVLRQQPPDLVEFAVEYFTRLREARA (SEQ ID NO: 20)

SHIQIPPGLTELLQGYSVEVLRQQPPDLVEFAVEYFTRLREARA (SEQ ID NO: 21)

SHIQIPPGLTELLQGYTVDVLRQQPPDLVEFAVEYFTRLREARA (SEQ ID NO: 22)

SHIQIPPGLTELLQGYTVEVLKQQPPDLVEFAVEYFTRLREARA (SEQ ID NO: 23)

SHIQIPPGLTELLQGYTVEVLRNQPPDLVEFAVEYFTRLREARA (SEQ ID NO: 24)

SHIQIPPGLTELLQGYTVEVLRQNPPDLVEFAVEYFTRLREARA (SEQ ID NO: 25)

SHIQIPPGLTELLQGYTVEVLRQQPPELVEFAVEYFTRLREARA (SEQ ID NO: 26)

SHIQIPPGLTELLQGYTVEVLRQQPPDLVDFAVEYFTRLREARA (SEQ ID NO: 27)

SHIQIPPGLTELLQGYTVEVLRQQPPDLVEFLVEYFTRLREARA (SEQ ID NO: 28)

SHIQIPPGLTELLQGYTVEVLRQQPPDLVEFIVEYFTRLREARA (SEQ ID NO: 29)

SHIQIPPGLTELLQGYTVEVLRQQPPDLVEFVVEYFTRLREARA (SEQ ID NO: 30)

SHIQIPPGLTELLQGYTVEVLRQQPPDLVEFAVDYFTRLREARA (SEQ ID NO: 31)

Alto et al. (2003, *Proc Natl Acad Sci USA* 100:4445-50) performed a bioinformatic analysis of the AD sequence of various AKAP proteins to design an RII selective AD sequence called AKAP-IS (SEQ ID NO:3), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:3 below. The skilled artisan will realize that in designing sequence variants of the AD sequence, one would desirably avoid changing any of the underlined residues, while conservative amino acid substitutions might be made for residues that are less critical for DDD binding. Table 3 shows potential conservative amino acid substitutions in the sequence of AKAP-IS (AD1, SEQ ID NO:3), similar to that shown for DDD1 (SEQ ID NO:1) in Table 2 above.

A limited number of such potential alternative AD moiety sequences are shown in SEQ ID NO:32 to SEQ ID NO:49 below. Again, a very large number of species within the genus of possible AD moiety sequences could be made, tested and used by the skilled artisan, based on the data of Alto et al. (2003). It is noted that FIG. 2 of Alto (2003) shows an even large number of potential amino acid substitutions that may be made, while retaining binding activity to DDD moieties, based on actual binding experiments.

(AKAP-IS)

(SEQ ID NO: 3)

QIEYLAKQIVDNAIQQA

TABLE 3

Conservative Amio Acid Substitutions in AD1 (SEQ ID NO: 3). Consensus sequence disclosed as SEQ ID NO: 88.

| Q | I | E | Y | L | A | K | Q | I | V | D | N | A | I | Q | Q | A |
|---|---|---|---|---|---|---|---|---|---|---|---|---|---|---|---|---|
| N | L<br>V | D | F<br>T<br>S | I<br>V | | R | N | | | E | Q | | | N | N | L<br>I<br>V |

NIEYLAKQIVDNAIQQA (SEQ ID NO: 32)

QLEYLAKQIVDNAIQQA (SEQ ID NO: 33)

QVEYLAKQIVDNAIQQA (SEQ ID NO: 34)

QIDYLAKQIVDNAIQQA (SEQ ID NO: 35)

QIEFLAKQIVDNAIQQA (SEQ ID NO: 36)

QIETLAKQIVDNAIQQA (SEQ ID NO: 37)

QIESLAKQIVDNAIQQA (SEQ ID NO: 38)

QIEYIAKQIVDNAIQQA (SEQ ID NO: 39)

QIEYVAKQIVDNAIQQA (SEQ ID NO: 40)

QIEYLARQIVDNAIQQA (SEQ ID NO: 41)

QIEYLAKNIVDNAIQQA (SEQ ID NO: 42)

QIEYLAKQIVENAIQQA (SEQ ID NO: 43)

QIEYLAKQIVDQAIQQA (SEQ ID NO: 44)

QIEYLAKQIVDNAINQA (SEQ ID NO: 45)

QIEYLAKQIVDNAIQNA (SEQ ID NO: 46)

QIEYLAKQIVDNAIQQL (SEQ ID NO: 47)

QIEYLAKQIVDNAIQQI (SEQ ID NO: 48)

QIEYLAKQIVDNAIQQV (SEQ ID NO: 49)

Gold et al. (2006, *Mol Cell* 24:383-95) utilized crystallography and peptide screening to develop a SuperAKAP-IS sequence (SEQ ID NO:50), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL™ constructs. Other alternative sequences that might be substituted for the AKAP-IS AD sequence are shown in SEQ ID NO:51-53. Substitutions relative to the AKAP-IS sequence are underlined. It is anticipated that, as with the AD2 sequence shown in SEQ ID NO:4, the AD moiety may also include the additional N-terminal residues cysteine and glycine and C-terminal residues glycine and cysteine.

SuperAKAP-IS (SEQ ID NO: 50)

QIEYVAKQIVDYAIHQA

-continued

Alternative AKAP sequences (SEQ ID NO: 51)

QIEYKAKQIVDHAIHQA (SEQ ID NO: 52)

QIEYHAKQIVDHAIHQA (SEQ ID NO: 53)

QIEYVAKQIVDHAIHQA

Figure 2:
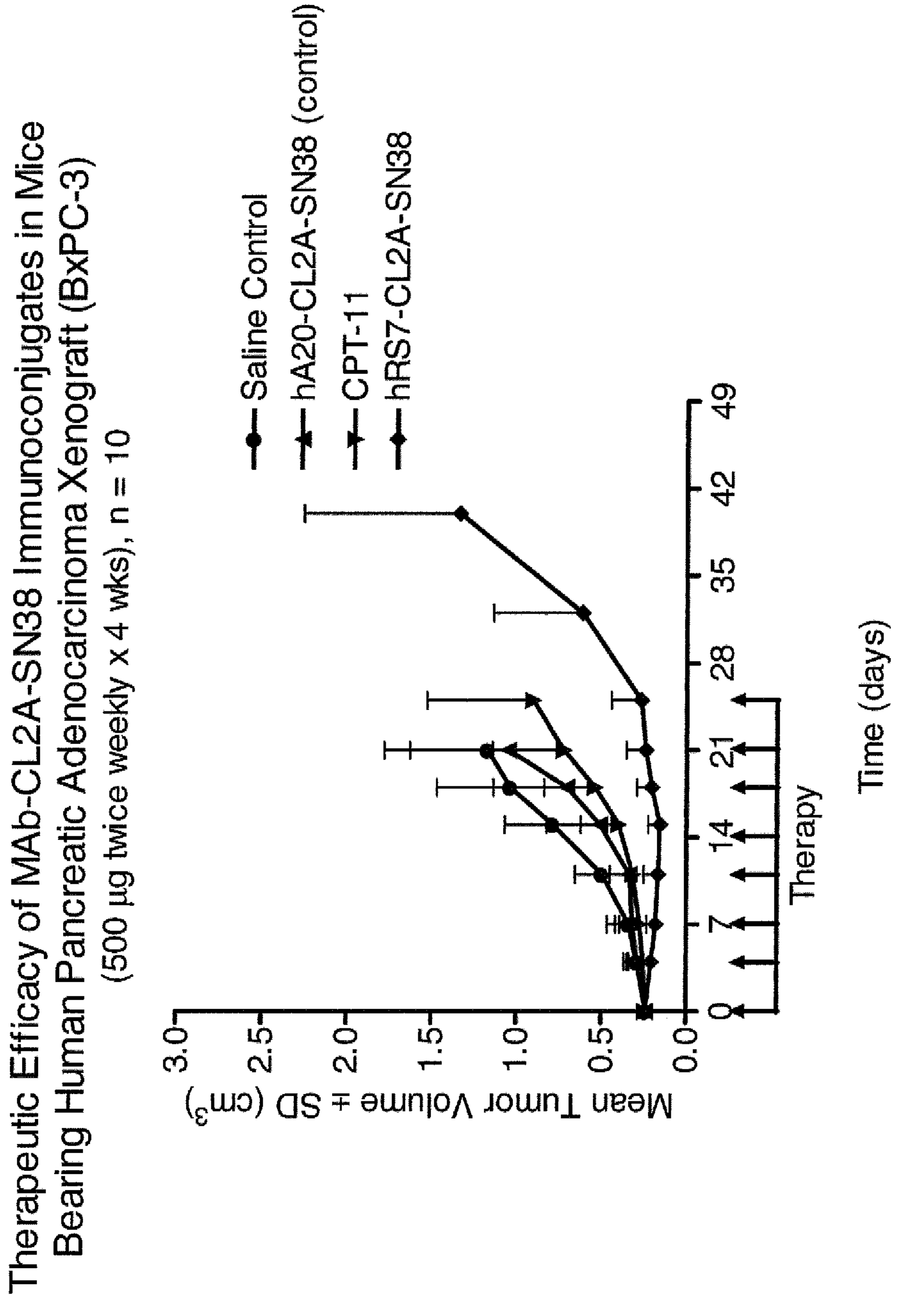
FIG. 2. In vivo therapy of athymic nude mice, bearing BxPC3 human pancreatic carcinoma, with MAb-CL2A-SN-38 conjugates.

FIG. 2 of Gold et al. disclosed additional DDD-binding sequences from a variety of AKAP proteins, shown below.

RII-Specific AKAPs

AKAP-KL (SEQ ID NO: 54)

PLEYQAGLLVQNAIQQAI

AKAP79

(SEQ ID NO: 55)

LLIETASSLVKNAIQLSI

AKAP-Lbc (SEQ ID NO: 56)

LIEEAASRIVDAVIEQVK

-continued

RI-Specific AKAPs

AKAPce
(SEQ ID NO: 57)
ALYQFADRFSELVISEAL

RIAD
(SEQ ID NO: 58)
LEQVANQLADQIIKEAT

PV38
(SEQ ID NO: 59)
FEELAWKIAKMIWSDVF

Dual-Specificity AKAPs

AKAP7
(SEQ ID NO: 60)
ELVRLSKRLVENAVLKAV

MAP2D
(SEQ ID NO: 61)
TAEEVSARIVQVVTAEAV

DAKAP1
(SEQ ID NO: 62)
QIKQAAFQLISQVILEAT

DAKAP2
(SEQ ID NO: 63)
LAWKIAKMIVSDVMQQ

Stokka et al. (2006, *Biochem J* 400:493-99) also developed peptide competitors of AKAP binding to PKA, shown in SEQ ID NO:64-66. The peptide antagonists were designated as Ht31 (SEQ ID NO:64), RIAD (SEQ ID NO:65) and PV-38 (SEQ ID NO:66). The Ht-31 peptide exhibited a greater affinity for the RII isoform of PKA, while the RIAD and PV-38 showed higher affinity for RI.

Ht31
(SEQ ID NO: 64)
DLIEEAASRIVDAVIEQVKAAGAY

RIAD
(SEQ ID NO: 65)
LEQYANQLADQIIKEATE

PV-38
(SEQ ID NO: 66)
FEELAWKIAKMIWSDVFQQC

Hundsrucker et al. (2006, *Biochem J* 396:297-306) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 4 below. AKAPIS represents a synthetic RII subunit-binding peptide. All other peptides are derived from the RII-binding domains of the indicated AKAPs.

TABLE 4

AKAP Peptide sequences

| | Peptide Sequence |
|---|---|
| AKAPIS | QIEYLAKQIVDNAIQQA (SEQ ID NO: 3) |
| AKAPIS-P | QIEYLAKQIPDNAIQQA (SEQ ID NO: 67) |
| Ht31 | KGADLIEEAASRIVDAVIEQVKAAG (SEQ ID NO: 68) |
| Ht31-P | KGADLIEEAASRIPDAPIEQVKAAG (SEQ ID NO: 69) |
| AKAP7δ-wt-pep | PEDAELVRLSKRLVENAVLKAVQQY (SEQ ID NO: 70) |
| AKAP7δ-L304T-pep | PEDAELVRTSKRLVENAVLKAVQQY (SEQ ID NO: 71) |
| AKAP7δ-L308D-pep | PEDAELVRLSKRDVENAVLKAVQQY (SEQ ID NO: 72) |
| AKAP7δ-P-pep | PEDAELVRLSKRLPENAVLKAVQQY (SEQ ID NO: 73) |
| AKAP7δ-PP-pep | PEDAELVRLSKRLPENAPLKAVQQY (SEQ ID NO: 74) |
| AKAP7δ-L314E-pep | PEDAELVRLSKRLVENAVEKAVQQY (SEQ ID NO: 75) |
| AKAP1-pep | EEGLDRNEEIKRAAFQIISQVISEA (SEQ ID NO: 76) |
| AKAP2-pep | LVDDPLEYQAGLLVQNAIQQAIAEQ (SEQ ID NO: 77) |
| AKAP5-pep | QYETLLIETASSLVKNAIQLSIEQL (SEQ ID NO: 78) |
| AKAP9-pep | LEKQYQEQLEEEVAKVIVSMSIAFA (SEQ ID NO: 79) |
| AKAP10-pep | NTDEAQEELAWKIAKMIVSDIMQQA (SEQ ID NO: 80) |
| AKAP11-pep | VNLDKKAVLAEKIVAEAIEKAEREL (SEQ ID NO: 81) |
| AKAP12-pep | NGILELETKSSKLVQNIIQTAVDQF (SEQ ID NO: 82) |
| AKAP14-pep | TQDKNYEDELTQVALALVEDVINYA (SEQ ID NO: 83) |
| Rab32-pep | ETSAKDNINIEEAARFLVEKILVNH (SEQ ID NO: 84) |

Residues that were highly conserved among the AD domains of different AKAP proteins are indicated below by underlining with reference to the AKAP IS sequence (SEQ ID NO:3). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

AKAP-IS
(SEQ ID NO: 3)
QIEYLAKQIVDNAIQQA

Carr et al. (2001, *J Biol Chem* 276:17332-38) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:1. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

(SEQ ID NO: 1)
SHIQIPPGLTELLQGYTVEVLRQQPPDLVEFAVEYFTRLREARA

A modified set of conservative amino acid substitutions for the DDD1 (SEQ ID NO:1) sequence, based on the data of Carr et al. (2001) is shown in Table 5. Even with this reduced set of substituted sequences, there are numerous possible alternative DDD moiety sequences that may be produced, tested and used by the skilled artisan without undue experimentation. The skilled artisan could readily derive such alternative DDD amino acid sequences as disclosed above for Table 2 and Table 3.

TABLE 5

Conservative Amino Acid Substitutions in DDD1 (SEQ ID NO: 1). Consensus sequence disclosed as SEQ ID NO: 89.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T | | | N | | | | | | S | | | | | | | | I<br>L<br>A | | | | |
| **Q** | **Q** | **P** | **P** | **D** | **L** | **V** | **E** | **F** | **A** | **V** | **E** | **Y** | **F** | **T** | **R** | **L** | **R** | **E** | **A** | **R** | **A** |
| N | | | | | | | | | | I<br>L<br>A | D | | | S | K | | K | | L<br>I<br>V | | L<br>I<br>V |

The skilled artisan will realize that these and other amino acid substitutions in the DDD or AD amino acid sequences may be utilized to produce alternative species within the genus of AD or DDD moieties, using techniques that are standard in the field and only routine experimentation.

Antibody Allotypes

Immunogenicity of therapeutic antibodies is associated with increased risk of infusion reactions and decreased duration of therapeutic response (Baert et al., 2003, *N Engl J Med* 348:602-08). The extent to which therapeutic antibodies induce an immune response in the host may be determined in part by the allotype of the antibody (Stickler et al., 2011, *Genes and Immunity* 12:213-21). Antibody allotype is related to amino acid sequence variations at specific locations in the constant region sequences of the antibody. The allotypes of IgG antibodies containing a heavy chain γ-type constant region are designated as Gm allotypes (1976, *J Immunol* 117:1056-59).

For the common IgG1 human antibodies, the most prevalent allotype is G1m1 (Stickler et al., 2011, *Genes and Immunity* 12:213-21). However, the G1m3 allotype also occurs frequently in Caucasians (Id.). It has been reported that G1m1 antibodies contain allotypic sequences that tend to induce an immune response when administered to non-G1m1 (nG1m1) recipients, such as G1m3 patients (Id.). Non-G1m1 allotype antibodies are not as immunogenic when administered to G1m1 patients (Id.).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown for the exemplary antibodies rituximab (SEQ ID NO:85) and veltuzumab (SEQ ID NO:86).

Rituximab heavy chain variable region sequence
(SEQ ID NO: 85)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKAEPKSCDKTHTCPPCPAPELLGG

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFFLYSKLTVDK

SRWQQGNVFSCSVMHEALHNHYTQKSLSLSPGK

Veltuzumab heavy chain variable region
(SEQ ID NO: 86)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKRVEPKSCDKTHTCPPCPAPELLGG

-continued

```
PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

EEMTKNQVSLTCLVKGFYPSDIAVEWESNGQPENNYKTTPPVLDSDGSFFLYSKLTVDK

SRWQQGNVFSCSVMHEALHNHYTQKSLSLSPGK
```

Jefferis and Lefranc (2009, *mAbs* 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotype characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies. Table 6 compares the allotype sequences of rituximab vs. veltuzumab. As shown in Table 6, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, *J Clin Oncol* 27:3346-53; Goldenberg et al., 2009, *Blood* 113:1062-70; Robak & Robak, 2011, *BioDrugs* 25:13-25), an effect that has been attributed to the difference between humanized and chimeric antibodies. However, the difference in allotypes between the EEM and DEL allotypes likely also accounts for the lower immunogenicity of veltuzumab.

TABLE 6

Allotypes of Rituximab vs. Veltuzumab

| | | Heavy chain position and associated allotypes | | | | | |
|---|---|---|---|---|---|---|---|
| | Complete allotype | 214 (allotype) | | 356/358 (allotype) | | 431 (allotype) | |
| Rituximab | G1m17, 1 | K | 17 | D/L | 1 | A | — |
| Veltuzumab | G1m3 | R | 3 | E/M | — | A | — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Amino Acid Substitutions

In alternative embodiments, the disclosed methods and compositions may involve production and use of proteins or peptides with one or more substituted amino acid residues. For example, the DDD and/or AD sequences used to make DNL™ constructs may be modified as discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, *J. Mol. Biol.*, 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, *Biochemistry,* 13:222-245; 1978, *Ann. Rev. Biochem.,* 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Avimers

In certain embodiments, the binding moieties described herein may comprise one or more avimer sequences. Avimers are a class of binding proteins somewhat similar to antibodies in their affinities and specificities for various target molecules. They were developed from human extracellular receptor domains by in vitro exon shuffling and phage display. (Silverman et al., 2005, *Nat. Biotechnol.* 23:1493-94; Silverman et al., 2006, *Nat. Biotechnol.* 24:220). The resulting multidomain proteins may comprise multiple independent binding domains, that may exhibit improved affinity (in some cases sub-nanomolar) and specificity compared with single-epitope binding proteins. (Id.) In various embodiments, avimers may be attached to, for example, DDD and/or AD sequences for use in the claimed methods and compositions. Additional details concerning methods of construction and use of avimers are disclosed, for example, in U.S. Patent Application Publication Nos. 20040175756, 20050048512, 20050053973, 20050089932 and 20050221384, the Examples section of each of which is incorporated herein by reference.

Phage Display

Certain embodiments of the claimed compositions and/or methods may concern binding peptides and/or peptide mimetics of various target molecules, cells or tissues. Binding peptides may be identified by any method known in the art, including but not limiting to the phage display technique. Various methods of phage display and techniques for producing diverse populations of peptides are well known in the art. For example, U.S. Pat. Nos. 5,223,409; 5,622,699 and 6,068,829 disclose methods for preparing a phage library. The phage display technique involves genetically manipulating bacteriophage so that small peptides can be expressed on their surface (Smith and Scott, 1985, *Science* 228:1315-1317; Smith and Scott, 1993, *Meth. Enzymol.* 21:228-257). In addition to peptides, larger protein domains such as single-chain antibodies may also be displayed on the surface of phage particles (Arap et al., 1998, *Science* 279: 377-380).

Targeting amino acid sequences selective for a given organ, tissue, cell type or target molecule may be isolated by panning (Pasqualini and Ruoslahti, 1996, *Nature* 380:364-366; Pasqualini, 1999, *The Quart. J. Nucl. Med.* 43:159-162). In brief, a library of phage containing putative targeting peptides is administered to an intact organism or to isolated organs, tissues, cell types or target molecules and samples containing bound phage are collected. Phage that bind to a target may be eluted from a target organ, tissue, cell type or target molecule and then amplified by growing them in host bacteria.

In certain embodiments, the phage may be propagated in host bacteria between rounds of panning Rather than being lysed by the phage, the bacteria may instead secrete multiple copies of phage that display a particular insert. If desired, the amplified phage may be exposed to the target organs, tissues, cell types or target molecule again and collected for additional rounds of panning Multiple rounds of panning may be performed until a population of selective or specific binders is obtained. The amino acid sequence of the peptides may be determined by sequencing the DNA corresponding to the targeting peptide insert in the phage genome. The identified targeting peptide may then be produced as a synthetic peptide by standard protein chemistry techniques (Arap et al., 1998, Smith et al., 1985).

In some embodiments, a subtraction protocol may be used to further reduce background phage binding. The purpose of subtraction is to remove phage from the library that bind to targets other than the target of interest. In alternative embodiments, the phage library may be prescreened against a control cell, tissue or organ. For example, tumor-binding peptides may be identified after prescreening a library against a control normal cell line. After subtraction the library may be screened against the molecule, cell, tissue or organ of interest. Other methods of subtraction protocols are known and may be used in the practice of the claimed methods, for example as disclosed in U.S. Pat. Nos. 5,840,841, 5,705,610, 5,670,312 and 5,492,807.

Aptamers

In certain embodiments, a targeting moiety of use may be an aptamer. Methods of constructing and determining the binding characteristics of aptamers are well known in the art. For example, such techniques are described in U.S. Pat. Nos. 5,582,981, 5,595,877 and 5,637,459, the Examples section of each incorporated herein by reference. Methods for preparation and screening of aptamers that bind to particular targets of interest are well known, for example U.S. Pat.

Nos. 5,475,096 and 5,270,163, the Examples section of each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, $P(O)NR_2$, P(O)R, P(O)OR', CO, or $CNR_2$, wherein R is H or alkyl (1-20C) and R' is alkyl (1-20C); in addition, this group may be attached to adjacent nucleotides through O or S. Not all linkages in an oligomer need to be identical.

Affibodies and Fynomers

Certain alternative embodiments may utilize affibodies in place of antibodies. Affibodies are commercially available from Affibody AB (Solna, Sweden). Affibodies are small proteins that function as antibody mimetics and are of use in binding target molecules. Affibodies were developed by combinatorial engineering on an alpha helical protein scaffold (Nord et al., 1995, *Protein Eng* 8:601-8; Nord et al., 1997, *Nat Biotechnol* 15:772-77). The affibody design is based on a three helix bundle structure comprising the IgG binding domain of protein A (Nord et al., 1995; 1997). Affibodies with a wide range of binding affinities may be produced by randomization of thirteen amino acids involved in the Fc binding activity of the bacterial protein A (Nord et al., 1995; 1997). After randomization, the PCR amplified library was cloned into a phagemid vector for screening by phage display of the mutant proteins. The phage display library may be screened against any known antigen, using standard phage display screening techniques (e.g., Pasqualini and Ruoslahti, 1996, *Nature* 380:364-366; Pasqualini, 1999, *Quart. J. Nucl. Med.* 43:159-162), in order to identify one or more affibodies against the target antigen.

A $^{177}$Lu-labeled affibody specific for HER2/neu has been demonstrated to target HER2-expressing xenografts in vivo (Tolmachev et al., 2007, *Cancer Res* 67:2773-82). Although renal toxicity due to accumulation of the low molecular weight radiolabeled compound was initially a problem, reversible binding to albumin reduced renal accumulation, enabling radionuclide-based therapy with labeled affibody (Id.).

The feasibility of using radiolabeled affibodies for in vivo tumor imaging has been recently demonstrated (Tolmachev et al., 2011, *Bioconjugate Chem* 22:894-902). A maleimide-derivatized NOTA was conjugated to the anti-HER2 affibody and radiolabeled with $^{111}$In (Id.). Administration to mice bearing the HER2-expressing DU-145 xenograft, followed by gamma camera imaging, allowed visualization of the xenograft (Id.).

Fynomers can also bind to target antigens with a similar affinity and specificity to antibodies. Fynomers are based on the human Fyn SH3 domain as a scaffold for assembly of binding molecules. The Fyn SH3 domain is a fully human, 63 amino acid protein that can be produced in bacteria with high yields. Fynomers may be linked together to yield a multispecific binding protein with affinities for two or more different antigen targets. Fynomers are commercially available from COVAGEN AG (Zurich, Switzerland).

The skilled artisan will realize that affibodies or fynomers may be used as targeting molecules in the practice of the claimed methods and compositions.

Conjugation Protocols

The preferred conjugation protocol is based on a thiol-maleimide, a thiol-vinylsulfone, a thiol-bromoacetamide, or a thiol-iodoacetamide reaction that is facile at neutral or acidic pH. This obviates the need for higher pH conditions for conjugations as, for instance, would be necessitated when using active esters. Further details of exemplary conjugation protocols are described below in the Examples section.

Therapeutic Treatment

In another aspect, the invention relates to a method of treating a subject, comprising administering a therapeutically effective amount of a therapeutic conjugate as described herein to a subject. Diseases that may be treated with the therapeutic conjugates described herein include, but are not limited to B-cell malignancies (e.g., non-Hodgkin's lymphoma, mantle cell lymphoma, multiple myeloma, Hodgkin's lymphoma, diffuse large B cell lymphoma, Burkitt lymphoma, follicular lymphoma, acute lymphocytic leukemia, chronic lymphocytic leukemia, hairy cell leukemia) using, for example an anti-CD22 antibody such as the hLL2 MAb (epratuzumab, see U.S. Pat. No. 6,183,744), against another CD22 epitope (hRFB4) or antibodies against other B cell antigens, such as CD19, CD20, CD21, CD22, CD23, CD37, CD40, CD40L, CD52, CD74, CD80 or HLA-DR. Other diseases include, but are not limited to, adenocarcinomas of endodermally-derived digestive system epithelia, cancers such as breast cancer and non-small cell lung cancer, and other carcinomas, sarcomas, glial tumors, myeloid leukemias, etc. In particular, antibodies against an antigen, e.g., an oncofetal antigen, produced by or associated with a malignant solid tumor or hematopoietic neoplasm, e.g., a gastrointestinal, stomach, colon, esophageal, liver, lung, breast, pancreatic, liver, prostate, ovarian, testicular, brain, bone or lymphatic tumor, a sarcoma or a melanoma, are advantageously used. Such therapeutics can be given once or repeatedly, depending on the disease state and tolerability of the conjugate, and can also be used optionally in combination with other therapeutic modalities, such as surgery, external radiation, radioimmunotherapy, immunotherapy, chemotherapy, antisense therapy, interference RNA therapy, gene therapy, and the like. Each combination will be adapted to the tumor type, stage, patient condition and prior therapy, and other factors considered by the managing physician.

As used herein, the term "subject" refers to any animal (i.e., vertebrates and invertebrates) including, but not limited to mammals, including humans. It is not intended that the term be limited to a particular age or sex. Thus, adult and newborn subjects, as well as fetuses, whether male or female, are encompassed by the term. Doses given herein are for humans, but can be adjusted to the size of other mammals, as well as children, in accordance with weight or square meter size.

In a preferred embodiment, therapeutic conjugates comprising an anti-EGP-1 (anti-TROP-2) antibody such as the hRS7 MAb can be used to treat carcinomas such as carcinomas of the esophagus, pancreas, lung, stomach, colon and rectum, urinary bladder, breast, ovary, uterus, kidney and prostate, as disclosed in U.S. Pat. Nos. 7,238,785; 7,517,964 and 8,084,583, the Examples section of which is incorporated herein by reference. An hRS7 antibody is a humanized antibody that comprises light chain complementarity-determining region (CDR) sequences CDR1 (KASQDVSIAVA, SEQ ID NO:90); CDR2 (SASYRYT, SEQ ID NO:91); and CDR3 (QQHYITPLT, SEQ ID NO:92) and heavy chain CDR sequences CDR1 (NYGMN, SEQ ID NO:93); CDR2 (WINTYTGEPTYTDDFKG, SEQ ID NO:94) and CDR3 (GGFGSSYWYFDV, SEQ ID NO:95)

In another preferred embodiment, therapeutic conjugates comprising an anti-CEACAM5 antibody (e.g., hMN-14, labretuzumab) and/or an anti-CEACAM6 antibody (e.g., hMN-3 or hMN-15) may be used to treat any of a variety of cancers that express CEACAM5 and/or CEACAM6, as disclosed in U.S. Pat. Nos. 7,541,440; 7,951,369; 5,874,540; 6,676,924 and 8,267,865, the Examples section of each incorporated herein by reference. Solid tumors that may be treated using anti-CEACAM5, anti-CEACAM6, or a combination of the two include but are not limited to breast, lung, pancreatic, esophageal, medullary thyroid, ovarian, colon, rectum, urinary bladder, mouth and stomach cancers. A majority of carcinomas, including gastrointestinal, respiratory, genitourinary and breast cancers express CEACAM5 and may be treated with the subject immunoconjugates. An hMN-14 antibody is a humanized antibody that comprises light chain variable region CDR sequences CDR1 (KASQDVGTSVA; SEQ ID NO:96), CDR2 (WTSTRHT; SEQ ID NO:97), and CDR3 (QQYSLYRS; SEQ ID NO:98), and the heavy chain variable region CDR sequences CDR1 (TYWMS; SEQ ID NO:99), CDR2 (EIHPDSSTINYAPSLKD; SEQ ID NO:100) and CDR3 (LYFGFPWFAY; SEQ ID NO:101). An hMN-3 antibody is a humanized antibody that comprises light chain variable region CDR sequences CDR1 (RSSQSIVHSNGNTYLE, SEQ ID NO:102), CDR2 (KVSNRFS, SEQ ID NO:103) and CDR3 (FQGSHVPPT, SEQ ID NO:104) and the heavy chain CDR sequences CDR1 (NYGMN, SEQ ID NO:105), CDR2 (WINTYTGEPTYADDFKG, SEQ ID NO:106) and CDR3 (KGWMDFNSSLDY, SEQ ID NO:107). An hMN-15 antibody is a humanized antibody that comprises light chain variable region CDR sequences SASSRVSYIH (SEQ ID NO:108); GTSTLAS (SEQ ID NO:109); and QQWSYNPPT (SEQ ID NO:110); and heavy chain variable region CDR sequences DYYMS (SEQ ID NO:111); FIANKANGHTTDYSPSVKG (SEQ ID NO:112); and DMGIRWNFDV (SEQ ID NO:113).

In another preferred embodiment, therapeutic conjugates comprising an anti-CD74 antibody (e.g., hLL1, milatuzumab, disclosed in U.S. Pat. Nos. 7,074,403; 7,312,318; 7,772,373; 7,919,087 and 7,931,903, the Examples section of each incorporated herein by reference) may be used to treat any of a variety of cancers that express CD74, including but not limited to renal, lung, intestinal, stomach, breast, prostate or ovarian cancer, as well as several hematological cancers, such as multiple myeloma, chronic lymphocytic leukemia, acute lymphoblastic leukemia, non-Hodgkin lymphoma, and Hodgkin lymphoma. An hLL1 antibody is a humanized antibody comprising the light chain CDR sequences CDR1 (RSSQSLVHRNGNTYLH; SEQ ID NO:114), CDR2 (TVSNRFS; SEQ ID NO:115), and CDR3 (SQSSHVPPT; SEQ ID NO:116) and the heavy chain variable region CDR sequences CDR1 (NYGVN; SEQ ID NO:117), CDR2 (WINPNTGEPTFDDDFKG; SEQ ID NO:118), and CDR3 (SRGKNEAWFAY; SEQ ID NO:119).

In another preferred embodiment, therapeutic conjugates comprising an anti-CD22 antibody (e.g., hLL2, epratuzumab, disclosed in U.S. Pat. Nos. 5,789,554; 6,183,744; 6,187,287; 6,306,393; 7,074,403 and 7,641,901, the Examples section of each incorporated herein by reference, or the chimeric or humanized RFB4 antibody) may be used to treat any of a variety of cancers that express CD22, including but not limited to indolent forms of B-cell lymphomas, aggressive forms of B-cell lymphomas, chronic lymphatic leukemias, acute lymphatic leukemias, non-Hodgkin's lymphoma, Hodgkin's lymphoma, Burkitt lymphoma, follicular lymphoma or diffuse B-cell lymphoma. An hLL2 antibody is a humanized antibody comprising light chain CDR sequences CDR1 (KSSQSVLYSANHKYLA, SEQ ID NO:120), CDR2 (WASTRES, SEQ ID NO:121), and CDR3 (HQYLSSWTF, SEQ ID NO:122) and the heavy chain CDR sequences CDR1 (SYWLH, SEQ ID NO:123), CDR2 (YINPRNDYTEYNQNFKD, SEQ ID NO:124), and CDR3 (RDITTFY, SEQ ID NO:125)

In a preferred embodiment, therapeutic conjugates comprising anti-CSAp antibodies, such as the hMu-9 MAb, can be used to treat colorectal, as well as pancreatic and ovarian cancers as disclosed in U.S. Pat. Nos. 6,962,702; 7,387,772; 7,414,121; 7,553,953; 7,641,891 and 7,670,804, the Examples section of each incorporated herein by reference. In addition, therapeutic conjugates comprising the hPAM4 MAb can be used to treat pancreatic cancer or other solid tumors, as disclosed in U.S. Pat. Nos. 7,238,786 and 7,282,567, the Examples section of each incorporated herein by reference. An hMu-9 antibody is a humanized antibody comprising light chain CDR sequences CDR1 (RSSQSIVHSNGNTYLE, SEQ ID NO:126), CDR2 (KVSNRFS, SEQ ID NO:127), and CDR3 (FQGSRVPYT, SEQ ID NO:128), and heavy chain variable CDR sequences CDR1 (EYVIT, SEQ ID NO:129), CDR2 (EIYPGSGSTSYNEKFK, SEQ ID NO:130), and CDR3 (EDL, SEQ ID NO:131). An hPAM4 antibody is a humanized antibody comprising light chain variable region CDR sequencs CDR1 (SASSSVSSSYLY, SEQ ID NO:132); CDR2 (STSNLAS, SEQ ID NO:133); and CDR3 (HQWNRYPYT, SEQ ID NO:134); and heavy chain CDR sequences CDR1 (SYVLH, SEQ ID NO:135); CDR2 (YINPYNDGTQYNEKFKG, SEQ ID NO:136) and CDR3 (GFGGSYGFAY, SEQ ID NO:137).

In another preferred embodiment, therapeutic conjugates comprising an anti-AFP MAb, such as IMMU31, can be used to treat hepatocellular carcinoma, germ cell tumors, and other AFP-producing tumors using humanized, chimeric and human antibody forms, as disclosed in U.S. Pat. No. 7,300,655, the Examples section of which is incorporated herein by reference. An IMMU31 antibody is a humanized antibody comprising the heavy chain CDR sequences CDR1 (SYVIH, SEQ ID NO:138), CDR2 (YIHPYNGGTKYNEKFKG, SEQ ID NO:139) and CDR3 (SGGGDPFAY, SEQ ID NO:140) and the light chain CDR1 (KASQDINKYIG, SEQ ID NO:141), CDR2 (YTSALLP, SEQ ID NO:142) and CDR3 (LQYDDLWT, SEQ ID NO:143).

In another preferred embodiment, therapeutic conjugates comprising an anti-HLA-DR MAb, such as hL243, can be used to treat lymphoma, leukemia, cancers of the skin, esophagus, stomach, colon, rectum, pancreas, lung, breast, ovary, bladder, endometrium, cervix, testes, kidney, liver, melanoma or other HLA-DR-producing tumors, as disclosed in U.S. Pat. No. 7,612,180, the Examples section of which is incorporated herein by reference. An hL243 antibody is a humanized antibody comprising the heavy chain CDR sequences CDR1 (NYGMN, SEQ ID NO:144), CDR2 (WINTYTREPTYADDFKG, SEQ ID NO:145), and CDR3 (DITAVVPTGFDY, SEQ ID NO:146) and light chain CDR sequences CDR1 (RASENIYSNLA, SEQ ID NO:147), CDR2 (AASNLAD, SEQ ID NO:148), and CDR3 (QHFWTTPWA, SEQ ID NO:149).

In another preferred embodiment, therapeutic conjugates comprising an anti-CD20 MAb, such as veltuzumab (hA20), 1F5, obinutuzumab (GA101), or rituximab, can be used to treat lymphoma, leukemia, immune thrombocytopenic purpura, systemic lupus erythematosus, Sjögren's syndrome, Evans syndrome, arthritis, arteritis, pemphigus vulgaris, renal graft rejection, cardiac graft rejection, rheumatoid arthritis, Burkitt lymphoma, non-Hodgkin's lymphoma, follicular lymphoma, small lymphocytic lymphoma, diffuse B-cell lymphoma, marginal zone lymphoma, chronic lymphocytic leukemia, acute lymphocytic leukemia, Type I diabetes mellitus, GVHD, multiple sclerosis or multiple myeloma, as disclosed in U.S. Pat. Nos. 7,435,803 or 8,287,864, the Examples section of each incorporated herein by reference. An hA20 (veltuzumab) antibody is a humanized antibody comprising the light chain CDR sequences CDRL1 (RASSSVSYIH, SEQ ID NO:150), CDRL2 (ATSNLAS, SEQ ID NO:151) and CDRL3 (QQWTSNPPT, SEQ ID NO:152) and heavy chain CDR sequences CDRH1 (SYNMH, SEQ ID NO:153), CDRH2 (AIYPGNGDTSYNQKFKG, SEQ ID NO:154) and CDRH3 (STYYGGDWYFDV, SEQ ID NO:155).

In another preferred embodiment, therapeutic conjugates comprising an anti-CD19 MAb, such as hA19, can be used to treat B-cell related lymphomas and leukemias, such as non-Hodgkin's lymphoma, chronic lymphocytic leukemia or acute lymphoblastic leukemia. Other disease states that may be treated include autoimmune diseases, such as acute or chronic immune thrombocytopenia, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosurn, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis ubiterans, Sjögren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, and fibrosing alveolitis, as disclosed in U.S. Pat. Nos. 7,109,304, 7,462,352, 7,902,338, 8,147,831 and 8,337,840, the Examples section of each incorporated herein by reference. An hA19 antibody is a humanized antibody comprising the light chain CDR sequences CDR1 KASQSVDYDGDSYLN (SEQ ID NO: 156); CDR2 DASNLVS (SEQ ID NO: 157); and CDR3 QQSTEDPWT (SEQ ID NO: 158) and the heavy chain CDR sequences CDR1 SYWMN (SEQ ID NO: 159); CDR2 QIWPGDGDTNYNGKFKG (SEQ ID NO: 160) and CDR3 RETTTVGRYYYAMDY (SEQ ID NO: 161).

In another preferred embodiment, therapeutic conjugates comprising anti-tenascin antibodies can be used to treat hematopoietic and solid tumors, and conjugates comprising antibodies to tenascin can be used to treat solid tumors, preferably brain cancers like glioblastomas.

In a preferred embodiment, the antibodies that are used in the treatment of human disease are human or humanized (CDR-grafted) versions of antibodies; although murine and chimeric versions of antibodies can be used. Same species IgG molecules as delivery agents are mostly preferred to minimize immune responses. This is particularly important when considering repeat treatments. For humans, a human or humanized IgG antibody is less likely to generate an anti-IgG immune response from patients. Antibodies such as hLL1 and hLL2 rapidly internalize after binding to internalizing antigen on target cells, which means that the chemotherapeutic drug being carried is rapidly internalized into cells as well. However, antibodies that have slower rates of internalization can also be used to effect selective therapy.

In another preferred embodiment, the therapeutic conjugates can be used against pathogens, since antibodies against pathogens are known. For example, antibodies and antibody fragments which specifically bind markers produced by or associated with infectious lesions, including viral, bacterial, fungal and parasitic infections, for example caused by pathogens such as bacteria, rickettsia, mycoplasma, protozoa, fungi, and viruses, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444,744, 4,818,709 and 4,624,846, the Examples section of each incorporated herein by reference, and in Reichert and Dewitz, cited above. In a preferred embodiment, the pathogens are selected from the group consisting of HIV virus, *Mycobacterium tuberculosis, Streptococcus agalactiae*, methicillin-resistant *Staphylococcus aureus, Legionella pneumophilia, Streptococcus pyogenes, Escherichia coli, Neisseria gonorrhoeae, Neisseria meningitidis, Pneumococcus, Cryptococcus neoformans, Histoplasma capsulatum, Hemophilis influenzae* B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae*, as disclosed in U.S. Pat. No. 6,440,416, the Examples section of which is incorporated herein by reference.

In a more preferred embodiment, drug conjugates of the present invention comprising anti-gp120 and other such anti-HIV antibodies can be used as therapeutics for HIV in AIDS patients; and drug conjugates of antibodies to *Mycobacterium tuberculosis* are suitable as therapeutics for drug-refractive tuberculosis. Fusion proteins of anti-gp120 MAb (anti HIV MAb) and a toxin, such as *Pseudomonas* exotoxin, have been examined for antiviral properties (Van Oigen et al., *J Drug Target,* 5:75-91, 1998). Attempts at treating HIV infection in AIDS patients failed, possibly due to insufficient efficacy or unacceptable host toxicity. The drug conjugates of the present invention advantageously lack such toxic side effects of protein toxins, and are therefore advantageously used in treating HIV infection in AIDS patients. These drug conjugates can be given alone or in combination with other antibiotics or therapeutic agents that are effective in such patients when given alone. Candidate anti-HIV antibodies include the P4/D10 anti-envelope antibody described by Johansson et al. (AIDS. 2006 Oct. 3; 20(15):1911-5), as well as the anti-HIV antibodies described and sold by Polymun (Vienna, Austria), also described in U.S. Pat. Nos. 5,831, 034, 5,911,989, and Vcelar et al., AIDS 2007; 21(16):2161-2170 and Joos et al., *Antimicrob. Agents Chemother.* 2006; 50(5):1773-9, all incorporated herein by reference. A preferred targeting agent for HIV is various combinations of these antibodies in order to overcome resistance.

In a preferred embodiment, a more effective incorporation into cells and pathogens can be accomplished by using multivalent, multispecific or multivalent, monospecific antibodies. Examples of such bivalent and bispecific antibodies are found in U.S. Pat. Nos. 7,387,772; 7,300,655; 7,238,785; and 7,282,567, the Examples section of each of which is incorporated herein by reference. These multivalent or multispecific antibodies are particularly preferred in the targeting of cancers and infectious organisms (pathogens), which express multiple antigen targets and even multiple epitopes of the same antigen target, but which often evade antibody targeting and sufficient binding for immunotherapy because of insufficient expression or availability of a single antigen target on the cell or pathogen. By targeting multiple antigens or epitopes, said antibodies show a higher binding and residence time on the target, thus affording a higher saturation with the drug being targeted in this invention.

In another preferred embodiment, the therapeutic conjugates can be used to treat autoimmune disease or immune system dysfunction (e.g., graft-versus-host disease, organ transplant rejection). Antibodies of use to treat autoimmune/immune dysfunction disease may bind to exemplary antigens including, but not limited to, BCL-1, BCL-2, BCL-6, CD1a, CD2, CD3, CD4, CD5, CD7, CD8, CD10, CD11b, CD11c, CD13, CD14, CD15, CD16, CD19, CD20, CD21, CD22, CD23, CD25, CD33, CD34, CD38, CD40, CD40L, CD41a, CD43, CD45, CD55, CD56, CCD57, CD59, CD64, CD71, CD74, CD79a, CD79b, CD117, CD138, FMC-7 and HLA-DR. Antibodies that bind to these and other target antigens, discussed above, may be used to treat autoimmune or immune dysfunction diseases. Autoimmune diseases that may be treated with immunoconjugates may include acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, bullous pemphigoid, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis or fibrosing alveolitis.

In another preferred embodiment, a therapeutic agent used in combination with the camptothecin conjugate of this invention may comprise one or more isotopes. Radioactive isotopes useful for treating diseased tissue include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, $^{227}$Th and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Th-227 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

Radionuclides and other metals may be delivered, for example, using chelating groups attached to an antibody or conjugate. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates, such as macrocyclic polyethers for complexing $^{223}$Ra, may be used.

Therapeutic agents of use in combination with the camptothecin conjugates described herein also include, for example, chemotherapeutic drugs such as vinca alkaloids, anthracyclines, epidophyllotoxins, taxanes, antimetabolites, tyrosine kinase inhibitors, alkylating agents, antibiotics, Cox-2 inhibitors, antimitotics, antiangiogenic and proapoptotic agents, particularly doxorubicin, methotrexate, taxol, other camptothecins, and others from these and other classes of anticancer agents, and the like. Other cancer chemotherapeutic drugs include nitrogen mustards, alkyl sulfonates, nitrosoureas, triazenes, folic acid analogs, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Exemplary drugs of use include, but are not limited to, 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), transplatinum, thalidomide, thioguanine, thiotepa, teniposide, topotecan, uracil mustard, vatalanib, vinorelbine, vinblastine, vincristine, vinca alkaloids and ZD1839. Such agents may be part of the conjugates described herein or may alternatively be administered in combination with the described conjugates, either prior to, simultaneously with or after the conjugate. Alternatively, one or more therapeutic naked antibodies as are known in the art may be used in combination with the described conjugates. Exemplary therapeutic naked antibodies are described above.

Therapeutic agents that may be used in concert with the camptothecin conjugates also may comprise toxins conjugated to targeting moieties. Toxins that may be used in this regard include ricin, abrin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin. (See, e.g., Pastan. et al., *Cell* (1986), 47:641, and Sharkey and Goldenberg, *CA Cancer J Clin.* 2006 July-August; 56(4):226-43.) Additional toxins suitable for use herein are known to those of skill in the art and are disclosed in U.S. Pat. No. 6,077,499.

Yet another class of therapeutic agent may comprise one or more immunomodulators. Immunomodulators of use may be selected from a cytokine, a stem cell growth factor, a lymphotoxin, an hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β, -γ or -λ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and lymphotoxin (LT). As used herein, the term cytokine includes proteins from natural sources or from recombinant cell culture and biologically active equivalents of the native sequence cytokines.

Chemokines of use include RANTES, MCAF, MIP 1-alpha, MIP 1-Beta and IP-10.

The person of ordinary skill will realize that the subject immunoconjugates, comprising a camptothecin conjugated to an antibody or antibody fragment, may be used alone or in combination with one or more other therapeutic agents, such as a second antibody, second antibody fragment, second immunoconjugate, radionuclide, toxin, drug, chemotherapeutic agent, radiation therapy, chemokine, cytokine, immunomodulator, enzyme, hormone, oligonucleotide, RNAi or siRNA. Such additional therapeutic agents may be administered separately, in combination with, or attached to the subject antibody-drug immunoconjugates.

Formulation and Administration

Suitable routes of administration of the conjugates include, without limitation, oral, parenteral, subcutaneous, rectal, transmucosal, intestinal administration, intramuscular, intramedullary, intrathecal, direct intraventricular, intravenous, intravitreal, intraperitoneal, intranasal, or intraocular injections. The preferred routes of administration are parenteral. Alternatively, one may administer the compound in a local rather than systemic manner, for example, via injection of the compound directly into a solid tumor.

Immunoconjugates can be formulated according to known methods to prepare pharmaceutically useful compositions, whereby the immunoconjugate is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

In a preferred embodiment, the immunoconjugate is formulated in Good's biological buffer (pH 6-7), using a buffer selected from the group consisting of N-(2-acetamido)-2-aminoethanesulfonic acid (ACES); N-(2-acetamido)iminodiacetic acid (ADA); N,N-bis(2-hydroxyethyl)-2-aminoethanesulfonic acid (BES); 4-(2-hydroxyethyl)piperazine-1-ethanesulfonic acid (HEPES); 2-(N-morpholino) ethanesulfonic acid (MES); 3-(N-morpholino) propanesulfonic acid (MOPS); 3-(N-morpholinyl)-2-hydroxypropanesulfonic acid (MOPSO); and piperazine-N,N'-bis(2-ethanesulfonic acid) [Pipes]. More preferred buffers are MES or MOPS, preferably in the concentration range of 20 to 100 mM, more preferably about 25 mM. Most preferred is 25 mM MES, pH 6.5. The formulation may further comprise 25 mM trehalose and 0.01% v/v polysorbate 80 as excipients, with the final buffer concentration modified to 22.25 mM as a result of added excipients. The preferred method of storage is as a lyophilized formulation of the conjugates, stored in the temperature range of −20° C. to 2° C., with the most preferred storage at 2° C. to 8° C.

The immunoconjugate can be formulated for intravenous administration via, for example, bolus injection, slow infusion or continuous infusion. Preferably, the antibody of the present invention is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic conjugate. Control release preparations can be prepared through the use of polymers to complex or adsorb the immunoconjugate. For example, biocompatible polymers include matrices of poly (ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate from such a matrix depends upon the molecular weight of the immunoconjugate, the amount of immunoconjugate within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

Generally, the dosage of an administered immunoconjugate for humans will vary depending upon such factors as the patient's age, weight, height, sex, general medical condition and previous medical history. It may be desirable to provide the recipient with a dosage of immunoconjugate that is in the range of from about 1 mg/kg to 24 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m$^2$ for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy. Preferred dosages may include, but are not limited to, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 22 mg/kg and 24 mg/kg. Any amount in the range of 1 to 24 mg/kg may be used. The dosage is preferably administered multiple times, once or twice a week. A minimum dosage schedule of 4 weeks, more preferably 8 weeks, more preferably 16 weeks or longer may be used. The schedule of administration may comprise administration once or twice a week, on a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five week off; (vi) four weeks of therapy followed by one, two, three, four or five week off; (vii) five weeks of therapy followed by one, two, three, four or five week off; and (viii) monthly. The cycle may be repeated 4, 6, 8, 10, 12, 16 or 20 times or more.

Alternatively, an immunoconjugate may be administered as one dosage every 2 or 3 weeks, repeated for a total of at least 3 dosages. Or, twice per week for 4-6 weeks. If the dosage is lowered to approximately 200-300 mg/m$^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 12 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

In preferred embodiments, the immunoconjugates are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's macroglobulinemia, Wilms' tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias; e.g., acute lymphocytic leukemia, acute myelocytic leukemia [including myeloblastic, promyelocytic, myelomonocytic, monocytic, and erythroleukemia]) and chronic leukemias (e.g., chronic myelocytic [granulocytic] leukemia and chronic lymphocytic leukemia), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Autoimmune diseases that may be treated with immunoconjugates may include acute and chronic immune thrombocytopenias, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, poststreptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, bullous pemphigoid, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis or fibrosing alveolitis.

Kits

Various embodiments may concern kits containing components suitable for treating diseased tissue in a patient. Exemplary kits may contain at least one conjugated antibody or other targeting moiety as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

Various embodiments of the present invention are illustrated by the following examples, without limiting the scope thereof.

General

Abbreviations used below are: DCC, dicyclohexylcarbodiimide; NHS, N-hydroxysuccinimide, DMAP, 4-dimethylaminopyridine; EEDQ, 2-ethoxy-1-ethoxycarbonyl-1,2-dihydroquinoline; MMT, monomethoxytrityl; PABOH, p-aminobenzyl alcohol; PEG, polyethylene glycol; SMCC, succinimidyl 4-(N-maleimidomethyl)cyclohexane-1-carboxylate; TBAF, tetrabutylammonium fluoride; TBDMS, tert-butyldimethylsilyl chloride.

Chloroformates of hydroxy compounds in the following examples were prepared using triphosgene and DMAP according to the procedure described in Moon et al. (J. Medicinal Chem. 51:6916-6926, 2008). Extractive work-up refers to extraction with chloroform, dichloromethane or ethyl acetate, and washing optionally with saturated bicarbonate, water, and with saturated sodium chloride. Flash chromatography was done using 230-400 mesh silica gel and methanol-dichloromethane gradient, using up to 15% v/v methanol-dichloromethane, unless otherwise stated. Reverse phase HPLC was performed by Method A using a 7.8×300 mm C18 HPLC column, fitted with a precolumn filter, and using a solvent gradient of 100% solvent A to 100% solvent B in 10 minutes at a flow rate of 3 mL per minute and maintaining at 100% solvent B at a flow rate of 4.5 mL per minute for 5 or 10 minutes; or by Method B using a 4.6×30 mm Xbridge C18, 2.5 μm, column, fitted with a precolumn filter, using the solvent gradient of 100% solvent A to 100% of solvent B at a flow rate of 1.5 mL per minutes for 4 min and 100% of solvent B at a flow rate of 2 mL per minutes for 1 minutes. Solvent A was 0.3% aqueous ammonium acetate, pH 4.46 while solvent B was 9:1 acetonitrile-aqueous ammonium acetate (0.3%), pH 4.46. HPLC was monitored by a dual in-line absorbance detector set at 360 nm and 254 nm.

Example 1

Preparation of CL6-SN-38

CL6-SN-38 is represented in Scheme-1. Commercially available O-(2-azidoethyl)-O'—(N-diglycolyl-2-aminoethyl)heptaethyleneglycol ('PEG-$N_3$'; 227 mg) was activated with DCC (100 mg), NHS (56 mg), and a catalytic amount of DMAP in 10 mL of dichloromethane for 10 min. To this mixture was added L-valinol (46.3 mg), and the reaction mixture was stirred for 1 h at ambient temperature. Filtration, followed by solvent removal and flash chromatography yielded 214 mg of clear oily material. This intermediate (160 mg) was reacted with 10-O-BOC-SN-38-20-O-chloroformate, the latter generated from 10-O-BOC-SN-38 (123 mg) using triphosgene and DMAP. The coupling reaction was done in 4 mL of dichloromethane for 10 min, and the reaction mixture was purified by flash chromatography to obtain 130 mg (45% yield) of product as foamy material. HPLC: $t_R$ 11.80 min; electrospray mass spectrum: M+Na: m/z 1181.

The maleimide-containing acetylenic reagent, namely 4-(N-maleimidomethyl)-N-(2-propynyl)cyclohexane-1-carboxamide, required for click cycloaddition, was prepared by reacting 0.107 g of SMCC and 0.021 mL of propargylamine (0.018 g; 1.01 equiv.) in dichloromethane using 1.1 equiv. of diisopropylethylamine. After 1 h, the solvent was removed and the product was purified by flash chromatography to obtain 83 mg of the product (colorless powder). Electrospray mass spectrum showed peaks at m/e 275 (M+H) and a base peak at m/e 192 in the positive ion mode, consistent with the structure calculated for $C_{15}H_{18}N_2O_3$: 275.1390 (M+H), found: 275.1394 (exact mass).

The azido intermediate (126 mg) was dissolved in DMSO (1.5 mL) and water (0.4 mL), and reacted with 60 mg of 4-(N-maleimidomethyl)-N-(2-propynyl)cyclohexane-1-carboxamide and 15 mg of cuprous bromide and stirred for 30 min at ambient temperature. Flash chromatography, after work up of the reaction mixture, furnished 116 mg (75% yield) of the cycloaddition product. HPLC: $t_R$ 11.20 min; electrospray mass spectrum: M+H and M+Na at m/z 1433 and 1456, respectively. Finally, deprotection with a mixture of TFA (5 mL), dichloromethane (1 mL), anisole (0.1 mL) and water (0.05 mL), followed by precipitation with ether and subsequent flash chromatography yielded the product, CL6-SN-38, as a gummy material. HPLC: $t_R$ 9.98 min; electrospray mass spectrum: M+H and M−H (negative ion mode) at m/z 1333 and 1356, respectively.

Scheme-1
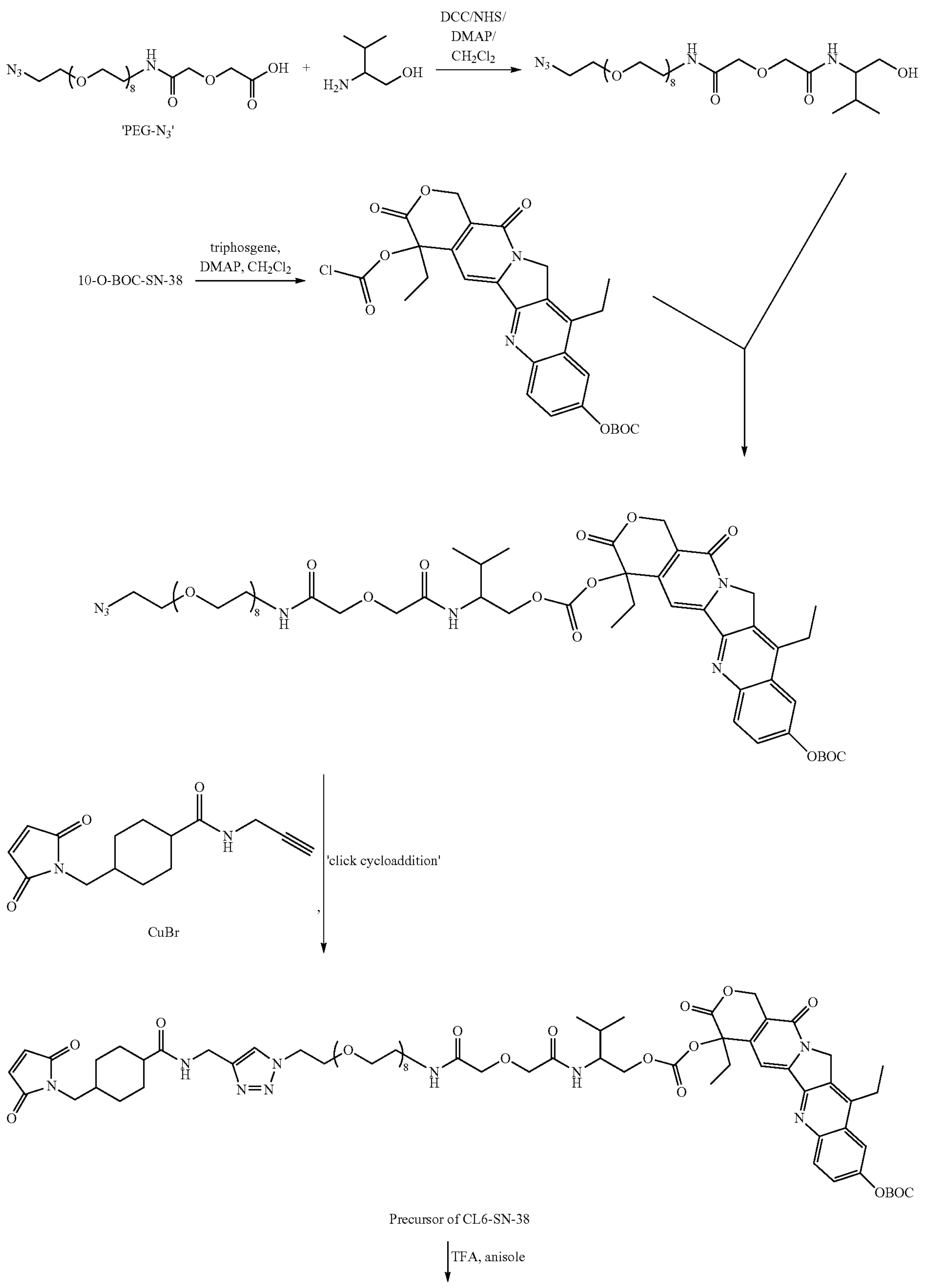

-continued

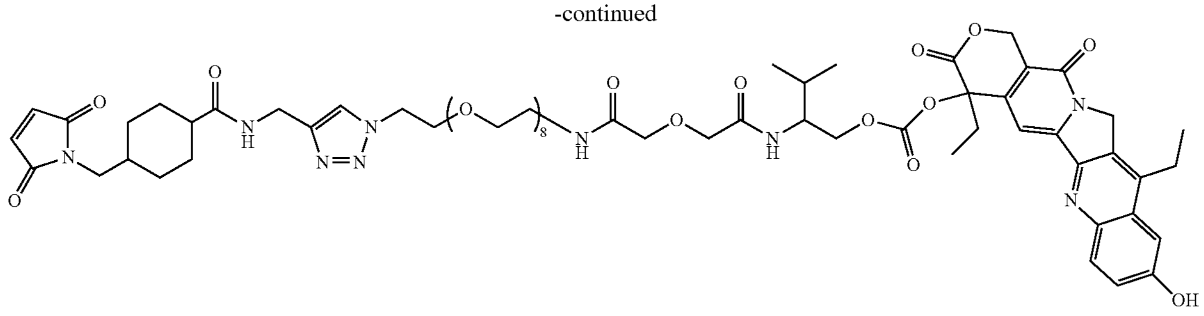

CL6-SN-38

Example 2

Preparation of CL7-SN-38

The synthesis is schematically shown in Scheme-2. L-Valinol (40 mg) was reacted with commercially available Fmoc-Lys(MMT)-OH (253 mg) and EEDQ (107 mg) in 10 mL of anhydrous dichloromethane at ambient temperature, under argon, for 3 h. Extractive work up followed by flash chromatography furnished the product Fmoc-Lys(MMT)-valinol as a pale yellow liquid (200 mg; ~70% yield). HPLC: $t_R$14.38 min; electrospray mass spectrum: M+H: m/z 727. This intermediate (200 mg) was deprotected with diethylamine (10 mL), and the product (135 mg) was obtained in ~90% purity after flash chromatography. HPLC: $t_R$ 10.91 min; electrospray mass spectrum: M+Na at m/z 527. This product (135 mg) was coupled with the commercially available O-(2-azidoethyl)-O'—(N-diglycolyl-2-aminoethyl) heptaethyleneglycol ('PEG-$N_3$'; 150 mg, 1.1 equiv.) in presence of EEDQ (72 mg, 1.1 equiv.) in 10 mL of dichloromethane, and stirred overnight at ambient temperature. The crude material was purified by flash chromatography to obtain 240 mg of the purified product as a light yellow oil (~87% yield). HPLC: $t_R$ 11.55 min; electrospray mass spectrum: M+H and M+Na at m/z 1041 and 1063, respectively.

This intermediate (240 mg) was reacted with 10-O-TBDMS-SN-38-20-O-chloroformate, the latter generated from 10-O-TBDMS-SN-38 (122 mg) using triphosgene and DMAP. The coupling reaction was done in 5 mL of dichloromethane for 10 min, and the reaction mixture was purified by flash chromatography to obtain 327 mg of product as pale yellow foam. Electrospray mass spectrum: M+H at m/z 1574. The entire product was reacted with 0.25 mmol of TBAF in 10 mL of dichloromethane for 5 min, and the reaction mixture was diluted to 100 mL and washed with brine.

Crude product (250 mg) was dissolved in DMSO (2 mL) and water (0.4 mL), and reacted with 114 mg of 4-(N-maleimidomethyl)-N-(2-propynyl)cyclohexane-1-carboxamide (prepared as described in Example 1) and 30 mg of cuprous bromide and stirred for 1 h at ambient temperature. Flash chromatography furnished 150 mg of the penultimate intermediate. Finally, deprotection of the MMT group with a mixture of TFA (0.5 mL) and anisole (0.05 mL) in dichloromethane (5 mL) for 3 min, followed by purification by flash chromatography yielded 69 mg of CL7-SN-38 as a gummy material. HPLC: $t_R$ 9.60 min; electrospray mass spectrum: M+H and M−H (negative ion mode) at m/z 1461 and 1459, respectively.

Scheme-2

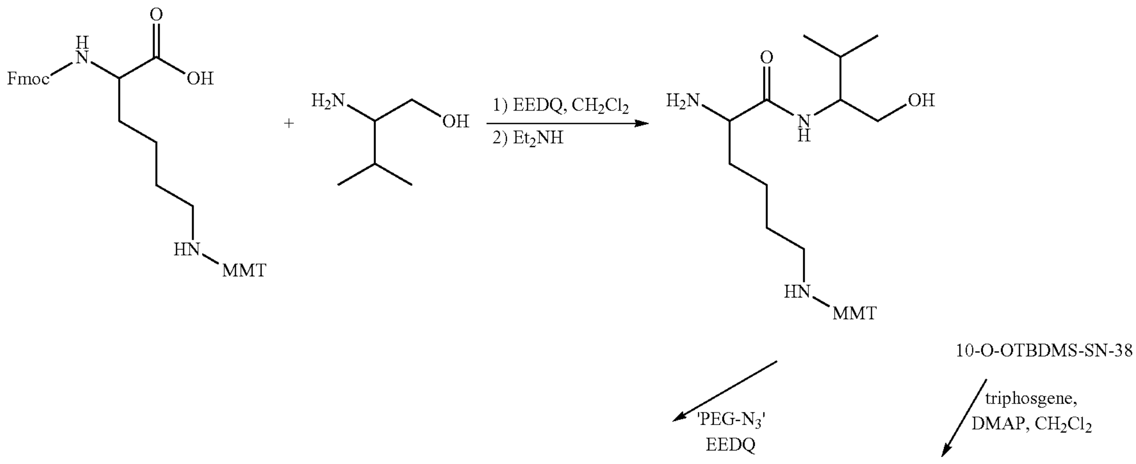

-continued
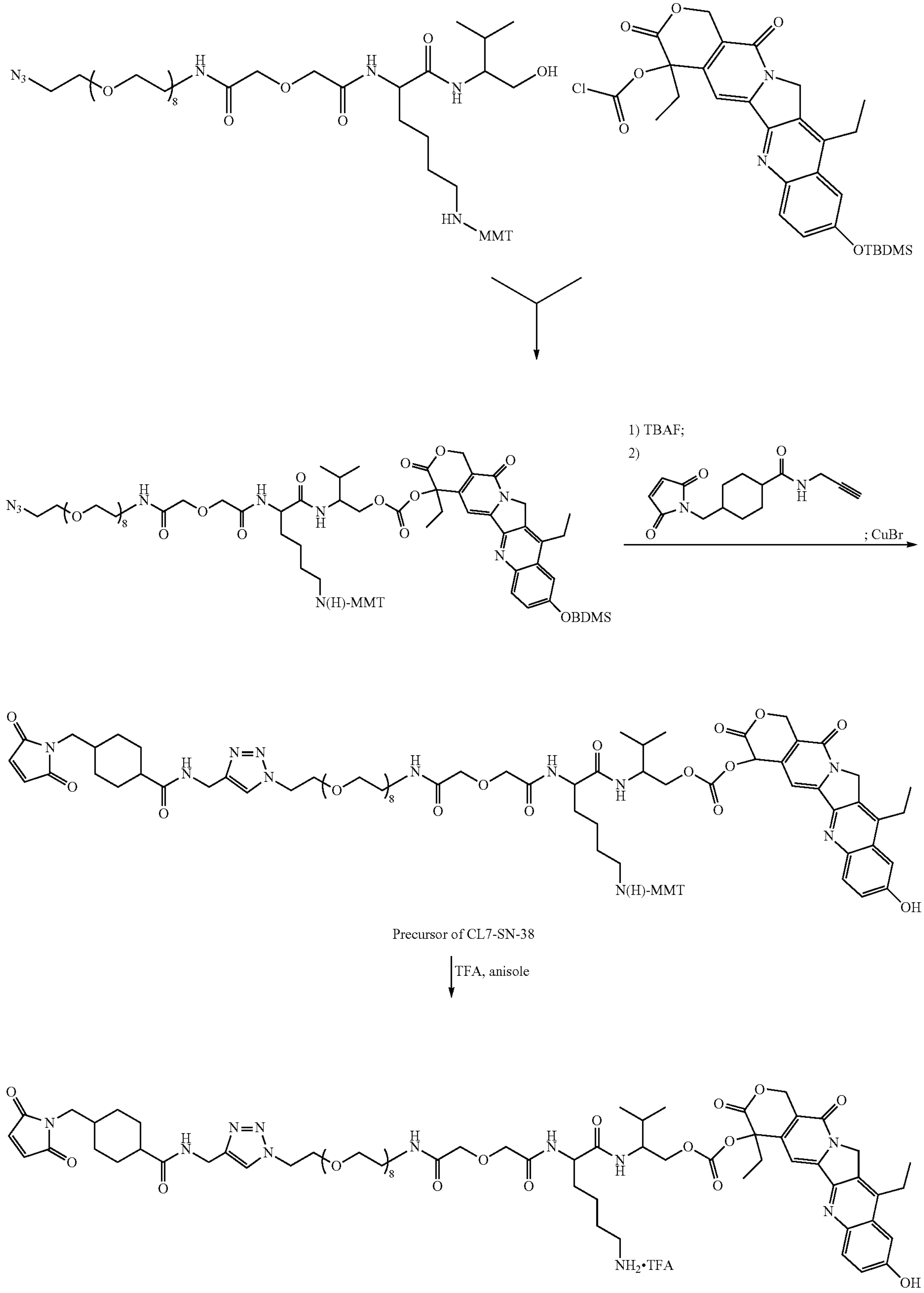
Precursor of CL7-SN-38
CL7-SN-38

Example 3

Preparation of CL6-SN-38-10-O—$CO_2$Et

The CL6-SN-38 of Example 1 (55.4 mg) was dissolved in dichloromethane (5 mL), and reacted with ethylchloroformate (13.1 mg; 11.5 μL) and diisopropylethylamine (52.5 mg; 71 μL), and stirred for 20 min under argon. The reaction mixture was diluted with 100 mL of dichloromethane, and washed with 100 mL each of 0.1 M HCl, half saturated sodium bicarbonate and brine, and dried. Flash chromatography, after solvent removal, furnished 59 mg of the title product. HPLC: $t_R$ 10.74 min; exact mass: calc. 1404.6457 (M+H) and 1426.6276 (M+Na); found: 1404.6464 (M+H) and 1426.6288 (M+Na).

Example 4

Preparation of CL7-SN-38-10-O—$CO_2$Et

The precursor of CL7-SN-38 of Example 2 (80 mg) was converted to the 10-O-chloroformate using the procedure and purification as described in Example 3. Yield: 60 mg. HPLC: $t_R$ 12.32 min; electrospray mass spectrum: M+H and M−H (negative ion mode) at m/z 1806 and 1804, respectively. Deprotection of this material using dichloroacetic acid and anisole in dichloromethane gave the title product. HPLC: $t_R$ 10.37 min; electrospray mass spectrum: M+H at m/z 1534.

Example 5

Preparations of CL6-SN-38-10-O—COR and CL7-SN-38-10-O—COR

This Example shows that the 10-OH group of SN-38 is protected as a carbonate or an ester, instead of as 'BOC', such that the final product is ready for conjugation to antibodies without need for deprotecting the 10-OH protecting group. This group is readily deprotected under physiological pH conditions after in vivo administration of the protein conjugate. In these conjugates, 'R' can be a substituted alkyl such as $(CH_2)_n$—$N(CH_3)_2$ where n is 2-10, or a simple alkyl such as $(CH_2)$n-$CH_3$ where n is 0-10, or it can be an alkoxy moiety such as "$CH_3$—$(CH_2)$n-O—" where n is 0-10, or a substituted alkoxy moiety such as such as O—$(CH_2)_n$—$N(CH_3)_2$ where n is 2-10 and wherein the terminal amino group is optionally in the form of a quaternary salt for enhanced aqueous solubility, or "$R_1$O—($CH_2$—$CH_2$—O$)_n$—$CH_2$—$CH_2$—O—" where $R_1$ is ethyl or methyl and n is an integer with values of 0-10. In the simplest version of the latter category, R="—O—$(CH_2)_2$—$OCH_3$". These 10-hydroxy derivatives are readily prepared by treatment with the chloroformate of the chosen reagent, if the final derivative is to be a carbonate. Typically, the 10-hydroxy-containing camptothecin such as SN-38 is treated with a molar equivalent of the chloroformate in dimethylformamide using triethylamine as the base. Under these conditions, the 20-OH position is unaffected. For forming 10-O-esters, the acid chloride of the chosen reagent is used. Such derivatizations are conveniently accomplished using advanced intermediates as illustrated for simple ethyl carbonates of Examples 3 and 4.

Example 6

Preparation of CL2A-SN-38

To the mixture of commercially available Fmoc-Lys (MMT)-OH (0.943 g), p-aminobenzyl alcohol (0.190 g) in methylene choloride (10 mL) was added EEDQ (0.382 g) at room temperature and stirred for 4 h. Extractive work up followed by flash chromatograph yielded 1.051 g of material as white foam. All HPLC analyses were performed by Method B as stated in 'General' section. HPLC ret. time: 3.53 min., Electrospray mass spectrum showed peaks at m/e 745.8 (M+H) and m/e 780.3 ($M+Cl^-$), consistent with structure. This intermediate (0.93 g) was dissolved in diethylamine (10 mL) and stirred for 2 h. After solvent removal, the residue was washed in hexane to obtain 0.6 g of the intermediate ((2) in Scheme-3) as colorless precipitate (91.6% pure by HPLC). HPLC ret. time: 2.06 min. Electrospray mass spectrum showed peaks at m/e 523.8 (M+H), m/e 546.2 (M+Na) and m/e 522.5 (M−H).

This crude intermediate (0.565 g) was coupled with commercially available O-(2-azidoethyl)-O'—(N-diglycolyl-2-aminoethyl)heptaethyleneglycol ('PEG-N3', 0.627 g) using EEDQ in methylene chloride (10 mL). Solvent removal and flash chromatography yielded 0.99 g of the product ((3) in Scheme-3; light yellow oil; 87% yield). HPLC ret. time: 2.45 min. Electrospray mass spectrum showed peaks at m/e 1061.3 (M+H), m/e 1082.7 (M+Na) and m/e 1058.8 (M−H), consistent with structure. This intermediate (0.92 g) was reacted with 10-O-TBDMS-SN-38-20-O-chloroformate ((5) in Scheme-3) in methylene chloride (10 mL) for 10 min under argon. The mixture was purified by flash chromatography to obtain 0.944 g as light yellow oil ((6) in Scheme-3; yield=68%). HPLC ret. time: 4.18 min. To this intermediate (0.94 g) in methylene chloride (10 mL) was added the mixture of TBAF (1M in THF, 0.885 mL) and acetic acid (0.085 mL) in methylene chloride (3 mL), then stirred for 10 min. The mixture was diluted with methylene chloride (100 mL), washed with 0.25 M sodium citrate and brine. The solvent removal yielded 0.835 g of yellow oily product. HPLC ret. time: 2.80 min., (99% purity). Electrospray mass spectrum showed peaks at m/e 1478 (M+H), m/e 1500.6 (M+Na), m/e 1476.5 (M−H), m/e 1590.5 (M+TFA), consistent with structure.

Scheme-3:
Preparartion of CL2A-SN-38
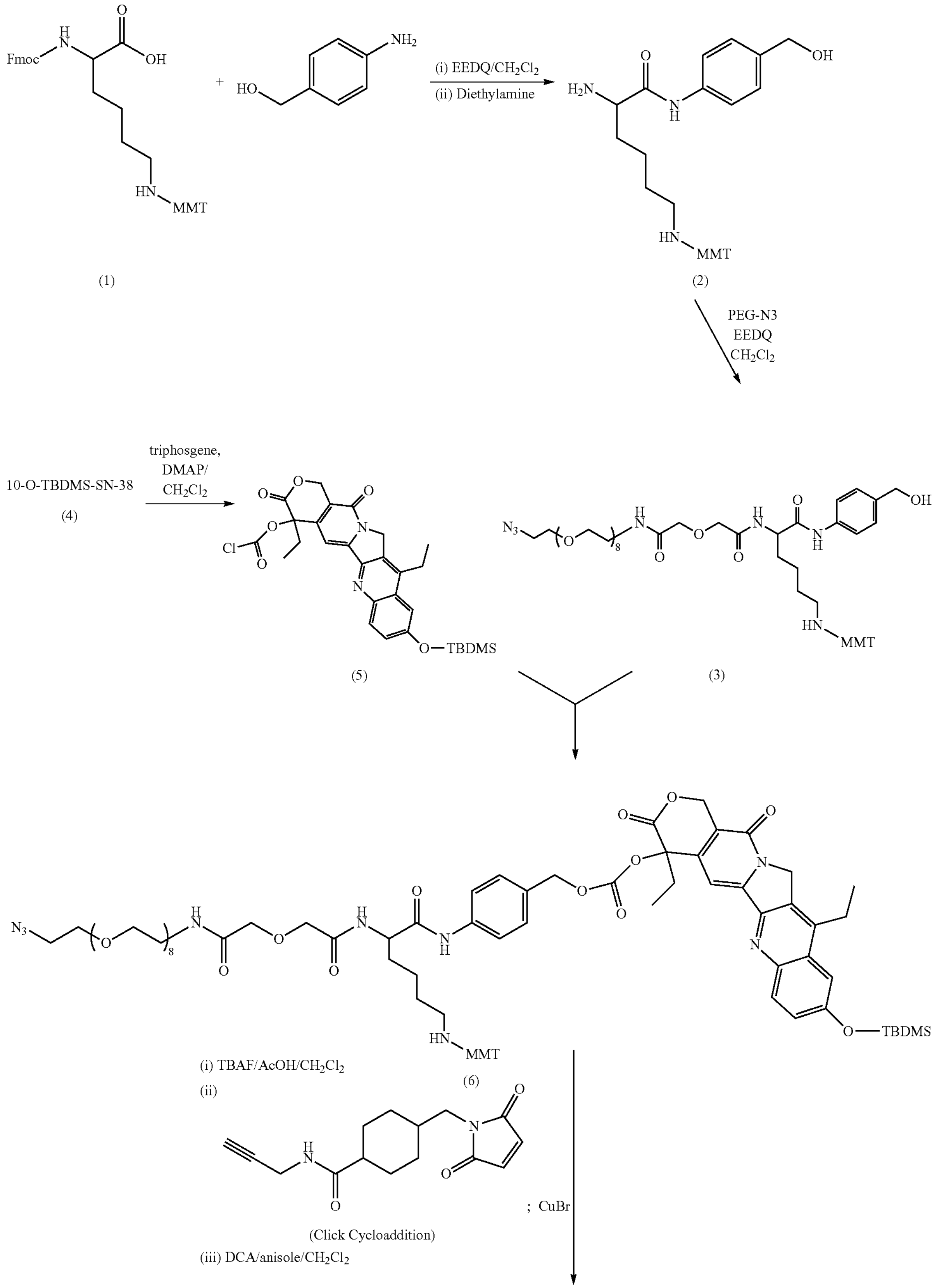
(1) (2) (3) (4) (5) (6)

-continued

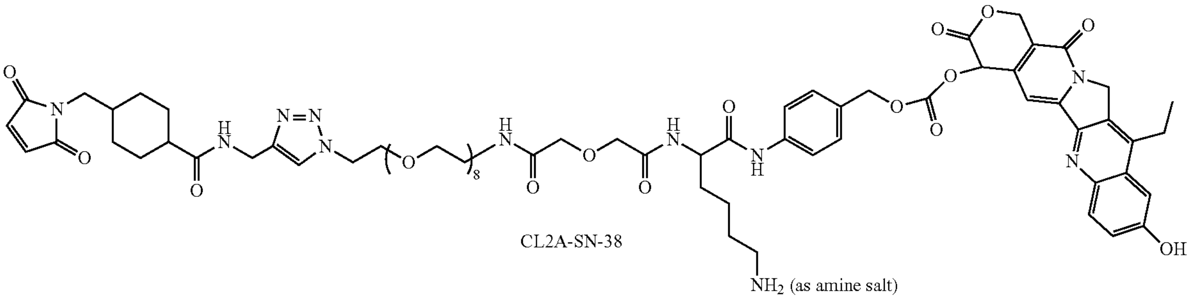

CL2A-SN-38

(7)

This azido-derivatized SN-38 intermediate (0.803 g) was reacted with 4-(N-maleimidomethyl)-N-(2-propynyl)cyclohexane-1-carboxamide (0.233 g) in methylene chloride (10 mL) in presence of CuBr (0.0083 g), DIEA (0.01 mL) and triphenylphosphine (0.015 g), for 18 h. Extractive work up, including washing with and 0.1 M EDTA (10 mL), and flash chromatography yielded 0.891 g as yellow foam. (yield=93%), HPLC ret. time: 2.60 min. Electrospray mass spectrum showed peaks at m/e 1753.3 (M+H), m/e 1751.6 (M−H), 1864.5 (M+TFA), consistent with structure. Finally, deprotection of the penultimate intermediate (0.22 g) with a mixture of dichloroacetic acid (0.3 mL) and anisole (0.03 mL) in methylene chloride (3 mL), followed by precipitation with ether yielded 0.18 g (97% yield) of CL2A-SN-38; (7) in Scheme-3) as light yellow powder. HPLC ret. time: 1.88 min. Electrospray mass spectrum showed peaks at m/e 1480.7 (M+H), 1478.5 (M−H), consistent with structure.

Example 7

Preparation of CL2E-SN-38

N,N'-dimethylethylenediamine (3 mL) in methylene chloride (50 mL) was reacted with monomethoxytrityl chloride (1.7 g). After 1 h of stirring, the solvent was removed under reduced pressure, and the crude product was recovered by extractive work up (yellow oil; 2.13 g). All HPLC analyses were performed by Method B as stated in ‘General’ section. HPLC ret. time: 2.28 min. This intermediate ((1) in Scheme-4; 0.93 g) was added in situ to activated SN-38, and the latter ((2) in Scheme-4) was prepared by reacting SN-38 (0.3 g) with p-nitrophenylchloroformate (0.185 g) and DIEA (0.293 mL) in DMF for 1 h. After removing solvent, the residue was purified on deactivated silica gel to obtain 0.442 g as white solid.

This intermediate (0.442 g) was deprotected with a mixture of trifluoroacetic acid (1 mL) and anisole (0.1 mL) in methylene chloride (5 mL), followed by precipitation with ether to obtain 0.197 g of the product ((3) in Scheme-4) as white solid. This intermediate ((3); 0.197 g) was coupled with activated azide-containing-dipeptide incorporated-PEG-linker ((5) in Scheme-4), which activation was done by reacting PEG-linker ((4) in Scheme-4; 0.203 g) with bis(4-nitrophenyl) carbonate (0.153 g) and DIEA (0.044 mL) in methylene chloride (8 mL). Flash chromatography yielded 0.2 g of azide-derivatized SN-38 intermediate product ((6) in Scheme-4) as glassy solid. HPLC ret. time: 2.8 min. Electrospray mass spectrum showed peaks at m/e 1740.5 (M+H), m/e 1762.9 (M+Na), m/e 1774.9 (M+Cl$^-$), consistent with structure. This intermediate ((6) in Scheme-4; 0.2 g) was subjected to click cycloaddition with 4-(N-maleimidomethyl)-N-(2-propynyl)cyclohexane-1-carboxamide (0.067 g) in methylene chloride in presence of CuBr (0.007 g), DIEA (0.008 mL) and triphenylphosphine (0.012 g) for 18 h. Work up of reaction mixture, which included treatment with 0.1M EDTA, followed by flash chromatography yielded 0.08 g of the penultimate intermediate as light yellow foam. HPLC: $t_R$=2.63 min. Electrospray mass spectrum showed peaks at m/e 2035.9 (M+Na$^+$), m/e 2047.9 (M+Cl$^-$), consistent with structure. Finally, deprotection of this intermediate (0.08 g) with a mixture of trifluoroacetic acid (0.2 mL), anisole (0.12 mL) and water (0.06 mL) in methylene chloride (2 mL), followed by precipitation with ether yielded 0.051 g of product, CL17-SN-38 (also referred to as CL2E-SN-38), as light yellow powder (yield=69%). HPLC ret. time: 1.95 min., ~99% purity. Electrospray mass spectrum showed peaks at m/e 1741.1 (M+H), 1775.5 (M+Cl$^-$), consistent with structure.

Scheme-4:
Prepararation of CL2E-SN-38

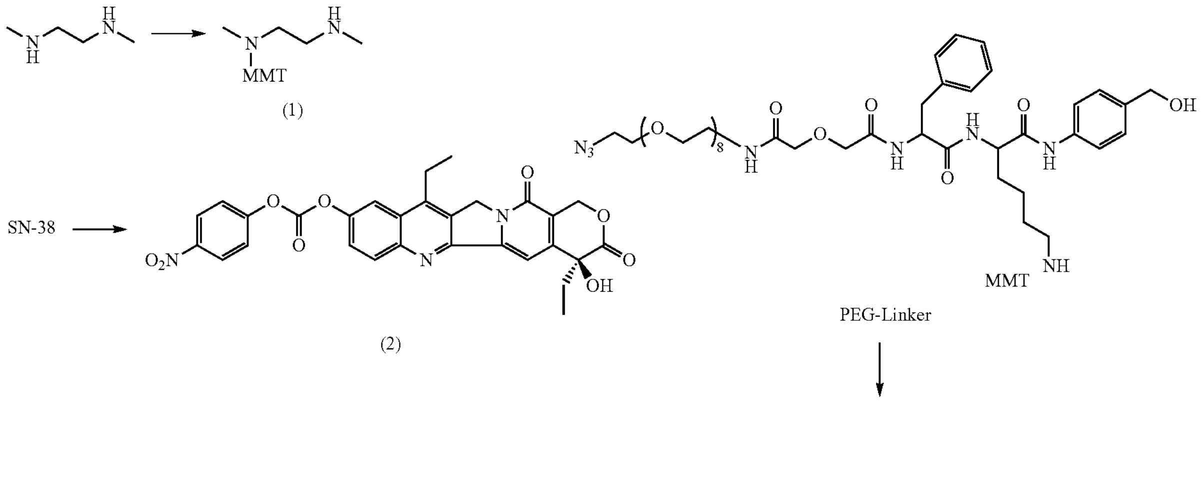

(1)

SN-38

(2)

PEG-Linker

-continued

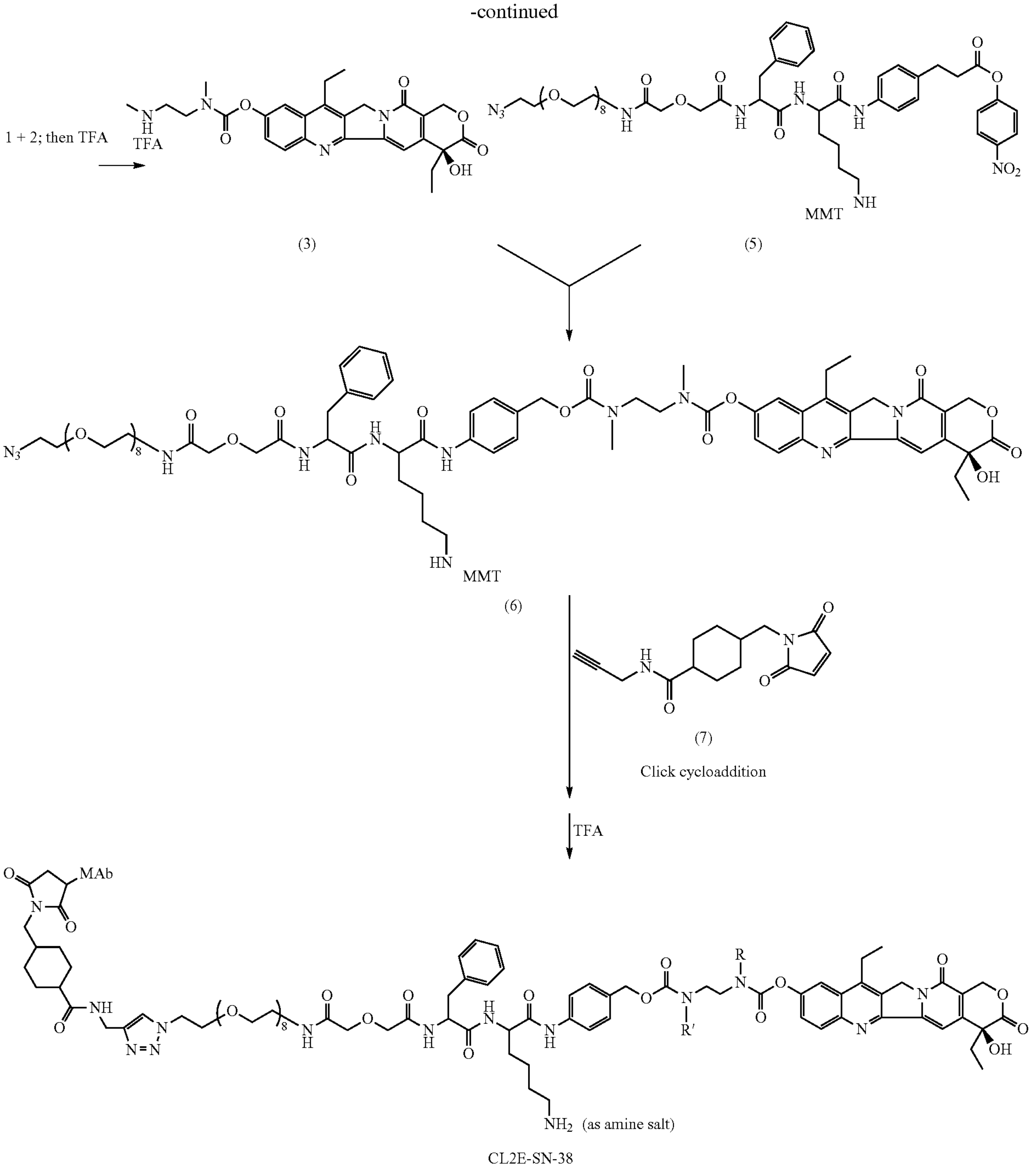

(3) (5) (6) (7)

CL2E-SN-38
(R = R' = $CH_3$)

Example 8

Conjugation of Bifunctional SN-38 Products to Mildly Reduced Antibodies

The anti-CEACAM5 humanized MAb, hMN-14 (also known as labetuzumab), the anti-CD22 humanized MAb, hLL2 (also known as epratuzumab), the anti-CD20 humanized MAb, hA20 (also known as veltuzumab), the anti-EGP-1 humanized MAb, hRS7, and anti-mucin humanized MAb, hPAM4 (also known as clivatuzumab), were used in these studies. Each antibody was reduced with dithiothreitol (DTT), used in a 50-to-70-fold molar excess, in 40 mM PBS, pH 7.4, containing 5.4 mM EDTA, at 37° C. (bath) for 45 min. The reduced product was purified by size-exclusion chromatography and/or diafiltration, and was buffer-exchanged into a suitable buffer at pH 6.5. The thiol content was determined by Ellman's assay, and was in the 6.5-to-8.5 SH/IgG range. Alternatively, the antibodies were reduced with Tris(2-carboxyethyl)phosphine (TCEP) in phosphate buffer at pH in the range of 5-7, followed by in situ conjugation. The reduced MAb was reacted with ~10-to-15-fold molar excess of 'CL6-SN-38' of Example 1, or 'CL7-SN-38' of Example 2, or 'CL6-SN-38-10-O—$CO_2$Et' of Example 3, or 'CL7-SN-38-10-O—$CO_2$Et' of Example 4, CL2A-SN-38 of Example 6, or CL2E-SN-38 of Example 7 using DMSO at 7-15% v/v as co-solvent, and incubating for 20 min at ambient temperature. The conjugate was purified by centrifuged SEC, passage through a hydrophobic column, and finally by ultrafiltration-diafiltration. The product was assayed for SN-38 by absorbance at 366 nm and correlating with standard values, while the protein concentration was deduced from absorbance at 280 nm, corrected for spillover of SN-38 absorbance at this wavelength. This way, the SN-38/MAb substitution ratios were determined. The purified conjugates were stored as lyophilized formulations in glass vials, capped under vacuum and stored in a −20° C. freezer. SN-38 molar substitution ratios (MSR) obtained for some of these conjugates, which were typically in the 5-to-7 range, are shown in Table 7.

TABLE 7

SN-38/MAb Molar substitution ratios (MSR) in some conjugates

| MAb | Conjugate | MSR |
|---|---|---|
| hMN-14 | hMN-14-[CL2A-SN-38], using drug-linker of Example 10 | 6.1 |
| | hMN-14-[CL6-SN-38], using drug-linker of Example 1 | 6.8 |
| | hMN-14-[CL7-SN-38], using drug-linker of Example 2 | 5.9 |
| | hMN-14-[CL7-SN-38-10-O-$CO_2$Et], using drug-linker of Example 4 | 5.8 |
| | hMN-14-[CL2E-SN-38], using drug-linker of Example 11 | 5.9 |
| hRS7 | hRS7-CL2A-SN-38 using drug-linker of Example 10 | 5.8 |
| | hRS7-CL7-SN-38 using drug-linker of Example 2 | 5.9 |
| | hRS7-CL7-SN-38 (Et) using drug-linker of Example 4 | 6.1 |
| hA20 | hA20-CL2A-SN-38 using drug-linker of Example 10 | 5.8 |
| hLL2 | hLL2-CL2A-SN-38 using drug-linker of Example 10 | 5.7 |
| hPAM4 | hPAM4-CL2A-SN-38 using drug-linker of Example 10 | 5.9 |

Example 9

Figure 1:
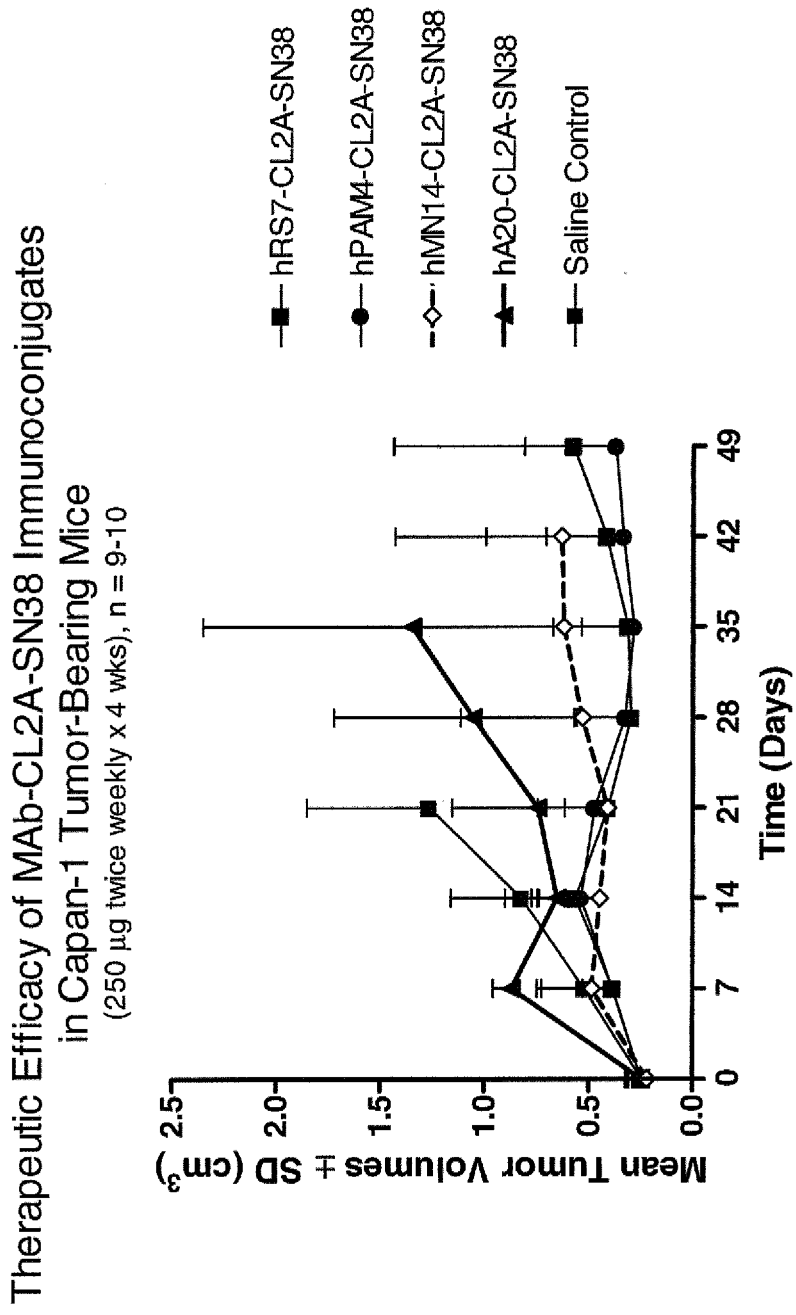
FIG. 1. In vivo therapy of athymic nude mice, bearing Capan 1 human pancreatic carcinoma, with MAb-CL2A-SN-38 conjugates.
Figure 3:
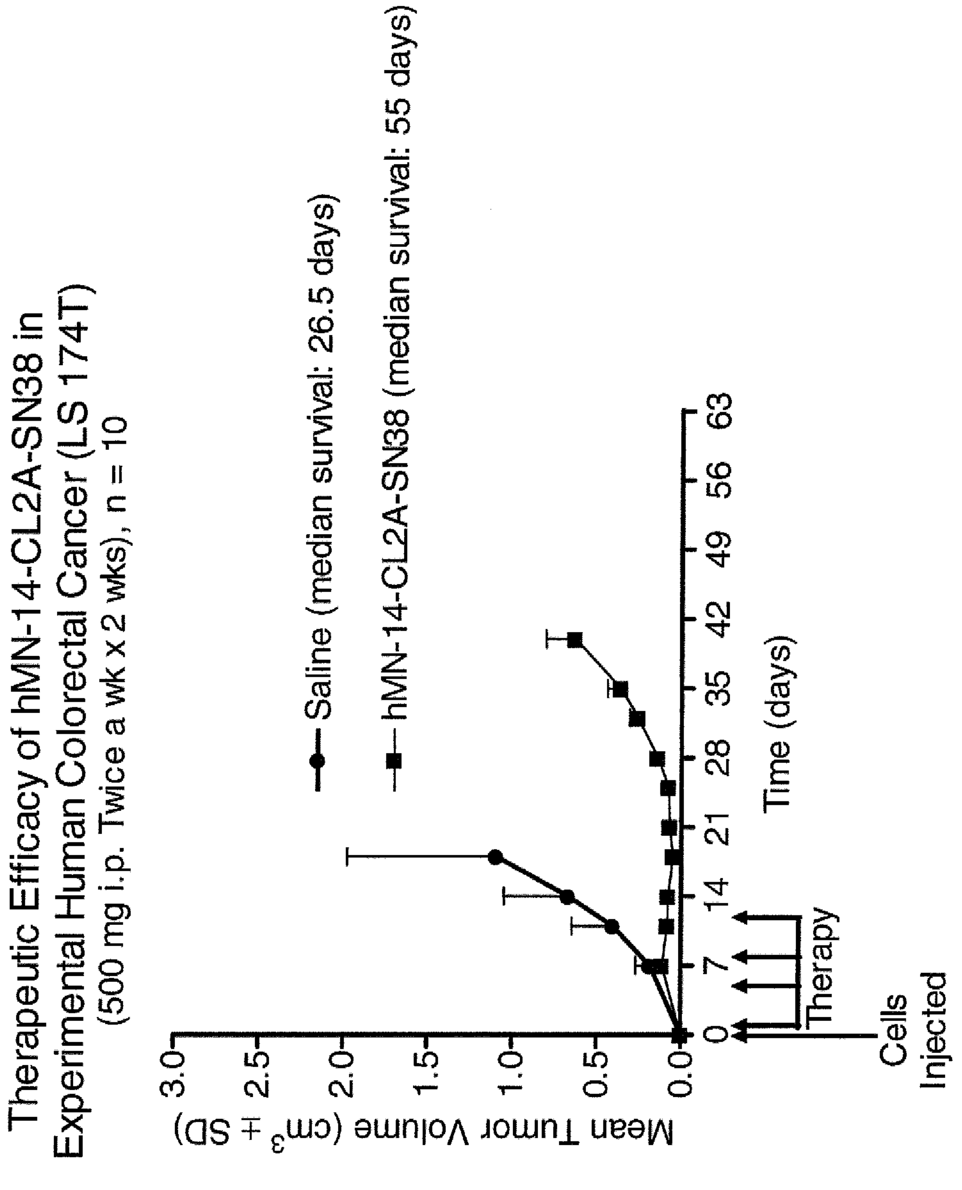
FIG. 3. In vivo therapy of athymic nude mice, bearing LS174T human colon carcinoma, with hMN-14-CL2A-SN-38 conjugate.

In vivo Therapeutic Efficacies in Preclinical Models of Human Pancreatic or Colon Carcinoma Immune-compromised athymic nude mice (female), bearing subcutaneous human pancreatic or colon tumor xenografts were treated with either specific CL2A-SN-38 conjugate or control conjugate or were left untreated. The therapeutic efficacies of the specific conjugates were observed. FIG. 1 shows a Capan 1 pancreatic tumor model, wherein specific CL2A-SN-38 conjugates of hRS7 (anti-EGP-1), hPAM4 (anti-mucin), and hMN-14 (anti-CEACAM5) antibodies showed better efficacies than control hA20-CL2A-SN-38 conjugate (anti-CD20) and untreated control. Similarly in a BXPC3 model of human pancreatic cancer, the specific hRS7-CL2A-SN-38 showed better therapeutic efficacy than control treatments (FIG. 2). Likewise, in an aggressive LS174T model of human colon carcinoma, treatment with specific hMN-14-CL2A-SN-38 was more efficacious than non-treatment (FIG. 3).

Example 10

In vivo Therapy of Lung Metastases of GW-39 Human Colonic Tumors in Nude Mice Using hMN-14-[CL1-SN-38] and hMN-14-[CL2-SN-38]

Figure 4:
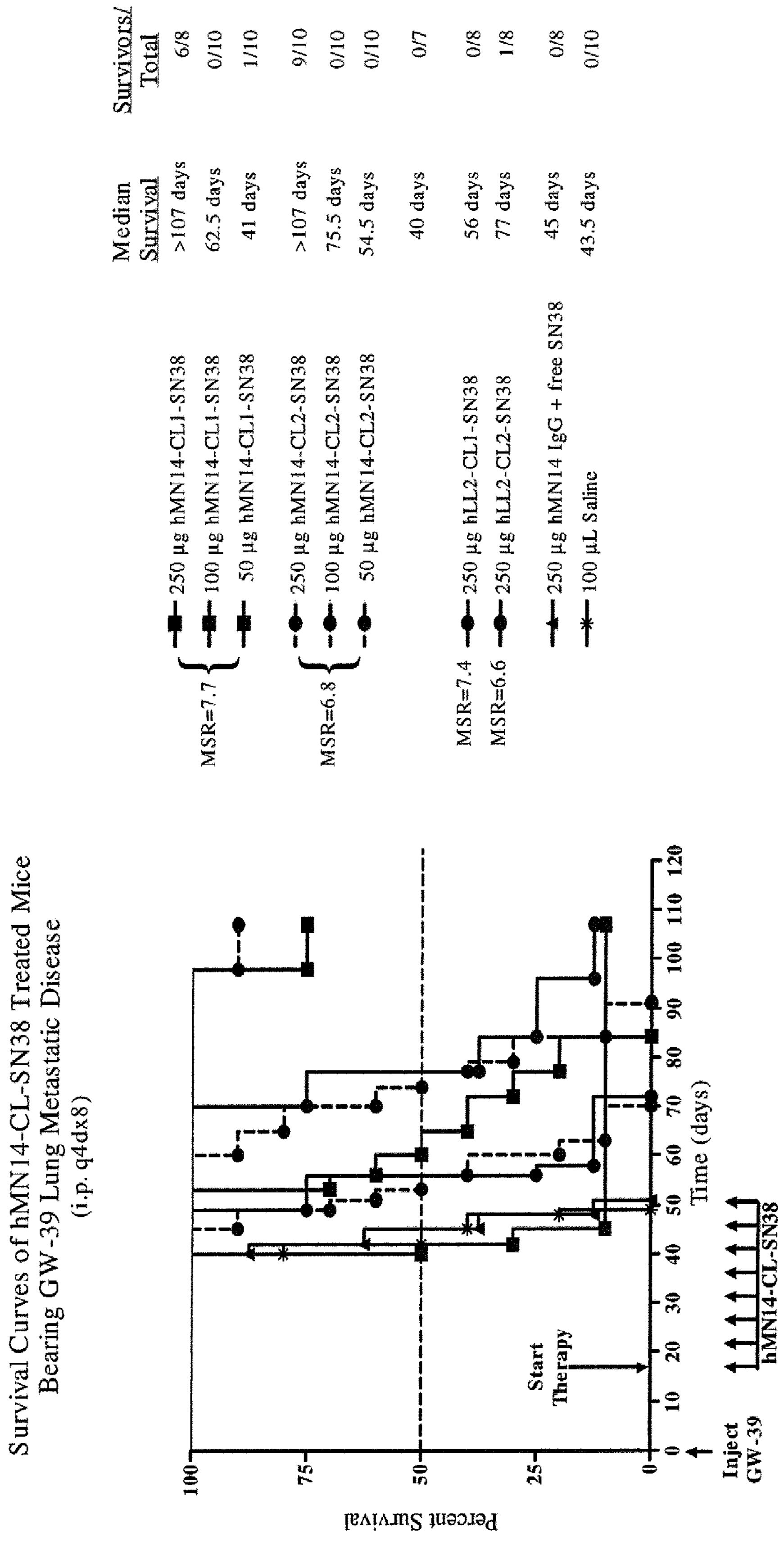
FIG. 4. Survival curves of hMN14-CL-SN-38 treated mice bearing GW-39 lung metastatic disease.

A lung metastatic model of colonic carcinoma was established in nude mice by i.v. injection of GW-39 human colonic tumor suspension, and therapy was initiated 14 days later. Specific anti-CEACAM5 antibody conjugates, hMN14-CL1-SN-38 and hMN14-CL2-SN-38, as well as nontargeting anti-CD22 MAb control conjugates, hLL2-CL1-SN-38 and hLL2-CL2-SN-38 and equidose mixtures of hMN14 and SN-38 were injected at a dose schedule of q4d×8, using different doses. FIG. 4 (MSR=SN-38/antibody molar substitution ratio) shows selective therapeutic effects due to hMN-14 conjugates. At equivalent dosages of 250 μg, the mice treated with hMN14-CL1-SN-38 or hMN14-CL2-SN-38 showed a median survival of greater than 107 days. Mice treated with the control conjugated antibodies hLL2-CL1-SN-38 and hLL2-CL2-SN-38, which do not specifically target lung cancer cells, showed median survival of 56 and 77 days, while mice treated with unconjugated hMN14 IgG and free SN-38 showed a median survival of 45 days, comparable to the untreated saline control of 43.5 days. A significant and surprising increase in effectiveness of the conjugated, cancer cell targeted antibody-SN-38 conjugate, which was substantially more effective than unconjugated antibody and free chemotherapeutic agent alone, was clearly seen. The dose-responsiveness of therapeutic effect of conjugated antibody was also observed. These results demonstrate the clear superiority of the SN-38-antibody conjugates compared to the combined effect of both unconjugated antibody and free SN-38 in the same in vivo human lung cancer system.

Example 11

Use of Humanized Anti-TROP-2 IgG-SN-38 Conjugate for Effective Treatment of Diverse Epithelial Cancers Abstract The purpose of this study was to evaluate the efficacy of an SN-38-anti-TROP-2 antibody-drug conjugate (ADC) against several human solid tumor types, and to assess its tolerability in mice and monkeys, the latter with tissue cross-reactivity to hRS7 similar to humans. Two SN-38 derivatives, CL2-SN-38 and CL2A-SN-38, were conjugated to the anti-TROP-2-humanized antibody, hRS7. The immunoconjugates were characterized in vitro for stability, binding, and cytotoxicity. Efficacy was tested in five different human solid tumor-xenograft models that expressed TROP-2 antigen. Toxicity was assessed in mice and in Cynomolgus monkeys.

The hRS7 conjugates of the two SN-38 derivatives were equivalent in drug substitution (~6), cell binding ($K_d$~1.2 nmol/L), cytotoxicity ($IC_{50}$~2.2 nmol/L), and serum stability in vitro ($t/_{1/2}$~20 hours). Exposure of cells to the ADC demonstrated signaling pathways leading to PARP cleavage, but differences versus free SN-38 in p53 and p21 upregulation were noted. Significant antitumor effects were produced by hRS7-SN-38 at nontoxic doses in mice bearing Calu-3 ($P \leq 0.05$), Capan-1 ($P<0.018$), BxPC-3 ($P<0.005$), and COLO 205 tumors ($P<0.033$) when compared to non-targeting control ADCs. Mice tolerated a dose of 2×12 mg/kg (SN-38 equivalents) with only short-lived elevations in ALT and AST liver enzyme levels. Cynomolgus monkeys infused with 2×0.96 mg/kg exhibited only transient decreases in blood counts, although, importantly, the values did not fall below normal ranges.

We conclude that the anti-TROP-2 hRS7-CL2A-SN-38 ADC provided significant and specific antitumor effects against a range of human solid tumor types. It was well tolerated in monkeys, with tissue TROP-2 expression similar to humans. (Cardillo et al., 2011, Clin Cancer Res 17:3157-69.)

Translational Relevance

Successful irinotecan treatment of patients with solid tumors has been limited due in large part to the low conversion rate of the CPT-11 prodrug into the active SN-38 metabolite. Others have examined nontargeted forms of SN-38 as a means to bypass the need for this conversion and to deliver SN-38 passively to tumors. We conjugated SN-38 covalently to a humanized anti-TROP-2 antibody, hRS7. This antibody-drug conjugate has specific antitumor effects in a range of s.c. human cancer xenograft models, including non-small cell lung carcinoma, pancreatic, colorectal, and squamous cell lung carcinomas, all at nontoxic doses (e.g., ≤3.2 mg/kg cumulative SN-38 equivalent dose).

TROP-2 is widely expressed in many epithelial cancers, but also some normal tissues, and therefore a dose escalation study in Cynomolgus monkeys was performed to assess the clinical safety of this conjugate. Monkeys tolerated 24 mg SN-38 equivalents/kg with only minor, reversible, toxicities. Given its tumor-targeting and safety profile, hRS7-SN-38 may provide an improvement in the management of solid tumors responsive to irinotecan.

Introduction

Human trophoblast cell-surface antigen (TROP-2), also known as GA733-1 (gastric antigen 733-1), EGP-1 (epithelial glycoprotein-1), and TACSTD2 (tumor-associated calcium signal transducer), is expressed in a variety of human carcinomas and has prognostic significance in some, being associated with more aggressive disease (see, e.g., Alberti et al., 1992, Hybridoma 11:539-45; Stein et al., 1993, Int J Cancer 55:938-46; Stein et al., 1994, Int J Cancer Suppl. 8:98-102). Studies of the functional role of TROP-2 in a mouse pancreatic cancer cell line transfected with murine TROP-2 revealed increased proliferation in low serum conditions, migration, and anchorage-independent growth in vitro, and enhanced growth rate with evidence of increased Ki-67 expression in vivo and a higher likelihood to metastasize (Cubas et al., 2010, Mol Cancer 9:253).

TROP-2 antigen's distribution in many epithelial cancers makes it an attractive therapeutic target. Stein and colleagues (1993, Int J Cancer 55:938-46) characterized an antibody, designated RS7-3G11 (RS7), that bound to EGP-1, which was present in a number of solid tumors, but the antigen was also expressed in some normal tissues, usually in a lower intensity, or in restricted regions. Targeting and therapeutic efficacies were documented in a number of human tumor xenografts using radiolabeled RS7 (Shih et al., 1995, Cancer Res 55:5857s-63s; Stein et al., 1997, Cancer 80:2636-41; Govindan et al., 2004, Breast Cancer Res Treat 84:173-82), but this internalizing antibody did not show therapeutic activity in unconjugated form (Shih et al., 1995, Cancer Res 55:5857s-63s). However, in vitro it has demonstrated antibody-dependent cellular cytotoxicity (ADCC) activity against TROP-2 positive carcinomas.

We reported the preparation of antibody-drug conjugates (ADC) using an anti-CEACAM5 (CD66e) IgG coupled to several derivatives of SN-38, a topoisomerase-I inhibitor that is the active component of irinotecan, or CPT-11 (Moon et al., 2008, J Med Chem 51:6916-26; Govindan et al., 2009, Clin Cancer Res 15:6052-61). The derivatives varied in their in vitro serum stability properties, and in vivo studies found one form (designated CL2) to be more effective in preventing or arresting the growth of human colonic and pancreatic cancer xenografts than other linkages with more or less stability.

Importantly, these effects occurred at nontoxic doses, with initial testing failing to determine a dose-limiting toxicity (Govindan et al., 2009, Clin Cancer Res 15:6052-61). These results were encouraging, but also surprising, because the CEACAM5 antibody does not internalize, a property thought to be critical to the success of an ADC. We speculated that the therapeutic activity of the anti-CEACAM5-SN-38 conjugate might be related to the slow release of SN-38 within the tumor after the antibody localized. Because irinotecan performs best when cells are exposed during the S-phase of their growth cycle, a sustained release is expected to improve responses. Indeed, SN-38 coupled to nontargeting, plasma extending agents, such as polyethylene glycol (PEG) or micelles, has shown improved efficacy over irinotecan or SN-38 alone (e.g., Koizumi et al., 2006, Cancer Res 66:10048-56), lending additional support to this mechanism.

Given the RS7 antibody's broad reactivity with epithelial cancers and its internalization ability, we hypothesized that an RS7-SN-38 conjugate could benefit not only from the sustained release of the drug, but also from direct intracellular delivery. Therefore, we prepared and tested the efficacy of SN-38 conjugates using a humanized version of the murine RS7 antibody (hRS7). A slight modification was made to the SN-38 derivative (Govindan et al., 2009, Clin Cancer Res 15:6052-61), which improved the quality of the conjugate without altering its in vitro stability or its efficacy in vivo. This new derivative (designated CL2A) is currently the preferred agent for SN-38 coupling to antibodies. Herein, we show the efficacy of the hRS7-SN-38 conjugate in several epithelial cancer cell lines implanted in nude mice at nontoxic dosages, with other studies revealing that substantially higher doses could be tolerated. More importantly, toxicity studies in monkeys that also express TROP-2 in similar tissues as humans showed that hRS7-SN-38 was tolerated at appreciably higher amounts than the therapeutically effective dose in mice, providing evidence that this conjugate is a promising agent for treating patients with a wide range of epithelial cancers.

Materials and Methods

Cell lines, antibodies, and chemotherapeutics. All human cancer cell lines used in this study were purchased from the American Type Culture Collection. These include Calu-3 (non-small cell lung carcinoma), SK-MES-1 (squamous cell lung carcinoma), COLO 205 (colonic adenocarcinoma), Capan-1 and BxPC-3 (pancreatic adenocarcinomas), and PC-3 (prostatic adenocarcinomas). Humanized RS7 IgG and control humanized anti-CD20 (hA20 IgG, veltuzumab) and anti-CD22 (hLL2 IgG, epratuzumab) antibodies were prepared at Immunomedics, Inc. Irinotecan (20 mg/mL) was obtained from Hospira, Inc.

SN-38 immunoconjugates and in vitro aspects. Synthesis of CL2-SN-38 has been described previously (Moon et al., 2008, *J Med Chem* 51:6916-26). Its conjugation to hRS7 IgG and serum stability were performed as described (Moon et al., 2008, *J Med Chem* 51:6916-26; Govindan et al., 2009, *Clin Cancer Res* 15:6052-61). Preparations of CL2A-SN-38 (M.W. 1480) and its hRS7 conjugate, and stability, binding, and cytotoxicity studies, were conducted as described previously (Moon et al., 2008, *J Med Chem* 51:6916-26). Cell lysates were prepared and immunoblotting for $p21^{Waf1/Cip}$, p53, and PARP (poly-ADP-ribose polymerase) was performed.

In vivo therapeutic studies. For all animal studies, the doses of SN-38 immunoconjugates and irinotecan are shown in SN-38 equivalents. Based on a mean SN-38/IgG substitution ratio of 6, a dose of 500 μg ADC to a 20-g mouse (25 mg/kg) contains 0.4 mg/kg of SN-38. Irinotecan doses are likewise shown as SN-38 equivalents (i.e., 40 mg irinotecan/kg is equivalent to 24 mg/kg of SN-38). NCr female athymic nude (nu/nu) mice, 4 to 8 weeks old, and male Swiss-Webster mice, 10 weeks old, were purchased from Taconic Farms. Tolerability studies were performed in Cynomolgus monkeys (*Macaca fascicularis;* 2.5-4 kg male and female) by SNBL USA, Ltd. Animals were implanted subcutaneously with different human cancer cell lines. Tumor volume (TV) was determined by measurements in 2 dimensions using calipers, with volumes defined as: $L \times w^2/2$, where L is the longest dimension of the tumor and w is the shortest. Tumors ranged in size between 0.10 and 0.47 $cm^3$ when therapy began. Treatment regimens, dosages, and number of animals in each experiment are described in the Results. The lyophilized hRS7-CL2A-SN-38 and control ADC were reconstituted and diluted as required in sterile saline. All reagents were administered intraperitoneally (0.1 mL), except irinotecan, which was administered intravenously. The dosing regimen was influenced by our prior investigations, where the ADC was given every 4 days or twice weekly for varying lengths of time (Moon et al., 2008, *J Med Chem* 51:6916-26; Govindan et al., 2009, *Clin Cancer Res* 15:6052-61). This dosing frequency reflected a consideration of the conjugate's serum half-life in vitro, to allow a more continuous exposure to the ADC.

Statistics. Growth curves were determined as percent change in initial TV over time. Statistical analysis of tumor growth was based on area under the curve (AUC). Profiles of individual tumor growth were obtained through linear-curve modeling. An f-test was employed to determine equality of variance between groups before statistical analysis of growth curves. A 2-tailed t-test was used to assess statistical significance between the various treatment groups and controls, except for the saline control, where a 1-tailed t-test was used (significance at $P \leq 0.05$). Statistical comparisons of AUC were performed only up to the time that the first animal within a group was euthanized due to progression.

Pharmacokinetics and biodistribution. $^{111}$In-radiolabeled hRS7-CL2A-SN-38 and hRS7 IgG were injected into nude mice bearing s.c. SK-MES-1 tumors (~0.3 $cm^3$). One group was injected intravenously with 20 μCi (250-m protein) of $^{111}$In-hRS7-CL2A-SN-38, whereas another group received 20 μCi (250-μg protein) of $^{111}$In-hRS7 IgG. At various timepoints mice (5 per timepoint) were anesthetized, bled via intracardiac puncture, and then euthanized. Tumors and various tissues were removed, weighed, and counted by γ scintillation to determine the percentage injected dose per gram tissue (% ID/g). A third group was injected with 250 μg of unlabeled hRS7-CL2A-SN-38 3 days before the administration of $^{111}$In-hRS7-CL2A-SN-38 and likewise necropsied. A 2-tailed t-test was used to compare hRS7-CL2A-SN-38 and hRS7 IgG uptake after determining equality of variance using the f-test. Pharmacokinetic analysis on blood clearance was performed using WinNonLin software (Parsight Corp.).

Tolerability in Swiss-Webster mice and Cynomolgus monkeys. Briefly, mice were sorted into 4 groups each to receive 2-mL i.p. injections of either a sodium acetate buffer control or 3 different doses of hRS7-CL2A-SN-38 (4, 8, or 12 mg/kg of SN-38) on days 0 and 3 followed by blood and serum collection, as described in Results. Cynomolgus monkeys (3 male and 3 female; 2.5-4.0 kg) were administered 2 different doses of hRS7-CL2A-SN-38. Dosages, times, and number of monkeys bled for evaluation of possible hematologic toxicities and serum chemistries are described in the Results.

Results

Stability and potency of hRS7-CL2A-SN-38. Two different linkages were used to conjugate SN-38 to hRS7 IgG. The first is termed CL2-SN-38 and has been described previously (Moon et al., 2008, J Med Chem 51:6916-26; Govindan et al., 2009, Clin Cancer Res 15:6052-61). A minor change was made to the synthesis of the CL2 linker in that the phenylalanine moiety was removed. This change simplified the synthesis, but did not affect the conjugation outcome (e.g., both CL2-SN-38 and CL2A-SN-38 incorporated ~6 SN-38 per IgG molecule). Side-by-side comparisons found no significant differences in serum stability, antigen binding, or in vitro cytotoxicity (not shown).

To confirm that the change in the SN-38 linker from CL2 to CL2A did not impact in vivo potency, hRS7-CL2A and hRS7-CL2-SN-38 were compared in mice bearing COLO 205 or Capan-1 tumors (not shown), using 0.4 mg or 0.2 mg/kg SN-38 twice weekly×4 weeks, respectively, and with starting tumors of 0.25 $cm^3$ size in both studies. Both the hRS7-CL2A and CL2-SN-38 conjugates significantly inhibited tumor growth compared to untreated ($AUC_{14\ days}$ $P<0.002$ vs. saline in COLO 205 model; $AUC_{21\ days}$ $P<0.001$ vs. saline in Capan-1 model), and a nontargeting anti-CD20 control ADC, hA20-CL2A-SN-38 ($AUC_{14\ days}$ $P<0.003$ in COLO-205 model; $AUC_{35\ days}$: $P<0.002$ in Capan-1 model). At the end of the study (day 140) in the Capan-1 model, 50% of the mice treated with hRS7-CL2A-SN-38 and 40% of the hRS7-CL2-SN-38 mice were tumor-free, whereas only 20% of the hA20-ADC-treated animals had no visible sign of disease. Importantly, there were no differences in efficacy between the 2 specific conjugates in both the tumor models.

Mechanism of action. In vitro cytotoxicity studies demonstrated that hRS7-CL2A-SN-38 had $IC_{50}$ values in the nmol/L range against several different solid tumor lines (Table 8). The $IC_{50}$ with free SN-38 was lower than the conjugate in all cell lines. Although there was no correlation between TROP-2 expression and sensitivity to hRS7-CL2A-SN-38, the $IC_{50}$ ratio of the ADC versus free SN-38 was lower in the higher TROP-2-expressing cells, most likely reflecting the enhanced ability to internalize the drug when more antigen is present.

TABLE 8

Expression of TROP-2 and in vitro cytotoxicity of SN-38 and hRS7-SN-38 in several solid tumor lines

| | TROP-2 expression via FACS | | Cytotoxicity results | | | | |
|---|---|---|---|---|---|---|---|
| Cell line | Median fluorescence (background) | Percent positive | SN-38 $IC_{50}$ (nmol/L) | 95% CI $IC_{50}$ (nmol/L) | hRS7-SN-38[a] $IC_{50}$ (nmol/L) | 95% CI $IC_{50}$ (nmol/L) | ADC/free SN-38 ratio |
| Calu-3 | 282.2 (4.7) | 99.6% | 7.19 | 5.77-8.95 | 9.97 | 8.12-12.25 | 1.39 |
| COLO 205 | 141.5 (4.5) | 99.5% | 1.02 | 0.66-1.57 | 1.95 | 1.26-3.01 | 1.91 |

TABLE 8-continued

Expression of TROP-2 and in vitro cytotoxicity of SN-38 and hRS7-SN-38 in several solid tumor lines

| | TROP-2 expression via FACS | | Cytotoxicity results | | | | |
|---|---|---|---|---|---|---|---|
| Cell line | Median fluorescence (background) | Percent positive | SN-38 $IC_{50}$ (nmol/L) | 95% CI $IC_{50}$ (nmol/L) | hRS7-SN-38[a] $IC_{50}$ (nmol/L) | 95% CI $IC_{50}$ (nmol/L) | ADC/free SN-38 ratio |
| Capan-1 | 100.0 (5.0) | 94.2% | 3.50 | 2.17-5.65 | 6.99 | 5.02-9.72 | 2.00 |
| PC-3 | 46.2 (5.5) | 73.6% | 1.86 | 1.16-2.99 | 4.24 | 2.99-6.01 | 2.28 |
| SK-MES-1 | 44.0 (3.5) | 91.2% | 8.61 | 6.30-11.76 | 23.14 | 17.98-29.78 | 2.69 |
| BxPC-3 | 26.4 (3.1) | 98.3% | 1.44 | 1.04-2.00 | 4.03 | 3.25-4.98 | 2.80 |

[a]$IC_{50}$-value is shown as SN-38 equivalents of hRS7-SN-38

SN-38 is known to activate several signaling pathways in cells, leading to apoptosis. Our initial studies examined the expression of 2 proteins involved in early signaling events ($p21^{Waf1/Cip1}$ and p53) and 1 late apoptotic event [cleavage of poly-ADP-ribose polymerase (PARP)] in vitro (not shown). In BxPC-3, SN-38 led to a 20-fold increase in $p21^{Waf1/Cip1}$ expression, whereas hRS7-CL2A-SN-38 resulted in only a 10-fold increase, a finding consistent with the higher activity with free SN-38 in this cell line (Table 8). However, hRS7-CL2A-SN-38 increased $p21^{Waf1/Cip1}$ expression in Calu-3 more than 2-fold over free SN-38 (not shown).

A greater disparity between hRS7-CL2A-SN-38- and free SN-38-mediated signaling events was observed in p53 expression. In both BxPC-3 and Calu-3, upregulation of p53 with free SN-38 was not evident until 48 hours, whereas hRS7-CL2A-SN-38 upregulated p53 within 24 hours (not shown). In addition, p53 expression in cells exposed to the ADC was higher in both cell lines compared to SN-38 (not shown). Interestingly, although hRS7 IgG had no appreciable effect on $p21^{Waf1/Cip1}$ expression, it did induce the upregulation of p53 in both BxPC-3 and Calu-3, but only after a 48-hour exposure. In terms of later apoptotic events, cleavage of PARP was evident in both cell lines when incubated with either SN-38 or the conjugate (not shown). The presence of the cleaved PARP was higher at 24 hours in BxPC-3, which correlates with high expression of p21 and its lower $IC_{50}$. The higher degree of cleavage with free SN-38 over the ADC was consistent with the cytotoxicity findings.

Efficacy of hRS7-SN-38. Because TROP-2 is widely expressed in several human carcinomas, studies were performed in several different human cancer models, which started with an evaluation of the hRS7-CL2-SN-38 linkage, but later, conjugates with the CL2A-linkage were used. Calu-3-bearing nude mice given 0.04 mg SN-38/kg of the hRS7-CL2-SN-38 every 4 days×4 had a significantly improved response compared to animals administered the equivalent amount of hLL2-CL2-SN-38 (TV=0.14±0.22 $cm^3$ vs. 0.80±0.91 $cm^3$, respectively; $AUC_{42\ days}$P<0.026; FIG. 5A). A dose-response was observed when the dose was increased to 0.4 mg/kg SN-38. At this higher dose level, all mice given the specific hRS7 conjugate were "cured" within 28 days, and remained tumor-free until the end of the study on day 147, whereas tumors regrew in animals treated with the irrelevant ADC (specific vs. irrelevant $AUC_{98\ days}$: P=0.05). In mice receiving the mixture of hRS7 IgG and SN-38, tumors progressed >4.5-fold by day 56 (TV=1.10±0.88 $cm^3$; $AUC_{56\ days}$P<0.006 vs. hRS7-CL2-SN-38).

Efficacy also was examined in human colonic (COLO 205) and pancreatic (Capan-1) tumor xenografts. In COLO 205 tumor-bearing animals, (FIG. 5B), hRS7-CL2-SN-38 (0.4 mg/kg, q4d×8) prevented tumor growth over the 28-day treatment period with significantly smaller tumors compared to control anti-CD20 ADC (hA20-CL2-SN-38), or hRS7 IgG (TV=0.16±0.09 $cm^3$, 1.19±0.59 $cm^3$, and 1.77±0.93 $cm^3$, respectively; $AUC_{28\ days}$P<0.016). The MTD of irinotecan (24 mg SN-38/kg, q2d×5) was as effective as hRS7-CL2-SN-38, because mouse serum can more efficiently convert irinotecan to SN-38 than human serum, but the SN-38 dose in irinotecan (2,400 μg cumulative) was 37.5-fold greater than with the conjugate (64 μg total).

Animals bearing Capan-1 showed no significant response to irinotecan alone when given at an SN-38-dose equivalent to the hRS7-CL2-SN-38 conjugate (e.g., on day 35, average tumor size was 0.04±0.05 $cm^3$ in animals given 0.4 mg SN-38/kg hRS7-SN-38 vs. 1.78±0.62 $cm^3$ in irinotecan-treated animals given 0.4 mg/kg SN-38; $AUC_{day\ 35}$P<0.001; FIG. 5C). When the irinotecan dose was increased 10-fold to 4 mg/kg SN-38, the response improved, but still was not as significant as the conjugate at the 0.4 mg/kg SN-38 dose level (TV=0.17±0.18 $cm^3$ vs. 1.69±0.47 $cm^3$, $AUC_{day\ 49}$P<0.001). An equal dose of nontargeting hA20-CL2-SN-38 also had a significant antitumor effect as compared to irinotecan-treated animals, but the specific hRS7 conjugate was significantly better than the irrelevant ADC (TV=0.17±0.18 $cm^3$ vs. 0.80±0.68 $cm^3$, $AUC_{day\ 49}$P<0.018).

Studies with the hRS7-CL2A-SN-38 ADC were then extended to 2 other models of human epithelial cancers. In mice bearing BxPC-3 human pancreatic tumors (FIG. 5D), hRS7-CL2A-SN-38 again significantly inhibited tumor growth in comparison to control mice treated with saline or an equivalent amount of nontargeting hA20-CL2A-SN-38 (TV=0.24±0.11 $cm^3$ vs. 1.17±0.45 $cm^3$ and 1.05±0.73 $cm^3$, respectively; $AUC_{day\ 21}$P<0.001), or irinotecan given at a 10-fold higher SN-38 equivalent dose (TV=0.27±0.18 $cm^3$ vs. 0.90±0.62 $cm^3$, respectively; $AUC_{day\ 25}$P<0.004). Interestingly, in mice bearing SK-MES-1 human squamous cell lung tumors treated with 0.4 mg/kg of the ADC (FIG. 5E), tumor growth inhibition was superior to saline or unconjugated hRS7 IgG (TV=0.36±0.25 $cm^3$ vs. 1.02±0.70 $cm^3$ and 1.30±1.08 $cm^3$, respectively; $AUC_{28\ days}$, P<0.043), but nontargeting hA20-CL2A-SN-38 or the MTD of irinotecan provided the same antitumor effects as the specific hRS7-

SN-38 conjugate. In all murine studies, the hRS7-SN-38 ADC was well tolerated in terms of body weight loss (not shown).

Biodistribution of hRS7-CL2A-SN-38. The biodistributions of hRS7-CL2A-SN-38 or unconjugated hRS7 IgG were compared in mice bearing SK-MES-1 human squamous cell lung carcinoma xenografts (not shown), using the respective $^{111}$In-labeled substrates. A pharmacokinetic analysis was performed to determine the clearance of hRS7-CL2A-SN-38 relative to unconjugated hRS7 (not shown). The ADC cleared faster than the equivalent amount of unconjugated hRS7, with the ADC exhibiting ~40% shorter half-life and mean residence time. Nonetheless, this had a minimal impact on tumor uptake (not shown). Although there were significant differences at the 24- and 48-hour timepoints, by 72 hours (peak uptake) the amounts of both agents in the tumor were similar. Among the normal tissues, hepatic and splenic differences were the most striking (not shown). At 24 hours postinjection, there was >2-fold more hRS7-CL2A-SN-38 in the liver than hRS7 IgG. Conversely, in the spleen there was 3-fold more parental hRS7 IgG present at peak uptake (48-hour timepoint) than hRS7-CL2A-SN-38. Uptake and clearance in the rest of the tissues generally reflected differences in the blood concentration.

Because twice-weekly doses were given for therapy, tumor uptake in a group of animals that first received a predose of 0.2 mg/kg (250 μg protein) of the hRS7 ADC 3 days before the injection of the $^{111}$In-labeled antibody was examined. Tumor uptake of $^{111}$In-hRS7-CL2A-SN-38 in predosed mice was substantially reduced at every timepoint in comparison to animals that did not receive the predose (e.g., at 72 hours, predosed tumor uptake was 12.5%±3.8% ID/g vs. 25.4%±8.1% ID/g in animals not given the predose; P=0.0123). Predosing had no appreciable impact on blood clearance or tissue uptake (not shown). These studies suggest that in some tumor models, tumor accretion of the specific antibody can be reduced by the preceding dose(s), which likely explains why the specificity of a therapeutic response could be diminished with increasing ADC doses and why further dose escalation is not indicated.

Tolerability of hRS7-CL2A-SN-38 in Swiss-Webster mice and Cynomolgus monkeys. Swiss-Webster mice tolerated 2 doses over 3 days, each of 4, 8, and 12 mg SN-38/kg of the hRS7-CL2A-SN-38, with minimal transient weight loss (not shown). No hematopoietic toxicity occurred and serum chemistries only revealed elevated aspartate transaminase (AST) and alanine transaminase (not shown). Seven days after treatment, AST rose above normal levels (>298 U/L) in all 3 treatment groups (not shown), with the largest proportion of mice being in the 2×8 mg/kg group. However, by 15 days posttreatment, most animals were within the normal range. ALT levels were also above the normal range (>77 U/L) within 7 days of treatment (not shown) and with evidence of normalization by Day 15. Livers from all these mice did not show histologic evidence of tissue damage (not shown). In terms of renal function, only glucose and chloride levels were somewhat elevated in the treated groups. At 2×8 mg/kg, 5 of 7 mice had slightly elevated glucose levels (range of 273-320 mg/dL, upper end of normal 263 mg/dL) that returned to normal by 15 days postinjection. Similarly, chloride levels were slightly elevated, ranging from 116 to 127 mmol/L (upper end of normal range 115 mmol/L) in the 2 highest dosage groups (57% in the 2×8 mg/kg group and 100% of the mice in the 2×12 mg/kg group), and remained elevated out to 15 days postinjection. This also could be indicative of gastrointestinal toxicity, because most chloride is obtained through absorption by the gut; however, at termination, there was no histologic evidence of tissue damage in any organ system examined (not shown).

Because mice do not express TROP-2 bound by hRS7, a more suitable model was required to determine the potential of the hRS7 conjugate for clinical use. Immunohistology studies revealed binding in multiple tissues in both humans and Cynomolgus monkeys (breast, eye, gastrointestinal tract, kidney, lung, ovary, fallopian tube, pancreas, parathyroid, prostate, salivary gland, skin, thymus, thyroid, tonsil, ureter, urinary bladder, and uterus; not shown). Based on this cross-reactivity, a tolerability study was performed in monkeys.

The group receiving 2×0.96 mg SN-38/kg of hRS7-CL2A-SN-38 had no significant clinical events following the infusion and through the termination of the study. Weight loss did not exceed 7.3% and returned to acclimation weights by day 15. Transient decreases were noted in most of the blood count data (not shown), but values did not fall below normal ranges. No abnormal values were found in the serum chemistries. Histopathology of the animals necropsied on day 11 (8 days after last injection) showed microscopic changes in hematopoietic organs (thymus, mandibular and mesenteric lymph nodes, spleen, and bone marrow), gastrointestinal organs (stomach, duodenum, jejunum, ileum, cecum, colon, and rectum), female reproductive organs (ovary, uterus, and vagina), and at the injection site. These changes ranged from minimal to moderate and were fully reversed at the end of the recovery period (day 32) in all tissues, except in the thymus and gastrointestinal tract, which were trending towards full recovery at this later timepoint.

At the 2×1.92 mg SN-38/kg dose level of the conjugate, there was 1 death arising from gastrointestinal complications and bone marrow suppression, and other animals within this group showed similar, but more severe adverse events than the 2×0.96 mg/kg group. These data indicate that dose-limiting toxicities were identical to that of irinotecan; namely, intestinal and hematologic. Thus, the MTD for hRS7-CL2A-SN-38 lies between 2×0.96 and 1.92 mg SN-38/kg, which represents a human equivalent dose of 2×0.3 to 0.6 mg/kg SN-38.

Discussion

TROP-2 is a protein expressed on many epithelial tumors, including lung, breast, colorectal, pancreas, prostate, and ovarian cancers, making it a potentially important target for delivering cytotoxic agents. The RS7 antibody internalizes when bound to TROP-2 (Shih et al., 1995, Cancer Res 55:5857s-63s), which enables direct intracellular delivery of cytotoxics.

Conjugation of chemotherapeutic drugs to antibodies has been explored for over 30 years. Because a substantial portion of an ADC is not processed by the tumor, but by normal tissues, there is a risk that these agents will be too toxic to normal organ systems before reaching the therapeutic level in tumors. As with any therapeutic, the therapeutic window is a key factor determining the potential of an ADC, and thus rather than examining "ultratoxic" drugs, we chose SN-38 as the drug component of the TROP-2-targeted ADC.

SN-38 is a potent topoisomerase-I inhibitor, with $IC_{50}$ values in the nanomolar range in several cell lines. It is the active form of the prodrug, irinotecan, that is used for the treatment of colorectal cancer, and which also has activity in lung, breast, and brain cancers. We reasoned that a directly targeted SN-38, in the form of an ADC, would be a significantly improved therapeutic over CPT-11, by overcoming the latter's low and patient-variable bioconversion to active SN-38.

The Phe-Lys peptide inserted in the original CL2 derivative allowed for possible cleavage via cathepsin B. In an effort to simplify the synthetic process, in CL2A, phenylalanine was eliminated, and thus the cathepsin B cleavage site was removed. Interestingly, this product had a better-defined chromatographic profile compared to the broad profile obtained with CL2 (not shown), but more importantly, this change had no impact on the conjugate's binding, stability, or potency in side-by-side testing. These data suggest that SN-38 in CL2 was released from the conjugate primarily by the cleavage at the pH-sensitive benzyl carbonate bond to SN-38's lactone ring and not the cathepsin B cleavage site.

In vitro cytotoxicity of hRS7 ADC against a range of solid tumor cell lines consistently had $IC_{50}$ values in the nmol/L range. However, cells exposed to free SN-38 demonstrated a lower $IC_{50}$ value compared to the ADC. This disparity between free and conjugated SN-38 was also reported for ENZ-2208 (Sapra et al., 2008, *Clin Cancer Res* 14:1888-96) and NK012 (Koizumi et al., 2006, *Cancer Res* 66:10048-56). ENZ-2208 utilizes a branched PEG to link about 3.5 to 4 molecules of SN-38 per PEG, whereas NK012 is a micelle nanoparticle containing 20% SN-38 by weight. With our ADC, this disparity (i.e., ratio of potency with free vs. conjugated SN-38) decreased as the TROP-2 expression levels increased in the tumor cells, suggesting an advantage to targeted delivery of the drug. In terms of in vitro serum stability, both the CL2- and CL2A-SN-38 forms of hRS7-SN-38 yielded a $t/_{1/2}$ of ~20 hours, which is in contrast to the short $t/_{1/2}$ of 12.3 minutes reported for ENZ-2208 (Zhao et al., 2008, *Bioconjug Chem* 19:849-59), but similar to the 57% release of SN-38 from NK012 under physiological conditions after 24 hours (Koizumi et al., 2006, *Cancer Res* 66:10048-56).

Treatment of tumor-bearing mice with hRS7-SN-38 (either with CL2-SN-38 or CL2A-SN-38) significantly inhibited tumor growth in 5 different tumor models. In 4 of them, tumor regressions were observed, and in the case of Calu-3, all mice receiving the highest dose of hRS7-SN-38 were tumor-free at the conclusion of study. Unlike in humans, irinotecan is very efficiently converted to SN-38 by a plasma esterase in mice, with a greater than 50% conversion rate, and yielding higher efficacy in mice than in humans. When irinotecan was administered at 10-fold higher or equivalent SN-38 levels, hRS7-SN-38 was significantly better in controlling tumor growth. Only when irinotecan was administered at its MTD of 24 mg/kg q2d×5 (37.5-fold more SN-38) did it equal the effectiveness of hRS7-SN-38. In patients, we would expect this advantage to favor hRS7-CL2A-SN-38 even more, because the bioconversion of irinotecan would be substantially lower.

We also showed in some antigen-expressing cell lines, such as SK-MES-1, that using an antigen-binding ADC does not guarantee better therapeutic responses than a nonbinding, irrelevant conjugate. This is not an unusual or unexpected finding. Indeed, the nonbinding SN-38 conjugates mentioned earlier enhance therapeutic activity when compared to irinotecan, and so an irrelevant IgG-SN-38 conjugate is expected to have some activity. This is related to the fact that tumors have immature, leaky vessels that allow the passage of macromolecules better than normal tissues. With our conjugate, 50% of the SN-38 will be released in ~13 hours when the pH is lowered to a level mimicking lysosomal levels (e.g., pH 5.3 at 37° C.; data not shown), whereas at the neutral pH of serum, the release rate is reduced nearly 2-fold. If an irrelevant conjugate enters an acidic tumor microenvironment, it is expected to release some SN-38 locally. Other factors, such as tumor physiology and innate sensitivities to the drug, will also play a role in defining this "baseline" activity. However, a specific conjugate with a longer residence time should have enhanced potency over this baseline response as long as there is ample antigen to capture the specific antibody. Biodistribution studies in the SK-MES-1 model also showed that if tumor antigen becomes saturated as a consequence of successive dosing, tumor uptake of the specific conjugate is reduced, which yields therapeutic results similar to that found with an irrelevant conjugate.

Although it is challenging to make direct comparisons between our ADC and the published reports of other SN-38 delivery agents, some general observations can be made. In our therapy studies, the highest individual dose was 0.4 mg/kg of SN-38. In the Calu-3 model, only 4 injections were given for a total cumulative dose of 1.6 mg/kg SN-38 or 32 μg SN-38 in a 20 g mouse. Multiple studies with ENZ-2208 were done using its MTD of 10 mg/kg×5, and preclinical studies with NK012 involved its MTD of 30 mg/kg×3. Thus, significant antitumor effects were obtained with hRS7-SN-38 at 30-fold and 55-fold less SN-38 equivalents than the reported doses in ENZ-2208 and NK012, respectively. Even with 10-fold less hRS7 ADC (0.04 mg/kg), significant antitumor effects were observed, whereas lower doses of ENZ-2208 were not presented, and when the NK012 dose was lowered 4-fold to 7.5 mg/kg, efficacy was lost (Koizumi et al., 2006, *Cancer Res* 66:10048-56). Normal mice showed no acute toxicity with a cumulative dose over 1 week of 24 mg/kg SN-38 (1,500 mg/kg of the conjugate), indicating that the MTD was higher. Thus, tumor-bearing animals were effectively treated with 7.5- to 15-fold lower amounts of SN-38 equivalents.

As a topoisomerase-I inhibitor, SN-38 induces significant damage to a cell's DNA, with upregulation of p53 and $p21^{WAF1/Cip1}$ resulting in caspase activation and cleavage of PARP. When we exposed BxPC-3 and Calu-3 cells to our ADC, both p53 and $p21^{WAF1/Cip1}$ were upregulated above basal levels. In addition, PARP cleavage was also evident in both cell lines, confirming an apoptotic event in these cells. Of interest was the higher upregulation of $p21^{Waf1/Cip1}$ in BxPC-3 and Calu-3 relative to p53 by both free SN-38 and our hRS7-SN-38. This may be indicative of the mutational status of p53 in these 2 cell lines and the use of a p53-independent pathway for $p21^{WAF1/Cip1}$-mediated apoptosis.

An interesting observation was the early upregulation of p53 in both BxPC-3 and Calu-3 at 24 hours mediated by the hRS7-ADC relative to free SN-38. Even the naked hRS7 IgG could upregulate p53 in these cell lines, although only after a 48-hour exposure. TROP-2 overexpression and cross-linking by antibodies has been linked to several MAPK-related signaling events, as well as intracellular calcium release. While binding of hRS7 was not sufficient to induce apoptosis in BxPC-3 and Calu-3, as evidenced by the lack of PARP cleavage, it may be enough to prime a cell, such that the inclusion of SN-38 conjugated to hRS7 may lead to a greater effect on tumor growth inhibition. Studies are currently underway to understand which pathways are involved with hRS7-delivery of SN-38 and how they may differ from free SN-38, and what effect p53 status may play in this signaling.

Biodistribution studies revealed the hRS7-CL2A-SN-38 had similar tumor uptake as the parental hRS7 IgG, but cleared substantially faster with 2-fold higher hepatic uptake, which may be due to the hydrophobicity of SN-38. With the ADC being cleared through the liver, hepatic and gastrointestinal toxicities were expected to be dose limiting. Although mice had evidence of increased hepatic transaminases, gastrointestinal toxicity was mild at best, with only transient loss in weight and no abnormalities noted upon histopathologic examination. Interestingly, no hematological toxicity was noted. However, monkeys showed an identical toxicity profile as expected for irinotecan, with gastrointestinal and hematological toxicity being dose-limiting.

Because TROP-2 recognized by hRS7 is not expressed in mice, it was critically important to perform toxicity studies in monkeys that have a similar tissue expression of TROP-2 as humans. Monkeys tolerated 0.96 mg/kg/dose (~12 $mg/m^2$) with mild and reversible toxicity, which extrapolates to a human dose of ~0.3 mg/kg/dose (~11 $mg/m^2$). In a Phase I clinical trial of NK012, patients with solid tumors tolerated 28 $mg/m^2$ of SN-38 every 3 weeks with Grade 4 neutropenia as dose-limiting toxicity (Hamaguchi et al., 2010, *Clin Cancer Res* 16:5058-66). Similarly, Phase I clinical trials with ENZ-2208 revealed dose-limiting febrile neutropenia, with a recommendation to administer 10 $mg/m^2$ every 3 weeks or 16 $mg/m^2$ if patients were administered G-CSF. Because monkeys tolerated a cumulative human equivalent dose of 22 $mg/m^2$, it is possible that even though hRS7 binds to a number of normal tissues, the MTD for a single treatment of the hRS7 ADC could be similar to that of the other nontargeting SN-38 agents. Indeed, the specificity of the anti-TROP-2 antibody did not appear to play a role in defining the DLT, because the toxicity profile was similar to that of irinotecan. More importantly, if antitumor activity can be achieved in humans as in mice that responded with human equivalent dose of just at 0.03 mg SN-38 equivalents/kg/dose, then significant antitumor responses could be realized clinically.

In conclusion, toxicology studies in monkeys, combined with in vivo human cancer xenograft models in mice, have indicated that this ADC targeting TROP-2 is an effective therapeutic in several tumors of different epithelial origin.

Example 12

Anti-CD22 (Epratuzumab) Conjugated-SN-38 for the Therapy of Hematologic Malignancies Abstract We previously found that slowly internalizing antibodies conjugated with SN-38 could be used successfully when prepared with a linker that allows approximately 50% of the IgG-bound SN-38 to dissociate in serum every 24 hours. In this study, the efficacy of SN-38 conjugates prepared with epratuzumab (rapidly internalizing) and veltuzumab (slowly internalizing), humanized anti-CD22 and anti-CD20 IgG, respectively, was examined for the treatment of B-cell malignancies. Both antibody-drug conjugates had similar nanomolar activity against a variety of human lymphoma/leukemia cell lines, but slow release of SN-38 compromised potency discrimination in vitro even against an irrelevant conjugate. When SN-38 was stably linked to the anti-CD22 conjugate, its potency was reduced 40- to 55-fold. Therefore, further studies were conducted only with the less stable, slowly dissociating linker. In vivo, similar antitumor activity was found between CD22 and CD20 antibody-drug conjugate in mice-bearing Ramos xenografts, even though Ramos expressed 15-fold more CD20 than CD22, suggesting that the internalization of the epratuzumab-SN-38 conjugate (Emab-SN-38) enhanced its activity. Emab-SN-38 was more efficacious than a nonbinding, irrelevant IgG-SN-38 conjugate in vivo, eliminating a majority of well-established Ramos xenografts at nontoxic doses. In vitro and in vivo studies showed that Emab-SN-38 could be combined with unconjugated veltuzumab for a more effective treatment. Thus, Emab-SN-38 is active in lymphoma and leukemia at doses well below toxic levels and therefore represents a new promising agent with therapeutic potential alone or combined with anti-CD20 antibody therapy. (Sharkey et al., 2011, *Mol Cancer Ther* 11:224-34.)

Introduction

A significant effort has focused on the biologic therapy of leukemia and lymphoma, where unconjugated antibodies (e.g., rituximab, alemtuzumab, ofatumumab), radioimmunoconjugates ($^{90}$Y-ibritumomab tiuxetan, $^{131}$I-tositumomab), and a drug conjugate (gemtuzumab ozogamicin) received U.S. Food and Drug Administration (FDA) approval. Another antibody-drug conjugate (ADC), brentuximab vedotin (SGN-35; anti-CD30-auristatin E), recently received accelerated approval by the FDA for Hodgkin lymphoma and anaplastic large-cell lymphomas. There are also a number of other ADCs in preclinical and clinical development that target CD19, CD22, CD37, CD74, and CD79b.

Antibodies against all of these targets are logical choices for carriers of drugs, because they are internalizing. Internalization and specificity of CD22 have made it a particularly important target for leukemia and lymphomas, with at least 3 different anti-CD22 conjugates in clinical investigation, including CMC-544 (acid-labile-conjugated calicheamicin), an anti-CD22-maytansine conjugate (stably linked MCC-DM1), and CAT-3888 (formally BL22; a *Pseudomonas* exotoxin single-chain fusion protein). The active agent in all of these conjugates has subnanomolar potency (i.e., so called ultra-toxics).

We recently developed methods to conjugate antibodies with SN-38, a topoisomerase I inhibitor with low nanomolar potency that is derived from the prodrug, irinotecan (Govindan et al., 2009, *Clin Cancer Res* 15:6052-62; Moon et al., 2008, *J Med Chem* 51:6916-26). Four SN-38 linkage chemistries were examined initially using conjugates prepared with a slowly internalizing anti-CEACAM5 antibody (Govindan et al., 2009, *Clin Cancer Res* 15:6052-62; Moon et al., 2008, *J Med Chem* 51:6916-26). The conjugates retained CEACAM5 binding but differed in the dissociation rate of SN-38 in human serum, with half-lives varying from approximately 10 to 67 hours (Govindan et al., 2009, *Clin Cancer Res* 15:6052-62). Ultimately, the linker designated CL2, with intermediate stability (~50% dissociated in 24-35 hours), was selected for further development. CL2 was modified recently, eliminating the phenylalanine in the cathepsin B-cleavable dipeptide to simplify and improve manufacturing yields. The new derivative, designated CL2A, retains the pH-sensitive carbonate linkage to the SN-38, but it is no longer selectively cleaved by cathepsin B. Nevertheless, it has identical serum stability and in vivo activity as the original CL2 linker (Cardillo et al., 2011, *Clin Cancer Res* 17:3157-69). Because significant efficacy without toxicity was found with the slowly internalizing anti-CEACAM5-SN-38, we postulated that its activity was aided by the slow release of SN-38 from the antibody after it localized in a tumor. Thus, the main objective in this report was to evaluate the therapeutic prospects of conjugates prepared using the CL2A linker with two antibodies that are highly specific for B-cell cancers but differ in their antigen expression and internalization properties.

Epratuzumab (Emab) is a rapidly internalizing (e.g., ≥50% within 1 hour), humanized anti-CD22 IgG1 that has been evaluated extensively in lymphoma and leukemia in an unconjugated or conjugated form. Veltuzumab (Vmab) is a humanized anti-CD20 antibody that is also being studied clinically but internalizes slowly (e.g., ~10% in 1 hour). CD20 is usually expressed at much higher levels than CD22 in non-Hodgkin lymphoma, whereas CD22 is preferentially expressed in acute lymphoblastic leukemia (ALL) but not in multiple myeloma. Both antibodies are effective in patients as unconjugated agents, but only veltuzumab is active in murine xenograft models (Stein et al., 2004, *Clin Cancer Res* 10:2868-76). On the basis of previous studies that showed $^{90}$Y-Emab combined with unconjugated veltuzumab had enhanced efficacy in NHL models (Mattes et al., 2008, *Clin Cancer Res* 14:6154-60), we also examined the Emab-SN-38+Vmab combination, as this could provide additional benefit without competing for the same target antigen or having additional toxicity.

Materials and Methods

Cell lines. Ramos, Raji, Daudi (Burkitt lymphomas), and JeKo-1 (mantle cell lymphoma) were purchased from American Type Culture Collection. REH, RS4;11, MN-60, and 697 (ALL) were purchased from Deutsche Sammlung von Mikroorganismen and Zellkulturen. WSU-FSCCL (follicular NHL) was the gift of Dr. Mitchell R. Smith (Fox Chase Cancer Center, Philadelphia, Pa.). All cell lines were cultured in a humidified $CO_2$ incubator (5%) at 37° C. in recommended supplemented media containing 10 to 20% fetal calf serum and were checked periodically for *Mycoplasma*.

Antibodies and conjugation methods. Epratuzumab and veltuzumab are humanized anti-CD22 and anti-CD20 IgG1 monoclonal antibodies, respectively. Labetuzumab (Lmab), a humanized anti-CEACAM5 IgG1, and RS7, a humanized anti-TROP-2 antibody (both from Immunomedics, Inc.), were used as nonbinding, irrelevant controls. Herein, Emab-SN-38, Vmab-SN-38, and Lmab-SN-38 refer to conjugates prepared using the CL2A linker that was described above. In vitro studies in human serum showed that approximately 50% of the active SN-38 moiety is released from the IgG each day (Cardillo et al., 2011, *Clin Cancer Res* 17:3157-69). Another linker, designated CL2E, is stable in human serum over 14 days, but it contains a cathepsin B cleavage site to facilitate the release of SN-38 when processed in lysosomes. The method to prepare CL2E and the structures of the CL2A and CL2E linkers are given in the Examples above. The conjugates contained approximately 6 SN-38 units per IgG (e.g., 1.0 mg of the IgG-SN-38 conjugate contains ~16 μg of SN-38).

In vitro cell binding and cytotoxicity. Flow cytometry was carried out using the unconjugated specific and irrelevant antibodies incubated for 1 hour at 4° C., with binding revealed using fluorescein isothiocyanate (FITC)-Fcγ fragment-specific goat anti-human IgG (Jackson ImmunoResearch), also incubated for 1 hour at 4° C. Median fluorescence was determined on a FACSCALIBUR® flow cytometer (Becton Dickinson) using a CellQuest software package.

Cytotoxicity was determined using the MTS dye reduction assay (Promega). Dose-response curves [with/without goat anti-human Fcγ F(ab')$_2$; Jackson ImmunoResearch] were generated from the mean of triplicate determinations, and $IC_{50}$-values were calculated using PRISM® GraphPad software (v5), with statistical comparisons using an F test on the best fit curves for the data. Significance was set at $P<0.05$.

Immunoblotting. After 24- or 48-hour exposure to the test agents, markers of early (p21 expression) and late (PARP cleavage) apoptosis were revealed by Western blotting.

In vivo studies. The subcutaneous Ramos model was initiated by implanting $1\times10^7$ cells (0.2 mL) from culture (>95% viability) into 4- to 6-week-old female nude mice (Taconic). Three weeks from implantation, animals with tumors ranging from 0.4 to 0.8 cm$^3$ (measured by caliper, L×W×D) were segregated into groups of animals, each with the same range of tumor sizes. Tumor size and body weights were measured at least once weekly, with animals removed from the study when tumors grew to 3.0 cm$^3$ or if they experienced 20% or greater body weight loss. The intravenous WSU-FSCCL and 697 models were initiated by intravenous injection of $2.5\times10^6$ and $1\times10^7$ cells, respectively, in female severe combined immunodeficient (SCID) mice (Taconic). Treatment began 5 days after administration of the WSU-FSCCL cells and 7 days after the 697 inoculation. Animals were observed daily, using hind leg paralysis or other signs of morbidity as surrogate survival endpoints. All treatments were given intraperitoneally in ≤0.2 mL. The specific dosages and frequency are given in the Results section. Because mice convert irinotecan to SN-38 efficiently, irinotecan dosing was adjusted on the basis of SN-38 equivalents; SN-38 mole equivalents are based on 1.6% of ADC mass and 60% of irinotecan mass.

Efficacy was expressed in a Kaplan-Meier curve, using time to progression (TTP) as surrogate survival endpoints as indicated above. Statistical analysis was conducted by a log-rank test using PRISM® GraphPad software (significance, $P<0.05$).

Results

Antigen expression and cytotoxicity in vitro. All cell lines were highly susceptible to SN-38, with $EC_{50}$ values ranging from 0.13 nmol/L for Daudi to 2.28 nmol/L for RS4;11 (Table 9). Except for 697 and RS4;11, the Emab-SN-38 anti-CD22 conjugate was 2- to 7-fold less effective than SN-38. This is a common finding with our targeted, as well as other nontargeted, SN-38 conjugates. Despite differences in antigen expression, the Emab-SN-38 and Vmab-SN-38 had similar potencies as the nonbinding, Lmab-SN-38 anti-CEACAM5 conjugate, which was likely due to dissociation of approximately 90% of SN-38 during the 4-day MTS assay. Other in vitro procedures using shorter exposure times were also ineffective in discriminating differences in the potencies of conjugates. For example, Annexin V staining after a 1-day exposure failed to find differences between untreated and treated cells (not shown). Upregulation of p21 and PARP cleavage was also examined as early and late markers of apoptosis, respectively. Ramos did not express p21. However, PARP cleavage was detected, but only after a 48-hour exposure, being more strongly expressed in SN-38-treated cells (not shown). The WSU-FSCCL cell line expressed p21, but neither p21 upregulation nor PARP cleavage was evident until 48 hours after Emab-SN-38 exposure. However, both were observed after a 24-hour exposure with free SN-38 (not shown). While the enhanced intensity and earlier activation of apoptotic events with free SN-38 are consistent with its lower $EC_{50}$ over the IgG-conjugated form, the results indicated that an exposure period of at least 48 hours would be required, but at this time, approximately 75% of the SN-38 would be released from the conjugate.

TABLE 9

Expression of CD20 and CD22 by FACScan and in vitro cytotoxicity by MTS assay of SN-38 and specific Emab anti-CD22-SN-38, Vmab anti-CD20-SN-38, and Lmab anti-CEACAM5-SN-38 conjugates against several hematopoietic tumor cell lines

| | CD20 expression | CD22 expression | $EC_{50}$ values[a] | | | | | | | |
|---|---|---|---|---|---|---|---|---|---|---|
| Cell line | Median fluorescence (background) | Median fluorescence (background) | SN-38, nmol/L | 95% CI | Emab-SN-38 nmol/L | 95% CI | Vmab-SN-38, nmol/L | 95% CI | Lmab-SN-38, nmol/L | 95% CI |
| NHL:Burkitt | | | | | | | | | | |
| Raji | 422.2 (6.8) | 45.9 (6.8) | 1.42 | 0.8-2.4 | 2.10 | 1.2-3.8 | ND | — | ND | — |
| | | | | | 4.61 | 2.2-9.5 | 4.88 | 2.7-9.0 | 3.73 | 1.8-7.6 |
| Ramos | 620.4 (4.1) | 40.8 (4.1) | 0.40 | 0.2-0.7 | 2.92 | 1.6-5.4 | ND | — | ND | — |
| | | | | | 9.84 | 4.5-21.6 | 13.56 | 4.9-37.2 | 8.08 | 2.9-22.2 |
| Daudi | 815.1 (5.9) | 145.0 (5.9) | 0.13 | 0.1-0.2 | 0.52 | 0.4-0.7 | ND | — | ND | — |
| NHL:follicular | | | | | | | | | | |
| WSU-FSCCL | 97.4 (4.9) | 7.7 (4.9) | 0.50 | 0.3-1.0 | 0.68 | 0.4-1.1 | ND | — | ND | — |
| | | | | | 1.05 | 0.8-1.4 | 0.83 | 0.6-1.1 | 1.17 | 0.8-1.7 |
| NHL:mantle cell | | | | | | | | | | |
| Jeko-1 | 604.6 (6.5) | 11.2 (6.5) | ND | — | 2.25 | 1.3-3.8 | 1.98 | 1.1-3.5 | 2.27 | 1.3-3.9 |
| ALL:B cell | | | | | | | | | | |
| REH | 12.3 (4.1) | 22.9 (4.1) | 0.47 | 0.3-0.9 | 1.22 | 0.8-1.9 | ND | — | ND | — |
| 697 | 6.9 (4.2) | 16.0 (4.2) | 2.23 | 1.3-3.9 | 2.67 | 1.7-3.7 | ND | — | ND | — |
| RS4; 11 | 3.7 (4.1) | 23.3 (4.1) | 2.28 | 1.1-4.9 | 1.68 | 1.0-3.0 | ND | — | ND | — |
| MN-60 | 21.5 (5.8) | 10.3 (5.8) | 1.23 | 0.6-2.1 | 3.65 | 2.2-6.2 | ND | — | ND | — |

Abbreviations:
CI, confidence interval;
ND, not determined,
[a]$EC_{50}$ expressed as mole equivalents of SN-38 in Emab-SN-38.

We again examined PARP cleavage and p21 expression, this time in cells treated with Emab-SN-38+Vmab. Confirming the earlier study in Ramos, PARP cleavage first occurs only after a 48-hour exposure to the conjugate, with expression unchanged in the presence of a cross-linking antibody (not shown). Exposure to veltuzumab for more than 48 hours had no effect on PARP cleavage, but cleavage was strong within 24 hours when a cross-linking antibody was added (not shown). However, when veltuzumab alone (no cross-linker) was combined with Emab-SN-38, PARP cleavage occurred after a 24-hour exposure (not shown), indicating veltuzumab could induce a more rapid onset of apoptosis, even in the absence of cross-linking. The only notable difference in the WSU-FSCCL cell line was that the combination greatly enhanced p21 expression at 48 hours (not shown), again suggesting an acceleration of apoptosis induction when veltuzumab is combined with the Emab-SN-38 conjugate. The delay in apoptosis induction in WSU-FSCCL as compared with Ramos is likely explained by the lower expression of CD22 and CD20.

Ultratoxic agents often use linkers that are highly stable in serum, as their premature release would increase toxicity, but these conjugates must be internalized for the drug to be delivered optimally. Because epratuzumab internalizes rapidly, we examined whether it might benefit from a more stably linked SN-38, comparing in vitro cytotoxicity of the CL2A-linked Emab-SN-38 conjugate with the serum-stable CL2E-SN-38 conjugate. Both conjugates had a similar binding affinity (not shown), but the more stable Emab-CL2E-SN-38 was approximately 40- to 55-times less potent than the CL2A conjugate in 3 cell lines (not shown). While specificity was lacking with the CL2A conjugates, the Emab-CL2E-SN-38 consistently was approximately two times more potent than the nonbinding Lmab-anti-CEACAM5-CL2E-SN-38 conjugate (not shown). We concluded that it was unlikely that the more stably linked conjugate would be appropriate for a slowly internalizing veltuzumab conjugate and therefore continued our investigation only with CL2A-linked SN-38 conjugates.

Because of limitations of the in vitro assays, efficacy was assessed in xenograft models. As indicated in Table 9, all of the lymphoma cell lines have much higher expression of CD20 than CD22. Daudi had the highest expression of CD22 and CD20, but it is very sensitive in vivo to unconjugated veltuzumab and in vitro testing revealed the highest sensitivity to SN-38 (Table 9). These properties would likely make it difficult to assess differences in activity attributed to the SN-38 conjugate versus the unconjugated antibody, particularly when unconjugated epratuzumab is not an effective therapeutic in animals. Because Ramos had been used previously to show an advantage for combining $^{90}$Y-Emab with veltuzumab (Mattes et al., 2008, *Clin Cancer Res* 14:6154-60), we elected to start with a comparison of the Emab-SN-38 and Vmab-SN-38 conjugates in the Ramos human Burkitt cell line. Despite flow cytometry showing a 15-fold higher expression of CD20 over CD22, immunohistology of Ramos xenografts showed abundant CD22 and CD20, with CD22 seemingly expressed more uniformly than CD20 (not shown).

Ramos xenografts in untreated animals progressed rapidly, reaching the 3.0-$cm^3$ termination size from their starting size of 0.4 $cm^3$ within 6 days (not shown), and as reported previously, neither veltuzumab nor epratuzumab appreciably affected the progression of well-established Ramos xenografts (Sharkey et al., 2009, *J Nucl Med* 50:444-53). Consistent with previous findings using other SN-38 conjugates, none of the animals treated with a 4-week, twice-weekly, 0.5 mg/dose treatment regimen had appreciable weight loss. Both conjugates were highly effective in controlling tumor growth, with 80% or more of the animals having no evidence of tumor by the end of the 4-week treatment (FIG. 6). The 0.25-mg Vmab-SN-38 dose was better at controlling growth over the first 4 weeks, but at 0.5 mg, similar early growth control was observed for both conjugates. Thus, despite a 15-fold higher expression of CD20 than CD22, Emab-SN-38 compared favorably with Vmab-SN-38. Therefore, the remaining studies focused on Emab-SN-38 alone or in combination with unconjugated veltuzumab.

Emab-SN-38 dose-response and specificity. A dose-response relationship was seen for the specific Emab-SN-38 and irrelevant Lmab-SN-38 conjugates, but Emab-SN-38 had significantly better growth control at 2 of the 3 levels tested, and with a strong trend favoring the specific conjugate at the intermediate dose (FIG. 7). Again, 0.25 mg of Emab-SN-38 ablated a majority of the tumors; here, 7 of 10 animals were tumor-free at the end of the 12-week monitoring period, with no change in body weight. Animals given irinotecan alone (6.5 μg/dose; approximately the same SN-38 equivalents as 0.25 mg of conjugate) had a median survival of 1.9 weeks, with 3 of 11 animals tumor-free at the end of the study, which was not significantly different from the 3.45-week median survival for the irrelevant Lmab-SN-38 conjugate (P=0.452; FIG. 7C).

In the 697-disseminated leukemia model, the median survival of saline-treated animals was just 17 days from tumor inoculation. Animals given unconjugated epratuzumab plus irinotecan (same mole equivalents of SN-38 as 0.5 mg of the conjugate) had the same median survival, whereas animals given 0.5 mg of Emab-SN-38 twice weekly starting 7 days from tumor inoculation survived to 24.5 days, significantly longer than untreated animals (P<0.0001) or for unconjugated epratuzumab given with irinotecan (P=0.016). However, Emab-SN-38 was not significantly better than the irrelevant conjugate (median survival=22 days; P=0.304), most likely reflecting the low expression of CD22 in this cell line.

Emab-SN-38 combined with unconjugated Vmab anti-CD20. We previously reported improved responses when $^{90}$Y-Emab was combined with unconjugated veltuzumab in the subcutaneous Ramos model (Mattes et al., 2008, *Clin Cancer Res* 14:6154-60) and thus this possibility was examined with Emab-SN-38. In a pilot study, 5 animals bearing subcutaneous Ramos tumors averaging approximately 0.3 $cm^3$ were given veltuzumab (0.1 mg), 0.1 mg of Emab-SN-38, or Emab-SN-38+Vmab (all agents given twice weekly for 4 weeks). The median TTP to 2.0 $cm^3$ was 22, 14, and more than 77 days, respectively (veltuzumab vs. Emab-SN-38 alone, P=0.59; Emab-SN-38+Vmab vs. Emab-SN-38, P=0.0145), providing an initial indication that the combination of veltuzumab with Emab-SN-38 improved the overall therapeutic response. In a follow-up study that also used a twice-weekly, 4-week treatment regimen, 6 of 11 animals given 0.1 mg of Emab-SN-38 plus 0.1 mg of veltuzumab had no evidence of tumors 16 weeks from the start of treatment, whereas the median survival for animals receiving veltuzumab alone or with 0.1 mg of the control Lmab-SN-38 was 1.9 and 3.3 weeks, respectively, with 3 of 11 animals being tumor-free at 16 weeks in each of these groups (not shown). Despite the longer median TTP and more survivors, no significant differences were found between the groups. Thus, in the Ramos model, which has abundant CD20 and moderate levels of CD22, the Emab-SN-38 conjugate given at nontoxic dose levels was not significantly better than unconjugated anti-CD20 therapy, but the addition of Emab-SN-38 to unconjugated anti-CD20 therapy appeared to improve the response without toxicity. It is important to emphasize that the SN-38 conjugates are given at levels far less than their maximum tolerated dose, and therefore these results should not be interpreted that the unconjugated anti-CD20 therapy is equal to that of the Emab-SN-38 conjugate.

Two additional studies were conducted in an intravenous implanted model using the WSU-FSCCL follicular NHL cell line that has a low expression of CD20 and CD22 (not shown). The median survival time for saline-treated animals was 40 to 42 days from tumor implantation. Irinotecan alone (not shown), given at a dose containing the same SN-38 equivalents as 0.3 mg of the ADC, increased the median survival (49 vs. 40 days, respectively; P=0.042), but 14 of 15 animals succumbed to disease progression on day 49, the same day the final 4 of 15 animals in the saline group were eliminated (not shown). Despite its relatively low CD20 expression, veltuzumab alone (35 μg twice weekly×4 weeks) was effective in this model. The median survival increased to 91 days in the first study, with 2 cures (day 161), and to 77 days in the second, but with no survivors after 89 days (veltuzumab alone vs. saline-treated, P<0.001 in both studies). Unconjugated epratuzumab (0.3 mg/dose) combined with irinotecan and veltuzumab had the same median survival as veltuzumab alone, suggesting that neither epratuzumab nor irinotecan contributed to the net response.

As expected because of the low CD22 expression by WSU-FSCCL, Emab-SN-38 alone was not as effective as in Ramos. At the 0.15-mg dose, no significant benefit over the saline group was seen, but at 0.3 mg, the median survival increased to 63 days, providing a significant improvement compared with the saline-treated animals (P=0.006). The second study, using 0.3 mg of Emab-SN-38, confirmed an enhanced survival compared with the saline group (75 vs. 40 days; P<0.0001). The specificity of this response was not apparent in the first study, where the median survival of the irrelevant Lmab-SN-38 conjugate and Emab-SN-38 were not different at either 0.15- or 0.3-mg dose levels (42 vs. 49 days and 63 vs. 63 days for the Emab-SN-38 vs. anti-CEACAM5-SN-38 conjugates at the 2 doses levels, respectively). However, in the second study, the 0.3-mg dose of Emab-SN-38 provided a significantly improved survival over the irrelevant conjugate (75 vs. 49 days; P<0.0001). Again, the difficulty in showing specificity in this model is most likely related to low CD22 expression.

Combining the specific Emab-SN-38 with veltuzumab substantially increases survival, with evidence of more robust responses than the control Lmab-SN-38. For example, in the first study, animals treated with veltuzumab plus 0.15 or 0.3 mg of the control conjugate had a median survival of 98 and 91 days, respectively, which was similar to that of veltuzumab alone (91 days; not shown). However, veltuzumab plus 0.15 mg of the specific Emab-SN-38 conjugate increased the median survival to 140 days. While this improvement was not significantly higher than veltuzumab alone (P=0.257), when the Emab-SN-38 dose was increased to 0.3 mg with veltuzumab, 6 of 10 animals remained alive at the end of the study, providing a significant survival advantage over the control conjugate plus veltuzumab (P=0.0002). In a second study, the median survival of veltuzumab alone was shorter than in the first (77 vs. 91 days), yet the median survival for the control conjugate with veltuzumab was again 91 days, which now yielded a significant survival advantage over veltuzumab alone (P<0.0001). Combining the specific Emab-SN-38 conjugate with veltuzumab extended the median survival to 126 days, which was significantly longer than the median survival of 75 and 77 days for Emab-SN-38 and veltuzumab alone, respectively (P<0.0001 for each). However, in this study, it did not quite meet the requirements for a statistical improvement over the combination with control anti-CEACAM5-SN-38 conjugate (P=0.078).

Discussion

Over the past 10 years, ADCs have made substantial gains in cancer therapy, yet there also have been some setbacks. The gains occurred largely when investigators chose to examine agents that were too toxic to be used alone, but when coupled to an antibody, these so-called ultratoxics produced substantially improved responses in preclinical testing. The recent approval of brentuximab vedotin, an auristatin conjugate, in Hodgkin lymphoma and the clinical success with trastuzumab-DM1 anti-HER2-maytansine conjugate as a single agent in breast cancer refractive to unconjugated trastuzumab suggest that these ADCs bearing ultratoxic agents are becoming accepted treatment modalities. However, conjugates prepared with agents that are themselves potent in the picomolar range can have an increased risk for toxicity, as the recent decision to withdraw gemtuzumab ozogamicin, the anti-CD33-calicheamicin conjugate, from the market suggests (Ravandi, 2011, *J Clin Oncol* 29:349-51). Thus, the success of an ADC may depend on identifying appropriate chemistries to bind the drug and antibody together, as well as defining a suitable target that is sufficiently expressed to allow an adequate and selective delivery of the cytotoxic agent.

We developed a linker for coupling SN-38 to IgG that allows SN-38 to be released slowly from the conjugate in serum (about 50% per day). With this linker, an antibody that is slowly internalized could be an effective therapeutic, perhaps because the conjugate localized to a tumor releases a sufficient amount of drug locally, even without being internalized. The CL2A linker also was used recently with an antibody to TROP-2 that was reported to be internalized rapidly (Cardillo et al., 2011, *Clin Cancer Res* 17:3157-69.). Thus, it appears that the slow release mechanism is beneficial for internalizing and noninternalizing antibodies.

In this report, we expanded our assessment of the CL2A linker by comparing SN-38 conjugates prepared with epratuzumab, a rapidly internalizing anti-CD22 IgG, and veltuzumab, a slowly internalizing anti-CD20 IgG, for the treatment of B-cell malignancies. Prior studies with the murine parent of epratuzumab had indicated that most of the antibody internalizes within 1 hour and 50% of CD22 is reexpressed on the cell surface within 5 hours (Shih et al., 1994, *Int J Cancer* 56:538-45). This internalization and reexpression process would permit intracellular delivery that might compensate for lower surface expression of CD22. Because many of the B-cell malignancies express much more CD20 than CD22, a conjugate targeting CD20 might deliver more moles of drug by releasing its toxic payload after being localized in the tumor.

In vitro cytotoxicity studies could not discriminate the potency of the specific conjugates or even an irrelevant conjugate because of the release of SN-38 from the conjugate into the media. Indeed, SN-38 alone was somewhat more potent than the conjugates, which may reflect its accelerated ability to enter the cell and engage topoisomerase I. Because other studies revealed that the conjugates required a 48-hour exposure before early signs of apoptosis could be seen, we concluded that in vitro testing would not be able to discriminate the potency of these 2 conjugates and therefore resorted to in vivo studies.

In xenograft models, both conjugates had similar antitumor activity against Ramos tumors, which flow cytometry had indicated expressed nearly 15-fold more CD20 than CD22. This lent support to selecting the Emab anti-CD22-SN-38 conjugate especially because it could be combined with unconjugated Vmab anti-CD20 therapy without concern that either agent would interfere with the binding of the other agent. Indeed, if an anti-CD20-SN-38 conjugate were used, the total IgG protein dose given likely would be below a level typically needed for effective unconjugated anti-CD20 antibody treatments, as the dose-limiting toxicity would be driven by the SN-38 content. Adding more unlabeled anti-CD20 to an anti-CD20-SN-38 conjugate would risk reducing the conjugate's uptake and potentially diminishing its efficacy. However, as we showed previously in combination studies using radiolabeled epratuzumab with unconjugated veltuzumab, benefit can be derived from both agents given at their maximum effective and safe dosages. In vitro studies showed veltuzumab, even in the absence of cross-linking that is used to enhance signaling, accelerated apoptotic events initiated with Emab-SN-38. Thus, as long as the Emab-SN-38 conjugate was as effective as the anti-CD20 conjugate, selecting the Emab-SN-38 conjugate is a logical choice because it allows for a more effective combination therapy, even in tumors where one or both of the antigens are low in expression.

Because most ADCs using ultratoxic drugs are stably linked, we also tested a serum-stable, but intracellularly cleavable, anti-CD22-SN-38 conjugate, but determined it was 40- to 55-fold less potent than the CL2A linker Others have examined a variety of ultratoxic drugs conjugated to anti-CD20 or anti-CD22 antibodies, finding that internalizing conjugates are generally more active, but also observing that even slowly internalizing antibodies could be effective if the released drug penetrated the cell membrane. While the CL2A-type linker may be appropriate for SN-38, it may not be optimal for a more toxic agent, where even a small, sustained release in the serum would increase toxicity and compromise the therapeutic window.

Emab-SN-38 was active at a cumulative dose of 0.6 mg in mice bearing Ramos (75 μg twice weekly for 4 weeks), which extrapolates to a human dose of just 2.5 mg/kg. Thus, Emab-SN-38 should have an ample therapeutic window in patients. Furthermore, an effective and safe dose of the anti-TROP-2-SN-38 conjugate was combined with a maximum tolerated dose of a $^{90}$Y-labeled antibody without an appreciable increase in toxicity but with improved efficacy (Sharkey et al., 2011, *Mol Cancer Ther* 10:1072-81). Thus, the safety and efficacy profile of these SN-38 antibody conjugates are very favorable for other combination therapies.

Even though irinotecan is not used routinely for the treatment of hematopoietic cancers, SN-38 was as potent in lymphoma and leukemia cell lines as in solid tumors (Cardillo et al., 2011, *Clin Cancer Res* 17:3157-69.). In the WSU-FSCCL cell line, the specific and irrelevant IgG conjugates were significantly better than irinotecan, whereas in Ramos, the median TTP with the irrelevant conjugate was longer but not significantly better than irinotecan. These results are consistent with other studies that have shown that a nonspecific IgG is an excellent carrier for drugs and more potent in vivo than free drug or conjugates prepared with albumin or polyethylene glycol (PEG)-Fc. While the PEG-SN-38 conjugate had significant antitumor effects, it was given at its maximum tolerated amounts, ranging from 10 to 30 mg/kg SN-38 equivalents (Sapra et al., 2009, *Haematologica* 94:1456-9). In contrast, the maximum cumulative dose of SN-38 given over 4 weeks to animals bearing Ramos was only 1.6 mg/kg (i.e., dosing of 0.25 mg of Emab-SN-38 given twice weekly over 4 weeks) and this was nontoxic.

The specific therapeutic activity of Emab-SN-38 appeared to improve in cell lines with higher CD22 expression. For example, in Ramos, specific therapeutic effects of Emab-SN-38 alone were recorded at 2 of the 3 different dose levels examined, and a sizeable number of tumors were completely ablated. In contrast, in WSU-FSCCL that had about 2.5-fold lower expression of CD22, Emab-SN-38 improved survival significantly compared with the irrelevant anti-CEACAM5-SN-38 conjugate in 1 of 2 studies. However, it is important to emphasize that when used in combination with unconjugated anti-CD20 therapy, Emab-SN-38 amplifies the therapeutic response. Thus, the combination of these two treatments could augment the response even in situations where CD22 is not highly expressed.

In conclusion, using the less-stable CL2A-SN-28 linker, Emab anti-CD22-SN-38 conjugate was equally active at nontoxic doses in vivo as a similar anti-CD20-SN-38 conjugate, despite the fact that CD20 expression was more than a log-fold higher than CD22. Therapeutic responses benefited by the combination of Emab-SN-38 with unconjugated Vmab anti-CD20 therapy, even when CD22 expression was low, suggesting that the combination therapy could improve responses in a number of B-cell malignancies when both antigens are present The current studies suggest that this combination is very potent in diverse lymphoma and leukemia preclinical models, yet appears to have less host toxicity.

Example 13

Anti-CD74 (Milatuzumab)SN-38 Conjugates for Treatment of CD74+Human Cancers

Abstract

CD74 is an attractive target for antibody-drug conjugates (ADC), because it internalizes and recycles after antibody binding. CD74 mostly is associated with hematological cancers, but is expressed also in solid cancers. Therefore, the utility of ADCs prepared with the humanized anti-CD74 antibody, milatuzumab, for the therapy CD74-expressing solid tumors was examined. Milatuzumab-doxorubicin and two milatuzumab-SN-38 conjugates were prepared with cleavable linkers (CL2A and CL2E), differing in their stability in serum and how they release SN-38 in the lysosome. CD74 expression was determined by flow cytometry and immunohistology. In vitro cytotoxicity and in vivo therapeutic studies were performed in the human cancer cell lines A-375 (melanoma), HuH-7 and Hep-G2 (hepatoma), Capan-1 (pancreatic), and NCI-N87 (gastric), and Raji Burkitt lymphoma. The milatuzumab-SN-38 ADC was compared to SN-38 ADCs prepared with anti-TROP-2 and anti-CEACAM6 antibodies in xenografts expressing their target antigens.

Milatuzumab-doxorubicin was most effective in the lymphoma model, while in A-375 and Capan-1, only the milatuzumab-CL2A-SN-38 showed a therapeutic benefit. Despite much lower surface expression of CD74 than TROP-2 or CEACAM6, milatuzumab-CL2A-SN-38 had similar efficacy in Capan-1 as anti-TROP-2 CL2A-SN-38, but in NCI-N87, the anti-CEACAM6 and anti-TROP-2 conjugates were superior. Studies in 2 hepatoma cell lines at a single dose level showed significant benefit over saline-treated animals, but not against an irrelevant IgG conjugate. CD74 is a suitable target for ADCs in some solid tumor xenografts, with efficacy largely influenced by uniformity of CD74 expression, and with CL2A-linked SN-38 conjugates providing the best therapeutic responses.

Introduction

CD74, referred to as invariant chain or Ii, is a type II transmembrane glycoprotein that associates with HLA-DR and inhibits the binding of antigenic peptides to the class II antigen presentation structure. It serves as a chaperone molecule, directing the invariant chain complexes to endosomes and lysosomes, an accessory molecule in the maturation of B cells, using a pathway mediated by NF-kB, and in T-cell responses via interactions with CD44 (Naujokas et al., 1993, Cell 74:257-68), and it is a receptor for the pro-inflammatory cytokine, macrophage migration inhibitory factor (Leng et al., 2003, *J Exp Med* 197:1467-76), which is involved in activating cell proliferation and survival pathways.

In normal human tissues, CD74 is primarily expressed in B cells, monocytes, macrophages, dendritic cells, Langerhans cells, subsets of activated T cells, and thymic epithelium (not shown), and it is expressed in over 90% of B-cell tumors (Burton et al., 2004, *Clin Cancer Res* 10:6606-11; Stein et al., 2004, *Blood* 104:3705-11). Early studies had conflicting data on whether CD74 is present on the membrane, in part because the antibodies to the invariant chain were specific for the cytoplasmic portion of the molecule, but also because there are relatively few copies on the surface, and its half-life on the cell surface is very short. Approximately 80% of the CD74 on the cell surface is associated with the MHC II antigen HLA-DR (Roche et al., 1993, *PNAS USA* 90:8581-85). Using the murine anti-CD74 antibody, LL1, the Raji Burkitt lymphoma cell line was estimated to have $4.8\times10^4$ copies/cell, but because of rapid intracellular transit, ~$8\times10^6$ antibody molecules were internalized and catabolized per day (Hansen et al., 1996, *Biochem J* 320:293-300). Thus, CD74 internalization is highly dynamic, with the antibody being moved quickly from the surface and unloaded inside the cell, followed by CD74 re-expression on the surface. Fab' internalization occurs just as rapidly as IgG binding, indicating that bivalent binding is not required. Later studies with a CDR-grafted version of murine LL1, milatuzumab (hLL1), found that the antibody could alter B-cell proliferation, migration, and adhesion molecule expression (Stein et al., 2004, *Blood* 104:3705-11; Qu et al., 2002, *Proc Am Assoc Cancer Res* 43:255; Frolich et al., 2012, *Arthritis Res Ther* 14:R54), but the exceptional internalization properties of the anti-CD74 antibody made it an efficient carrier for the intracellular delivery of cancer therapeutics (e.g., Griffiths et al., 2003, *Clin Cancer Res* 9:6567-71). Based on preclinical efficacy and toxicology results, Phase I clinical trials with milatuzumab-doxorubicin in multiple myeloma (Kaufman et al., 2008, *ASH Annual Meeting Abstracts,* 112:3697), as well as non-Hodgkin lymphoma and chronic lymphocytic leukemia, have been initiated.

Interestingly, CD74 also is expressed in non-hematopoietic cancers, such as gastric, renal, urinary bladder, non-small cell lung cancers, certain sarcomas, and glioblastoma (e.g., Gold et al., 2010, *Int J Clin Exp Pathol* 4:1-12), and therefore it may be a therapeutic target for solid tumors expressing this antigen. Since a milatuzumab-doxorubicin conjugate was highly active in models of hematological cancers, it was a logical choice for this assessment. However, we recently developed procedures for coupling the highly potent topoisomerase I inhibitor, SN-38, to antibodies. SN-38 is the active form of irinotecan, whose pharmacology and metabolism are well known. These conjugates have nanomolar potency in solid tumor cell lines, and were found to be active with antibodies that were not actively internalized. Prior studies indicated a preference for a linker (CL2A) that allowed SN-38 to dissociate from the conjugate in serum with a half-life of ~1 day, rather than other linkers that were either more or less stable in serum. However, given milatuzumab's exceptional internalization capability, a new linker that is highly stable in serum, but can release SN-38 when taken into the lysosome, was developed.

The current investigation examines the prospects for using these three milatuzumab anti-CD74 conjugates, one with doxorubicin, and two SN-38 conjugates, for effective therapy primarily against solid tumors.

Materials and Methods

Human tumor cell lines. Raji Burkitt lymphoma, A-375 (melanoma), Capan-1 (pancreatic adenocarcinoma), NCI-N87 (gastric carcinoma), Hep-G2 hepatoma and MC/CAR myeloma cell lines were purchased from American Tissue Culture Collection (Manassas, Va.). HuH-7 hepatoma cell line was purchased from Japan Health Science Research Resources Bank (Osaka, Japan). All cell lines were cultured in a humidified $CO_2$ incubator (5%) at 37° C. in recommended media containing 10% to 20% fetal-calf serum and supplements. Cells were passaged <50 times and checked regularly for mycoplasma.

Antibodies and conjugation methods. Milatuzumab (anti-CD74 MAb), epratuzumab (anti-CD22), veltuzumab (anti-CD20), labetuzumab (anti-CEACAM5), hMN15 (anti-CEACAM6), and hRS7 (anti-TROP-2) are humanized $IgG_1$ monoclonal antibodies. CL2A and CL2E linkers and their SN-38 derivatives were prepared and conjugated to antibodies as described in the Examples above. The milatuzumab-doxorubicin conjugates were prepared as previously described (Griffiths et al., 2003, *Clin Cancer Res* 9:6567-71). All conjugates were prepared by disulfide reduction of the IgG, followed by reaction with the corresponding maleimide derivatives of these linkers. Spectrophotometric analyses estimated the drug:IgG molar substitution ratio was 5-7 (1.0 mg of the protein contains ~16 μg of SN-38 or 25 μg of doxorubicin equivalent).

In vitro cell binding and cytotoxicity. Assays to compare cell binding of the unconjugated and conjugated milatuzumab to antigen-positive cells and cytotoxicity testing used the MTS dye reduction method (Promega, Madison, Wis.).

Flow cytometry and immunohistology. Flow cytometry was performed in a manner that provided an assessment of only membrane-bound or membrane and cytoplasmic antigen. Immunohistology was performed on formalin-fixed, paraffin-embedded sections of subcutaneous tumor xenografts, staining without antigen retrieval methods, using antibodies at 10 μg/mL that were revealed with an anti-human IgG conjugate.

In vivo studies. Female nude mice (4-8 weeks old) or female SCID mice (7 weeks old) were purchased from Taconic (Germantown, N.Y.) and used after a 1-week quarantine. All agents, including saline controls, were administered intraperitoneally twice-weekly for 4 weeks. Specific doses are given in Results. Toxicity was assessed by weekly weight measurements. For the Raji Burkitt lymphoma model, SCID mice were injected intravenously with $2.5\times10^6$ Raji cells in 0.1 mL media. Five days later, animals received a single intravenous injection (0.1 mL) of the conjugate or saline (N=10/group). Mice were observed daily for signs of distress and paralysis, and were euthanized when either hind-limb paralysis developed, >15% loss of initial weight, or if otherwise moribund (surrogate survival endpoints).

Subcutaneous tumors were measure by caliper in two dimensions, and the tumor volume (TV) calculated as $L\times w^2/2$, where L is the longest diameter and w is the shortest. Measurements were made at least once weekly, with animals terminated when tumors grew to 1.0 $cm^3$ (i.e., surrogate survival end-point). The A-375 melanoma cell line ($6\times10^6$ cells in 0.2 mL) was implanted in nude mice and therapy was initiated when tumors averaged 0.23±0.06 $cm^3$ (N=8/group). Capan-1 was implanted subcutaneously in nude mice using a combination of tumor suspension from serially-passaged tumors (0.3 mL of a 15% w/v tumor suspension) combined with $8\times10^6$ cells from tissue culture. Treatments were initiated when TV averaged 0.27±0.05 $cm^3$ (N=10/group). NCI-N87 gastric tumor xenografts were initiated by injecting 0.2 mL of a 1:1 (v/v) mixture of matrigel and $1\times10^7$ cells from terminal culture subcutaneously. Therapy was started when the TV averaged 0.249±0.045 $cm^3$ (N=7/group). The same procedure was followed for developing the Hep-G2 and HuH-7 hepatoma xenografts in nude mice. Therapy was started when Hep-G2 averaged 0.364±0.062 $cm^3$ (N=5/group) and HuH-7 averaged 0.298±0.055 $cm^3$ (N=5/group).

Efficacy is expressed in Kaplan-Meier survival curves, using the surrogate end-points mentioned above for determining the median survival times. Analysis was performed by a log-rank (Mantel-Cox) test using Prism GraphPad software (LaJolla, Calif.), with significance at P<0.05.

Results

CD74 expression in human tumor cell lines and xenografts. Six cell lines derived from 4 different solid tumor types were identified as CD74-positive based primarily on the analysis of permeabilized cells (Table 10), since the MFI of membrane-only CD74 in the solid tumor cell lines very often was <2-fold higher than the background MFI (except A-375 melanoma cell line). Surface CD74 expression in Raji was >5-fold higher than the solid tumor cell lines, but total CD74 in permeabilized Raji cells was similar to most of the solid tumor cell lines.

TABLE 10

CD74 expression by flow cytometry expressed as mean fluorescent intensity (MFI) of milatuzumab-positive gated cells.

| Cell line | | Surface | | Surface and cytoplasmic | |
|---|---|---|---|---|---|
| | | hLL1 (bkgd)[a] | MFI Ratio hLL1:bkgd | hLL1 (bkgd)[b] | MFI Ratio hLL1:bkgd |
| Panc CA[c] | Capan-1 | 22 (12) | 1.8 | 248 (5) | 49.6 |
| Gastric | Hs746T | 17 (8) | 2.1 | 144 (5) | 28.8 |
| | NCI-N87 | 5 (4) | 1.3 | 220 (6) | 36.7 |
| Melanoma | A-375 | 16 (3) | 5.3 | 185 (6) | 30.8 |
| Hepatoma | Hep-G2 | 9 (6) | 1.5 | 156 (5) | 31.2 |
| | HuH-7 | 8 (5) | 1.6 | 114 (4) | 28.5 |
| Lymphoma | Raji | 59 (3) | 19.6 | 143 (5) | 28.6 |

ND, not done
[a]Background MFI of cells incubated with GAH-FITC only.

Immunohistology showed Raji subcutaneous xenografts had a largely uniform and intense staining, with prominent cell surface labeling (not shown). The Hep-G2 hepatoma cell line had the most uniform uptake of the solid tumors, with moderately strong, but predominantly cytoplasmic, staining (not shown), followed by the A-375 melanoma cell line that had somewhat less uniform staining with more intense, yet mostly cytoplasmic, expression (not shown). The Capan-1 pancreatic (not shown) and NCI-N87 (not shown) gastric carcinoma cell lines had moderate (Capan-1) to intense (NCI-N87) CD74 staining, but it was not uniformly distributed. The HuH-7 hepatoma cell line (not shown) had the least uniform and the weakest staining.

Immunoreactivity of the conjugates. $K_d$ values for unconjugated milatuzumab, milatuzumab-CL2A- and CL2E-SN-38 conjugates were not significantly different, averaging 0.77 nM, 0.59 nM, and 0.80 nM, respectively. $K_d$ values for the unconjugated and doxorubicin-conjugated milatuzumab measured in the MC/CAR multiple myeloma cell line were 0.5±0.02 nM and 0.8±0.2 nM, respectively (Sapra et al., 2008, *Clin Cancer Res* 14:1888-96).

In vitro drug release and serum stabilities of conjugates. The release mechanisms of SN-38 from the mercaptoethanol-capped CL2A and CL2E linkers were determined in an environment partially simulating lysosomal conditions, namely, low pH (pH 5.0), and in the presence or absence of cathepsin B. The CL2E-SN-38 substrate was inert at pH 5 in the absence of the enzyme (not shown), but in the presence of cathepsin B, cleavage at the Phe-Lys site proceeded quickly, with a half-life of 34 min (not shown). The formation of active SN-38 requires intramolecular cyclization of the carbamate bond at the $10^{th}$ position of SN-38, which occurred more slowly, with a half-life of 10.7 h (not shown).

As expected, cathepsin B had no effect on the release of active SN-38 in the CL2A linker. However, CL2A has a cleavable benzyl carbonate bond, releasing active SN-38 at a rate similar to the CL2E linker at pH 5.0, with a half-life of ~10.2 h (not shown). The milatuzumab-doxorubicin conjugate, which has a pH-sensitive acylhydrazone bond, had a half-life of 7 to 8 h at pH 5.0 (not shown).

While all of these linkers release the drug at relatively similar rates under lysosomally-relevant conditions, they have very different stabilities in serum. Milatuzumab-CL2A-SN-38 released 50% of free SN-38 in 21.55±0.17 h (not shown), consistent with other CL2A-SN-38 conjugates. The CL2E-SN-38 conjugate, however, was highly inert, with a half-life extrapolated to ~2100 h. The milatuzumab-doxorubicin conjugate released 50% of the doxorubicin in 98 h, which was similar to 2 other antibody-doxorubicin conjugates (not shown).

Cytotoxicity. A significant issue related to the evaluation of these conjugates was the relative potency of free doxorubicin and SN-38 in hematopoietic and solid tumor cell lines. Our group previously reported that SN-38 was active in several B-cell lymphoma and acute leukemia cell lines, with potencies ranging from 0.13 to 2.28 nM (Sharkey et al., 2011, *Mol Cancer Ther* 11:224-34). SN-38 potency in 4 of the solid tumor cell lines that were later used for in vivo therapy studies ranged from 2.0 to 6 nM (not shown). Doxorubicin had a mixed response, with 3-4 nM potency in the Raji lymphoma and the A-375 melanoma cell lines, but it was nearly 10 times less potent against Capan-1, NCI-N87, and Hep G2 cell lines. Other studies comparing the potency of SN-38 to doxorubicin found: LS174T colon cancer, 18 vs. 18 (nM potency of SN-38 vs. doxorubicin, respectively); MDA-MB-231 breast cancer, 2 vs. 2 nM; SK-OV-4 ovarian cancer, 18 vs. 90 nM; Calu-3 lung adenocarcinoma, 32 vs. 582 nM; Capan-2 pancreatic cancer, 37 vs. 221 nM; and NCI-H466 small cell lung cancer, 0.1 vs. 2 nM. Thus, SN-38 was 5- to 20-fold more potent than doxorubicin in 4 of these 6 cell lines, with similar potency in LS174T and MDA-MB-231. Collectively, these data indicate that doxorubicin is less effective against solid tumors than SN-38, while SN-38 appears to be equally effective in solid and hematopoietic tumors.

As expected, the 3 conjugate forms were often some order of magnitude less potent than the free drug in vitro, since both drugs are expected to be transported readily into the cells, while drug conjugates require antibody binding to transport drug inside the cell (not shown). The CL2A-linked SN-38 conjugate is an exception, since more than 90% of the SN-38 is released from the conjugate into the media over the 4-day assay period (Cardillo et al., 2011, *Clin Cancer Res* 17:3157-69; Sharkey et al., 2011, *Mol Cancer Ther* 11:224-34). Thus, even if the conjugate was internalized rapidly, it would be difficult to discern differences between the free drug and the CL2A-linked drug.

The stable CL2E-linked SN-38 performed comparatively well in the Raji cell line, compared to free SN-38, but it had substantially (7- to 16-fold) lower potency in the 4 solid tumor cell lines, suggesting the relatively low surface expression of CD74 may be playing a role in minimizing drug transport in these solid tumors. The milatuzumab-doxorubicin conjugate had substantial differences in its potency when compared to the free doxorubicin in all cell lines, which was of similar magnitude as the CL2E-SN-38 conjugates to free SN-38 in the solid tumor cell lines.

In the 6 additional cell lines mentioned above, the milatuzumab-CL2A-SN-38 conjugate was 9- to 60-times more potent than the milatuzumab-doxorubicin conjugate (not shown), but again, this result was influenced largely by the fact that the CL2A-linked conjugate releases most of its SN-38 into the media over the 4-day incubation period, whereas the doxorubicin conjugate would at most release 50% of its drug over this same time. The CL2E-linked milatuzumab was not examined in these other cell lines.

In vivo therapy of human tumor xenografts. Previous in vivo studies with the milatuzumab-doxorubicin or SN-38 conjugates prepared with various antibodies had indicated they were efficacious at doses far lower than their maximum tolerated dose (Griffiths et al., 2003, *Clin Cancer Res* 9:6567-71; Sapra et al., 2005, *Clin Cancer Res* 11:5257-64; Govindan et al., 2009, *Clin Cancer Res* 15:6052-61; Cardillo et al., 2011, *Clin Cancer Res* 17:3157-69; Sharkey et al., 2011, *Mol Cancer Ther* 11:224-34), and thus in vivo testing focused on comparing similar, but fixed, amounts of each conjugate at levels that were well-tolerated.

Initial studies first examined the doxorubicin and SN-38 conjugates in a disseminated Raji model of lymphoma in order to gauge how the milatuzumab-doxorubicin conjugate compared to the 2 SN-38 conjugates (not shown). All specific conjugates were significantly better than non-targeting labetuzumab-SN-38 conjugate or saline-treated animals, which had a median survival of only 20 days (P<0.0001). Despite in vitro studies indicating as much as an 8-fold advantage for the SN-38 conjugates in Raji, the best survival was seen with the milatuzumab-doxorubicin conjugates, where all animals given a single 17.5 mg/kg (350 μg) dose and 7/10 animals given 2.0 mg/kg (40 μg) were alive at the conclusion of the study (day 112) (e.g., 17.5 mg/kg dose milatuzumab-doxorubicin vs. milatuzumab-CL2A-SN-38, P=0.0012). Survival was significantly lower for the more stable CL2E-SN-38 conjugates (P<0.0001 and P=0.0197, 17.5 and 2.0 mg/kg doses for the CL2A vs. CL2E, respectively), even though in vitro studies suggested that both conjugates would release active SN-38 at similar rates when internalized.

Five solid tumor cell lines were examined, starting with the A-375 melanoma cell line, since it had the best in vitro response to both doxorubicin and SN-38. A-375 xenografts grew rapidly, with saline-treated control animals having a median survival of only 10.5 days (not shown). A 12.5 mg/kg (0.25 mg per animal) twice-weekly dose of the milatuzumab-CL2A-SN-38 conjugate extended survival to 28 days (P=0.0006), which was significantly better than the control epratuzumab-CL2A-SN-38 conjugate having a median survival of 17.5 days (P=0.0089), with the latter not being significantly different from the saline-treated animals (P=0.1967). The milatuzumab-CL2A conjugate provided significantly longer survival than the milatuzumab-CL2E-SN-38 conjugate (P=0.0014), which had the same median survival of 14 days as its control epratuzumab-CL2E-SN-38 conjugate. Despite giving a 2-fold higher dose of the milatuzumab-doxorubicin than the SN-38 conjugates, the median survival was no better than the saline-treated animals (10.5 days).

As with the A-375 melanoma model, in Capan-1, only the CL2A-linked SN-38 conjugate was effective, with a median survival of 35 days, significantly different from untreated animals (P<0.036) (not shown), even at a lower dose (5 mg/kg; 100 μg per animal) (P<0.02). Neither the milatuzumab-CL2E nor the non-targeting epratuzumab-CL2A-SN-38 conjugates, or a 2-fold higher dose of the milatuzumab-doxorubicin conjugate, provided any survival advantage (P=0.44 vs. saline). It is noteworthy that in the same study with animals given the same dose of the internalizing anti-TROP-2 CL2A-SN-38 conjugate (hRS7-SN-38; IMMU-132), the median survival was equal to milatuzumab-CL2A-SN-38 (not shown). The hRS7-CL2A-SN-38 conjugate had been identified previously as an ADC of interest for treating a variety of solid tumors (Cardillo et al., 2011, *Clin Cancer Res* 17:3157-69). The MFI for surface-binding hRS7 on Capan-1 was 237 (not shown), compared to 22 for milatuzumab (see Table 10). Thus, despite having a substantially lower surface antigen expression, the milatuzumab-CL2A-SN-38 conjugate performed as well as the hRS7-CL2A-SN-38 conjugate in this model.

With the milatuzumab-doxorubicin conjugate having inferior therapeutic results in 2 of the solid tumor xenografts, the focus shifted to compare the milatuzumab-SN-38 conjugates to SN-38 conjugates prepared with other humanized antibodies against TROP-2 (hRS7) or CEACAM6 (hMN-15), which are more highly expressed on the surface of many solid tumors (Blumenthal et al., 2007, *BMC Cancer* 7:2; Stein et al., 1993, *Int J Cancer* 55:938-46). Three additional xenograft models were examined.

In the gastric tumor model, NCI-N87, animals given 17.5 mg/kg/dose (350 μg) of milatuzumab-CL2A-SN-38 provided some improvement in survival, but it failed to meet statistical significance compared to the saline-treated animals (31 vs. 14 days; P=0.0760) or to the non-binding veltuzumab anti-CD20-CL2A-SN39 conjugate (21 days; P=0.3128) (not shown). However, the hRS7- and hMN-15-CL2A conjugates significantly improved the median survival to 66 and 63 days, respectively (P=0.0001). The MFI for surface-expressed TROP-2 and CEACAM6 were 795 and 1123, respectively, much higher than CD74 that was just 5 (see Table 10). Immunohistology showed a relatively intense cytoplasmic expression of CD74 in the xenograft of this cell line, but importantly it was scattered, appearing only in defined pockets within the tumor (not shown). CEACAM6 and TROP-2 were more uniformly expressed than CD74 (not shown), with CEACAM6 being more intensely present both cytoplasmically and on the membrane, and TROP-2 primarily found on the membrane. Thus, the improved survival with the anti-CEACAM6 and anti-TROP-2 conjugates most likely reflects both higher antigen density and more uniform expression in NCI-N87.

In the Hep-G2 hepatoma cell line (not shown), immunohistology showed a very uniform expression with moderate cytoplasmic staining of CD74, and flow cytometry indicated a relatively low surface expression (MFI=9). The MFI with hMN-15 was 175 and immunohistology showed a fairly uniform membrane and cytoplasmic expression of CEACAM6, with isolated pockets of very intense membrane staining (not shown). A study in animals bearing Hep-G2 xenografts found the milatuzumab-CL2A-SN-38 extended survival to 45 days compared to 21 days in the saline-treated group (P=0.0048), while the hMN-15-CL2A-SN-38 conjugate improved survival to 35 days. There was a trend favoring the milatuzumab conjugate over hMN-15-CL2A-SN-38, but it did not achieve statistical significance (46 vs. 35 days; P=0.0802). However, the non-binding veltuzumab-CL2A-SN-38 conjugate provided a similar survival advantage as the milatuzumab conjugate. We previously observed therapeutic results with non-binding conjugates could be similar to the specific CL2A-linked conjugate, particularly at higher protein doses, but titration of the specific and control conjugates usually revealed selectively. Thus, neither of the specific conjugates provided a selective therapeutic advantage at these doses in this cell line.

Another study using the HuH-7 hepatoma cell line (not shown), which had similar surface expression, but slightly lower cytoplasmic levels as Hep-G2 (see Table 10), found the hMN-15-SN-38 conjugate providing a longer (35 vs.18 days), albeit not significantly different, survival advantage than the milatuzumab-CL2A conjugate (P=0.2944). While both the hMN-15 and milatuzumab conjugates were significantly better than the saline-treated animals (P=0.008 and 0.009, respectively), again, neither conjugate was significantly different from the non-targeted veltuzumab-SN-38 conjugate at this dose level (P=0.4602 and 0.9033, respectively). CEACAM6 surface expression was relatively low in this cell line (MFI=81), and immunohistology showed that both CD74 (not shown) and CEACAM6 (not shown) were very faint and highly scattered.

Discussion

The antibody-drug conjugate (ADC) approach for tumor-selective chemotherapy is an area of considerable current interest (e.g., Govindan et al., 2012, *Expert Opin Biol Ther* 12:873-90; Sapra et al., 2011, *Expert Opin Biol Ther* 20:1131-49. The recent clinical successes (Pro et al., 2012, *Expert Opin Biol Ther* 12:1415-21; LoRusso et al., 2011, *Clin Cancer Res* 17:437-47) have occurred in a large part with the adoption of supertoxic drugs in place of the conventional chemotherapeutic agents that had been used previously. However, target selection, the antibody, and the drug linker are all factors that influence optimal performance of an ADC. For example, in the case of trastuzumab-DM1, HER2 is abundant on tumors expressing this antigen, the antibody is internalized, and the antibody itself has anti-tumor activity, all of which could combine to enhance therapeutic outcome. In stark contrast, CD74 is expressed at a much lower level on the surface of cells, but its unique internalization and surface re-expression properties has allowed a milatuzumab anti-CD74 ADC to be effective in hematopoietic cancer xenograft models even with a moderately toxic drug, such as doxorubicin (Griffiths et al., 2003, *Clin Cancer Res* 9:6567-71; Sapra et al., 2005, *Clin Cancer Res* 11:5257-64). Although doxorubicin is used more frequently in hematopoietic cancers, while SN-38 and other camptothecins are administered to patients with solid tumors, we decided to assess the utility of doxorubicin and SN-38 conjugates of milatuzumab in solid tumors. The milatuzumab-doxorubicin conjugate was effective in xenograft models of various hematological cancers, leading to its clinical testing (NCT01101594 and NCT01585688), while several SN-38 conjugates were effective in solid and hematological tumor models, leading to 2 new SN-38 conjugates being pursued in Phase I clinical trials of colorectal and diverse epithelial cancers (NCT01270698 and NCT01631552).

In vitro, unconjugated doxorubicin and SN-38 had similar potency as doxorubicin against the Raji lymphoma cell line, but SN-38 was more potent in a number of different solid tumor cell lines. Interestingly, in vivo, the milatuzumab-doxorubicin conjugate provided the best response in Raji as compared to the milatuzumab-SN-38 conjugates. However, in Capan-1 and A-375, milatuzumab-doxorubicin was less effective than the CL2A-linked SN-38 milatuzumab conjugate, even though in vitro testing had indicated that A-375 was equally sensitive to free doxorubicin as to free SN-38. Two other cell lines, MDA-MB-231 breast cancer and LS174T colon cancer, also had similar potency with free doxorubicin as SN-38 in vitro, but since in vitro testing indicated SN-38 was equally effective in solid and hematological cancers, and with SN-38 having a 5- to 20-fold higher potency than doxorubicin in most solid tumor cell lines evaluated, we decided to focus on the 2 milatuzumab-SN-38 conjugates for solid tumor therapy. However, to better gauge the utility of the milatuzumab-SN-38 conjugates, we included a comparative assessment to SN-38 ADCs prepared with antibodies against other antigens that are present in a variety of solid tumors.

We previously had investigated therapeutic responses with the internalizing hRS7 anti-TROP-2 CL2A-linked SN-38 conjugate in the Capan-1 cell line (Cardillo et al., 2011, *Clin Cancer Res* 17:3157-69), and therefore the efficacy of milatuzumab and hRS7 SN-38 conjugates were compared. In this study, both conjugates significantly improved survival compared to control antibodies, with the CL2A-linked SN-38 conjugates of each being superior to the CL2E-linked conjugates. Since flow cytometry had indicated TROP-2 expression was higher than CD74 in Capan-1, this result suggested that the transport capabilities of CD74, which were known to be exceptional, were more efficient than TROP-2. However, it is well known that antigen accessibility (i.e., membrane vs. cytoplasm, physiological and "binding-site" barriers) and distribution among cells within a tumor are critical factors influencing every form of targeted therapy, particularly those that depend on adequate intracellular delivery of a product to individual cells (Thurber et al., 2008, *Adv Drug Del Rev* 60:1421-34). In situations where the antigen is not uniformly expressed in all cells within the tumor, having a targeted agent that slowly releases its payload after localizing in the tumor, such as the CL2A-linked conjugates, would allow the drug to diffuse to non-targeted bystander cells, thereby enhancing its efficacy range. Indeed, high antigen expression could potentially impede tumor penetration as per the binding-site barrier effect, but the extracellular release mechanism could provide a mechanism for the drug to diffuse within the tumor. This mechanism also is thought to aid the efficacy of other conjugates that we have examined using poorly internalizing antibodies, such as anti-CEACAM5 and the anti-CEACAM6 used herein. Conjugates based on milatuzumab rely more heavily on the antibody's direct interaction with the tumor cell, taking advantage of CD74's rapid internalization and re-expression that can compensate for its lower abundance on the surface of cells. However, this advantage would be mitigated when CD74 is highly scattered within the tumor, and without a mechanism to retain the conjugate within the tumor, the benefit of the drug's slow release from the conjugate would be lost. A previous review of human gastrointestinal tumors by our group suggests that they often have a high level of expression with good uniformity (Gold et al., 2010, *Int J Clin Exp Pathol* 4:1-12).

During our initial assessment of suitable linkers for SN-38, a number of different derivatives were examined, including a 'CL2E'-like linker that was designed to be coupled at the 20-hydroxyl position of SN-38, similar to the CL2A linker. However, that antibody conjugate lacked sufficient antitumor activity and was not pursued. Given the exceptional internalization properties of milatuzumab, we decided to revisit the SN-38-linker chemistry, with the hypothesis that the rapid internalization of a CD74 conjugate would enhance drug loading of a more stable conjugate. We surmised that if the leaving group was phenolic, this could promote cyclization, and therefore, the CL2E-linker was designed to join at the phenolic 10-position of SN-38.

At the onset, the CL2E-linked SN-38 conjugate had a promisingly similar $IC_{50}$ as the CL2A conjugate in the Raji cell line, which was consistent with the view that if rapidly internalized, both conjugates would release the active form of SN-38 at approximately the same rate. However, as already mentioned, the in vitro activity of the CL2A conjugate is influenced largely by the release of SN-38 into the media, and does not necessarily reflect uptake by the intact conjugate. When the CL2E-linked conjugate was found to be much less potent in the solid tumor cell lines than the CL2A conjugate, this suggested that the lower surface expression of CD74 affected the internalization of SN-38 via milatuzumab binding. However, when in vivo studies in Raji showed the milatuzumab-CL2A-SN-38 was superior to the CL2E conjugate, some other factor had to be considered that would affect CL2E's efficacy. One possible explanation is that the linker design in CL2E-SN-38 leaves the 20-position of the drug underivatized, rendering the lactone group susceptible to ring-opening. Indeed, studies with irinotecan have shown SN-38's potency is diminished by a number of factors, with the lactone ring opening to the carboxylate form possessing only 10% of the potency of the intact lactone form. In contrast, the CL2A-linked SN-38 is derivatized at the 20-hydroxyl position, a process that stabilizes the lactone group in camptothecins under physiological conditions. Therefore, SN-38's lactone ring is likely protected from cleavage in the CL2A, but not the CL2E conjugate. Thus, the destabilization of the lactone ring could have contributed to CL2E's diminished efficacy in vivo. Since the in vitro stability studies and the analysis of serum stability were performed under acidic conditions, we do not have a direct measure of the carboxylate form of SN-38 in either of these conjugates.

In conclusion, in vitro and in vivo results indicate that the milatuzumab-doxorubicin conjugate is superior to the CL2A-SN-38 conjugate in the Raji lymphoma cell line, which may reflect the improved stability of the doxorubicin conjugate compared to the CL2A one. However, the finding that the CL2A-SN-38 conjugate was more effective than the highly stable CL2E-SN-38 conjugate suggests that other issues, potentially related to activation of the drug or cell line sensitivities, may be at play.

CD74 has multiple roles in cell biology; in antigen-presenting cells, it may have a more dominant role in processing antigenic peptides, where is solid tumors, its role might be related more to survival. These different roles could affect intracellular trafficking and processing. Alternatively, the lower efficacy of the CL2E-linked SN-38 could reflect drug inactivation by lactone ring-opening in SN-38, implicating the importance of the specific linker. Finally, in the solid tumor models, antigen accessibility appears to have a dominant role in defining milatuzumab-CL2A-SN-38's potency when measured against conjugates prepared with other internalizing (hRS7) or poorly internalizing antibodies (hMN15) that were more accessible (surface expressed) and abundant. We suspect this finding is universal for targeted therapies, but these studies have at least shown that the unique internalization properties of a CD74-targeted agent can provide significant efficacy even when surface expression of the target antigen is minimal.

Example 14

Use of hRS7-SN-38 (IMMU-132) to Treat Therapy-refractive Metastatic Colonic Cancer (mCRC)

The patient was a 62-year-old woman with mCRC who originally presented with metastatic disease in January 2012. She had laparoscopic ileal transverse colectomy as the first therapy a couple of weeks after diagnosis, and then received 4 cycles of FOLFOX (leucovorin, 5-fluorouracil, oxaliplatin) chemotherapy in a neoadjuvant setting prior to right hepatectomy in March 2012 for removal of metastatic lesions in the right lobe of the liver. This was followed by an adjuvant FOLFOX regimen that resumed in June, 2012, for a total of 12 cycles of FOLFOX. In August, oxaliplatin was dropped from the regimen due to worsening neurotoxicity. Her last cycle of 5-FU was on Sep. 25, 2012.

CT done in January 2013 showed metastases to liver. She was then assessed as a good candidate for enrollment to IMMU-132 (hRS7-SN-38) investigational study. Comorbidities in her medical history include asthma, diabetes mellitus, hypertension, hypercholesteremia, heart murmur, hiatal hernia, hypothyroidism, carpel tunnel syndrome, glaucoma, depression, restless leg syndrome, and neuropathy. Her surgical history includes tubo-ligation (1975), thyroidectomy (1983), cholescystectomy (2001), carpel tunnel release (2008), and glaucoma surgery.

At the time of entry into this trial, her target lesion was a 3.1-cm tumor in the left lobe of the liver. Non-target lesions included several hypo-attenuated masses in the liver. Her baseline CEA was 781 ng/m.

After the patient signed the informed consent, IMMU-132 was given on a once-weekly schedule by infusion for 2 consecutive weeks, then a rest of one week, this constituting a treatment cycle. These cycles were repeated as tolerated. The first infusion of IMMU-132 (8 mg/kg) was started on Feb. 15, 2013, and completed without notable events. She experienced nausea (Grade 2) and fatigue (Grade 2) during the course of the first cycle and has been continuing the treatment since then without major adverse events. She reported alopecia and constipation in March 2013. The first response assessment done (after 6 doses) on Apr. 8, 2013 showed a shrinkage of target lesion by 29% by computed tomography (CT). Her CEA level decreased to 230 ng/ml on Mar. 25, 2013. In the second response assessment (after 10 doses) on May 23, 2013, the target lesion shrank by 39%, thus constituting a partial response by RECIST criteria. She has been continuing treatment as of Jun. 14, 2013, receiving 6 cycles constituting 12 doses of hRS7-SN-38 (IMMU-132) at 8 mg/kg. Her overall health and clinical symptoms improved considerably since starting this investigational treatment.

Example 15

Use of hRS7-SN-38 (IMMU-132) to Treat Therapy-refractive Metastatic Breast Cancer The patient was a 57-year-old woman with stage IV, triple-negative, breast cancer (ER/PR negative, HER-neu negative), originally diagnosed in 2005. She underwent a lumpectomy of her left breast in 2005, followed by Dose-Dense ACT in adjuvant setting in September 2005. She then received radiation therapy, which was completed in November. Local recurrence of the disease was identified when the patient palpated a lump in the contralateral (right) breast in early 2012, and was then treated with CMF (cyclophosphamide, methotrexate, 5-fluorouracil) chemotherapy. Her disease recurred in the same year, with metastatic lesions in the skin of the chest wall. She then received a carboplatin+TAXOL® chemotherapy regimen, during which thrombocytopenia resulted. Her disease progressed and she was started on weekly doxorubicin, which was continued for 6 doses. The skin disease also was progressing. An FDG-PET scan on Sep. 26, 2012 showed progression of disease on the chest wall and enlarged, solid, axillary nodes. The patient was given oxycodone for pain control.

She was given IXEMPRA® from October 2012 until February 2013 (every 2 weeks for 4 months), when the chest wall lesion opened up and bled. She was then put on XELODA®, which was not tolerated well due to neuropathy in her hands and feet, as well as constipation. The skin lesions were progressive and then she was enrolled in the IMMU-132 trial after giving informed consent. The patient also had a medical history of hyperthyroidism and visual disturbances, with high risk of CNS disease (however, brain MRI was negative for CNS disease). At the time of enrollment to this trial, her cutaneous lesions (target) in the right breast measured 4.4 cm and 2.0 cm in the largest diameter. She had another non-target lesion in the right breast and one enlarged lymph node each in the right and left axilla.

The first IMMU-132 infusion (12 mg/kg) was started on Mar. 12, 2013, which was tolerated well. Her second infusion was delayed due to Grade 3 absolute neutrophil count (ANC) reduction (0.9) on the scheduled day of infusion, one week later. After a week delay and after receiving NEULASTA®, her second IMMU-132 was administered, with a 25% dose reduction at 9 mg/kg. Thereafter she has been receiving IMMU-132 on schedule as per protocol, once weekly for 2 weeks, then one week off. Her first response assessment on May 17, 2013, after 3 therapy cycles, showed a 43% decrease in the sum of the long diameter of the target lesions, constituting a partial response by RECIST criteria. She is continuing treatment at the 9 mg/kg dose level. Her overall health and clinical symptoms improved considerably since she started treatment with IMMU-132.

Example 16

Use of hRS7-SN-38 (IMMU-132) to Treat Refractory, Metastatic, Non-small Cell Lung Cancer This is a 60-year-old man diagnosed with non-small cell lung cancer. The patient is given chemotherapy regimens of carboplatin, bevacizumab for 6 months and shows a response, and then after progressing, receives further courses of chemotherapy with carboplatin, etoposide, TAXOTERE®, gemcitabine over the next 2 years, with occasional responses lasting no more than 2 months. The patient then presents with a left mediastinal mass measuring 6.5×4 cm and pleural effusion.

After signing informed consent, the patient is given IMMU-132 at a dose of 18 mg/kg every other week. During the first two injections, brief periods of neutropenia and diarrhea are experienced, with 4 bowel movements within 4 hours, but these resolve or respond to symptomatic medications within 2 days. After a total of 6 infusions of IMMU-132, CT evaluation of the index lesion shows a 22% reduction, just below a partial response but definite tumor shrinkage. The patient continues with this therapy for another two months, when a partial response of 45% tumor shrinkage of the sum of the diameters of the index lesion is noted by CT, thus constituting a partial response by RECIST criteria.

Example 17

Use of hRS7-SN-38 (IMMU-132) to Treat Refractory, Metastatic, Small-cell Lung Cancer This is a 65-year-old woman with a diagnosis of small-cell lung cancer, involving her left lung, mediastinal lymph nodes, and MRI evidence of a metastasis to the left parietal brain lobe. Prior chemotherapy includes carboplatin, etoposide, and topotecan, but with no response noted. Radiation therapy also fails to control her disease. She is then given IMMU-132 at a dose of 18 mg/kg once every three weeks for a total of 5 infusions. After the second dose, she experiences hypotension and a Grade 2 neutropenia, which improve before the next infusion. After the fifth infusion, a CT study shows 13% shrinkage of her target left lung mass. MRI of the brain also shows a 10% reduction of this metastasis. She continues her IMMU-132 dosing every 3 weeks for another 3 months, and continues to show objective and subjective improvement of her condition, with a 25% reduction of the left lung mass and a 21% reduction of the brain metastasis.

Example 18

Therapy of a Gastric Cancer Patient with Stage IV Metastatic Disease with hRS7-SN-38 (IMMU-132)

This patient is a 60-year-old male with a history of smoking and periods of excessive alcohol intake over a 40-year-period. He experiences weight loss, eating discomfort and pain not relieved by antacids, frequent abdominal pain, lower back pain, and most recently palpable nodes in both axilla. He seeks medical advice, and after a workup is shown to have an adenocarcinoma, including some squamous features, at the gastro-esophageal junction, based on biopsy via a gastroscope. Radiological studies (CT and FDG-PET) also reveal metastatic disease in the right and left axilla, mediastinal region, lumbar spine, and liver (2 tumors in the right lobe and 1 in the left, all measuring between 2 and 4 cm in diameter). His gastric tumor is resected and he is then put on a course of chemotherapy with epirubicin, cisplatin, and 5-fluorouracil. After 4 months and a rest period of 6 weeks, he is switched to docetaxel chemotherapy, which also fails to control his disease, based on progression confirmed by CT measurements of the metastatic tumors and some general deterioration.

The patient is then given therapy with IMMU-132 (hRS7-SN-38) at a dose of 10 mg/kg infused every-other-week for a total of 6 doses, after which CT studies are done to assess status of his disease. These infusions are tolerated well, with some mild nausea and diarrhea, controlled with symptomatic medications. The CT studies reveal that the sum of his index metastatic lesions has decreased by 28%, so he continues on this therapy for another 5 courses. Follow-up CT studies show that the disease remains about 35% reduced by RECIST criteria from his baseline measurements prior to IMMU-132 therapy, and his general condition also appears to have improved, with the patient regaining an optimistic attitude toward his disease being under control.

Example 19

Therapy of Advanced Colon Cancer Patient Refractory to Prior Chemo-immunotherapy, Using Only IMMU-130 (Labetuzumab-SN-38)

The patient is a 50-year-old man with a history of stage-IV metastatic colonic cancer, first diagnosed in 2008 and given a colectomy and partial hepatectomy for the primary and metastatic colonic cancers, respectively. He then received chemotherapy, as indicated FIG. 8, which included irinotecan, oxaliplatin, FOLFIRINOX (5-fluoruracil, leucovorin, irinotecan, oxaliplatin), and bevacizumab, as well as bevacizumab combined with 5-fluorouracil/leucovorin, for almost 2 years. Thereafter, he was given courses of cetuximab, either alone or combined with FOLFIRI (leucovorin, 5-flurouracil, irinotecan) chemotherapy during the next year or more. In 2009, he received radiofrequency ablation therapy to his liver metastasis while under chemo-immunotherapy, and in late 2010 he underwent a wedge resection of his lung metastases, which was repeated a few months later, in early 2011. Despite having chemo-immunotherapy in 2011, new lung metastases appeared at the end of 2011, and in 2012, both lung and liver metastases were visualized. His baseline plasma carcinoembryonic antigen (CEA) titer was 12.5 ng/mL just before undergoing the antibody-drug therapy with IMMU-130. The index lesions chosen by the radiologist for measuring tumor size change by computed tomography were the mid-lobe of the right lung and the liver metastases, both totaling 91 mm as the sum of their longest diameters at the baseline prior to IMMU-130 (anti-CEACAM5-SN-38) therapy.

This patient received doses of 16 mg/kg of IMMU-130 by slow IV infusion every other week for a total of 17 treatment doses. The patient tolerated the therapy well, having only a grade 1 nausea, diarrhea and fatigue after the first treatment, which occurred after treatments 4 and 5, but not thereafter, because he received medication for these side-effects. After treatment 3, he did show alopecia (grade 2), which was present during the subsequent therapy. The nausea, diarrhea, and occasional vomiting lasted only 2-3 days, and his fatigue after the first infusion lasted 2 weeks. Otherwise, the patient tolerated the therapy well. Because of the long duration of receiving this humanized (CDR-grafted) antibody conjugated with SN-38, his blood was measured for anti-labetuzumab antibody, and none was detected, even after 16 doses.

The first computed tomography (CT) measurements were made after 4 treatments, and showed a 28.6% change from the sum of the measurements made at baseline, prior to this therapy, in the index lesions. After 8 treatments, this reduction became 40.6%, thus constituting a partial remission according to RECIST criteria. This response was maintained for another 2 months, when his CT measurements indicated that the index lesions were 31.9% less than the baseline measurements, but somewhat higher than the previous decrease of 40.6% measured. Thus, based on careful CT measurements of the index lesions in the lung and liver, this patient, who had failed prior chemotherapy and immunotherapy, including irinotecan (parent molecule of SN-38), showed an objective response to the active metabolite of irintotecan (or camptotechin), SN-38, when targeted via the anti-CEACAM5 humanized antibody, labetuzumab (hMN-14). It was surprising that although irinotecan (CPT-11) acts by releasing SN-38 in vivo, the SN-38 conjugated anti- CEACAM5 antibody proved effective in a colorectal cancer patient by inducing a partial response after the patient earlier failed to respond to his last irinotecan-containing therapy. The patient's plasma CEA titer reduction also corroborated the CT findings: it fell from the baseline level of 12.6 ng/mL to 2.1 ng/mL after the third therapy dose, and was between 1.7 and 3.6 ng/mL between doses 8 and 12. The normal plasma titer of CEA is usually considered to be between 2.5 and 5.0 ng/mL, so this therapy effected a normalization of his CEA titer in the blood.

Example 20

Therapy of a Patient with Advanced Colonic Cancer with IMMU-130

This patient is a 75-year-old woman initially diagnosed with metastatic colonic cancer (Stage IV). She has a right partial hemicolectomy and resection of her small intestine and then receives FOLFOX, FOLFOX+bevacizumab, FOLFIRI+ramucirumab, and FOLFIRI+cetuximab therapies for a year and a half, when she shows progression of disease, with spread of disease to the posterior cul-de-sac, omentum, with ascites in her pelvis and a pleural effusion on the right side of her chest cavity. Her baseline CEA titer just before this therapy is 15 ng/mL. She is given 6 mg/kg IMMU-130 (anti-CEACAM5-SN-38) twice weekly for 2 consecutive weeks, and then one week rest (3-week cycle), for more than 20 doses, which is tolerated very well, without any major hematological or non-hematological toxicities. Within 2 months of therapy, her plasma CEA titer shrinks modestly to 1.3 ng/mL, but at the 8-week evaluation she shows a 21% shrinkage of the index tumor lesions, which increases to a 27% shrinkage at 13 weeks. Surprisingly, the patient's ascites and pleural effusion both decrease (with the latter disappearing) at this time, thus improving the patient's overall status remarkably. The patient continues her investigational therapy.

Example 21

Gastric Cancer Patient with Stage IV Metastatic Disease Treated with IMMU-130

The patient is a 52-year-old male who sought medical attention because of gastric discomfort and pain related to eating for about 6 years, and with weight loss during the past 12 months. Palpation of the stomach area reveals a firm lump which is then gastroscoped, revealing an ulcerous mass at the lower part of his stomach. This is biopsied and diagnosed as a gastric adenocarcinoma. Laboratory testing reveals no specific abnormal changes, except that liver function tests, LDH, and CEA are elevated, the latter being 10.2 ng/mL. The patent then undergoes a total-body PET scan, which discloses, in addition to the gastric tumor, metastatic disease in the left axilla and in the right lobe of the liver (2 small metastases). The patient has his gastric tumor resected, and then has baseline CT measurements of his metastatic tumors. Four weeks after surgery, he receives 3 courses of combination chemotherapy consisting of a regimen of cisplatin and 5-fluorouracil (CF), but does not tolerate this well, so is switched to treatment with docetaxel. It appears that the disease is stabilized for about 4 months, based on CT scans, but then the patient's complaints of further weight loss, abdominal pain, loss of appetite, and extreme fatigue cause repeated CT studies, which show increase in size of the metastases by a sum of 20% and a suspicious lesion at the site of the original gastric resection.

The patient is then given experimental therapy with IMMU-130 (anti-CEACAM5-SN-38) on a weekly schedule of 8 mg/kg. He tolerates this well, but after 3 weeks shows a grade 2 neutropenia and grade 1 diarrhea. His fourth infusion is postponed by one week, and then the weekly infusions are reinstituted, with no evidence of diarrhea or neutropenia for the next 4 injection. The patient then undergoes a CT study to measure his metastatic tumor sizes and to view the original area of gastric resection. The radiologist measures, according to RECIST criteria, a decrease of the sum of the metastatic lesions, compared to baseline prior to IMMU-130 therapy, of 23%. There does not seem to be any clear lesion in the area of the original gastric resection. The patient's CEA titer at this time is 7.2 ng/mL, which is much reduced from the pre-IMMU-130 baseline value of 14.5 ng/mL. The patient continues on weekly IMMU-130 therapy at the same dose of 8.0 mg/kg, and after a total of 13 infusions, his CT studies show that one liver metastasis has disappeared and the sum of all metastatic lesions is decreased by 41%, constituting a partial response by RECIST. The patient's general condition improves and he resumes his usual activities while continuing to receive a maintenance therapy of 8 mg/kg IMMU-130 every third week for another 4 injections. At the last measurement of blood CEA, the value is 4.8 ng/mL, which is within the normal range for a smoker, which is the case for this patient.

Example 22

Therapy of Relapsed Triple-negative Metastatic Breast Cancer with hMN-15-SN-38

A 58-year-old woman with triple-negative metastatic breast cancer formerly treated with bevacizumab plus paclitaxel, without response, presents with metastases to several ribs, lumbar vertebrae, a solitary lesion measuring 3 cm in diameter in her left lung, with considerable bone pain and fatigue. She is given an experimental therapy with the anti-CEACAM6 humanized monoclonal antibody, hMN-15 IgG, conjugated with 6 molecules of SN-38 per IgG. She is given an infusion of 12 mg/kg every third week, repeated for 4 doses, as a course of therapy. Except for transient grade 2 neutropenia and some initial diarrhea, she tolerates the therapy well, which is then repeated, after a rest of 2 months, for another course. Radiological examination indicates that she has partial response by RECIST criteria, because the sum of the diameters of the index lesions decrease by 39%. Her general condition, including bone pain, also improves, and she returns to almost the same level of activity as prior to her illness.

Example 23

Therapy of Relapsed, Generally Refractive, Metastatic Colonic Carcinoma with hMN-15-SN-38

A 46-year-old woman has Stage IV metastatic colonic cancer, with a prior history of resection of the primary lesion that also had synchronous liver metastases to both lobes of the liver, as well as a single focus of spread to the right lung; these metastases measured, by CT, between 2 and 5 cm in diameter. She undergoes various courses of chemotherapy over a period of 3 years, including 5-fluorouracil, leucovorin, irinotecan, oxaliplatin, cetuximab, and bevacizumab. On two occasions, there is evidence of stabilization of disease or a short-term response, but no reduction of 30% or more of her measured lesions. Her plasma CEA titer at baseline prior to hMN-14-SN-38 therapy is 46 ng/mL, and her total index lesions measure a sum of 92 mm.

Therapy with hMN-15-SN-38 is instituted at 12 mg/kg weekly for 2 weeks, with a rest period of one week thereafter, within a 21-day cycle. This cycle is repeated 3 times, with only transient neutropenia and gastrointestinal side effects (nausea, vomiting, diarrhea). Surprisingly, despite failing to respond to FOLFIRI therapy (which includes irinotecan, or CPT-11), the patient shows a partial response by RECIST criteria after completing her therapy. She is then placed on a maintenance schedule of this therapy at a dose of 16 mg/kg once every month for the next 6 months. Followup scans show that her disease remains under control as a partial response (PR), and the patient is generally in good condition with a 90% Kaaarnofsky performance status.

Example 24

Colonic Cancer Patient with Stage IV Metastatic Disease Treated with Anti-CSAp-SN-38 Conjugate This patient presents with colonic cancer metastases to the left lobe of the liver and to both lungs, after having a resection of a 9-cm sigmoid colon adenocarcinoma, followed by chemo-immunotherapy with FOLIFIRI and cetuximab for 6 months, and then FOLFOX followed by bevacizumab for an additional period of about 9 months. Ten months after the initial resection and then commencement of therapy, the stable disease thought to be present shows progression by the lesions growing and a new metastasis appearing in the left adrenal gland. Her plasma CEA at this time is 52 ng/mL, and her general condition appears to have deteriorated, with abdominal pains, fatigue, and borderline anemia, suggesting possibly internal bleeding.

She is now given an SN-38 conjugate of hMu-9 (anti-CSAp) antibody at a dose of 12 mg/kg weekly for two weeks, with one week rest, as a treatment cycle, and then repeated for additional treatment cycles, measuring her blood counts every week and receiving atropine medication to gastrointestinal reactions. Grade 2 alopecia is noted after the first treatment cycle, but only a Grade 1 neutropenia. After 3 treatment cycles, her plasma CEA titer is reduced to 19 ng/ml, and at this time her CT measurements show a decrease of the index lesions in the liver and lungs by 24.1%. After an additional 3 courses of therapy, she shows a CT reduction of the index lesions of 31.4%, and a decrease in the size of the adrenal mass by about 40%. This patient is considered to be responding to anti-CSAp-SN-38 antibody-drug therapy, and continues on this therapy. Her general condition appears to be improved, with less fatigue, no abdominal pain or discomfort, and generally more energy.

Example 25

Treatment of Breast Cancer with Anti-CEACAM6-SN-38 Immunoconjugate

This patient has triple-negative (does not express estrogen receptor, progesterone receptor or Her2/neu) metastatic breast cancer that is relapsed after several different therapies over the past 3 years. She presents with several small tumors in both lungs, as well as metastases to her C4, C5, T2, and T3 vertebrae, as well as the several ribs bilaterally. She is under standard therapy for her osteolytic lesions, and now begins treatment with hMN-15-SN-38 at a dose of 16 mg/kg once-weekly for 3 weeks, with a pause of one week, and then resumes this 3-weekly-cycle therapy two more times. At 2 weeks post therapy, CT scans are performed to evaluate response, and it is noted that 2 of the small lung metastases have disappeared while 1 of the larger lesions appears to have diminished by about 40%. The metastases to the vertebrae are still present, but the C4 and C5 lesions appear smaller by about 25%. Of the metastases to the ribs, 2 of 6 small lesions appear to be very much diminished in size, and are not certain as to being viable or small areas of scar or necrosis. The patient's tumor markers, as well as her LDH titers, appear to show either stable or reduced levels, indicating that disease progression has been halted and there is also some evidence of disease reduction. Subjectively, the patient is feeling much better, with less fatigue and bone pain and improved breathing. She has experienced some minimal nausea and vomiting after each therapy, which resolved within a week. The only other side effect has been a transient thrombocytopenia, which also resolves within 7 days. She is being observed and will resume therapy cycles within 2 months.

Example 26

Treatment of Metastatic Colon Cancer with Combination Anti-CEACAM5 and Anti-CEACAM6-SN-38 Immunoconjugates This patient has metastatic colonic cancer, with CT evidence of disease in the liver (5 cm lesion in right lobe and 3 cm lesion in left lobe), as well as 2 metastases (2- and 3-cm sizes) to the right lung. The primary cancer of the colon was previously resected and the patient had courses of post-operative therapy because of metachronous metastases to the liver and lungs. During therapy, the liver metastases grow and the one lung metastasis becomes two, so the patient is a candidate for experimental chemoimmunotherapy. He is then begun on a course of double antibody-drug conjugates, labetuzumab (hMN-14)-SN-38 and hMN-15-SN-38, each given on alternate days at doses of 8 mg/kg, once weekly for 2 weeks, and then repeated monthly for 4 months. Two weeks after therapy, the patient's status is evaluated by CT and lab tests. The CT scans reveal that the large tumor in the right liver lobe is reduced by 50%, the tumor in the left lobe by about 33%, and the lung metastases by about 20% cumulatively for both tumors. His blood CEA titer is diminished from 22 ng/mL at onset of therapy to 6 ng/mL at this followup. Subjectively, the patient states he is feeling stronger and also appears to have more vigor in daily activities. Side effects are transient thrombocytopenia and leukopenia, returning to normal ranges within 2 weeks after therapy, and several bouts of nausea and vomiting, controlled by anti-emetic medication. It is planned that the patient will resume these therapy cycles in about 2 months, following another workup for disease status.

Example 27

Continuous Infusion of Antibody-Drug Conjugates

The patient was previously resected for a rectal carcinoma and receives pre- and post-operative radiochemotherapy as per conventional treatment. She has been free of tumor for four years, but now presents with 3 small metastatic lesions to the right liver lobe, discovered by routine CT and followup blood CEA values, which rise to 6.3 ng/mL from the 3.0 ng/mL post initial therapy. She is given an indwelling catheter and a continuous infusion of labetuzumab-SN-28 at a dose of 2 mg/kg over 17 days. She then receives a repeat continuous infusion therapy 5 weeks later, now for 3 weeks, at 1 mg/kg. Three weeks later, CT scans and blood CEA monitoring reveal that 1 of the liver metastases has disappeared and the other two are the same or slightly smaller. The blood CEA titer now measures 2.4 ng/mL. She is not symptomatic, and only experiences grade 2 nausea and vomiting while under therapy, and grade 2 neutropenia, both resolving with time.

Example 28

Therapy of Advanced Metastatic Colon Cancer with Anti-CEACAM5 Immunoconjugate

The patient is a 50-year-old male who fails prior therapies for metastatic colon cancer. The first line of therapy is FOLFIRINOX+AVASTIN® (built up in a stepwise manner) starting with IROX (Irinotecan+Oxaliplatin) in the first cycle. After initiating this treatment the patient has a CT that shows decrease in the size of liver metastases. This is followed by surgery to remove tumor tissue. Adjuvant chemotherapy is a continuation of the first line regimen (without the IROX part) that resulted in a transient recurrence-free period. After about a 1 year interval, a CT reveals the recurrence of liver metastases. This leads to the initiation of the second line regimen (FOLFIRI+Cetuximab). Another CT shows a response in liver metastases. Then RF ablation of liver metastases is performed, followed by continuation of adjuvant chemotherapy with FOLFIRINOX+Cetuximab, followed by maintenance Cetuximab for approximately one year. Another CT scan shows no evidence of disease. A further scan shows possible lung nodules, which is confirmed. This leads to a wedge resection of the lung nodules. Subsequently FOLFIRI+Cetuximab is restarted and continued. Later CT scans show both lung and liver metastases.

At the time of administration of the hMN-14-SN-38 immunoconjugate, the patient has advanced metastatic colon cancer, with metastases of both lung and liver, which is unresponsive to irinotecan (camptothecin). The hMN-14-SN-38 immunoconjugate is administered at a dosage of 12 mg/kg, which is repeated every other week. The patient shows a partial response with reduction of metastatic tumors by RECIST criteria.

Of note is that only one patient in this 12 mg/kg (given every other week) cohort shows a grade 2 hematological (neutropenia) and most patients have grade 1 or 2 nausea, vomiting, or alopecia—which are signs of activity of the antibody-drug conjugate, but well tolerated. The effect of the antibody moiety in improved targeting of the camptothecin accounts for the efficacy of the SN-38 moiety in the cancer that had been previously resistant to unconjugated irinotecan.

Example 29

Treatment of Metastatic Pancreatic Cancer with Anti-MUC5ac-SN-38 Immunoconjugate This 44-year-old patient has a history of metastatic pancreatic carcinoma, with inoperable pancreas ductal adenocarcinoma in the pancreas head, and showing metastases to left and right lobes of the liver, the former measuring 3×4 cm and the latter measuring 2×3 cm. The patient is given a course of gemcitabine but shows no objective response. Four weeks later, he is given hPAM4-SN-38 i.v. at a dose of 8 mg/kg twice-weekly for 2 weeks, with one week off, and then repeated for another 2 cycles. CT studies are done one week later and show a total reduction in tumor mass (all sites) of 32% (partial response), alongside a drop in his blood CA19-9 titer from 220 at baseline to 75 at the time of radiological evaluation. The patient shows only grade 1 nausea and vomiting after each treatment with the antibody-drug conjugate, and a grade 2 neutropenia at the end of the last treatment cycle, which resolves 4 weeks later. No premedication for preventing infusion reactions is given.

Example 30

Use of hL243-SN-38 to Treat Therapy-refractive Metastatic Colonic Cancer (mCRC)

The patient is a 67-year-old man who presents with metastatic colon cancer. Following transverse colectomy shortly after diagnosis, the patient then receives 4 cycles of FOLFOX chemotherapy in a neoadjuvant setting prior to partial hepatectomy for removal of metastatic lesions in the left lobe of the liver. This is followed by an adjuvant FOLFOX regimen for a total of 10 cycles of FOLFOX.

CT shows metastases to liver. His target lesion is a 3.0-cm tumor in the left lobe of the liver. Non-target lesions included several hypo-attenuated masses in the liver. Baseline CEA is 685 ng/mL.

After the patient signs the informed consent, hL243-SN-38 (10 mg/kg) is given every other week for 4 months. The patient experiences nausea (Grade 2) and fatigue (Grade 2) following the first treatment and continues the treatment without major adverse events. The first response assessment done (after 8 doses) shows shrinkage of the target lesion by 26% by computed tomography (CT) and his CEA level decreases to 245 ng/mL. In the second response assessment (after 12 doses), the target lesion has shrunk by 35%. His overall health and clinical symptoms are considerably improved.

Example 31

Treatment of Relapsed Follicular Lymphoma with IMMU-114-SN-38 (Anti-HLA-DR-SN-38)

After receiving R-CHOP chemotherapy for follicular lymphoma presenting with extensive disease in various regional lymph nodes (cervical, axillary, mediastinal, inguinal, abdominal) and marrow involvement, this 68-year-old man is given the experimental agent, IMMU-114-SN-38 (anti-HLA-DR-SN-38) at a dose of 10 mg/kg weekly for 3 weeks, with a rest of 3 weeks, and then a second course for another 3 weeks. He is then evaluated for change in index tumor lesions by CT, and shows a 23% reduction according CHESON criteria. The therapy is repeated for another 2 courses, which then shows a 55% reduction of tumor by CT, which is a partial response.

Example 32

Treatment of Relapsed Chronic Lymphocytic Leukemia with IMMU-114-SN-38

A 67-year-old man with a history of CLL, as defined by the International Workshop on Chronic Lymphocytic Leukemia and World Health Organization classifications, presents with relapsed disease after prior therapies with fludarabine, dexamethasone, and rituximab, as well as a regimen of CVP. He now has fever and night sweats associated with generalized lymph node enlargement, a reduced hemoglobin and platelet production, as well as a rapidly rising leukocyte count. His LDH is elevated and the beta-2-microglobulin is almost twice normal. The patient is given therapy with IMMU-114-SN-38 conjugate at a dosing scheme of 8 mg/kg weekly for 4 weeks, a rest of 2 weeks, and then the cycle repeated again. Evaluation shows that the patient's hematological parameters are improving and his circulating CLL cells appear to be decreasing in number. The therapy is then resumed for another 3 cycles, after which his hematological and lab values indicate that he has a partial response.

Example 33

Use of hMN-15-SN-38 to Treat Refractory, Metastatic, Non-small Cell Lung Cancer The patient is a 58-year-old man diagnosed with non-small cell lung cancer. He is initially given chemotherapy regimens of carboplatin, bevacizumab for 6 months and shows a response, and then after progressing, receives further courses of chemotherapy with carboplatin, etoposide, TAXOTERE®, gemcitabine over the next 2 years, with occasional responses lasting no more than 2 months. The patient then presents with a left mediastinal mass measuring 5.5×3.5 cm and pleural effusion.

After signing informed consent, the patient is given hMN-15-SN-38 at a dose of 12 mg/kg every other week. During the first two injections, brief periods of neutropenia and diarrhea are experienced, but these resolve or respond to symptomatic medications within 2 days. After a total of 6 infusions of hMN-15-SN-38, CT evaluation of the target lesion shows a 22% reduction. The patient continues with this therapy for another two months, when a partial response of 45% is noted by CT.

Example 34

Treatment of Follicular Lymphoma Patient with hA19-SN-38

A 60-year-old male presents with abdominal pain and the presence of a palpable mass. The patient has CT and FDG-PET studies confirming the presence of the mass with pathologic adenopathies in the mediastinum, axillary, and neck nodes. Lab tests are unremarkable except for elevated LDH and beta-2-microglobulin. Bone marrow biopsy discloses several paratrabecular and perivascular lymphoid aggregates. These are lymphocytic with expression of CD20, CD19, and CD10 by immunostaining. The final diagnosis is grade-2 follicular lymphoma, stage IVA, with a FLIPI score of 4. The longest diameter of the largest involved node is 7 cm. The patient is given a humanized anti-CD19 monoclonal antibody IgG (hA19) conjugated with SN-38 (6 drug molecules per IgG). The dosing is 6 mg/kg weekly for 4 consecutive weeks, two weeks off, and then repeated cycles of 4 treatment weeks for every 6 weeks. After 5 cycles, bone marrow and imaging (CT) evaluations show a partial response, where the measurable lesions decrease by about 60% and the bone marrow is much less infiltrated. Also, LDH and beta-2-microglobulin titers also decrease.

Example 35

Treatment of Relapsed Precursor B-Cell ALL with hA19-SN-38

This 51-year-old woman has been under therapy for precursor, Philadelphia chromosome-negative, B-cell ALL, which shows the ALL cells stain for CD19, CD20, CD10, CD38, and CD45. More than 20% of the marrow and blood lymphoblasts express CD19 and CD20. The patient has received prior therapy with clofarabine and cytarabine, resulting in considerable hematological toxicity, but no response. A course of high-dose cytarabine (ara-C) was also started, but could not be tolerated by the patient. She is given hA19-SN-38 therapy at weekly doses by infusion of 6 mg/kg for 5 weeks, and then a 2-week rest, with repetition of this therapy two more times. Surprisingly, she shows improvement in her blood and marrow counts, sufficient for a partial response to be determined. After a rest of 2 months because of neutropenia (grade 3), therapy resumes at 8 mg/kg every other week for another 4 courses. At this time, she is much improved and is under consideration for maintenance therapy to try to bring her to a stage where she could be a candidate for stem-cell transplantation.

Example 36

Treatment of Lymphoma with Anti-CD22-SN-38 Immunoconjugate

The patient is a 62 year-old male with relapsed diffuse large B-cell lymphoma (DLBCL). After 6 courses of R-CHOP chemoimmunotherapy, he now presents with extensive lymph node spread in the mediastinum, axillary, and inguinal lymph nodes. He is given epratuzumab-SN-38 (anti-CD22) at a dose of 12 mg/kg weekly×3, with one week off, and then repeated again for another two cycles. One week later, the patient is evaluated by CT imaging, and his total tumor bulk is measured and shows a decrease of 35% (partial response), which appears to be maintained over the next 3 months. Side effects are only thrombocytopenia and grade 1 nausea and vomiting after therapy, which resolve within 2 weeks. No pretherapy for reducing infusion reactions is given.

Example 37

Combination Therapy of Follicular Lymphoma with Veltuzumab and Epratuzumab-SN-38 in the Frontline Setting A 35-year-old woman is diagnosed with a low-grade and good FLIPI score follicular lymphoma, presenting in her cervical lymph nodes, both axilla, and mediastinum. Her spleen is not enlarged, and bone marrow biopsy does not disclose disease involvement. She is symptomatically not much affected, with only periods of elevated temperature, night sweats, and somewhat more fatigued than usual. Her physician decides not to undertake a watch-and-wait process, but to give this woman a less-aggressive therapy combining a subcutaneous course of the humanized anti-CD20 monoclonal antibody, veltuzumab, weekly×4 weeks (200 mg/m$^2$) combined with two weekly courses of the anti-CD22 epratuzumab-SN-38, each infusion being a dose of 8 mg/kg. This combination therapy is repeated 2 months later, and after this the patient is evaluated by CT and FDG-PET imaging studies, as well as a bone marrow biopsy. Surprisingly, about a 90% reduction of all disease is noted, and she then is given another course of this combination therapy after a rest of 4 weeks. Evaluation 4 weeks later shows a radiological (and bone marrow biopsy) complete response. Her physician decides to repeat this course of therapy 8 months later, and radiological/pathological tests show a sustained complete remission.

Example 38

Frontline Therapy of Follicular Lymphoma Using Veltuzumab-SN-38

The patient is a 41-year-old woman presenting with low-grade follicular lymphoma, with measurable bilateral cervical and axillary lymph nodes (2-3 cm each), mediastinal mass of 4 cm diameter, and an enlarged spleen. She is given 3 courses of veltuzumab-SN-38 (anti-CD20-SN-38) therapy, with each course consisting of 10 mg/kg infused once every 3 weeks. After completion of therapy, her tumor measurements by CT show a reduction of 80%. She is then given 2 additional courses of therapy, and CT measurements indicate that a complete response is achieved. This is confirmed by FDG-PET imaging.

Example 39

Therapy of Relapsed DLBCL with 1F5 Humanized Antibody Conjugated with SN-38

A 53-year-old woman presents with recurrent diffuse large B-cell lymphoma at mediastinal and abdominal para-aortic sites 8 months after showing a partial response to R-CHOP chemotherapy given for 6 cycles. She refuses to have more cytotoxic chemotherapy, so is given a milder therapy consisting of 10 mg/kg humanized 1F5 anti-CD20 monoclonal antibody, conjugated to about 6 molecules of SN-28 per molecule of antibody, once weekly every other week for 5 infusions. CT and FDG-PET studies indicate a further reduction of her lymphomas by 40%, so after a rest period of 4 weeks, therapy is resumed at a dose of 8 mg/kg every 3 weeks for a total of 5 infusions. Evaluation of her disease reveals a reduction of about 80%.

Example 40

Therapy of Relapsed Chronic Lymphocytic Leukemia with Rituximab-SN-38

A 62-year-old man with an 8-year history of CLL, having responded in the past to fludarabine, cyclophosphamide, and rituximab therapy, and after relapse to ibrutinib for a partial response lasting 9 months, presents with progressing disease. The patient is given rituximab-SN-38 monotherapy at a schedule of 12 mg/kg every 2 weeks for 3 courses, reduced to 8 mg/kg every other week for another 4 courses. Sustained improvement in cytopenias, reflected by more than 50% or a hemoglobin level higher than 11 g per deciliter, an absolute neutrophil count higher than 1500 cells per cmm, or a platelet count higher than 11 k/cmm is observed, which was durable for about 9 months.

Example 41

Frontline Therapy of DLBCL with Veltuzumab-SN-38 Combined with Bendamustine

A 59-year-old man presents with multiple sites of DLBCL, including chest, abdominal, inguinal lymph nodes, and enlarged spleen, as confirmed by CT, FDG-PET, and immunohistological/pathological diagnoses. Bendamustine is given at a dose of 90 mg/$m^2$ on days 1 and 2, combined with veltuzumab-SN-38 at a dose of 6 mg/kg on days 7 and 14, given every 4 weeks for four cycles. Evaluation radiologically thereafter shows a partial response. After a rest of 2 months, the therapy is repeated for another 2 cycles, and radiological assessment then shows a complete response. Cytopenias, mostly neutropenia, is manageable and does not achieve a grade 3 level.

Example 42

Frontline Therapy of Mantle Cell Lymphoma (MCL) with Veltuzumab-SN-38 Combined with Lenalidomide The patient is a 68-year-old man diagnosed with MCL after presenting with a GI complaint and lethargy. Colonoscopy discloses a 7-cm cecal mass, and his workup reveals that he has Stage IV disease. He is given a combination therapy of lenalidomide, 25 mg orally daily on days 1 to 21 every 28 days. After two cycles, he is given veltuzumab-SN-38 every other week at a dose of 10 mg/kg for 3 treatments, with a 2-week rest. This is then repeated again. Two weeks after completion of this therapy, the patient shows a partial response of his measured index lesion and reduction of other lymph nodes visualized. Four months later, lenalidomide therapy is repeated for 21 days, followed by 2 courses of veltuzumab-SN-38. His disease is then shown to be reduced even further, although not yet a complete response.

Example 43

Epratuzumab-SN-38 Therapy of a Patient with Relapsed/Refractory Diffuse Large B-Cell Lymphoma (DLBCL)

A 65-year-old man with symptoms of weight loss undergoes a biopsy of an epigastric mass, which is diagnosed as a diffuse large B-cell lymphoma. He is treated with 6 cycles of standard R-CHOP (rituximab, cyclophosphamide, doxorubicin, vincristine, and prednisone). He has prolonged and persistent neutropenia (700 ANC) with mild thrombocytopenia (50-70 k/mL), but no real anemia. His IPI is high. The epigastric mass does not show any change following this therapy, and he is put on a mild treatment regimen of anti-CD22 epratuzumab-SN-38. This is a regimen of 4 mg/kg infused every other week for 4 infusions, then once every third week for another 3 infusions. His epigastric lymphoma is measured by CT one week later and shows a marked reduction by 52%. The patient is continues this treatment every third week for another 3 months, and continues to show this reduction of his lymphoma mass with stabilization of his weight and improvement of his energy and activities.

Example 44

Humanized RFB4 Therapy of a Patient with Relapsed Follicular Lymphoma

A 42-year-old woman presents with a sharp, constant and severe pain in her lower abdomen which radiates to her back. Laboratory tests are unremarkable, but an abdominal ultrasound shows a heterogeneous solid mass in the anterior lower left, measuring 7.5×6.2×7.0 cm. CT scans reveal a large mass within the left small-bowel mesentery, with involvement of adjacent lymph nodes. A CT-guided needle biopsy of the mass shows that it is a follicular lymphoma, grade 3. Immunohistochemistry shows a B-cell type with positive results for CD19, CD20, CD22, Bcl-2 and Bcl-6. PET studies reveal no disease above the diaphragm, in the bone marrow, or in the spleen, but bone marrow biopsy does confirm involvement of lymphoma. The patient undergoes 6 cycles of R-CHOP chemotherapy, resulting in a complete response to this therapy 4 months later. However, 10 months later, she undergoes a relapse, with recurrence of her abdominal mass and adjacent lymph nodes, as well as an enlarged spleen and more bone marrow involvement as determined by PET and biopsy studies. She now begins a course of therapy with the humanized anti-CD22 monoclonal antibody, RFB4, conjugated with 6 SN-38 molecules per IgG, at a dose of 8 mg/kg weekly for 3 weeks, and then continued at 8 mg/kg every other week for another 4 treatments. Two weeks later, she undergoes CT and FDG-PET studies, and her abdominal lesions and spleen show a reduction of 40%, and a general decrease of bone marrow involvement. After a rest of 4 weeks, therapy at 4 mg/kg weekly for 4 weeks, followed by 6 mg/kg every other week for another 5 treatments are implemented, with a further measurable reduction of the sum of the sizes of all measured lesions by a total of 60%. The patient continues on a maintenance therapy of hRFB4-SN-38 of 8 mg/kg once monthly for the next 5 months, and maintains her therapeutic response.

Example 45

Epratuzumab-SN-38 Therapy of a Patient with Relapsed/Refractory Acute Lymphoblastic Leukemia A 29-year-old male with CD22+ precursor B-cell acute lymphoblastic leukemia (ALL) has not responded to therapy with PEG-asparaginase, cyclophosphamide, daunorubicin, cytarabine (ara-C), vincristine, leucovorin, prednisone, methotrexate, and 6-mercaptopurine, and supportive therapy with G-CSF (Neupogen), given as induction/maintenance therapies under a modified Larson protocol. The patient's leukemia is Philadelphia chromosome-negative. Based on blood and marrow leukemia blast counts, the patient shows only a minimal response, with disease progressing 4 months later. He is then given weekly dosing of epratuzumab-SN-38 at an initial schedule of 6 mg/kg for 4 weeks, and then reduced to 6 mg/kg every-other-week for an additional 6 infusions. The patient is then evaluated by blood and marrow leukemic blasts as well as FDG studies of spleen size and bone marrow involvement, and it appears that a partial response is achieved, with concomitant improvement in the patient's general signs and symptoms. This therapy then continues over the next 8 months, but at 5 mg/kg every other week, with 3 weeks on therapy and 2 weeks rest, and a complete remission is achieved. The patient is now being evaluated as a candidate for hematopoietic stem cell transplantation.

Example 46

Humanized RFB4-SN-38 Therapy of a Patient with Relapsed/Refractory Acute Lymphoblastic Leukemia After failing to respond to HIDAC (high-dose ara-C therapy), this 20-year-old man with precursor B-cell acute lymphoblastic leukemia is given humanized anti-CD22 therapy with hRFB4 IgG conjugated to SN-38 (average of 6 drug molecules per IgG), at a dosing schedule of 10 mg/kg weekly for two weeks, then 1 week rest, followed by infusions of 10 mg/kg every other week for an additional 5 treatments. The patient is then evaluated for presence of blood and marrow leukemic blast cells, and shows a >90% reduction. After a rest of 4 weeks, this therapy course is repeated, and the evaluation 4 weeks later shows a complete response with no minimal residual disease, as measured by PCR.

Example 47

Consolidation Therapy with Epratuzumab-SN-38 in a DLBCL Patient Receiving R-CHOP Chemotherapy This 56-year-old woman with bilateral cervical adenopathy and cervical lymph nodes measuring 1.5 to 2.0 cm, as well as a right axillary lymph node of 3 cm, as well as retroperitoneal and bilateral pelvic lymph nodes measuring 2.5 to 3.0 cm, is diagnosed with stage 3 diffuse large B-cell lymphoma that is positive for CD20 and CD22. She is put on a standard R-CHOP chemotherapy regimen given every 21 days with filgrastim and prophylactic antibiotics. After receiving 6 cycles of this therapy, the patient is given a rest period of 2 months, and then is put on consolidation therapy with 8 mg/kg epratuzumab-SN-38, infused every other week for 3 treatments. Whereas the response after the R-CHOP chemotherapy is minimal (less than 30% change in measured lesions), consolidation therapy with epratuzumab-SN-38 results in a partial response (>50% decrease in sum of all index lesions). After a rest of 3 months, this course of therapy with epratuzumab-SN-38 is repeated, with the patient again given filgrastim and prophylactic antibiotics, and maintains her good remission.

Example 48

Treatment of Relapsed Metastatic Testicular Cancer with IMMU-31-SN-38

The patient is a 30-year-old man with a history of resected testicular cancer of his right testicle, with synchronous metastases to both lungs that respond well to combination chemotherapy. At diagnosis, his blood titer of alpha-fetoprotein (AFP) is elevated at 1,110 ng/mL, but decreases to 109 ng/mL after successful therapy. He now presents with a gradually rising AFP titer over a period of 3 years, so CT and FDG-PET scans of his body are made, revealing recurrence of lung metastases to both lungs. He receives therapy with the anti-AFP antibody, IMMU-31 IgG, conjugated with SN-38 at 6 drug molecules per IgG. He receives weekly doses of 12 mg/kg of this antibody-drug conjugate for 3 weeks of a 4-week cycle, repeated for another cycle but with a reduction of the therapeutic to 10 mg/kg. This is then repeated for another 2 cycles. Two weeks later, radiological examination of his lungs reveals that the metastases have disappeared. His blood AFP titer is now 18 ng/mL. The patient returns to normal activity with a complete response having been achieved.

Example 49

Treatment of Relapsed Metastatic Hepatocellular Carcinoma with IMMU-31-SN-38

A 58-year-old male with a history of hepatitis B infection, alcohol excess and smoking, leads first to liver cirrhosis and then a diagnosis of hepatocellular carcinoma. At the time he presents after having a portion of his liver resected, there are also regional lymph nodes involved. The patient receives a course of sorafenib therapy, indicates some general improvement, but does not have any reduction of his regional lymph node or 2 lung (right lung) metastases. CT of the liver also suggests that there may be a recurrence in the remaining liver parenchyma. This patient is now given 3 courses of therapy with IMMU-31-SN-38, each comprising a schedule of weekly 16 mg/kg for 2 weeks of a 4-week cycle. After the 3 courses comprising 6 doses, the patient is reevaluated and shows a decrease in his circulating AFP titer from the baseline value of 2,000 ng/mL to 170 ng/mL, as well as a 20% reduction of the sum of his measured index lesions. After a rest of 2 months, another course of therapy of 3 cycles, but with a reduction of the dose to 1 mg/kg per infusion, is instituted. One month later, there is a greater reduction of all measured lesion, to 35% of baseline, as well as a slight decrease in the AFP blood titer to 100 ng/mL. The patient is going on maintenance therapy of one dose per month for as long as there is no disease progression or limiting toxicities.

Example 50

Immunoconjugate Storage

The conjugates described in Example 8 were purified and buffer-exchanged with 2-(N-morpholino)ethanesulfonic acid (MES), pH 6.5, and further formulated with trehalose (25 mM final concentration) and polysorbate 80 (0.01% v/v final concentration), with the final buffer concentration becoming 22.25 mM as a result of excipient addition. The formulated conjugates were lyophilized and stored in sealed vials, with storage at 2° C.-8° C. The lyophilized immunoconjugates were stable under the storage conditions and maintained their physiological activities.

* * *

From the foregoing description, one skilled in the art can easily ascertain the essential characteristics of this invention, and without departing from the spirit and scope thereof, can make various changes and modifications of the invention to adapt it to various usage and conditions without undue experimentation. All patents, patent applications and publications cited herein are incorporated by reference.

We claim:

1. A method of treating breast, lung, pancreatic, esophageal, medullary thyroid, ovarian, uterine, prostatic, testicular, colon, rectal or stomach cancer comprising administering to a human patient with breast, lung, pancreatic, esophageal, medullary thyroid, ovarian, uterine, prostatic, testicular, colon, rectal or stomach cancer an immunoconjugate comprising SN-38 conjugated to an hMN-15 (anti-CEACAM6) antibody or antigen-binding fragment thereof; wherein the immunoconjugate is administered at a dosage of between 6 mg/kg and 18 mg/kg, wherein the patient has failed to respond to at least one other therapy, prior to treatment with the immunoconjugate.

2. The method of claim 1, further comprising administering to the patient an anti-CEACAM5-SN-38 immunoconjugate.

3. The method of claim 1, wherein the dosage is selected from the group consisting of 6 mg/kg, 8 mg/kg, 9 mg/kg, 10 mg/kg, 12 mg/kg, 16 mg/kg and 18 mg/kg.

4. The method of claim 1, wherein the cancer is a solid tumor and the treatment results in a reduction in tumor size of at least 15%, at least 20%, at least 30%, or at least 40%.

5. The method of claim 1, wherein the cancer is metastatic.

6. The method of claim 5, further comprising reducing in size or eliminating the metastases.

7. The method of claim 1, wherein the cancer is refractory to other therapies but responds to the immunoconjugate.

8. The method of claim 1, wherein the patient has failed to respond to therapy with a camptothecin, prior to treatment with the immunoconjugate.

9. The method of claim 8, wherein the camptothecin is selected from the group consisting of irinotecan, topotecan and SN-38.

10. The method of claim 1, wherein there is a linker between the SN-38 and the antibody.

11. The method of claim 10, wherein the linker is CL2A and the structure of the immunoconjugate is MAb-CL2A-SN-38

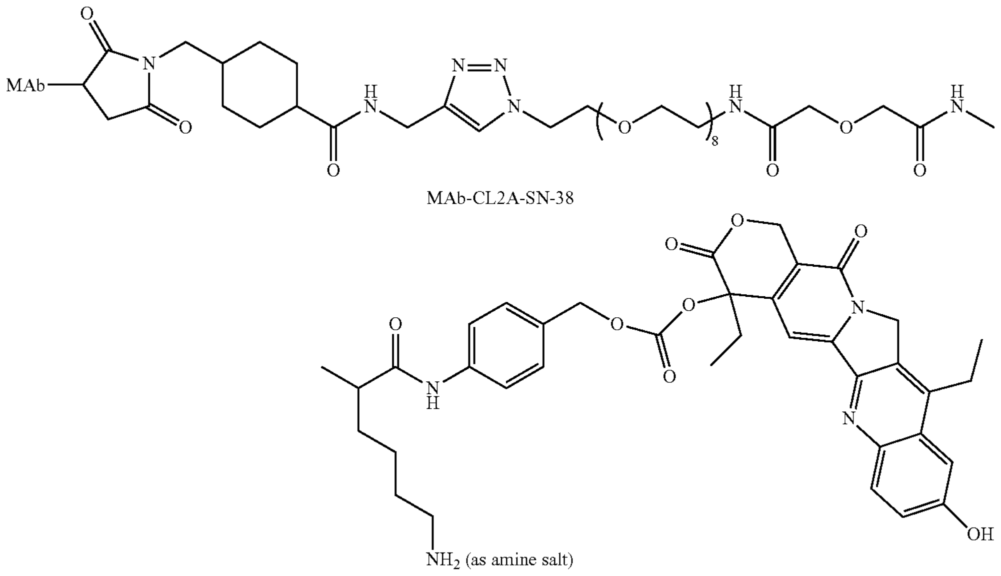

MAb-CL2A-SN-38

MAb-CL2A-SN-38.

12. The method of claim 11, wherein the 10-hydroxy position of SN-38 in MAb-CL2A-SN-38 is a 10-O-ester or 10-O-carbonate derivative using a 'COR' moiety, wherein "CO" is carbonyl and the "R" group is selected from (i) an N,N-disubstituted aminoalkyl group "$N(CH_3)_2$—$(CH_2)_n$—" wherein n is 1-10 and wherein the terminal amino group is optionally in the form of a quaternary salt; (ii) an alkyl residue "$CH_3$—$(CH_2)_n$—" wherein n is 0-10; (iii) an alkoxy moiety "$CH_3$—$(CH_2)$n-O—" wherein n is 0-10; (iv) an "$N(CH_3)_2$—$(CH_2)_n$—O—" wherein n is 2-10; or (v) an "$R_1O$—$(CH_2$—$CH_2$—$O)_n$—$CH_2$—$CH_2$—O—" wherein $R_1$ is ethyl or methyl and n is an integer with values of 0-10.

13. The method of claim 1, wherein there are at least 6 SN-38 molecules attached to each antibody molecule.

14. The method of claim 1, wherein there are 6 to 8 SN-38 molecules attached to each antibody molecule.

15. The method of claim 1, wherein the antibody is an IgG1 or IgG4 antibody.

16. The method of claim 1, wherein the antibody has an allotype selected from the group consisting of G1m3, G1m3,1, G1m3,2, G1m3,1,2, nG1m1, nG1m1,2 and Km3 allotypes.

17. The method of claim 1, wherein the immunoconjugate dosage is administered to the human patient once or twice a week on a schedule with a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five weeks off; (vi) four weeks of therapy followed by one, two, three, four or five weeks off; (vii) five weeks of therapy followed by one, two, three, four or five weeks off; and (viii) monthly.

18. The method of claim 17, wherein the cycle is repeated 4, 6, 8, 10, 12, 16 or 20 times.

19. The method of claim 1, wherein the immunoconjugate is administered in combination with one or more therapeutic modalities selected from the group consisting of unconjugated antibodies, radiolabeled antibodies, drug-conjugated antibodies, toxin-conjugated antibodies, gene therapy, chemotherapy, therapeutic peptides, cytokine therapy, oligonucleotides, localized radiation therapy, surgery and interference RNA therapy.

20. The method of claim 19, wherein the drug, toxin or chemotherapeutic agent is selected from the group consisting of 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, crizotinib, cytarabine, dacarbazine, dasatinib, dinaciclib, docetaxel, dactinomycin, daunorubicin, doxorubicin, 2-pyrrolinodoxorubicine (2P-DOX), cyanomorpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, flavopiridol, floxuridine (FUdR), 3',5'-O-dioleoyl-FudR (FUdR-dO), fludarabine, flutamide, farnesyl-protein transferase inhibitors, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), transplatinum, thalidomide, thioguanine, thiotepa, teniposide, topotecan, uracil mustard, vatalanib, vinorelbine, vinblastine, vincristine, vinca alkaloids and ZD1839.

* * * * *

UNITED STATES PATENT AND TRADEMARK OFFICE

CERTIFICATE OF CORRECTION

PATENT NO. : 9,475,884 B2
APPLICATION NO. : 14/669611
DATED : October 25, 2016
INVENTOR(S) : Serengulam V. Govindan et al.

It is certified that error appears in the above-identified patent and that said Letters Patent is hereby corrected as shown below:

In Column 1, below the paragraph ending at Line 11 and above the heading SEQUENCE LISTING, please insert the following heading and text:
--GOVERNMENT SUPPORT
This invention was made with government support under Grant Number CA171388 awarded by the National Institutes of Health. The government has certain rights in the invention.--

Signed and Sealed this
Tenth Day of April, 2018

Andrei Iancu
*Director of the United States Patent and Trademark Office*

SEQUENCE LISTING

```
<160> NUMBER OF SEQ ID NOS: 161

<210> SEQ ID NO 1
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40


<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45


<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 3

Gln Ile Glu Tyr Leu Ala Lys Gln Ile Val Asp Asn Ala Ile Gln Gln
1 5 10 15

Ala

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Cys Gly Gln Ile Glu Tyr Leu Ala Lys Gln Ile Val Asp Asn Ala Ile
1 5 10 15

Gln Gln Ala Gly Cys
20

<210> SEQ ID NO 5
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

Ser Leu Arg Glu Cys Glu Leu Tyr Val Gln Lys His Asn Ile Gln Ala
1 5 10 15

Leu Leu Lys Asp Ser Ile Val Gln Leu Cys Thr Ala Arg Pro Glu Arg
20 25 30

Pro Met Ala Phe Leu Arg Glu Tyr Phe Glu Arg Leu Glu Lys Glu Glu
35 40 45

Ala Lys
50

<210> SEQ ID NO 6
<211> LENGTH: 55
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Met Ser Cys Gly Gly Ser Leu Arg Glu Cys Glu Leu Tyr Val Gln Lys
1 5 10 15

His Asn Ile Gln Ala Leu Leu Lys Asp Ser Ile Val Gln Leu Cys Thr
20 25 30

Ala Arg Pro Glu Arg Pro Met Ala Phe Leu Arg Glu Tyr Phe Glu Arg
35 40 45

Leu Glu Lys Glu Glu Ala Lys
50 55

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Cys Gly Phe Glu Glu Leu Ala Trp Lys Ile Ala Lys Met Ile Trp Ser
1 5 10 15

Asp Val Phe Gln Gln Gly Cys
20

<210> SEQ ID NO 8
<211> LENGTH: 51
<212> TYPE: PRT
<213> ORGANISM: Homo sapiens

<400> SEQUENCE: 8

Ser Leu Arg Glu Cys Glu Leu Tyr Val Gln Lys His Asn Ile Gln Ala
1 5 10 15

Leu Leu Lys Asp Val Ser Ile Val Gln Leu Cys Thr Ala Arg Pro Glu
20 25 30

Arg Pro Met Ala Phe Leu Arg Glu Tyr Phe Glu Lys Leu Glu Lys Glu
35 40 45

Glu Ala Lys
50

<210> SEQ ID NO 9
<211> LENGTH: 54
<212> TYPE: PRT
<213> ORGANISM: Homo sapiens

<400> SEQUENCE: 9

Ser Leu Lys Gly Cys Glu Leu Tyr Val Gln Leu His Gly Ile Gln Gln
1 5 10 15

Val Leu Lys Asp Cys Ile Val His Leu Cys Ile Ser Lys Pro Glu Arg
20 25 30

Pro Met Lys Phe Leu Arg Glu His Phe Glu Lys Leu Glu Lys Glu Glu
35 40 45

Asn Arg Gln Ile Leu Ala
50

<210> SEQ ID NO 10
<211> LENGTH: 44
<212> TYPE: PRT
<213> ORGANISM: Homo sapiens

<400> SEQUENCE: 10

Ser His Ile Gln Ile Pro Pro Gly Leu Thr Glu Leu Leu Gln Gly Tyr
1 5 10 15

Thr Val Glu Val Gly Gln Gln Pro Pro Asp Leu Val Asp Phe Ala Val
20 25 30

Glu Tyr Phe Thr Arg Leu Arg Glu Ala Arg Arg Gln
35 40

<210> SEQ ID NO 11
<211> LENGTH: 44
<212> TYPE: PRT
<213> ORGANISM: Homo sapiens

<400> SEQUENCE: 11

Ser Ile Glu Ile Pro Ala Gly Leu Thr Glu Leu Leu Gln Gly Phe Thr
1 5 10 15

Val Glu Val Leu Arg His Gln Pro Ala Asp Leu Leu Glu Phe Ala Leu
20 25 30

```
Gln His Phe Thr Arg Leu Gln Gln Glu Asn Glu Arg
        35                  40


<210> SEQ ID NO 12
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40


<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Lys Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40


<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Arg Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40


<210> SEQ ID NO 15
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ser His Ile Asn Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30
```

```
Val Glu Tyr Phe Thr Arg Leu Arg Glu Ala Arg Ala
        35                  40


<210> SEQ ID NO 16
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ser His Ile Gln Ile Pro Pro Ala Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40


<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser His Ile Gln Ile Pro Pro Gly Leu Ser Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40


<210> SEQ ID NO 18
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser His Ile Gln Ile Pro Pro Gly Leu Thr Asp Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40


<210> SEQ ID NO 19
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser His Ile Gln Ile Pro Pro Gly Leu Thr Glu Leu Leu Asn Gly Tyr
1               5                   10                  15

Thr Val Glu Val Leu Arg Gln Gln Pro Pro Asp Leu Val Glu Phe Ala
```

```
            20                  25                  30

Val Glu Tyr Phe Thr Arg Leu Arg Glu Ala Arg Ala
        35                  40


<210> SEQ ID NO 20
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser His Ile Gln Ile Pro Pro Gly Leu Thr Glu Leu Leu Gln Ala Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40


<210> SEQ ID NO 21
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser His Ile Gln Ile Pro Pro Gly Leu Thr Glu Leu Leu Gln Gly Tyr
1               5                   10                  15

Ser Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40


<210> SEQ ID NO 22
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser His Ile Gln Ile Pro Pro Gly Leu Thr Glu Leu Leu Gln Gly Tyr
1               5                   10                  15

Thr Val Asp Val Leu Arg Gln Gln Pro Pro Asp Leu Val Glu Phe Ala
            20                  25                  30

Val Glu Tyr Phe Thr Arg Leu Arg Glu Ala Arg Ala
        35                  40


<210> SEQ ID NO 23
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser His Ile Gln Ile Pro Pro Gly Leu Thr Glu Leu Leu Gln Gly Tyr
1               5                   10                  15
```

-continued

```
Thr Val Glu Val Leu Lys Gln Gln Pro Pro Asp Leu Val Glu Phe Ala
            20                  25                  30

Val Glu Tyr Phe Thr Arg Leu Arg Glu Ala Arg Ala
        35                  40


<210> SEQ ID NO 24
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser His Ile Gln Ile Pro Pro Gly Leu Thr Glu Leu Leu Gln Gly Tyr
1               5                   10                  15

Thr Val Glu Val Leu Arg Asn Gln Pro Pro Asp Leu Val Glu Phe Ala
            20                  25                  30

Val Glu Tyr Phe Thr Arg Leu Arg Glu Ala Arg Ala
        35                  40


<210> SEQ ID NO 25
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser His Ile Gln Ile Pro Pro Gly Leu Thr Glu Leu Leu Gln Gly Tyr
1               5                   10                  15

Thr Val Glu Val Leu Arg Gln Asn Pro Pro Asp Leu Val Glu Phe Ala
            20                  25                  30

Val Glu Tyr Phe Thr Arg Leu Arg Glu Ala Arg Ala
        35                  40


<210> SEQ ID NO 26
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser His Ile Gln Ile Pro Pro Gly Leu Thr Glu Leu Leu Gln Gly Tyr
1               5                   10                  15

Thr Val Glu Val Leu Arg Gln Gln Pro Pro Glu Leu Val Glu Phe Ala
            20                  25                  30

Val Glu Tyr Phe Thr Arg Leu Arg Glu Ala Arg Ala
        35                  40


<210> SEQ ID NO 27
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser His Ile Gln Ile Pro Pro Gly Leu Thr Glu Leu Leu Gln Gly Tyr
1               5                   10                  15
```

Thr Val Glu Val Leu Arg Gln Gln Pro Pro Asp Leu Val Asp Phe Ala
20 25 30

Val Glu Tyr Phe Thr Arg Leu Arg Glu Ala Arg Ala
35 40

<210> SEQ ID NO 28
<211> LENGTH: 44
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

Ser His Ile Gln Ile Pro Pro Gly Leu Thr Glu Leu Leu Gln Gly Tyr
1 5 10 15

Thr Val Glu Val Leu Arg Gln Gln Pro Pro Asp Leu Val Glu Phe Leu
20 25 30

Val Glu Tyr Phe Thr Arg Leu Arg Glu Ala Arg Ala
35 40

<210> SEQ ID NO 29
<211> LENGTH: 44
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Ser His Ile Gln Ile Pro Pro Gly Leu Thr Glu Leu Leu Gln Gly Tyr
1 5 10 15

Thr Val Glu Val Leu Arg Gln Gln Pro Pro Asp Leu Val Glu Phe Ile
20 25 30

Val Glu Tyr Phe Thr Arg Leu Arg Glu Ala Arg Ala
35 40

<210> SEQ ID NO 30
<211> LENGTH: 44
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Ser His Ile Gln Ile Pro Pro Gly Leu Thr Glu Leu Leu Gln Gly Tyr
1 5 10 15

Thr Val Glu Val Leu Arg Gln Gln Pro Pro Asp Leu Val Glu Phe Val
20 25 30

Val Glu Tyr Phe Thr Arg Leu Arg Glu Ala Arg Ala
35 40

<210> SEQ ID NO 31
<211> LENGTH: 44
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Ser His Ile Gln Ile Pro Pro Gly Leu Thr Glu Leu Leu Gln Gly Tyr 1 5 10 15

Thr Val Glu Val Leu Arg Gln Gln Pro Pro Asp Leu Val Glu Phe Ala
20 25 30

Val Asp Tyr Phe Thr Arg Leu Arg Glu Ala Arg Ala
35 40

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Asn Ile Glu Tyr Leu Ala Lys Gln Ile Val Asp Asn Ala Ile Gln Gln
1 5 10 15

Ala

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Gln Leu Glu Tyr Leu Ala Lys Gln Ile Val Asp Asn Ala Ile Gln Gln
1 5 10 15

Ala

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Gln Val Glu Tyr Leu Ala Lys Gln Ile Val Asp Asn Ala Ile Gln Gln
1 5 10 15

Ala

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Gln Ile Asp Tyr Leu Ala Lys Gln Ile Val Asp Asn Ala Ile Gln Gln
1 5 10 15

Ala

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Gln Ile Glu Phe Leu Ala Lys Gln Ile Val Asp Asn Ala Ile Gln Gln
1 5 10 15

Ala

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 37

Gln Ile Glu Thr Leu Ala Lys Gln Ile Val Asp Asn Ala Ile Gln Gln
1 5 10 15

Ala

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Gln Ile Glu Ser Leu Ala Lys Gln Ile Val Asp Asn Ala Ile Gln Gln
1 5 10 15

Ala

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Gln Ile Glu Tyr Ile Ala Lys Gln Ile Val Asp Asn Ala Ile Gln Gln
1 5 10 15

Ala

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Gln Ile Glu Tyr Val Ala Lys Gln Ile Val Asp Asn Ala Ile Gln Gln
1 5 10 15

Ala

<210> SEQ ID NO 41
<211> LENGTH: 17
<212> TYPE: PRT
<213> ORGANISM: Artificial Sequence
<220> FEATURE:

<223> OTHER INFORMATION: Description of Artificial Sequence: Synthetic peptide

<400> SEQUENCE: 41

Gln Ile Glu Tyr Leu Ala Arg Gln Ile Val Asp Asn Ala Ile Gln Gln
1 5 10 15

Ala

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Gln Ile Glu Tyr Leu Ala Lys Asn Ile Val Asp Asn Ala Ile Gln Gln
1 5 10 15

Ala

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Gln Ile Glu Tyr Leu Ala Lys Gln Ile Val Glu Asn Ala Ile Gln Gln
1 5 10 15

Ala

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Gln Ile Glu Tyr Leu Ala Lys Gln Ile Val Asp Gln Ala Ile Gln Gln
1 5 10 15

Ala

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Gln Ile Glu Tyr Leu Ala Lys Gln Ile Val Asp Asn Ala Ile Asn Gln
1 5 10 15

Ala

<210> SEQ ID NO 46
<211> LENGTH: 17
<212> TYPE: PRT
<213> ORGANISM: Artificial Sequence -continued
<220> FEATURE:
<223> OTHER INFORMATION: Description of Artificial Sequence: Synthetic
peptide

<400> SEQUENCE: 46

Gln Ile Glu Tyr Leu Ala Lys Gln Ile Val Asp Asn Ala Ile Gln Asn
1 5 10 15

Ala

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Gln Ile Glu Tyr Leu Ala Lys Gln Ile Val Asp Asn Ala Ile Gln Gln
1 5 10 15

Leu

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Gln Ile Glu Tyr Leu Ala Lys Gln Ile Val Asp Asn Ala Ile Gln Gln
1 5 10 15

Ile

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 49

Gln Ile Glu Tyr Leu Ala Lys Gln Ile Val Asp Asn Ala Ile Gln Gln
1 5 10 15

Val

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 50

Gln Ile Glu Tyr Val Ala Lys Gln Ile Val Asp Tyr Ala Ile His Gln
1 5 10 15

Ala

<210> SEQ ID NO 51
<211> LENGTH: 17
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 51

Gln Ile Glu Tyr Lys Ala Lys Gln Ile Val Asp His Ala Ile His Gln
1               5                   10                  15

Ala

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Gln Ile Glu Tyr His Ala Lys Gln Ile Val Asp His Ala Ile His Gln
1               5                   10                  15

Ala

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 53

Gln Ile Glu Tyr Val Ala Lys Gln Ile Val Asp His Ala Ile His Gln
1               5                   10                  15

Ala

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Pro Leu Glu Tyr Gln Ala Gly Leu Leu Val Gln Asn Ala Ile Gln Gln
1               5                   10                  15

Ala Ile

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

Leu Leu Ile Glu Thr Ala Ser Ser Leu Val Lys Asn Ala Ile Gln Leu
1               5                   10                  15

Ser Ile

<210> SEQ ID NO 56
<211> LENGTH: 18

<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Leu Ile Glu Glu Ala Ala Ser Arg Ile Val Asp Ala Val Ile Glu Gln
1 5 10 15

Val Lys

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Ala Leu Tyr Gln Phe Ala Asp Arg Phe Ser Glu Leu Val Ile Ser Glu
1 5 10 15

Ala Leu

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Leu Glu Gln Val Ala Asn Gln Leu Ala Asp Gln Ile Ile Lys Glu Ala
1 5 10 15

Thr

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Phe Glu Glu Leu Ala Trp Lys Ile Ala Lys Met Ile Trp Ser Asp Val
1 5 10 15

Phe

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Glu Leu Val Arg Leu Ser Lys Arg Leu Val Glu Asn Ala Val Leu Lys
1 5 10 15

Ala Val

<210> SEQ ID NO 61

<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Thr Ala Glu Glu Val Ser Ala Arg Ile Val Gln Val Val Thr Ala Glu
1 5 10 15

Ala Val

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Gln Ile Lys Gln Ala Ala Phe Gln Leu Ile Ser Gln Val Ile Leu Glu
1 5 10 15

Ala Thr

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Leu Ala Trp Lys Ile Ala Lys Met Ile Val Ser Asp Val Met Gln Gln
1 5 10 15

<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Asp Leu Ile Glu Glu Ala Ala Ser Arg Ile Val Asp Ala Val Ile Glu
1 5 10 15

Gln Val Lys Ala Ala Gly Ala Tyr
20

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Leu Glu Gln Tyr Ala Asn Gln Leu Ala Asp Gln Ile Ile Lys Glu Ala
1 5 10 15

Thr Glu

<210> SEQ ID NO 66

<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Phe Glu Glu Leu Ala Trp Lys Ile Ala Lys Met Ile Trp Ser Asp Val
1 5 10 15

Phe Gln Gln Cys
20

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Gln Ile Glu Tyr Leu Ala Lys Gln Ile Pro Asp Asn Ala Ile Gln Gln
1 5 10 15

Ala

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Lys Gly Ala Asp Leu Ile Glu Glu Ala Ala Ser Arg Ile Val Asp Ala
1 5 10 15

Val Ile Glu Gln Val Lys Ala Ala Gly
20 25

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Lys Gly Ala Asp Leu Ile Glu Glu Ala Ala Ser Arg Ile Pro Asp Ala
1 5 10 15

Pro Ile Glu Gln Val Lys Ala Ala Gly
20 25

<210> SEQ ID NO 70
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Pro Glu Asp Ala Glu Leu Val Arg Leu Ser Lys Arg Leu Val Glu Asn
1 5 10 15

```
Ala Val Leu Lys Ala Val Gln Gln Tyr
            20                  25


<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25


<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25


<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25


<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25


<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 75

Pro Glu Asp Ala Glu Leu Val Arg Leu Ser Lys Arg Leu Val Glu Asn
1 5 10 15

Ala Val Glu Lys Ala Val Gln Gln Tyr
20 25

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Glu Glu Gly Leu Asp Arg Asn Glu Glu Ile Lys Arg Ala Ala Phe Gln
1 5 10 15

Ile Ile Ser Gln Val Ile Ser Glu Ala
20 25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Leu Val Asp Asp Pro Leu Glu Tyr Gln Ala Gly Leu Leu Val Gln Asn
1 5 10 15

Ala Ile Gln Gln Ala Ile Ala Glu Gln
20 25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

Gln Tyr Glu Thr Leu Leu Ile Glu Thr Ala Ser Ser Leu Val Lys Asn
1 5 10 15

Ala Ile Gln Leu Ser Ile Glu Gln Leu
20 25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 79

Leu Glu Lys Gln Tyr Gln Glu Gln Leu Glu Glu Glu Val Ala Lys Val
1 5 10 15

Ile Val Ser Met Ser Ile Ala Phe Ala
20 25

<210> SEQ ID NO 80

<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

```
Asn Thr Asp Glu Ala Gln Glu Glu Leu Ala Trp Lys Ile Ala Lys Met
1               5                   10                  15

Ile Val Ser Asp Ile Met Gln Gln Ala
            20                  25
```

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

```
Val Asn Leu Asp Lys Lys Ala Val Leu Ala Glu Lys Ile Val Ala Glu
1               5                   10                  15

Ala Ile Glu Lys Ala Glu Arg Glu Leu
            20                  25
```

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

```
Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25
```

<210> SEQ ID NO 83
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

```
Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25
```

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

```
Glu Thr Ser Ala Lys Asp Asn Ile Asn Ile Glu Glu Ala Ala Arg Phe
1               5                   10                  15
```

Leu Val Glu Lys Ile Leu Val Asn His
20 25

<210> SEQ ID NO 85
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Ala Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

```
<210> SEQ ID NO 86
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 87
<211> LENGTH: 44
<212> TYPE: PRT
<213> ORGANISM: Artificial Sequence
<220> FEATURE:
```

<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: His, Lys or Arg
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (8)..(8)
<223> OTHER INFORMATION: Gly or Ala
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (14)..(14)
<223> OTHER INFORMATION: Gln or Asn
<220> FEATURE:
<221> NAME/KEY: MOD_RES
<222> LOCATION: (15)..(15)
<223> OTHER INFORMATION: Gly or Ala
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (19)..(19)
<223> OTHER INFORMATION: Glu or Asp
<220> FEATURE:
<221> NAME/KEY: MOD_RES
<222> LOCATION: (22)..(22)
<223> OTHER INFORMATION: Arg or Lys
<220> FEATURE:
<221> NAME/KEY: MOD_RES
<222> LOCATION: (23)..(24)
<223> OTHER INFORMATION: Gln or Asn
<220> FEATURE:
<221> NAME/KEY: MOD_RES
<222> LOCATION: (27)..(27)
<223> OTHER INFORMATION: Asp or Glu
<220> FEATURE:
<221> NAME/KEY: MOD_RES
<222> LOCATION: (30)..(30)
<223> OTHER INFORMATION: Glu or Asp
<220> FEATURE:
<221> NAME/KEY: MOD_RES
<222> LOCATION: (32)..(32)
<223> OTHER INFORMATION: Ala, Leu, Ile or Val
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:

<221> NAME/KEY: MOD_RES
<222> LOCATION: (41)..(41)
<223> OTHER INFORMATION: Glu or Asp
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (43)..(43)
<223> OTHER INFORMATION: Arg or Lys
<220> FEATURE:
<221> NAME/KEY: MOD_RES
<222> LOCATION: (44)..(44)
<223> OTHER INFORMATION: Ala, Leu, Ile or Val

<400> SEQUENCE: 87

```
Xaa Xaa Ile Xaa Ile Pro Pro Xaa Leu Xaa Xaa Leu Leu Xaa Xaa Tyr
1               5                   10                  15

Xaa Val Xaa Val Leu Xaa Xaa Xaa Pro Pro Xaa Leu Val Xaa Phe Xaa
            20                  25                  30

Val Xaa Tyr Phe Xaa Xaa Leu Xaa Xaa Xaa Xaa Xaa
        35                  40
```

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(2)
<223> OTHER INFORMATION: Ile, Leu or Val
<220> FEATURE:
<221> NAME/KEY: MOD_RES
<222> LOCATION: (3)..(3)
<223> OTHER INFORMATION: Glu or Asp
<220> FEATURE:
<221> NAME/KEY: MOD_RES
<222> LOCATION: (4)..(4)
<223> OTHER INFORMATION: Tyr, Phe, Thr or Ser
<220> FEATURE:
<221> NAME/KEY: MOD_RES
<222> LOCATION: (5)..(5)
<223> OTHER INFORMATION: Leu, Ile or Val
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Gln or Asn
<220> FEATURE:
<221> NAME/KEY: MOD_RES
<222> LOCATION: (11)..(11)
<223> OTHER INFORMATION: Asp or Glu
<220> FEATURE:
<221> NAME/KEY: MOD_RES
<222> LOCATION: (12)..(12)
<223> OTHER INFORMATION: Asn or Gln
<220> FEATURE:
<221> NAME/KEY: MOD_RES
<222> LOCATION: (15)..(16)
<223> OTHER INFORMATION: Gln or Asn
<220> FEATURE:
<221> NAME/KEY: MOD_RES
<222> LOCATION: (17)..(17)
<223> OTHER INFORMATION: Ala, Leu, Ile or Val

<400> SEQUENCE: 88

Xaa Xaa Xaa Xaa Xaa Ala Xaa Xaa Ile Val Xaa Xaa Ala Ile Xaa Xaa
1 5 10 15

Xaa

<210> SEQ ID NO 89
<211> LENGTH: 44
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (18)..(18)
<223> OTHER INFORMATION: Val, Ile, Leu or Ala
<220> FEATURE:
<221> NAME/KEY: MOD_RES
<222> LOCATION: (23)..(23)
<223> OTHER INFORMATION: Gln or Asn
<220> FEATURE:
<221> NAME/KEY: MOD_RES
<222> LOCATION: (33)..(33)
<223> OTHER INFORMATION: Val, Ile, Leu or Ala
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (44)..(44)
<223> OTHER INFORMATION: Ala, Leu, Ile or Val

<400> SEQUENCE: 89

Xaa His Ile Xaa Ile Pro Pro Gly Leu Xaa Glu Leu Leu Gln Gly Tyr
1 5 10 15

Thr Xaa Glu Val Leu Arg Xaa Gln Pro Pro Asp Leu Val Glu Phe Ala
20 25 30

Xaa Xaa Tyr Phe Xaa Xaa Leu Xaa Glu Xaa Arg Xaa
35 40

<210> SEQ ID NO 90
<211> LENGTH: 11

<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Lys Ala Ser Gln Asp Val Ser Ile Ala Val Ala
1 5 10

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Ser Ala Ser Tyr Arg Tyr Thr
1 5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Gln Gln His Tyr Ile Thr Pro Leu Thr
1 5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Asn Tyr Gly Met Asn
1 5

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Trp Ile Asn Thr Tyr Thr Gly Glu Pro Thr Tyr Thr Asp Asp Phe Lys
1 5 10 15

Gly

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

```
Gly Gly Phe Gly Ser Ser Tyr Trp Tyr Phe Asp Val
1               5                   10


<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Lys Ala Ser Gln Asp Val Gly Thr Ser Val Ala
1               5                   10


<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Trp Thr Ser Thr Arg His Thr
1               5


<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Gln Tyr Ser Leu Tyr Arg Ser
1               5


<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Tyr Trp Met Ser
1               5


<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Glu Ile His Pro Asp Ser Ser Thr Ile Asn Tyr Ala Pro Ser Leu Lys
1               5                   10                  15

Asp


<210> SEQ ID NO 101
<211> LENGTH: 10
```

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Leu Tyr Phe Gly Phe Pro Trp Phe Ala Tyr
1 5 10

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Arg Ser Ser Gln Ser Ile Val His Ser Asn Gly Asn Thr Tyr Leu Glu
1 5 10 15

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Lys Val Ser Asn Arg Phe Ser
1 5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Phe Gln Gly Ser His Val Pro Pro Thr
1 5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

Asn Tyr Gly Met Asn
1 5

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 106

Trp Ile Asn Thr Tyr Thr Gly Glu Pro Thr Tyr Ala Asp Asp Phe Lys 1 5 10 15

Gly

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Lys Gly Trp Met Asp Phe Asn Ser Ser Leu Asp Tyr
1 5 10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Ser Ala Ser Ser Arg Val Ser Tyr Ile His
1 5 10

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Gly Thr Ser Thr Leu Ala Ser
1 5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Gln Gln Trp Ser Tyr Asn Pro Pro Thr
1 5

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Asp Tyr Tyr Met Ser
1 5

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 112

Phe Ile Ala Asn Lys Ala Asn Gly His Thr Thr Asp Tyr Ser Pro Ser
1 5 10 15

Val Lys Gly

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

Asp Met Gly Ile Arg Trp Asn Phe Asp Val
1 5 10

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 114

Arg Ser Ser Gln Ser Leu Val His Arg Asn Gly Asn Thr Tyr Leu His
1 5 10 15

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 115

Thr Val Ser Asn Arg Phe Ser
1 5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 116

Ser Gln Ser Ser His Val Pro Pro Thr
1 5

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 117

Asn Tyr Gly Val Asn 1 5

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 118

Trp Ile Asn Pro Asn Thr Gly Glu Pro Thr Phe Asp Asp Asp Phe Lys
1 5 10 15

Gly

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

Ser Arg Gly Lys Asn Glu Ala Trp Phe Ala Tyr
1 5 10

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 120

Lys Ser Ser Gln Ser Val Leu Tyr Ser Ala Asn His Lys Tyr Leu Ala
1 5 10 15

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 121

Trp Ala Ser Thr Arg Glu Ser
1 5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 122

His Gln Tyr Leu Ser Ser Trp Thr Phe
1 5

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 123

Ser Tyr Trp Leu His
1 5

<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 124

Tyr Ile Asn Pro Arg Asn Asp Tyr Thr Glu Tyr Asn Gln Asn Phe Lys
1 5 10 15

Asp

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 125

Arg Asp Ile Thr Thr Phe Tyr
1 5

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 126

Arg Ser Ser Gln Ser Ile Val His Ser Asn Gly Asn Thr Tyr Leu Glu
1 5 10 15

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 127

Lys Val Ser Asn Arg Phe Ser
1 5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Phe Gln Gly Ser Arg Val Pro Tyr Thr 1 5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Glu Tyr Val Ile Thr
1 5

<210> SEQ ID NO 130
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Glu Ile Tyr Pro Gly Ser Gly Ser Thr Ser Tyr Asn Glu Lys Phe Lys
1 5 10 15

<210> SEQ ID NO 131
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Glu Asp Leu
1

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Ser Ala Ser Ser Ser Val Ser Ser Ser Tyr Leu Tyr
1 5 10

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Ser Thr Ser Asn Leu Ala Ser
1 5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 134

His Gln Trp Asn Arg Tyr Pro Tyr Thr
1 5

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 135

Ser Tyr Val Leu His
1 5

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 136

Tyr Ile Asn Pro Tyr Asn Asp Gly Thr Gln Tyr Asn Glu Lys Phe Lys
1 5 10 15

Gly

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 137

Gly Phe Gly Gly Ser Tyr Gly Phe Ala Tyr
1 5 10

<210> SEQ ID NO 138
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 138

Ser Tyr Val Ile His
1 5

<210> SEQ ID NO 139
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 139

Tyr Ile His Pro Tyr Asn Gly Gly Thr Lys Tyr Asn Glu Lys Phe Lys
1 5 10 15

Gly

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

Ser Gly Gly Gly Asp Pro Phe Ala Tyr
1 5

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

Lys Ala Ser Gln Asp Ile Asn Lys Tyr Ile Gly
1 5 10

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

Tyr Thr Ser Ala Leu Leu Pro
1 5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 143

Leu Gln Tyr Asp Asp Leu Trp Thr
1 5

<210> SEQ ID NO 144
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 144

Asn Tyr Gly Met Asn
1 5

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

Trp Ile Asn Thr Tyr Thr Arg Glu Pro Thr Tyr Ala Asp Asp Phe Lys
1 5 10 15

Gly

<210> SEQ ID NO 146
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 146

Asp Ile Thr Ala Val Val Pro Thr Gly Phe Asp Tyr
1 5 10

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 147

Arg Ala Ser Glu Asn Ile Tyr Ser Asn Leu Ala
1 5 10

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 148

Ala Ala Ser Asn Leu Ala Asp
1 5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 149

Gln His Phe Trp Thr Thr Pro Trp Ala
1 5

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Arg Ala Ser Ser Ser Val Ser Tyr Ile His
1 5 10

```
<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Thr Ser Asn Leu Ala Ser
1               5


<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gln Gln Trp Thr Ser Asn Pro Pro Thr
1               5


<210> SEQ ID NO 153
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ser Tyr Asn Met His
1               5


<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Ile Tyr Pro Gly Asn Gly Asp Thr Ser Tyr Asn Gln Lys Phe Lys
1               5                   10                  15

Gly


<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Thr Tyr Tyr Gly Gly Asp Trp Tyr Phe Asp Val
1               5                   10


<210> SEQ ID NO 156
<211> LENGTH: 15
<212> TYPE: PRT
<213> ORGANISM: Artificial Sequence
```

<220> FEATURE:
<223> OTHER INFORMATION: Description of Artificial Sequence: Synthetic
peptide

<400> SEQUENCE: 156

Lys Ala Ser Gln Ser Val Asp Tyr Asp Gly Asp Ser Tyr Leu Asn
1               5                   10                  15

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 157

Asp Ala Ser Asn Leu Val Ser
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 158

Gln Gln Ser Thr Glu Asp Pro Trp Thr
1               5

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 159

Ser Tyr Trp Met Asn
1               5

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 160

Gln Ile Trp Pro Gly Asp Gly Asp Thr Asn Tyr Asn Gly Lys Phe Lys
1               5                   10                  15

Gly

<210> SEQ ID NO 161
<211> LENGTH: 15
<212> TYPE: PRT
<213> ORGANISM: Artificial Sequence -continued
<220> FEATURE:
<223> OTHER INFORMATION: Description of Artificial Sequence: Synthetic peptide

<400> SEQUENCE: 161

```
Arg Glu Thr Thr Thr Val Gly Arg Tyr Tyr Tyr Ala Met Asp Tyr
1               5                   10                  15
```